United States Patent
Conway et al.

(10) Patent No.: US 9,901,451 B2
(45) Date of Patent: Feb. 27, 2018

(54) IMPLANT COMPONENTS AND METHODS

(71) Applicant: Smith & Nephew, Inc., Memphis, TN (US)

(72) Inventors: Justin Steve Conway, Olive Branch, MS (US); David C. Kelman, Collierville, TN (US); Richard D. Lambert, Germantown, TN (US); Jeffrey A. Sharp, Salt Lake City, UT (US); Jeffrey Joel Shea, Memphis, TN (US); Brian Ronald Yokoo, Riverton, UT (US)

(73) Assignee: Smith & Nephew, Inc., Memphis, TN (US)

( * ) Notice: Subject to any disclaimer, the term of this patent is extended or adjusted under 35 U.S.C. 154(b) by 156 days.

(21) Appl. No.: 14/189,210

(22) Filed: Feb. 25, 2014

(65) Prior Publication Data

US 2014/0180431 A1  Jun. 26, 2014

Related U.S. Application Data

(62) Division of application No. 13/156,238, filed on Jun. 8, 2011, now abandoned.
(Continued)

(51) Int. Cl.
*A61F 2/34* (2006.01)
*G06F 9/455* (2018.01)
(Continued)

(52) U.S. Cl.
CPC ............ *A61F 2/34* (2013.01); *A61B 17/8066* (2013.01); *A61F 2/30734* (2013.01);
(Continued)

(58) Field of Classification Search
CPC ............... A61F 2/34; A61F 2002/3429; A61F 2002/343; A61F 2002/3432;
(Continued)

(56) References Cited

U.S. PATENT DOCUMENTS 3,874,003 A  4/1975  Moser et al.
3,882,550 A  5/1975  Karpf et al.
(Continued)

FOREIGN PATENT DOCUMENTS

CN  1728976 A  2/2006
CN  1756515 A  4/2006
(Continued)

OTHER PUBLICATIONS

Chinese Search Report (First); Chinese Patent Office (State Intellectual Property Office of People's Republic of China); Chinese Patent Application No. 201180039345.2; dated Sep. 19, 2014; 3 pages.
Chinese First Office Action; Chinese Patent Office (State Intellectual Property Office of People's Republic of China); Chinese Patent Application No. 201180039345.2; dated Sep. 28, 2014; 15 pages.
(Continued)

*Primary Examiner* — Christopher D Prone
(74) *Attorney, Agent, or Firm* — Taft Stettinius & Hollister LLP

(57) ABSTRACT

Systems, devices, and methods are provided for orthopedic implants. The implants may include a base member, such as an acetabular shell or an augment, that is configured to couple with an augment, flange cup, mounting member, or any other suitable orthopedic attachment. Mounting members include, for example, flanges, blades, hooks, and plates. In some embodiments, the orthopedic attachments may be adjustably positionable about the base member or other attachments, thereby providing modularity for assembling and implanting the device, and various securing and/or locking mechanisms may be used between the components of the implant.

25 Claims, 92 Drawing Sheets

Related U.S. Application Data

(60) Provisional application No. 61/352,705, filed on Jun. 8, 2010, provisional application No. 61/352,722, filed on Jun. 8, 2010, provisional application No. 61/422,903, filed on Dec. 14, 2010, provisional application No. 61/466,817, filed on Mar. 23, 2011.

(51) Int. Cl.
    *A61B 17/80*     (2006.01)
    *A61F 2/30*     (2006.01)
    *B33Y 80/00*     (2015.01)
    *A61B 17/82*     (2006.01)
    *A61B 17/86*     (2006.01)
    *A61F 2/46*     (2006.01)

(52) U.S. Cl.
CPC ...... *A61F 2/30749* (2013.01); *A61F 2/30771* (2013.01); *A61F 2/4609* (2013.01); *G06F 9/45533* (2013.01); *A61B 17/82* (2013.01); *A61B 17/866* (2013.01); *A61B 17/8685* (2013.01); *A61F 2/30907* (2013.01); *A61F 2/30965* (2013.01); *A61F 2002/30011* (2013.01); *A61F 2002/3038* (2013.01); *A61F 2002/3082* (2013.01); *A61F 2002/3092* (2013.01); *A61F 2002/3096* (2013.01); *A61F 2002/30169* (2013.01); *A61F 2002/30189* (2013.01); *A61F 2002/30326* (2013.01); *A61F 2002/30387* (2013.01); *A61F 2002/30449* (2013.01); *A61F 2002/30462* (2013.01); *A61F 2002/30471* (2013.01); *A61F 2002/30474* (2013.01); *A61F 2002/30507* (2013.01); *A61F 2002/30538* (2013.01); *A61F 2002/30578* (2013.01); *A61F 2002/30579* (2013.01); *A61F 2002/30611* (2013.01); *A61F 2002/30617* (2013.01); *A61F 2002/30736* (2013.01); *A61F 2002/30841* (2013.01); *A61F 2002/348* (2013.01); *A61F 2002/3412* (2013.01); *A61F 2002/3429* (2013.01); *A61F 2002/3441* (2013.01); *A61F 2002/3448* (2013.01); *A61F 2002/3487* (2013.01); *A61F 2002/4615* (2013.01); *A61F 2002/4619* (2013.01); *B33Y 80/00* (2014.12)

(58) Field of Classification Search
CPC ...... A61F 2002/3482; A61F 2002/3487; A61F 2002/349; A61F 2002/3491; A61F 2002/3498; A61F 2/30734; A61F 2/30739; A61B 17/8066
USPC ............ 623/22.22, 22.32, 22.34–22.39
See application file for complete search history.

(56) References Cited

U.S. PATENT DOCUMENTS

| | | |
|---|---|---|
| 3,894,297 A | 7/1975 | Mittelmeier et al. |
| 4,141,088 A | 2/1979 | Treace et al. |
| 4,298,993 A * | 11/1981 | Kovaleva ............ A61F 2/30721 623/22.36 |
| 4,437,193 A | 3/1984 | Oh |
| 4,473,068 A | 9/1984 | Oh |
| 4,475,549 A | 10/1984 | Oh |
| 4,623,352 A | 11/1986 | Oh |
| 4,632,111 A | 12/1986 | Roche |
| 4,673,409 A | 6/1987 | Van Kampen |
| 4,676,799 A | 6/1987 | Legrand |
| 4,695,282 A * | 9/1987 | Forte ............ A61F 2/34 623/22.29 |
| 4,718,908 A | 1/1988 | Wigginton et al. |
| 4,795,469 A | 1/1989 | Oh |
| 4,883,490 A | 11/1989 | Oh |
| 4,883,491 A | 11/1989 | Mallroy et al. |
| 4,990,149 A | 2/1991 | Fallin |
| 4,995,883 A | 2/1991 | Demane et al. |
| 4,997,447 A | 3/1991 | Shelley |
| 5,047,033 A | 9/1991 | Fallin |
| 5,078,746 A | 1/1992 | Garner |
| 5,080,677 A | 1/1992 | Shelley |
| 5,108,452 A | 4/1992 | Fallin |
| 5,193,679 A | 3/1993 | White |
| 5,217,499 A | 6/1993 | Shelley |
| 5,226,917 A | 7/1993 | Schryver |
| 5,310,408 A | 5/1994 | Schryver et al. |
| 5,314,487 A | 5/1994 | Schryver et al. |
| 5,324,291 A | 6/1994 | Ries et al. |
| 5,350,381 A | 9/1994 | Melton |
| 5,358,532 A | 10/1994 | Evans et al. |
| 5,405,005 A | 4/1995 | White |
| 5,405,392 A | 4/1995 | Deckner |
| 5,456,717 A | 10/1995 | Zweymuller et al. |
| 5,507,830 A | 4/1996 | Demane et al. |
| 5,549,702 A | 8/1996 | Ries et al. |
| 5,571,105 A | 11/1996 | Gundolf |
| 5,593,446 A | 1/1997 | Kuoni |
| 5,676,704 A | 10/1997 | Ries et al. |
| 5,782,928 A | 7/1998 | Ries et al. |
| 5,879,405 A | 3/1999 | Ries et al. |
| 5,906,234 A | 5/1999 | Mastrorio et al. |
| 5,931,870 A | 8/1999 | Cuckler et al. |
| 6,059,833 A | 5/2000 | Doets |
| 6,087,553 A | 7/2000 | Cohen et al. |
| 6,136,037 A | 10/2000 | Hassig et al. |
| 6,162,227 A | 12/2000 | Eckhardt et al. |
| 6,162,257 A | 12/2000 | Gustilo et al. |
| 6,209,621 B1 | 4/2001 | Treacy |
| 6,270,502 B1 | 8/2001 | Stulberg |
| 6,325,829 B1 | 12/2001 | Schmotzer |
| 6,344,060 B1 | 2/2002 | Schmotzer et al. |
| 6,364,910 B1 | 4/2002 | Shultz et al. |
| 6,383,228 B1 | 5/2002 | Schmotzer |
| 6,416,553 B1 | 7/2002 | White et al. |
| 6,436,147 B1 | 8/2002 | Zweymuller |
| 6,451,058 B2 | 9/2002 | Tuke et al. |
| RE38,058 E | 4/2003 | Fallin |
| 6,540,788 B1 | 4/2003 | Zweymuller |
| 6,613,094 B2 | 9/2003 | Zweymuller |
| 6,626,913 B1 | 9/2003 | McKinnon et al. |
| 6,652,589 B2 | 11/2003 | Schmotzer et al. |
| 6,746,452 B2 | 6/2004 | Tuke et al. |
| 6,808,539 B2 | 10/2004 | Zweymuller |
| 6,916,342 B2 | 7/2005 | Frederick et al. |
| 6,986,792 B2 | 1/2006 | McLean et al. |
| 7,004,973 B2 | 2/2006 | Zweymuller |
| 7,074,241 B2 | 7/2006 | McKinnon |
| 7,160,307 B2 | 1/2007 | Harwood et al. |
| 7,160,332 B2 | 1/2007 | Frederick et al. |
| 7,175,668 B2 | 2/2007 | Zweymuller |
| 7,179,297 B2 | 2/2007 | McLean |
| 7,250,054 B2 | 7/2007 | Allen et al. |
| 7,255,701 B2 | 8/2007 | Allen et al. |
| 7,335,231 B2 | 2/2008 | McLean |
| 7,374,576 B1 | 5/2008 | Ries et al. |
| 7,455,693 B2 | 11/2008 | Zweymuller |
| 7,494,510 B2 | 2/2009 | Zweymuller |
| 7,497,875 B1 | 3/2009 | Zweymuller |
| 7,534,271 B2 | 5/2009 | Ries et al. |
| 7,575,603 B2 | 8/2009 | Bergin et al. |
| 7,591,821 B2 | 9/2009 | Kelman |
| 7,621,915 B2 | 11/2009 | Frederick et al. |
| 7,682,398 B2 | 3/2010 | Croxton et al. |
| 7,749,277 B2 | 7/2010 | McLean |
| 7,749,278 B2 | 7/2010 | Frederick et al. |
| 7,780,667 B2 | 8/2010 | Watanabe et al. |
| 7,828,806 B2 | 11/2010 | Graf et al. |
| 7,863,410 B2 | 1/2011 | Smith et al. |
| 7,879,106 B2 | 2/2011 | McMinn |
| 7,892,290 B2 | 2/2011 | Bergin et al. |
| 7,901,411 B2 | 3/2011 | Frederick et al. |
| 2003/0045885 A1 | 3/2003 | Margulies et al. |

(56) References Cited

U.S. PATENT DOCUMENTS

| | | |
|---|---|---|
| 2003/0171818 A1 | 9/2003 | Lewallen |
| 2005/0267586 A1 | 12/2005 | Sidebotham |
| 2005/0288793 A1 | 12/2005 | Dong et al. |
| 2006/0178750 A1 | 8/2006 | Chieng |
| 2006/0282166 A1 | 12/2006 | Molz et al. |
| 2007/0129809 A1 | 6/2007 | Meridew et al. |
| 2007/0179627 A1 | 8/2007 | Gustilo et al. |
| 2008/0021568 A1* | 1/2008 | Tulkis ............... A61F 2/30734 623/22.35 |
| 2008/0065154 A1 | 3/2008 | Allard et al. |
| 2008/0312741 A1 | 12/2008 | Lee et al. |
| 2009/0240256 A1 | 9/2009 | Smith |
| 2009/0326670 A1 | 12/2009 | Keefer et al. |

FOREIGN PATENT DOCUMENTS

| | | |
|---|---|---|
| CN | 1826147 A | 8/2006 |
| CN | 101050053 A | 10/2007 |
| CN | 101161294 A | 4/2008 |
| EP | 0827726 A2 | 3/1998 |
| EP | 0838286 A1 | 4/1998 |
| EP | 0846453 A2 | 6/1998 |
| EP | 1870060 A1 | 12/2007 |
| EP | 2226408 A1 | 9/2010 |
| GB | 2057888 A | 4/1981 |
| JP | 05-200058 A | 8/1993 |
| JP | 2010-012254 A | 1/2010 |
| WO | 2009/022911 A2 | 2/2009 |
| WO | 2009022911 A2 | 2/2009 |

OTHER PUBLICATIONS

Chinese Search Report (Second); Chinese Patent Office (State Intellectual Property Office of People's Republic of China); Chinese Patent Application No. 201180039345.2; dated Jun. 25, 2015; 4 pages.

Chinese Second Office Action; Chinese Patent Office (State Intellectual Property Office of People's Republic of China); Chinese Patent Application No. 201180039345.2; dated Jul. 3, 2015; 25 pages.

Chinese Third Office Action; Chinese Patent Office (State Intellectual Property Office of People's Republic of China); Chinese Patent Application No. 201180039345.2; dated Mar. 1, 2016; 5 pages.

Australian Examination Report; Australian Patent Office; Australian Patent Application No. 2011264852; dated Oct. 26, 2015; 4 pages.

Australian Examination Report; Australian Patent Office; Australian Patent Application No. 2016202986; dated Feb. 9, 2017; 3 pages.

Korean Office Action; Korean Intellectual Property Office; Korean Patent Application No. 10-2013-7000339; dated Jun. 21, 2017; 8 pages.

Korean Notice of Preliminary Rejection; Korean Intellectual Property Office; Korean Patent Application No. 10-2013-7000385; Aug. 22, 2017; 8 pages.

European Examination Report; European Patent Office; European Patent Application No. 11793105.5; dated Nov. 7, 2017; 6 pages.

European Examination Report; European Patent Office; European Patent Application No. 11793107.1; dated Nov. 15, 2017; 8 pages.

Australian Examination Report; Australian Patent Office; Australian Patent Application No. 2016231485; dated Dec. 7, 2017; 5 pages.

European Examination Report; European Patent Office; European Patent Application No. 11793109.7; dated Jan. 2, 2018; 6 pages.

* cited by examiner

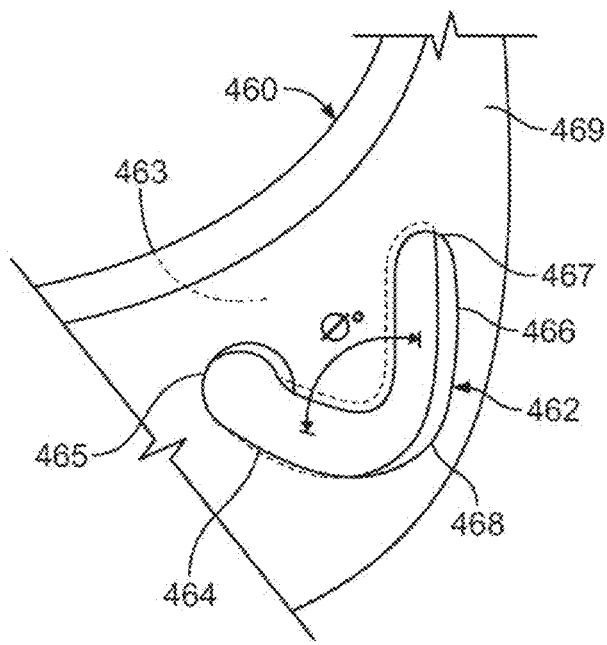
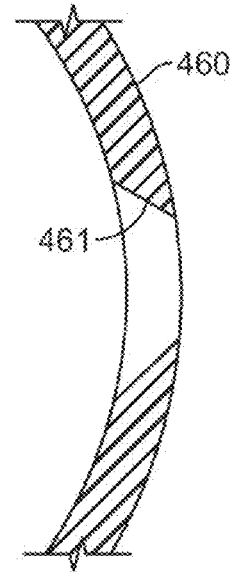
FIG. 37
FIG. 38
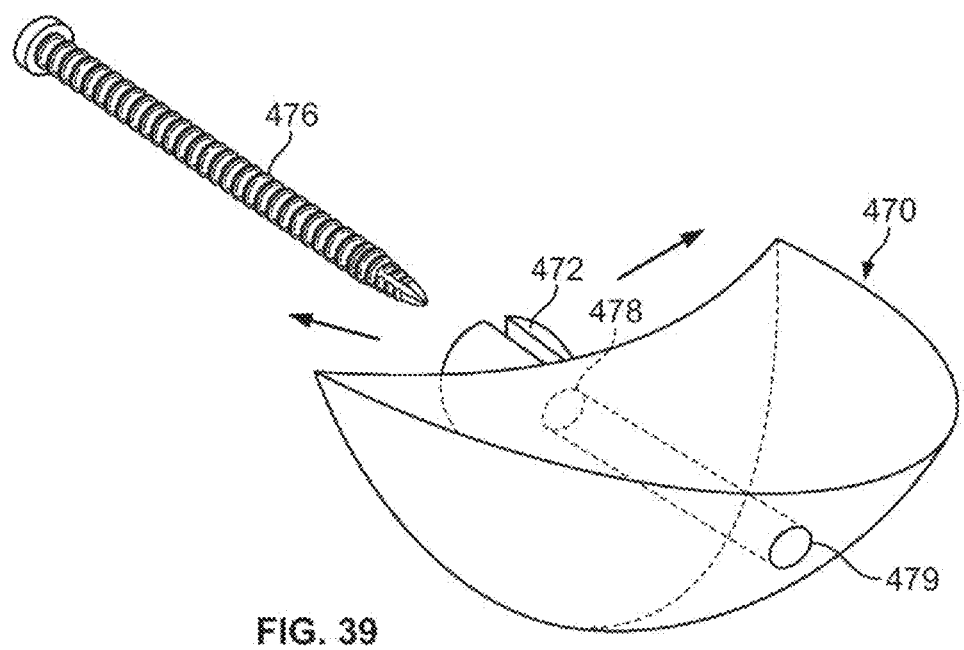
FIG. 39

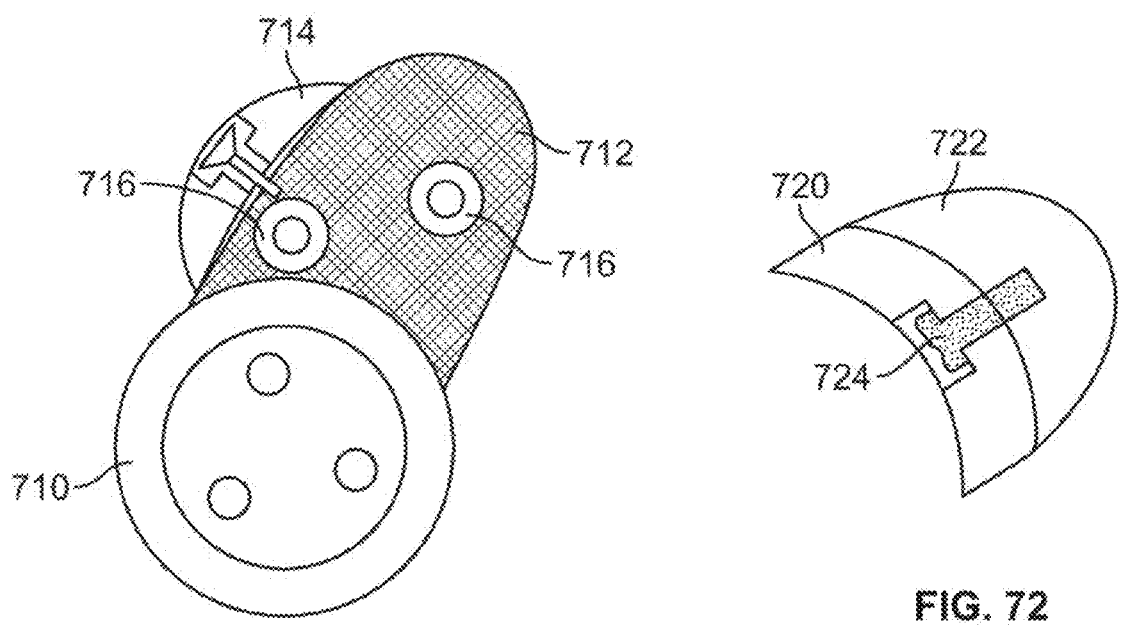
FIG. 71
FIG. 72
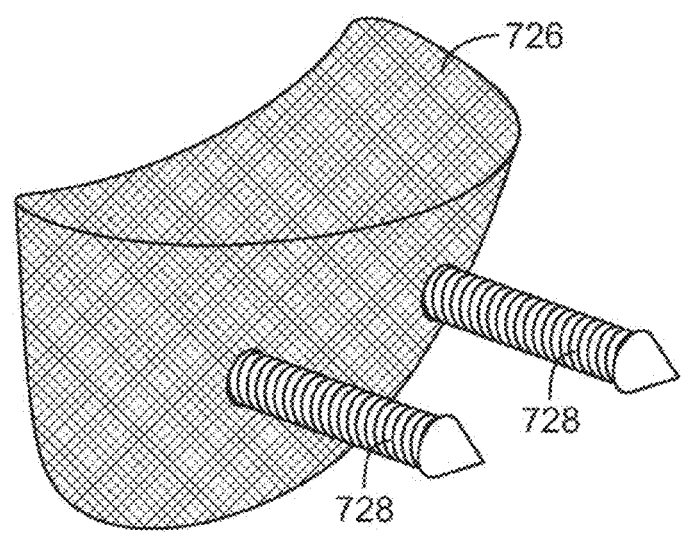
FIG. 73

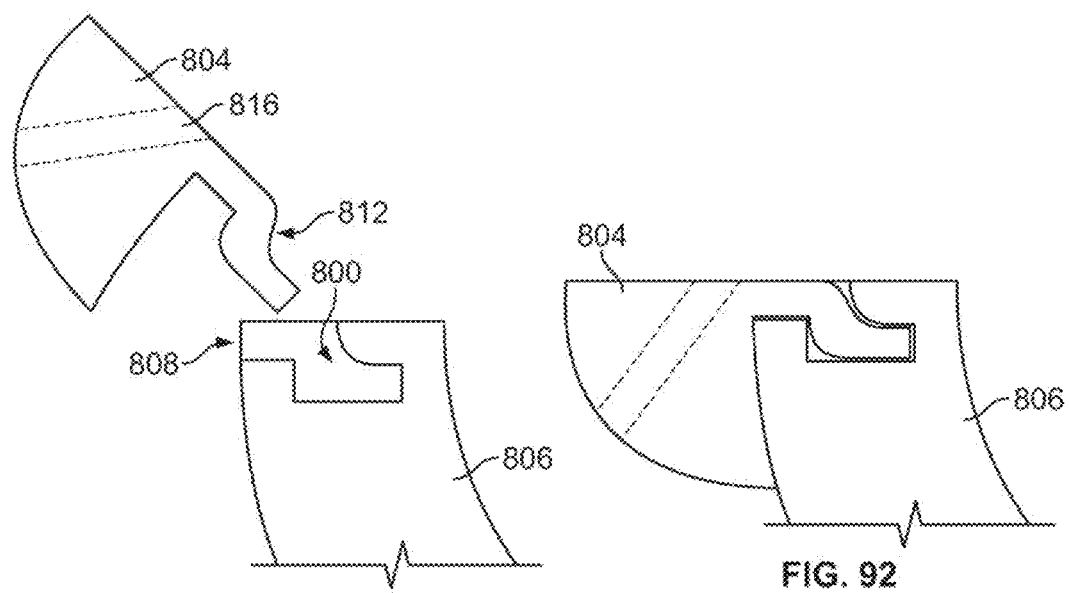
FIG. 91
FIG. 92
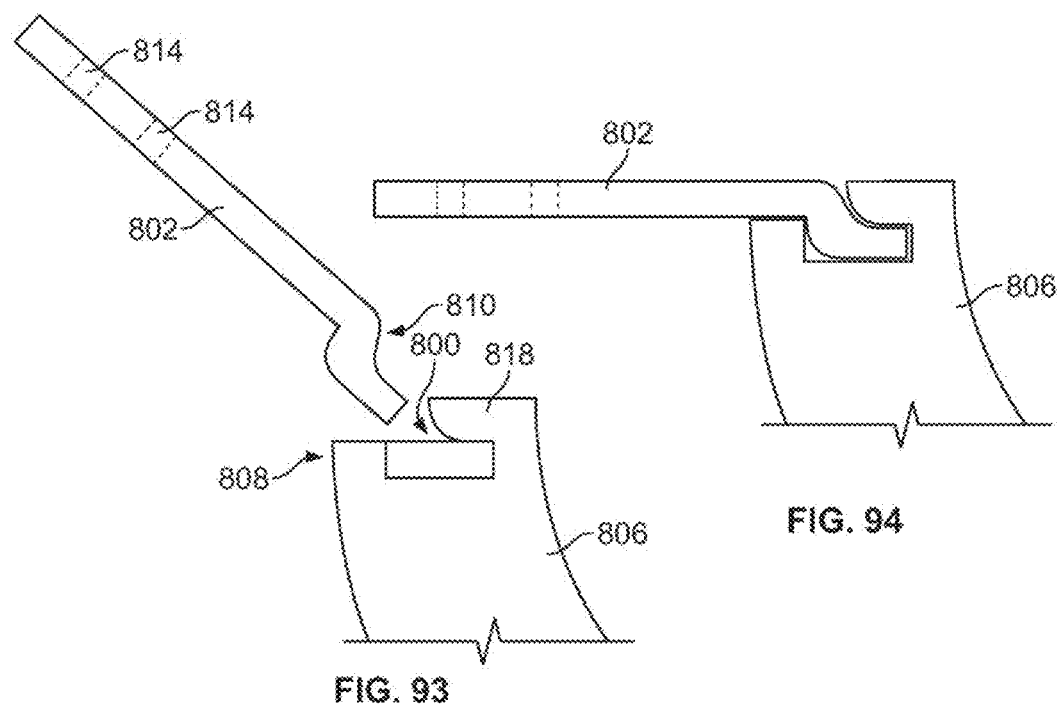
FIG. 93
FIG. 94

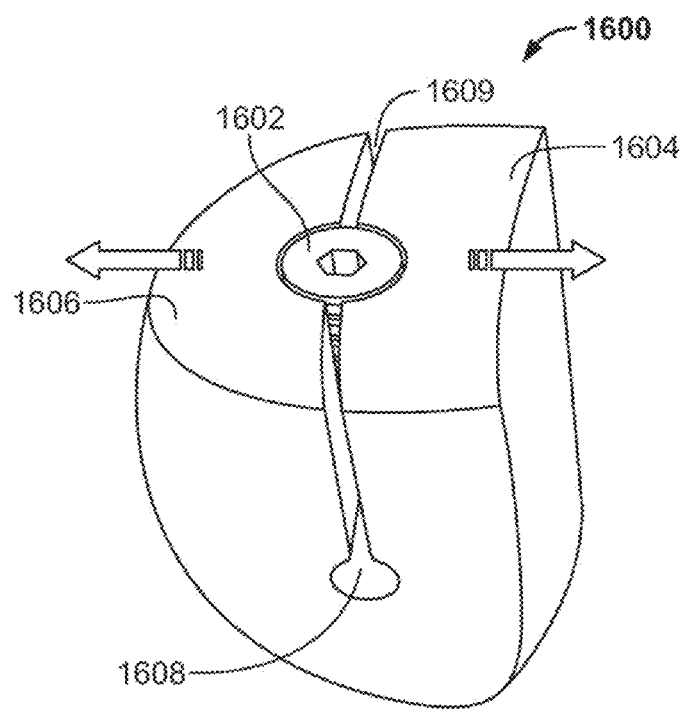
FIG. 103
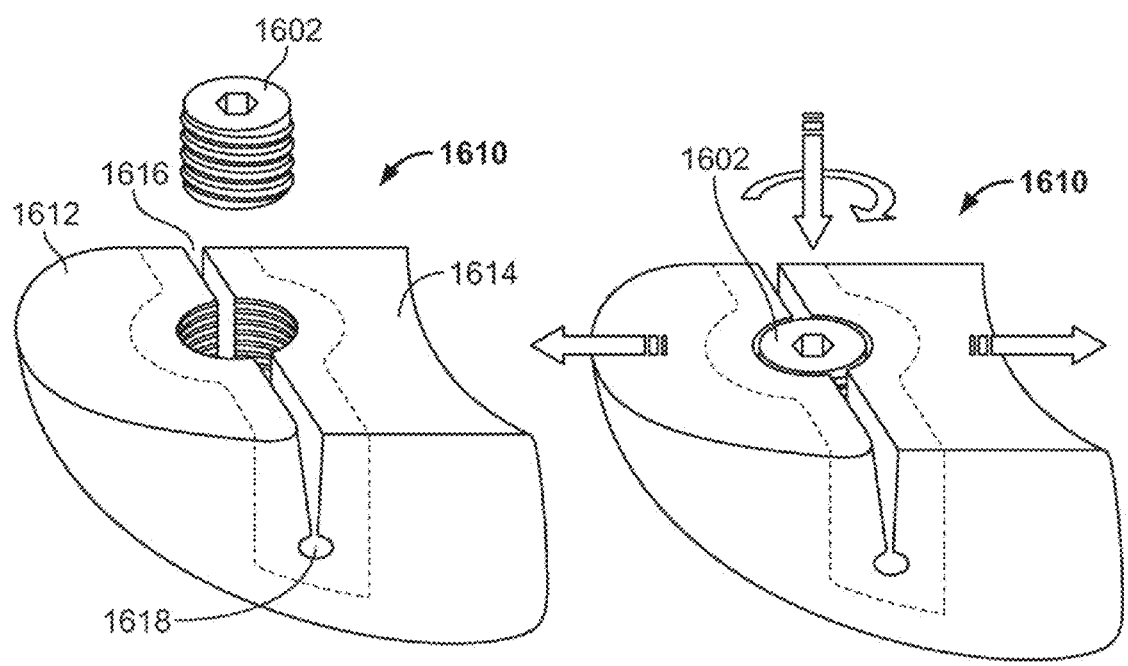
FIG. 104
FIG. 105

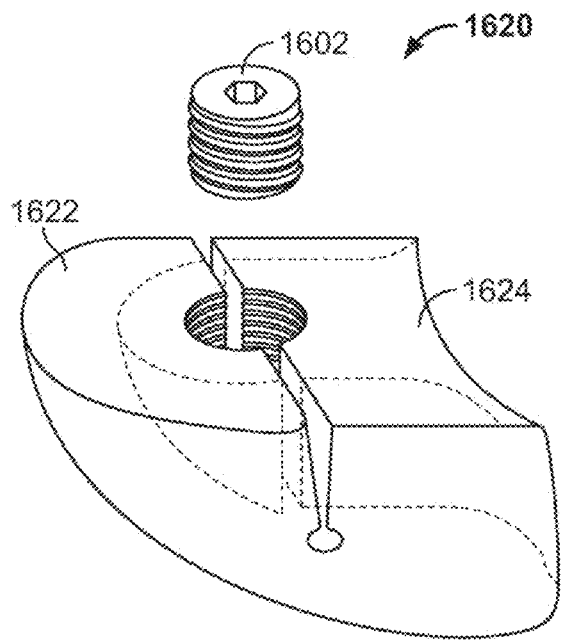
FIG. 106
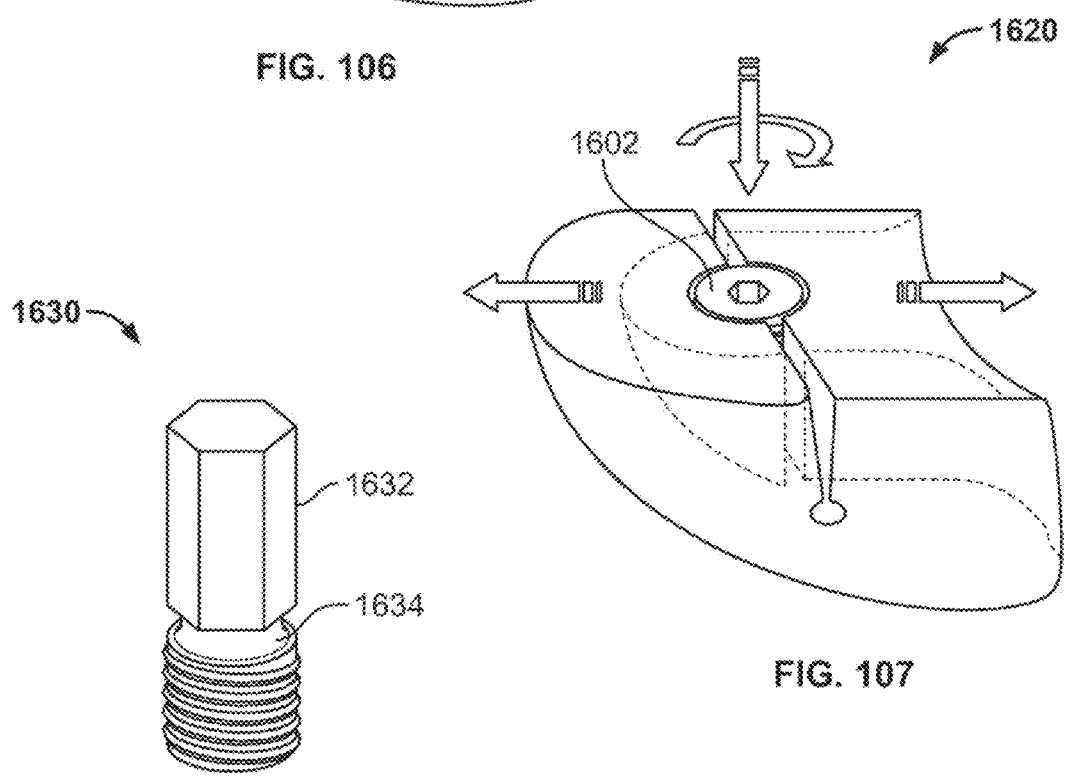
FIG. 108
FIG. 107

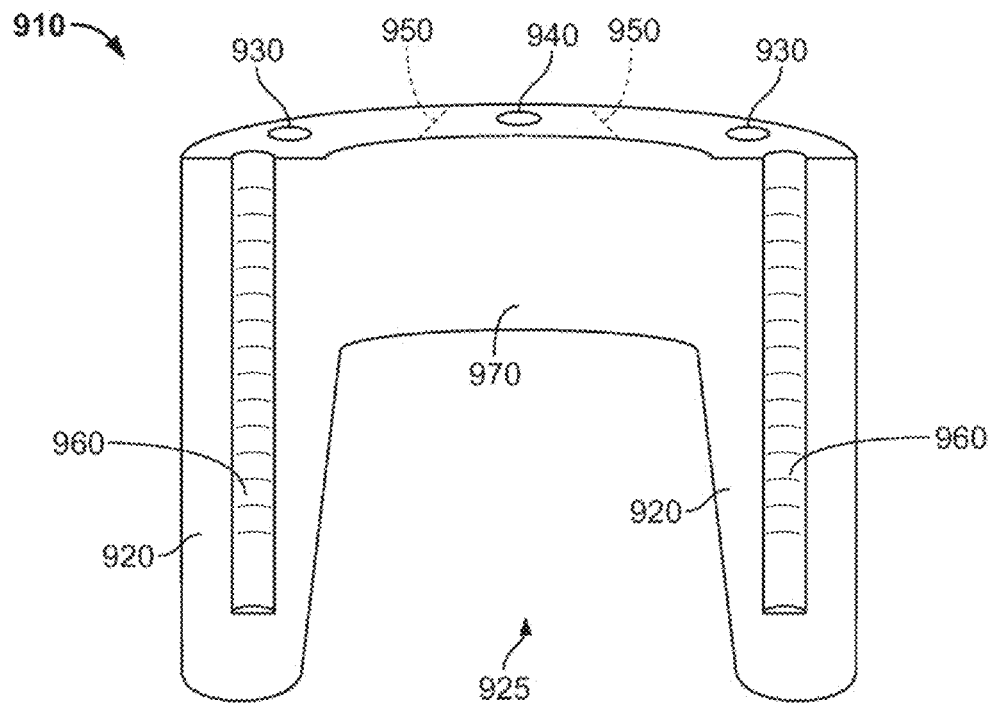
FIG. 116
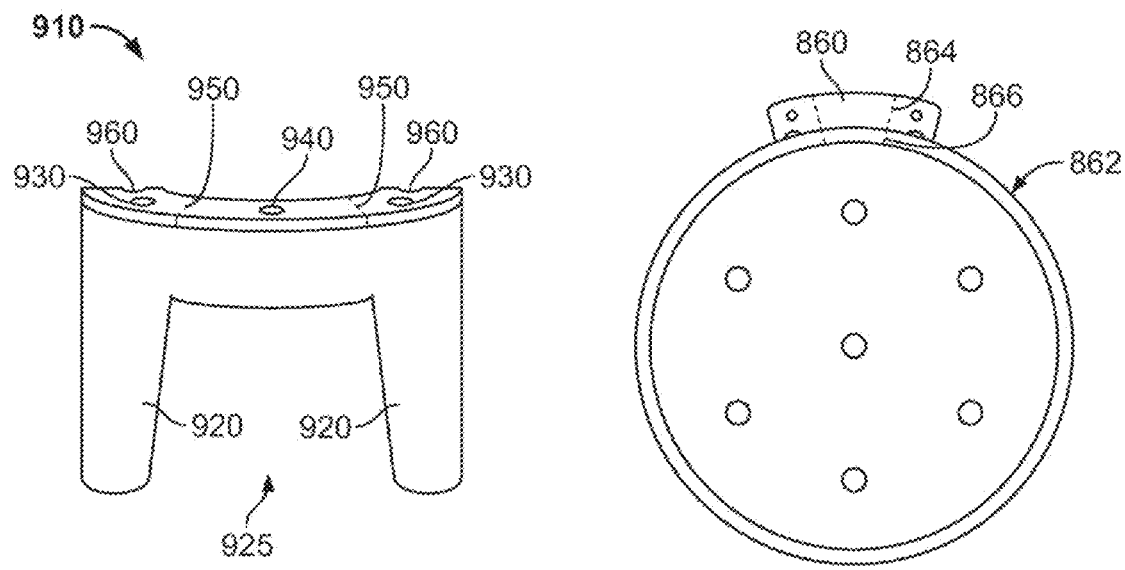
FIG. 117
FIG. 118

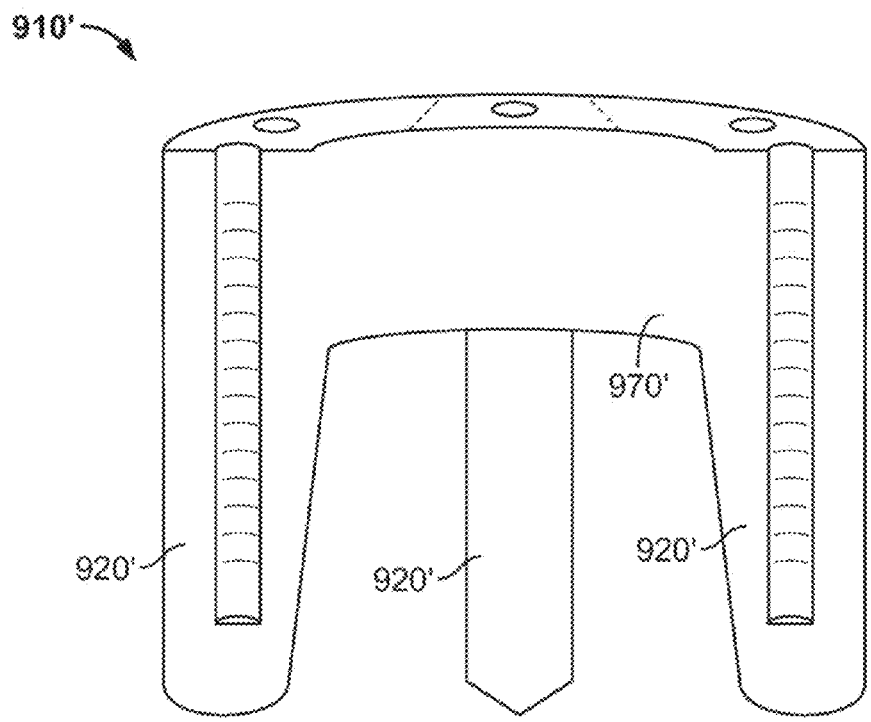
FIG. 123
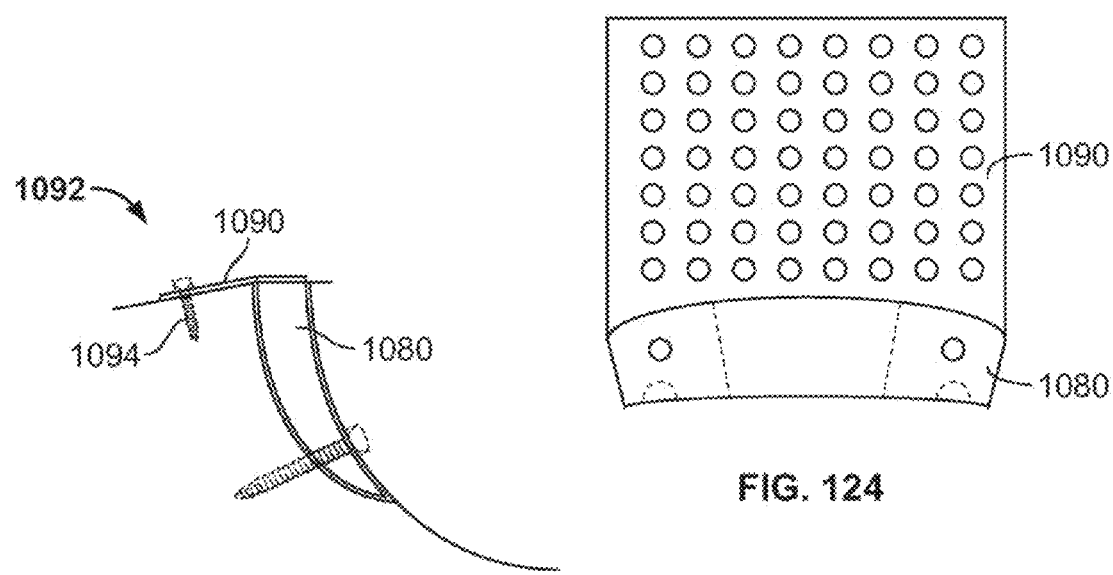
FIG. 125
FIG. 124

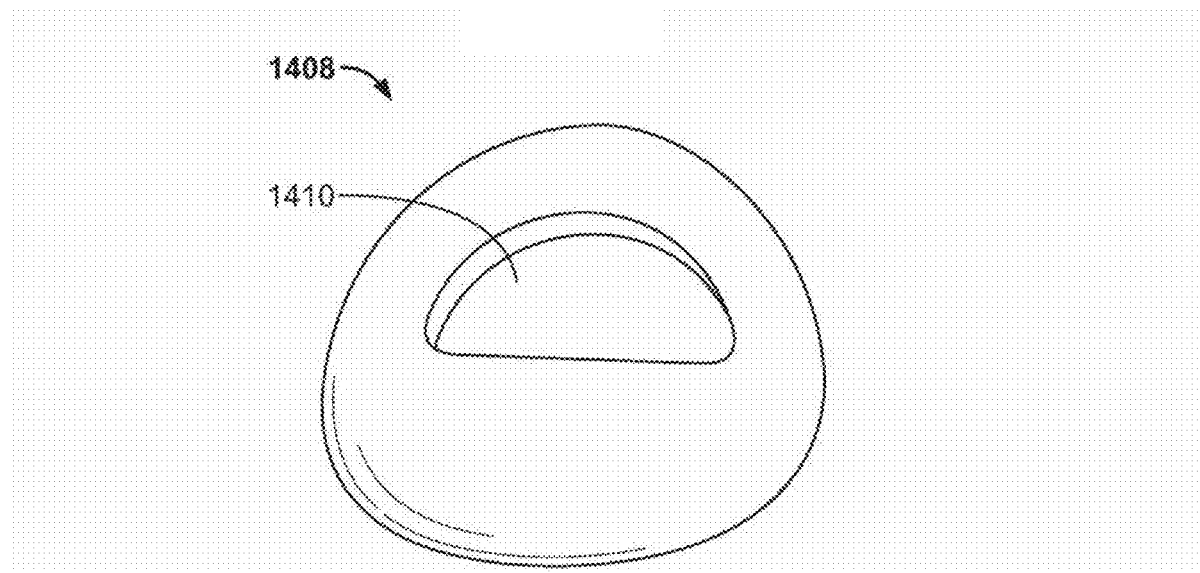
FIG. 187
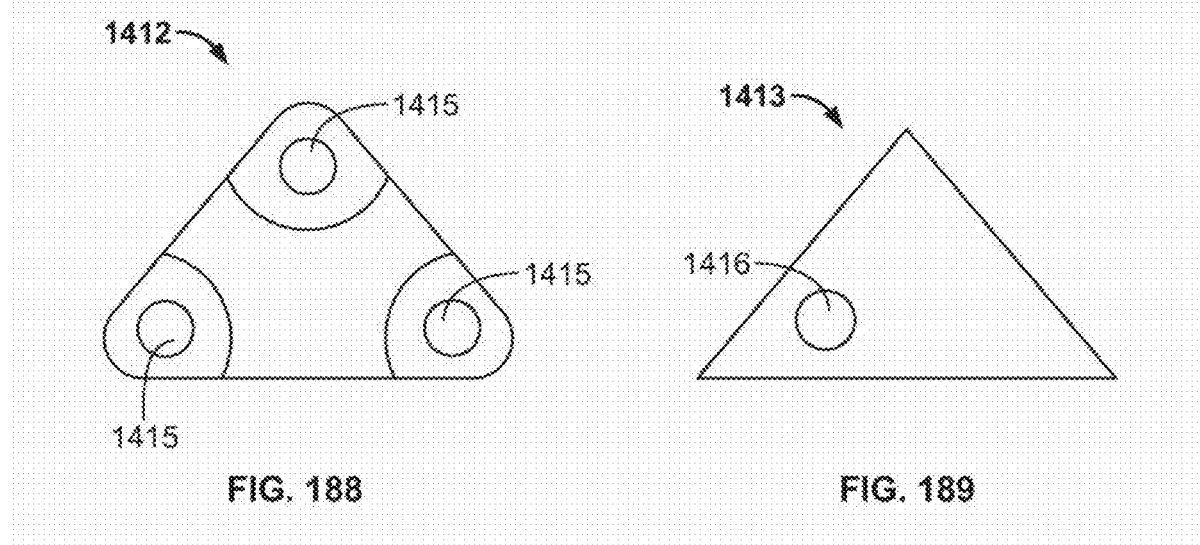
FIG. 188                    FIG. 189

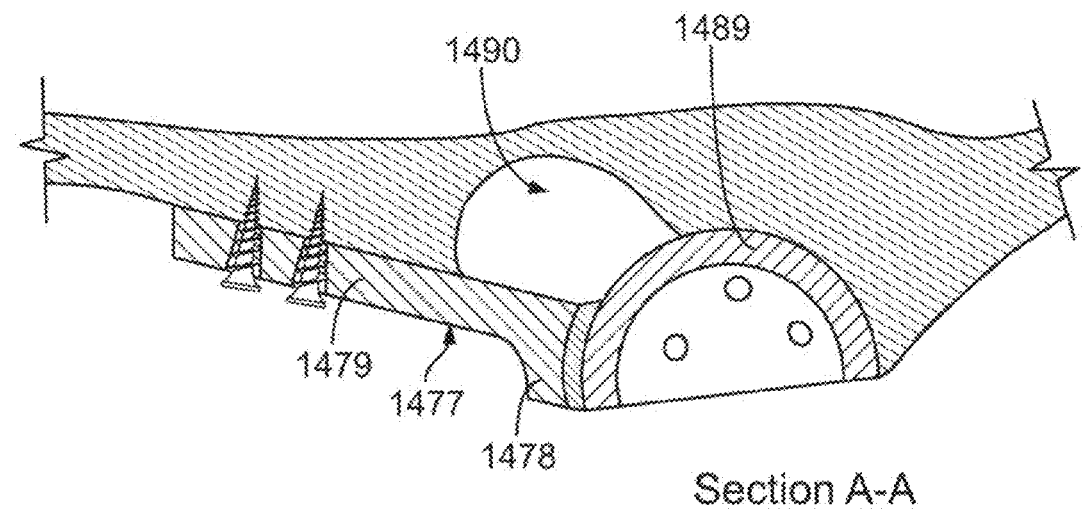
Section A-A
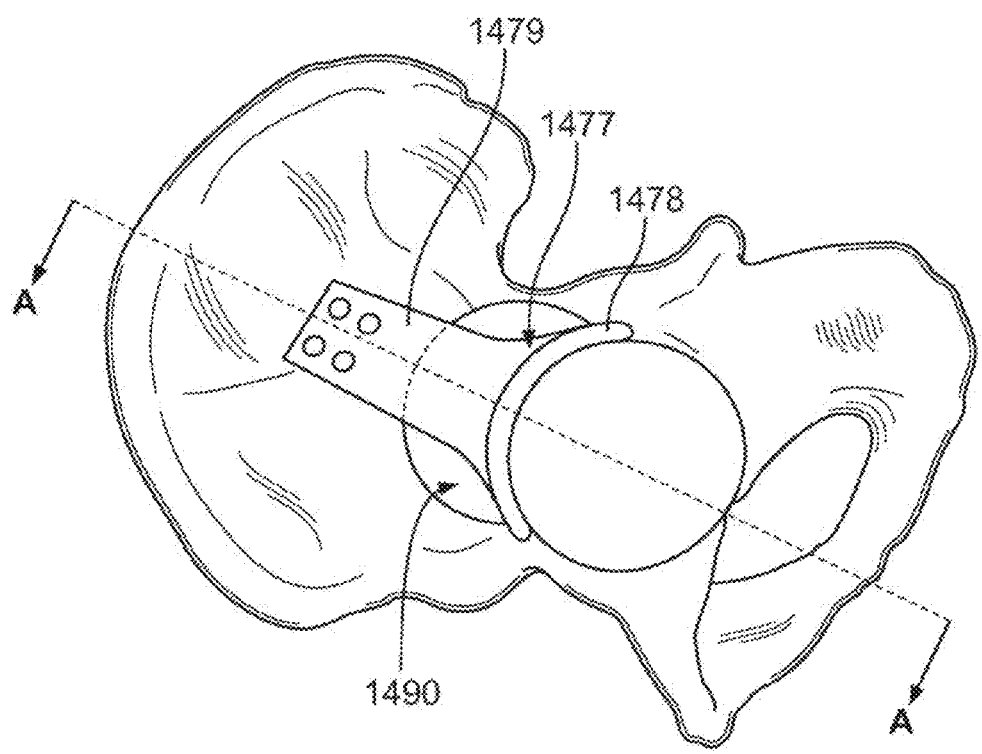
FIG. 209

IMPLANT COMPONENTS AND METHODS

CROSS-REFERENCE TO RELATED APPLICATIONS

This application is a division of U.S. patent application Ser. No. 13/156,238, filed Jun. 8, 2011, (now abandoned), which claims the benefit of U.S. Provisional Patent Application No. 61/352,705, filed Jun. 8, 2010, U.S. Provisional Patent Application No. 61/352,722, filed Jun. 8, 2010, U.S. Provisional Patent Application No. 61/422,903, filed. Dec. 14, 2010, and U.S. Provisional Patent Application No. 61/466,817, filed Mar. 23, 2011, each of which are hereby incorporated by reference herein in their entireties.

BACKGROUND

Joints often undergo degenerative changes due to a variety of reasons. When joint degeneration becomes advanced or irreversible, it may become necessary to replace the natural joint with a prosthetic joint. Artificial implants, including hip joints, shoulder joints, and knee joints are widely used in orthopedic surgery. Specifically, hip joint prostheses are common. The human hip joint acts mechanically as a ball and socket joint, wherein the ball-shaped head of the femur is positioned within the socket-shaped acetabulum of the pelvis. Various degenerative diseases and injuries may require replacement of all or a portion of a hip using synthetic materials, typically metals, ceramics, or plastics.

More particularly, natural hips often undergo degenerative changes, requiring replacement of the hip joint with a prosthetic joint. Often, the hip is replaced with two bearing surfaces between the femoral head and the acetabulum. The first bearing surface is typically a prosthesis shell or acetabular cup, which may be formed of metal, ceramic material, or as otherwise desired. A liner (conventionally formed of polyethylene material such as ultra high molecular weight polyethylene, a ceramic material, or in some cases, even a metal liner) is then fit tightly within the shell to provide an inner bearing surface that receives and cooperates with an artificial femoral head in an articulating relationship to track and accommodate the relative movement between the femur and the acetabulum.

The cup (or a cup and liner assembly) is typically fixed either by placing screws through apertures in the cup or by securing the cup with cement. In some cases, only a liner is cemented in a patient due to poor bone stock. In other cases, a cup having a porous surface may be press fit into the reamed acetabular surface.

It may become necessary to conduct a second or subsequent surgery in order to replace a prosthetic joint with a (often larger) replacement joint. Such surgeries often become necessary due to further degeneration of bone or advancement of a degenerative disease, requiring removal of further bone and replacement of the removed, diseased bone with a larger or enhanced prosthetic joint, often referred to as a revision prosthesis. For example, bone is often lost around the rim of the acetabulum, and this may provide less rim coverage to securely place a press-fit cup. Such surgeries may thus be referred to as revision surgeries.

In acetabular revision surgery, an acetabular prosthesis generally includes additional mounting elements, such as augments, flanges, hooks, plates, or any other attachment or mounting points or members that provide additional support and/or stability for the replacement prosthesis once positioned. These additional mounting or attachment members are often required due to bone degeneration, bone loss, or bone defects in the affected area (in this instance, the hip joint).

Various types of these mounting members (which term is intended to include but not be limited to flanges, blades, plates and/or hooks) may be provided in conjunction with a prosthesis system in order to help the surgeon achieve optimal fixation, non-limiting examples of which include iliac flanges (providing securement and fixation in and against the ilium region of the pelvis), ischial blades (providing securement and fixation in and against the ischium), and obturator hooks (providing securement and inferior fixation by engaging the obturator foramen). Although there have been attempts to provide such mounting attachments with modularity, the solutions to date have generally fatten short of providing true modularity. Instead, they typically provide a few discrete positions at which the mounting members may be positioned, without providing the surgeon a fuller range of decision options.

Additionally, in some primary surgeries and more often in revision surgeries, the acetabulum may have a bone defect or void that the surgeon must fill with bone grafts before inserting a new shell. This can be time consuming and expensive, and may subject the patient to additional health risks. Some techniques use an augment in connection with the acetabular shell, which can be coupled to or otherwise attached to the outer surface of the shell.

With current augments, the surgeon can attach the augment to the bone and then implant the cup. However, many acetabular shells rely on bone screws to achieve proper fixation and the augment often gets in the way of a screw. In short, surgeons need the freedom to place screws in the best location, but this compromises their ability to use augments. With current systems, it also takes an increased amount of time surgical time to trial the component orientation and then try to find good bone fixation for the cup. The surgeon will often have to free-hand the amount of bone removed while estimating the size of augment needed. In the cases where bone is often deficient, surgeons are hesitant to take away any more bone than necessary.

Various additional features and improved features intended for use and application with various types of joint implants are also described herein, such as improved bone screws, improved coatings, and various augment removal and insertion options.

SUMMARY

Disclosed herein are systems, devices, and methods for providing modular orthopedic implants. The implants may include a base member, such as an acetabular shell or an augment, that is configured to couple with an augment, flange cup, mounting member, any other suitable orthopedic attachment, or any combinations thereof. Mounting members include, for example, flanges, blades, hooks, and plates. In some embodiments, the orthopedic attachments may be adjustably positionable about the base member or other attachments thereby providing modularity for assembling and implanting the device. Various securing and/or locking mechanisms may be used between the components of the implant. In certain embodiments, the orthopedic attachments are removably coupled to the base member or other components. In certain embodiments, the orthopedic attachments are integrally provided on the base member or other components, yet may still be adjustably positionable thereabout. In some embodiments, expandable augments, base members, or other bone filling devices are provided. In some embodiments, surface features are provided that create friction and allow for surrounding bone ingrowth at the interface of the implants and a patient's bone.

Systems, devices, and methods described herein provide implants having attachment mechanisms that provide a plurality of positioning options for the orthopedic attachments. In certain embodiments, an orthopedic device includes an implant structured to fit with and stabilize a patient's orthopedic joint, the implant having a plurality of attachment sites, and a mounting member having a first end that anchors to the patient's bone or soft tissue and a second end that mates with the implant at each of the plurality of attachment sites. The plurality of attachment sites can include portions of a crossbar extending about an acetabular shell. Alternatively or additionally, the attachment sites can include a groove extending along a rim of the implant. In some embodiments, attached mounting members may include conventional holes, locking holes, or slots. The sites may be threaded, unthreaded, or partially threaded, and may be fixed or polyaxial. In some embodiments, attachment sites may include variable low-profile holes that allow for locking at a variety of angles. In some embodiments, a porous surface is disposed on a portion of the mounting member. In some embodiments, the mounting member is a flange that is adjustably positionable about the circumference of an acetabular implant. For example, the flange (or any other suitable mounting member) can pivot in a plane that is perpendicular to the circumference of an acetabular shell. The flange can include a split eye-let and/or a hook that joins a rail or groove on the implant. The flange can also include a key that removably inserts within a complementary rim on an acetabular shell. In certain embodiments, the flange is a flexible strap, or the flange may include a frangible portion that allows the flange to bend or break. In certain embodiments, the implant includes an annular recessed slot with an overhanging lip, where the mounting member includes a distal portion that fits within the annular recessed slot. The implant can be an augment that mounts to a surgical shell or cage, and the implant can fit within one of a shoulder, hip, or ankle joint. In certain embodiments, the mounting member includes a plurality of flanges, at least one flange being adjustably positionable with respect to more than one of the attachment sites.

In certain embodiments, a method of installing an orthopedic implant within a patient includes the steps of inserting the implant into the patient, selecting a site along the inserted implant to receive a first mounting member, attaching the first mounting member to the selected site, and anchoring the first mounting member to the patient. The selected site may be chosen from a plurality of-attachment sites that are angularly spaced about the implant. The method may further include the step of applying a porous surface to a portion of the first mounting member. In some embodiments, the inserting step may include the step of mounting an acetabular shell or cage within the patient's acetabulum. In some embodiments, the implant may be an acetabular augment, and the inserting step may include the step of mounting the acetabular augment to an acetabular shell. The method may further include the step of detaching a detachable portion of the first mounting member after attaching the first mounting member to the selected site. In some embodiments, the anchoring step includes the step of anchoring the first mounting member to a first entry point within the selected site. The method may further include the step of cementing the implant into the patient's acetabulum prior to attaching the first mounting member to the selected site. The method may further include the step of adjustably positioning the mounting member about the circumference of the implant and along the selected site. In some embodiments, the mounting member may include a flange, hook, or plate.

In certain embodiments, mounting members or augments shown and described in the figures contained herein may comprise tacks, spikes, coatings, or textured surfaces so as to improve initial fixation. The geographic locations of tacks, spikes, coatings, or textured surface structures may be strategically placed on select portions of a mounting member or implant so as to evenly load the mounting member or implant assembly and obtain the best biologic response initially, and over an extended period of time.

Systems, devices, and methods described herein provide implants that can include a flange cup. In certain embodiments, an acetabular implant system includes an acetabular shell, a cup member that fits positionably within the acetabular shell, and at least one mounting member coupled to the cup member, where the at least one mounting member has a first portion that is attachable to a patient's bone to thereby anchor to the patient's bone. The mounting member may include a flange that is adjustably positionable about the cup member and has a first end with an attachment portion that anchors to the patient's bone. In some embodiments, the cup member includes a distal tapered end that locks to an attachment site within the acetabular shell. In some embodiments, the attachment site within the acetabular shell is further configured to receive a liner. In some embodiments, the system includes a liner disposed within the cup member. The cup member may be configured as a band or as a full cup such that the liner is fully supported within the cup member. The at least one mounting member may include a flange, hook, or plate, and the at least one mounting member may be removably attached to the cup member. Alternatively, the at least one mounting member is integrally provided on the cup member.

In certain embodiments, a method of forming a surgical implant includes inserting an implant within a patient's acetabulum, providing a cup member, having at least one mounting member, within the inserted implant, aligning the cup member with the implant so that the at least one mounting member aligns with a patient bone site, and attaching the at least one mounting member to the patient's bone. The method may also include adjustably positioning the at least one mounting member about the cup member, wherein the at least one mounting member has a first end with an attachment portion that anchors to the patients bone, locking a distal tapered end of the cup member to an attachment site within the implant, and disposing a liner within the attachment site. In some embodiments, the method may further include disposing a liner within the cup member, where the cup member is provided as band or a full cup such that the liner is fully supported within the cup member. The at least one mounting member may include a flange, hook, or plate, and the method may further include removably attaching the at least one mounting member to the cup member. Alternatively, the at least one mounting member may be integrally provided on the cup member.

Systems, devices, and methods described herein provide implants having augments configured to attach to acetabular shells or cages, mounting members, or other augments with or without cement and configured to allow fine positional adjustments for best bone fit, coverage, and stability. In certain embodiments, an orthopedic implant includes an acetabular implant having a track that includes a plurality of slots and an exterior surface, an augment having a protrusion that moves within the plurality of slots, the augment having a first cam surface that forms an interface with the exterior surface, where the protrusion has an adjustable fastener that, upon adjusting, fixes the augment with respect to the implant to impede further movement. In some embodiment, the augment may rotate about the exterior surface. The adjustable fastener may be a tightening screw that extends through a through-hole in the augment and, upon tightening, expands the protrusion (which may be flared outwardly) and thereby tightens the augment within the track. In some embodiments, the tightening screw has a head that fits within a slot and faces an interior portion of the implant, where the slot has an interior opening that aligns with the head, and where the interior opening receives a tightening rod to tighten the screw. In some embodiments, the track includes a dovetail joint that receives the protrusion. In some embodiments, the track includes a straight portion and a curved portion. For example, the track can include two straight slots and a curved portion. In some embodiments, the track includes a J-shaped slot with a wall of the implant. The protrusion may be part of an intermediate locking member that is integral to the augment. In some embodiments, the first cam surface of the augment includes at least one trough that receives cement to bind the augment to the shell. In some embodiments, the augment includes a plurality of projections that form a gap and may farther include a flange attached to the augment.

In certain embodiments, a method of preparing an orthopedic implant includes the steps of providing an implant having a curved external surface and an opening in the surface, the opening having at least two portions that join at a common region but are separated by an angle of less than 180°, providing an augment having a first surface that interfaces with the curved external surface, coupling the augment and implant by an intermediate locking member, and tightening the intermediate locking member. In some embodiments, the method may further include the step of securing the augment to the implant by disposing cement within a trough located on the first surface. In some embodiments, the method may further include the step of rotating the augment with respect to the implant about the curved external surface prior to tightening the intermediate locking member, and moving the intermediate locking member within the opening prior to tightening. In some embodiments, the method may further include the steps of applying a fastener to the implant, so that the fastener extends outwardly from the external surface, and positioning the augment about the external surface so that the extended fastener fits between two protrusions of the augment, where the intermediate locking member is tightened with respect to the augment by a screw.

Systems, devices, and methods described herein provide implants that create friction and allow for surrounding bone ingrowth at the interface of the implants and a patient's bone. In certain embodiments, an implantable orthopedic device includes an implant that has a surface that contacts a patient's joint and has a plurality of protrusions connected to the surface that rise above the surface. The implant may also include pores dispersed throughout the surface at the bone interface. The protrusions located at the surface of the implant may be blunt, or may be any other suitable shape and configuration. The protrusions may extend from the surface to any suitable height, such as heights between about 50 μm and about 2000 μm, heights between about 100 μm and 1100 μm, or heights between about 200 μm and 400 μm. The protrusions may be spaced on the surface of the implant in any suitable concentration or density. The desired protrusion density may also be patient-specific, and may be determined based on the density of a native bone into which a component is implanted. An implant may have a large number of protrusion features on its surface, and one or more of these individual features may fall outside of a desired size or spacing without affecting the overall efficacy of the surface.

In certain embodiments, an implant includes internal or external strengthening features. A porous implant may include internal or external strengthening ribs to provide support to surrounding porous structures. A porous implant may also be coupled with a flange that has a first end for attaching the flange to the implant and a second end for attaching the flange to surrounding bone structure. The porous implant may also include a reticulated surface coating.

In certain embodiments, an implantable orthopedic device is created by providing a mold having a negative impression of a porous beaded surface and providing an implant substrate to be coated. Particles are interposed between the implant substrate and the mold, and a pressure or elevated temperature may be applied to the mold, implant substrate, and particles. The implant substrate provided may be solid or may be porous, and the particles interposed between, the implant substrate and the mold may be symmetric or asymmetric.

In certain embodiments, an implantable orthopedic device is created by creating a three-dimensional model simulating an outer surface profile of a porous beaded implant and creating a three-dimensional model of an implant substrate volume. The model simulating an outer surface profile of a porous beaded implant is applied to the model of an implant substrate volume to create a pre-form volume, and an algorithm is applied to fill the pre-form volume with a desired reticulated structure to create a porous implant model. An implant is formed using the porous implant model.

In certain embodiments, an implantable orthopedic device is created by providing a mold of an implant having an inner surface mimicking a negative image of an outer surface profile geometry of a porous beaded surface and providing a plurality of particles that are placed into the mold. Pressure or elevated temperature is applied to the mold and particles. The particles placed into the mold may be symmetric or asymmetric.

In certain embodiments, an implantable orthopedic device is created by providing a mold of an implant having an inner surface mimicking a negative image of an outer surface profile geometry of a porous beaded surface and loading one or more foaming agents into the mold. A porous foam component is created in the general shape or size of the implant that has an outer surface geometry mimicking an outer surface profile geometry of a porous beaded surface. The porous foam component is removed from the mold, and a binding agent is applied to the porous foam component. A plurality of symmetric or asymmetric particles are applied to the porous foam component having the binding agent and the porous foam component, binding agent, and particles are subjected to an elevated temperature to sinter the particles together and burn pit the foam component to form an implant having a roughened porous texture with an outer surface profile geometry mimicking a clinically-proven porous beaded structure. The porous foam component may be polymeric, and may be a polyurethane component.

Systems, devices, and methods described herein provide implants that can be expanded or adjusted to fill bone voids in a patient's anatomy surrounding the implant. In certain embodiments, an orthopedic implant includes an acetabular implant with first and second portions that are separated along a side of the implant by a slit and an expansion member disposed between the first and second portions and adjustable by a tightening tool to displace the two portions relative to each other. The implant may also include a hinge that joins the first and second portions along a side of the implant. The first and second portions of an implant may comprise a solid portion, and the volume of the implant not including the solid portion may be porous. Any number of portions may be provided in the implant, and the implant may have any number of intersecting perpendicular slits for dividing the portions. The implant may be a flange connected to an acetabular shell, or may be an acetabular shell or cage. The implant may include a screw that passes through the implant to connect the implant to a patient's acetabulum.

In certain embodiments, an expansion member used in an expandable or adjustable implant may be a shaped memory plug or a screw. The expansion member may be an augment with a curved side and a connection site that attaches to an acetabular shell.

In certain embodiments, an orthopedic device is implanted in a patient's joint by installing an acetabular shell or cage within the joint and placing an augment between the shell and the patient's bone. Two portions of the augment are expanded until a first portion abuts the patient's bone and a second bone abuts the acetabular shell or cage, and the augment is anchored to the bone. The portions of the augment may be expanded using a tightening fool coupled to an expansion member disposed between the portions of the augment to displace the portions relative to each other. The expansion member used may be a shaped memory plug, a screw, or a wedge, and the tightening tool may include a torque-limiting device. The two portions of the augment may be expanded along a hinge that joins the portions. The portions of the augment may be biased towards one another. A screw may be passed through the shell to connect the shell to the patient's acetabulum. A porous surface may be applied to a portion of the augment. The augment may be removed via slits or flexible hinge portions provided on the augment.

Systems, devices, and methods described herein provide implants having a plurality of projections and optional fixation elements. In certain embodiments, an orthopedic augment includes a base member to which at least two projections are coupled, the at least two projections having a gap therebetween, and a fixation element provided on one or more of the at least two projections. The fixation element may be a cement trough. In certain embodiments, the base member is shaped to couple with an implant. For example, a first surface of the base member mat contacts the implant may be substantially arcuate. The at least two projections may be disposed in substantially the same direction. The length of the at least two projections may be substantially the same, or the length of one of the at least two projections may be different than the respective length of another of the at least two projections. In some embodiments, the base member includes one or more fixation elements such as screw holes configured to receive a fastener. In some embodiments, the base member includes a connection element configured to receive a driver handle for placing the orthopedic augment into a patient's joint. In some embodiments, the base member includes timing marks configured to align with corresponding timing marks on an implant. In some embodiments, the augment may further include flanges, blades, plates, or hooks attached, thereto.

In certain embodiments, a method of implanting an orthopedic device in a patient's joint may include placing an implant within the patient's joint, the implant secured to the joint via a fixation device, preparing a space in the patient's bone proximate the implant and the fixation device, providing an augment that includes at least two projections having a gap therebetween, and inserting the augment into the prepared space by positioning the augment around the fixation member such that the fixation member extends through the gap between the at least two projections of the augment. The method may further include forming a cement trough on one or more of the at least two projections, and setting the augment by pouring cement into the cement trough. In some embodiments, the method includes setting the augment using screws. The preparing may include rasping or reaming the patient's bone with a broach. The broach may have approximately the same cross-sectional profile as the augment. In some embodiments, the amount of bone removed may be limited by using a depth stop disposed on the broach. The inserting may include attaching the augment to a driver handle for positioning the augment into the prepared space. The method may further include aligning timing marks disposed on the augment with timing marks disposed on the implant. In some embodiments, the augment further comprises flanges, blades, plates, or hooks attached thereto. In some embodiments, the placing includes mounting an acetabular shell or cage within the patient's acetabulum.

Systems, devices, and methods described herein provide modular orthopedic implants. In certain embodiments, an orthopedic device includes an implant having a plurality of attachment sites and a track that includes a plurality of slots, a mounting member having a first end that anchors to a patient's bone or soft tissue and a second end that mates with the implant at each of the plurality of attachment sites, and an augment having a protrusion that translates within the plurality of slots, the augment having a first cam surface that forms an interface with an exterior surface of the implant and rotates about that exterior surface. In some embodiments, the mounting member may be a flange, hook, or plate that may be adjustably positionable about the circumference of an acetabular implant. The flange, hook, or plate may pivot in a plane that is perpendicular to the circumference of an acetabular shell. In some embodiments, the mounting member is an acetabular augment that includes a base member to which at least two projections are coupled, the at least two projections having a gap therebetween. A cement trough may be provided on one or more of the at least two projections. In some embodiments, the orthopedic device further includes a cup member disposed within the implant, the cup member having one or more mounting members that are attachable to a patient's bone to thereby anchor to the patient's bone. The cup member may be a flange cup having one or more flanges attached thereto, and there may be a liner disposed within the cup member. In some embodiments, the protrusion has an adjustable fastener that, upon adjusting, fixes the augment with respect to the implant to impede further translation and rotation. In some embodiments, a porous surface is disposed on at least one of the implant, mounting member, and augment. The porous surface may include a plurality of protrusions that connect to the porous surface and rise above the porous surface and a plurality of pores dispersed within the porous surface. In some embodiments, the augment or the implant (or both) includes a first portion and a second portion, the first and second portions being separated along a first side of the augment by a slit, and an expansion member disposed between the first and second portions, the expansion member being adjustable by a tightening tool to displace the two portions relative to each other.

In certain embodiments, an orthopedic implant includes an implant having a plurality of attachment means and a track that includes positioning means, a mounting member having a first end that anchors to a patient's bone or soft tissue and a second end that mates with the implant at each of the plurality of attachment means; and an augment having a protrusion that translates within the positioning means, the augment having a first cam surface that forms an interface with an exterior surface of the implant and rotates about that exterior surface. In some embodiments, the mounting member may be a flange, hook, or plate that may be adjustably position able about the circumference of an acetabular implant. In some embodiments, the mounting member is an acetabular augment that includes a base member to which at least two projections are coupled, the at least two projections having a gap therebetween.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIGS. 37 and 38 show an illustrative acetabular shell or cage that includes a track;

FIG. 39 shows an illustrative augment that includes a through hole;

FIG. 71 shows an illustrative bi-lobe cup or shell;

FIG. 72 shows two augments attached together via an illustrative fastening device;

FIG. 73 shows an illustrative augment with integral spikes;

FIGS. 91 and 92 show an illustrative augment attached peripherally to an acetabular shell or cage via a recess;

FIGS. 93 and 94 show an illustrative mounting member attached peripherally to an acetabular shell or cage via a recess;

FIGS. 103-107 show illustrative expandable/adjustable augments;

FIG. 108 shows an illustrative expansion member;

FIGS. 116 and 117 show a front perspective view and a back view, respectively; of an illustrative augment;

FIG. 118 shows a top plan view of an augment illustratively installed on an acetabular shell;

FIG. 123 shows a front perspective view of an illustrative augment having three projections;

FIG. 124 shows a top plan view of an augment having an illustrative flange;

FIG. 125 shows a partial cross-section elevation view of an illustrative augment with a flange installed in an acetabulum;

FIGS. 185-187 show various illustrative augments in the shape of an acetabular cup and provided with a number of openings disposed circumferentially around the augment;

FIGS. 188-190 show illustrative triangular-shaped inserts that may be positioned in the openings of the augments of FIGS. 185-187;

FIGS. 204 and 205 show an illustrative supplemental augment coupled to an augment;

FIG. 206 shows an illustrative shell having a track that is undercut so as to form a dovetail joint with an augment;

FIG. 207 shows an illustrative augment including a channel shaped to receive a connecting member;

FIG. 208 shows an illustrative connecting member;

FIG. 209 shows an illustrative augment that spans a pelvic defect; and

FIG. 210 shows an illustrative secondary augment for use with a primary augment.

DETAILED DESCRIPTION

Figure 1:
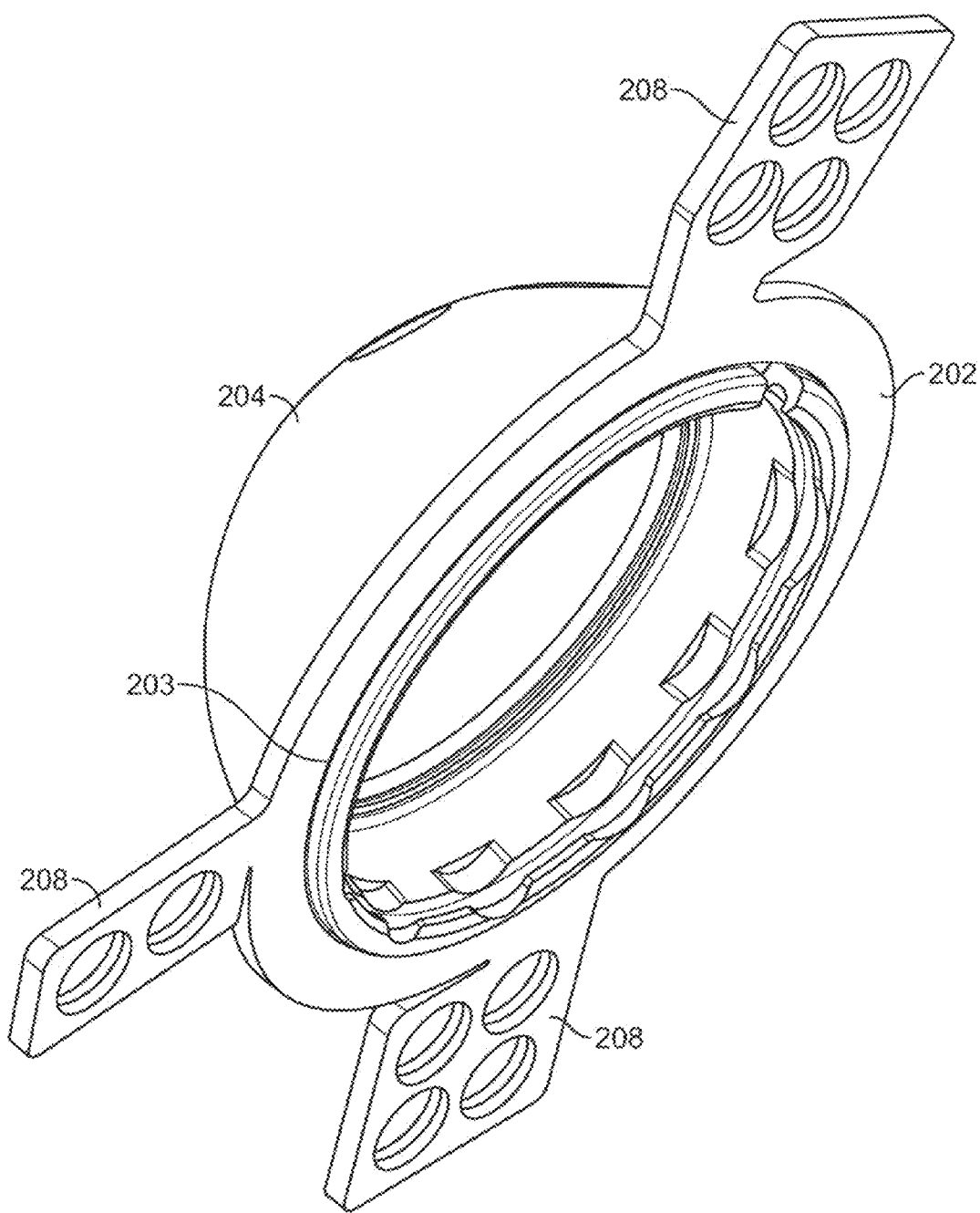
FIGS. 1-4 show various perspectives of an illustrative rim augment or mounting member.
Figure 2:
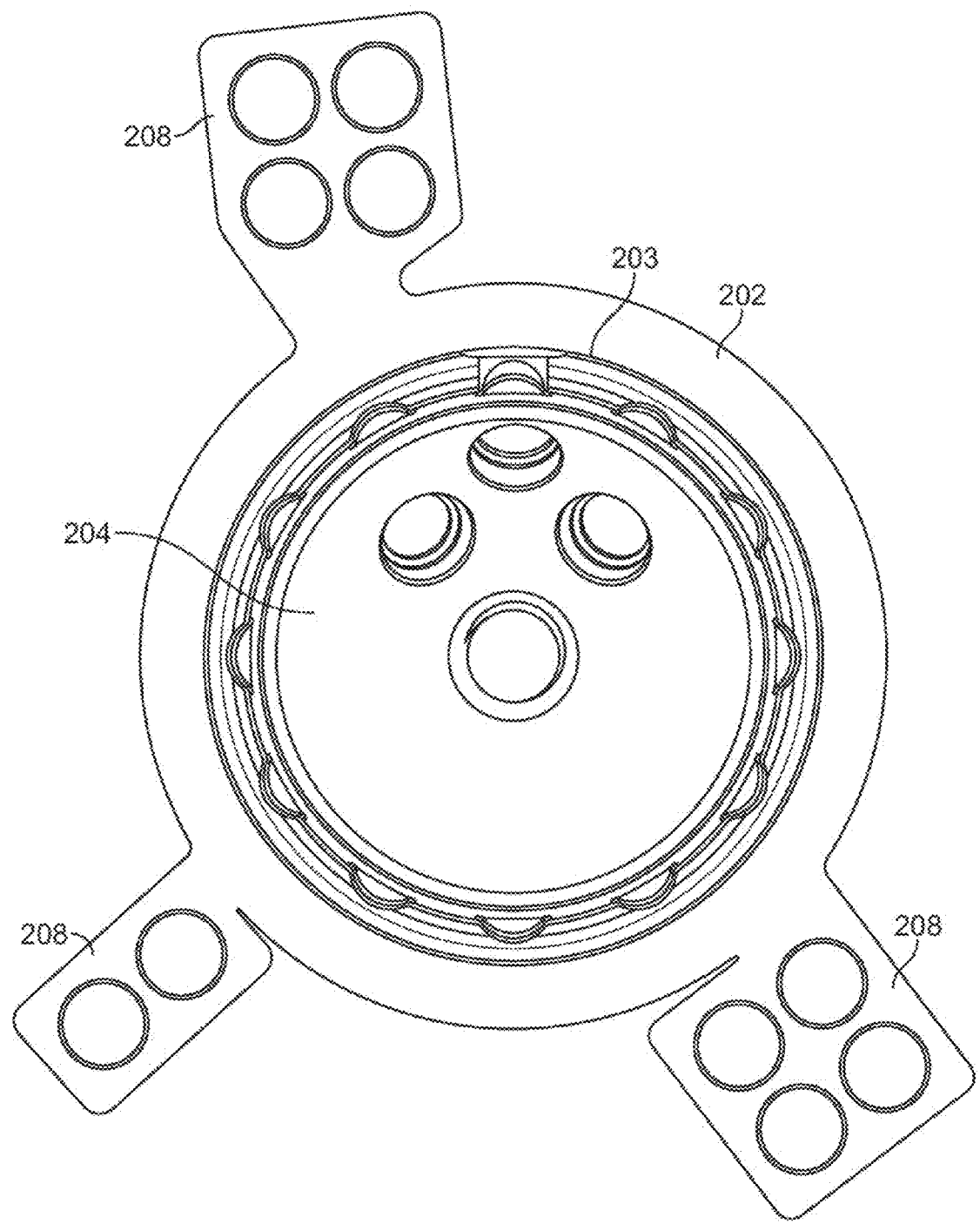
Figure 3:
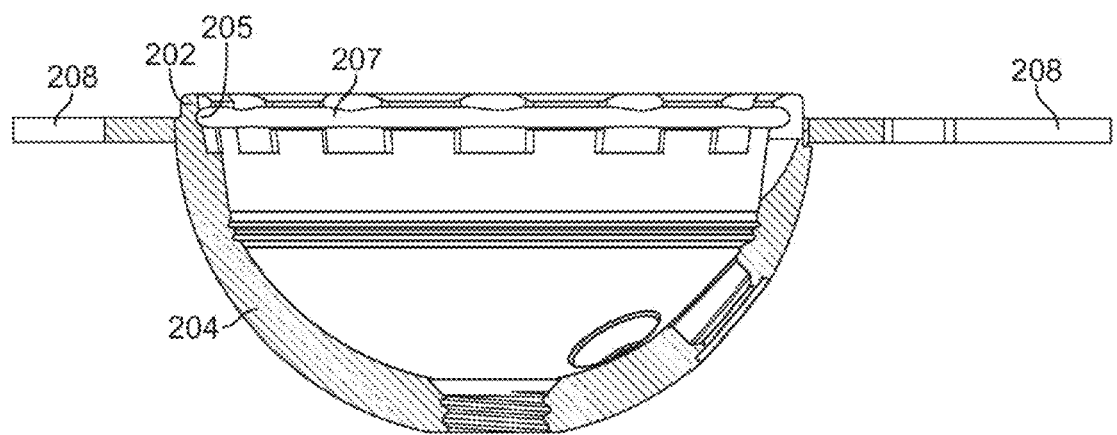
Figure 4:
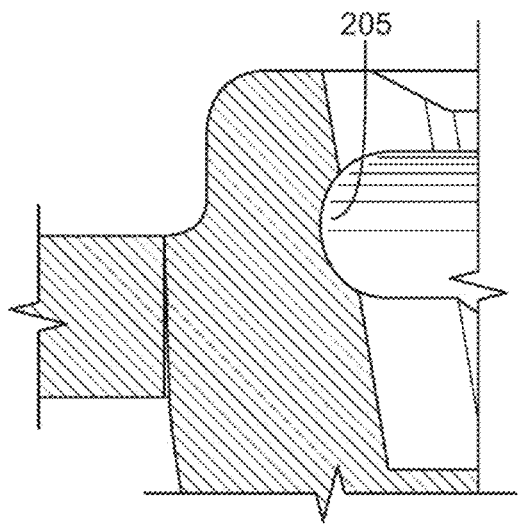

To provide an overall understanding of the systems, devices, and methods described herein, certain illustrative embodiments will be described. Although the embodiments and features described herein are specifically described for use in connection with acetabular systems, it will be understood that all the components, connection mechanisms, adjustable systems, fixation methods, manufacturing methods, coatings, and other features outlined below may be combined with one another in any suitable manner and may be adapted and applied to medical devices and implants to be used in other surgical procedures, including, but not limited to: spine arthroplasty, cranio-maxillofacial surgical procedures, knee arthroplasty, shoulder arthroplasty, as well as foot, ankle, hand, and other extremity procedures.

Various implants and other devices described herein in their various embodiments may be used in conjunction with any appropriate reinforcement material, non-limiting examples of which include bone cement, appropriate polymers, resorbable polyurethane, and/or any materials provided by PolyNovo Biomaterials Limited, or any suitable combinations thereof. Further non-limiting examples of potential materials that may be used are described in the following references: U.S. Patent Application Publication No. 2006/0051394, entitled "Biodegradable Polyurethane and Polyurethane Ureas," U.S. Patent Application Publication No. 2005/0197422, entitled "Biocompatible Polymer Compositions for Dual or Multi Staged Curing," U.S. Patent Application Publication No. 2005/0238683, entitled "Biodegradable Polyurethane/Urea Compositions," U.S. Patent Application Publication No. 2007/0225387, entitled "Polymer Compositions for Dual or Multi Staged Curing," U.S. Patent Application Publication No. 2009/0324675, entitled "Biocompatible Polymer Compositions," U.S. Patent Application Publication No. 2009/0175921, entitled "Chain Extenders," and U.S. Patent Application Publication No. 2009/0099600, entitled "High Modulus Polyurethane and Polyurethane/Urea Compositions." Each of the prior references is incorporated by reference herein in its entirety.

FIGS. 1-4 show some embodiments where a rim augment or a mounting member may be configured for a left hip. Rim mounting member 202 may be press-fit onto an outer diameter 203 of an acetabular cup 204 (e.g., acetabular shell, cup, cage, or augment). The rim mounting member 202 has at least one curved or spherical inner surface 205 that matches a contour profile 207 of an outer surface of the acetabular cup 204 to which the mounting member 202 is attached. In some embodiments, more than one opposing curved or spherical surfaces may be provided on the inner surface 205 of the rim mounting member 202, each curved or spherical surface comprising a similar radius of curvature. The size, shape, and profile of these one or more curved or spherical surfaces correspond to the outer diameter and outer surface profile of the acetabular cup 204.

By providing two curved or spherical surfaces, for example, the rim mounting member 202 may be configured for universal use and, therefore, may be flipped or inverted in order to allow its use with a left to a right acetabular cup. In other words, the rim mounting member 202 may be inverted when used in conjunction with a contralateral hip. It may further be provided in any suitable number of available sizes in order to fit multiple cup sizes (e.g., acetabular cups having outer diameter sizes ranging between approximately 30 mm and 90 mm).

One or more flanges or other mounting members, or any combinations thereof, may be provided on mounting member 202. In the particular embodiment shown, three mounting members 208 are shown, which extend radially from the rim of the acetabular cup 204. The mounting members 208 are configured to be bent, cut, or otherwise shaped as needed in order to conform to the pelvis of a particular patient's anatomy. Alternatively or additionally, one or more of the mounting members 208 may be oriented at predetermined radial locations circumferentially around the rim of the acetabular cup to correspond with, engage, or otherwise accommodate the ilium, ischium, superior ramus, or any other suitable patient anatomy. It should further be understood that any of the alternate and adjustable mounting and securement mechanisms described herein may also be used with these embodiments. The described rim mounting members are of particular use in acetabulums having defects and damage along the acetabular rim. The holes of the mounting members 208 may be threaded, unthreaded, or partially threaded, and may be fixed or polyaxial. In some embodiments, attachment sites may include variable low-profile holes that allow for locking at a variety of angles.

Figure 5:
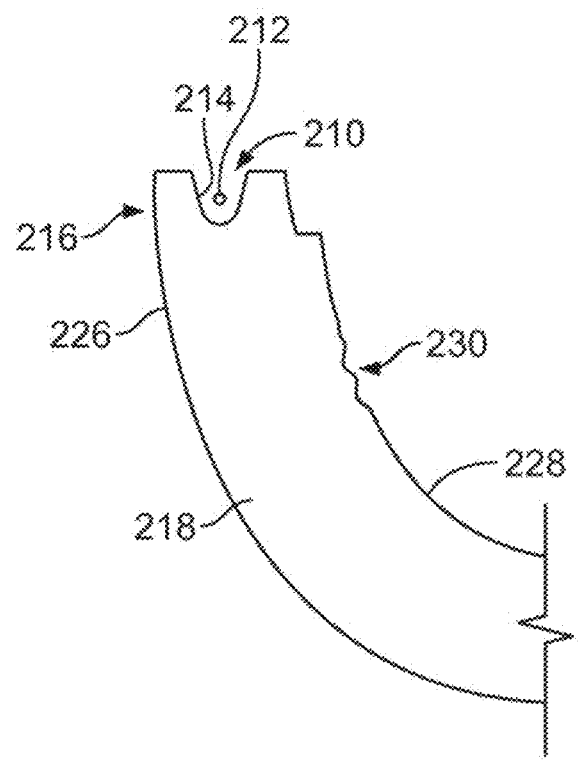
FIGS. 5 and 6 schematically show the use of an illustrative pivot joint to add a mounting member to an acetabular shell.
Figure 6:
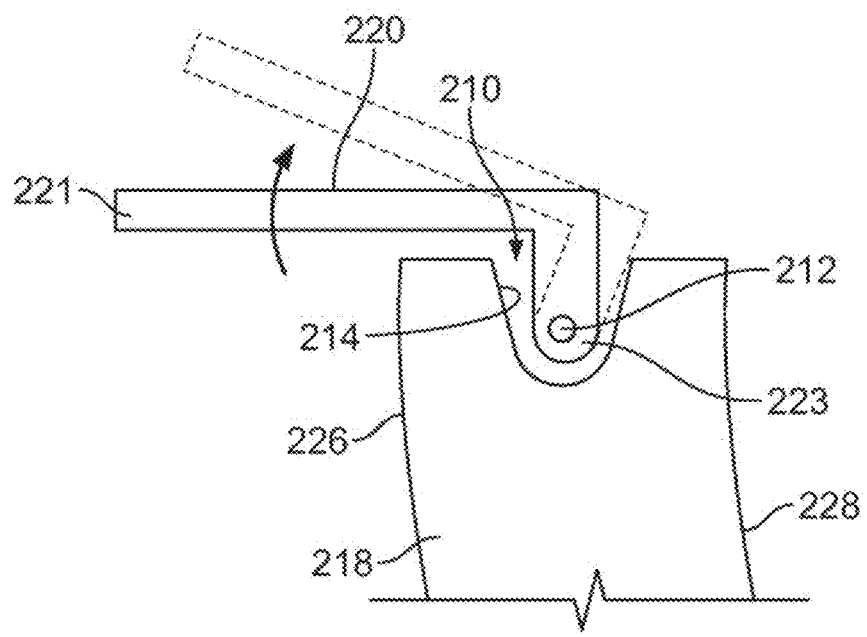
Figure 7:
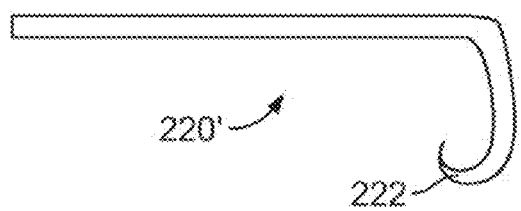
FIG. 7 shows an illustrative mounting member having a hook that receives a crossbar.
Figure 8:
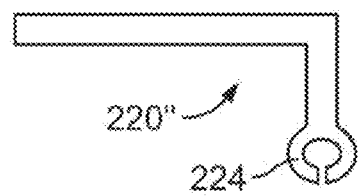
FIG. 8 shows an illustrative mounting member having a split opening that receives a crossbar.

FIGS. 5-8 schematically illustrate the use of a pivot joint 210 to add a mounting member (such as a flange, plate, or any other attachment or mounting member) to an acetabular shell, cup member, or augment according to some embodiments. For example, as shown in FIG. 5, a crossbar 212 may be provided in one or more recesses 214 on an upper shell surface of proximal rim portion 216 of the acetabular shell 218 and aligned generally parallel to a tangent of the shell 218 adjacent its rim. The one or more recesses 214 may comprise, for instance, a V-shaped slot, although any other suitably-shaped slot may be used. A plurality of attachment sites may be provided, with each being spaced angularly about the rim or other portion of the implant. This allows a plurality of positioning options for mounting members and gives the surgeon more flexibility to position the attachments along the implant for ease of anchoring. The acetabular shell 218 includes a ridge 230 on inner surface 228 that mates with a correspondingly-shaped ridge of a liner, for example, although any other suitable mounting member or augment may have a similarly-shaped ridge for mating with ridge 230. In some embodiments, the ridge 230 may be provided alternatively, or additionally, on outer surface 226.

A mounting member 220 has a first end 221 that anchors to the patient's bone or soft tissue and a second end or receiving portion 223 that mates with the implant, such as acetabular shell 218, at each of the plurality of attachment sites provided along, for example, the crossbar 212. The second end or receiving portion 223 of mounting member 220 may have a hook or a split opening that receives the crossbar 212. For example, mounting member 220' of FIG. 7 includes a hook 222, and mounting member 220" of FIG. 8 includes a split opening 224, which may also be referred to as a split eyelet. The mounting members shown in FIGS. 6-8 may be moved independently of the shell positioning. One of the advantages provided by this design is that the flanges and other mounting members are completely modular and do not have to be positioned in the same discrete place or in only one of a few predetermined locations, but can instead be positioned anywhere around the rim of the shell and can pivot in a plane that is perpendicular to the plane defined by the circumference of the shell.

Figure 9:
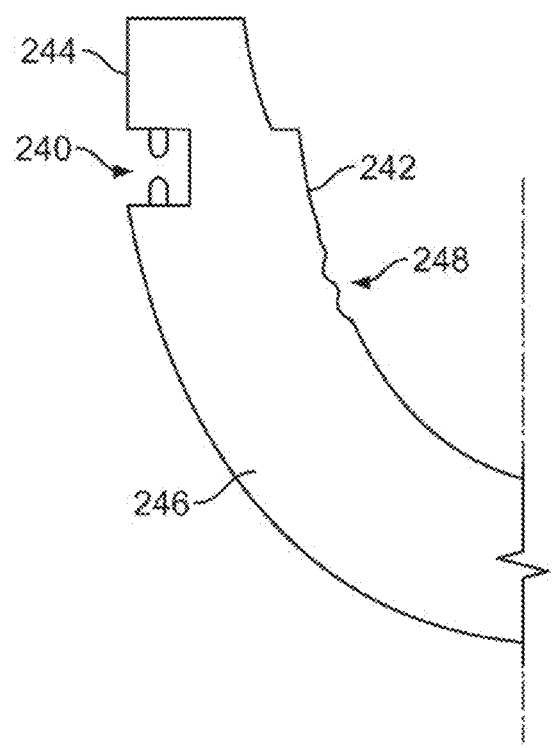
FIG. 9 shows an illustrative T-slot into which a correspondingly-shaped receiving portion may be disposed.
Figure 10:
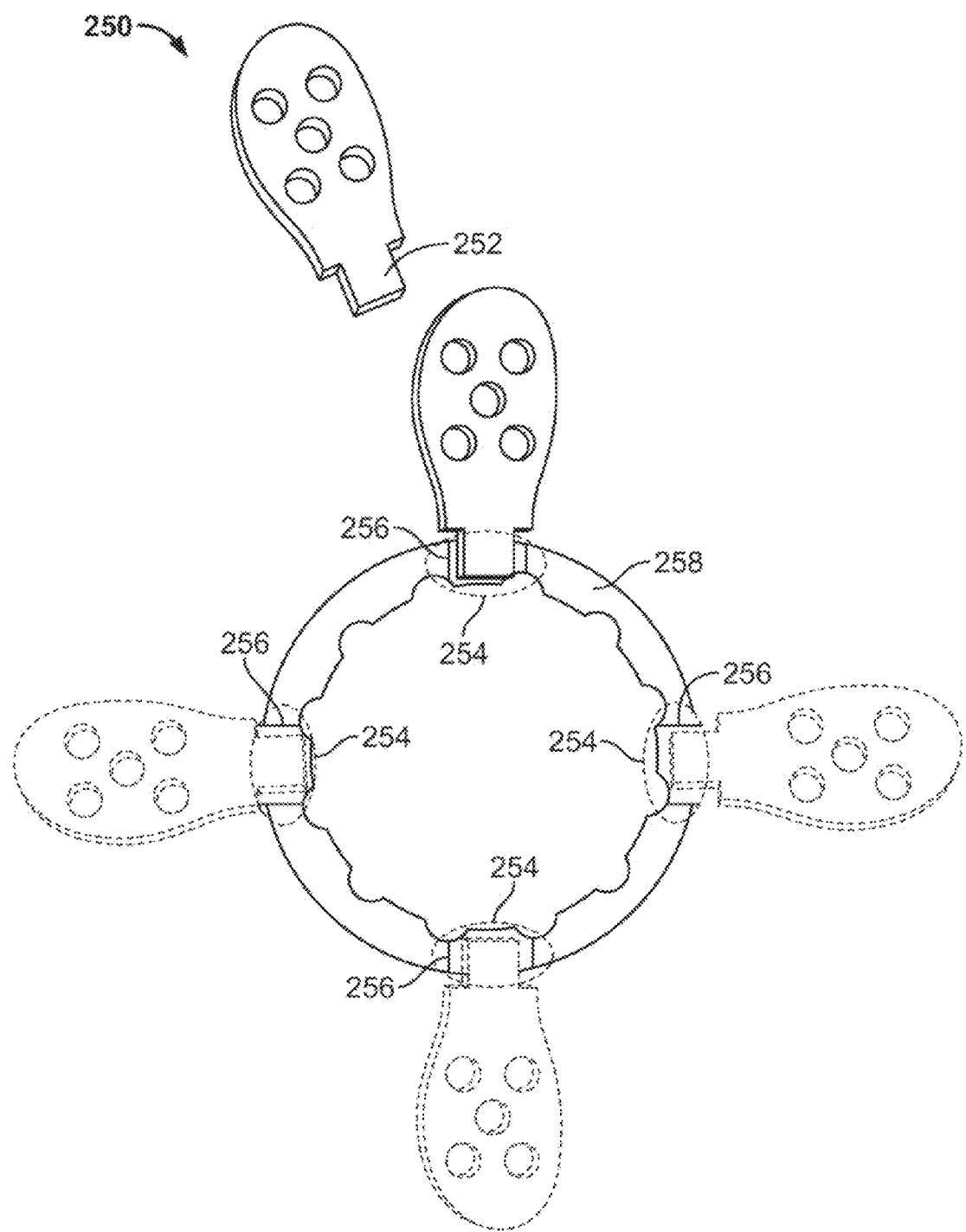
FIG. 10 shows a plurality of illustrative entry portions that may be provided around an acetabular shell.

FIGS. 9 and 10 illustrate some embodiments where one or more mounting members and/or augments translate or ride, or otherwise move, in a circumferentially-extending T-slot, dovetail slot, tongued groove, or undercut groove provided in an outer shell surface 244 proximate to the rim. The mounting members or augments may be configured with a receiving portion that may enter a portion of the shell 246 and slide within the circumferentially-extending T-slot, dovetail slot, tongued groove, or undercut groove. For example, FIG. 9 shows a T-slot 240 on an outer surface 244 of shell 246 into which a correspondingly-shaped receiving portion may be disposed. The mounting members or augments can revolve around the shell to the proper angular position around the rim and then be locked, retained, or otherwise secured in position. For example, the receiving portions may include a locking member or an expanding member that locks or expands, respectively, when the mounting member or augment is place in a particular location along the shell to thereby secure the mounting member or augment into position. A plurality of attachment sites may be provided, with each being spaced angularly about the rim or other portion of the implant. This allows a plurality of positioning options, as opposed to the discrete few options typically provided, for example, where the mounting member or augment must be positioned at the discrete location where attached. Similar to the acetabular shell 218 of FIG. 5, shell 246 may also include a ridge 248 on inner surface 242 that mates with a correspondingly-shaped ridge of a liner, for example, although any other suitable mounting member or augment may have a similarly-shaped ridge for mating with ridge 248. In some embodiments, the ridge 248 may be provided alternatively, or additionally, on outer surface 244.

One or more entry points may be provided within the T-slot, dovetail slot, tongued groove, undercut groove, or other attachment site to allow quick insertion, placement, access, or removal of the flanges, plates, or augments with respect to the shell. Particularly, multiple entry portions may be configured to allow one or more mounting members or augments to be engaged with the shell and positioned angularly around the shell even after the shell has been impacted into a prepared acetabulum and portions of the shell proximate to the rim are obstructed by bone, grafts, or cement. For example, as shown in FIG. 10, a plurality of entry portions 254 may be provided around shell 258. A mounting member 250 that includes a receiving portion 252 shaped as a key may be engaged with a reciprocally-shaped groove 256 at one of entry portions 254. The mounting member 250 may engage with the shell by placing mounting member 250 into one of the grooves 256 at an entry point 254 and then positioned angularly around the shell therefrom to one of a plurality of attachment sites. Furthermore, mounting member 250 may be inserted into a first entry point 254, rotated about the shell 258 to a second entry point 254, and then removed.

Figure 11:
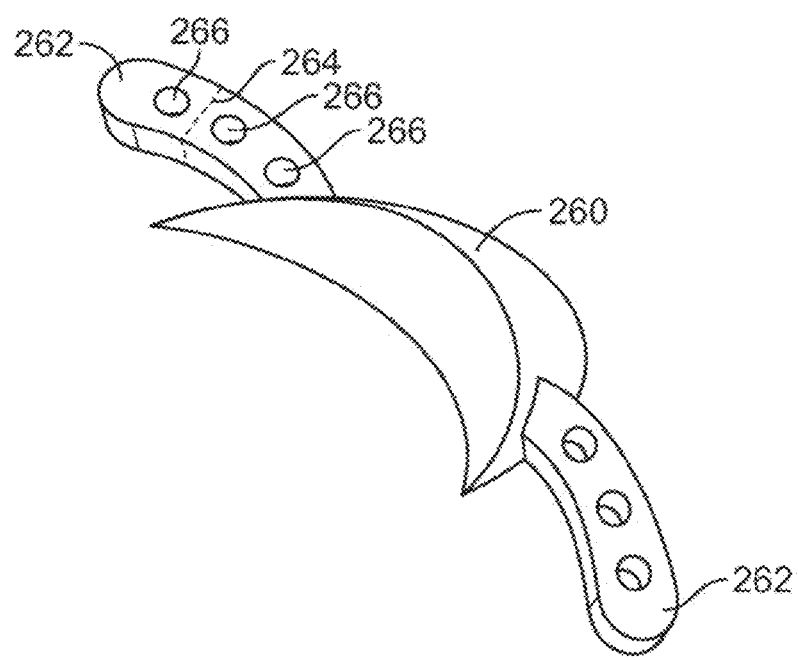
FIGS. 11-13 show an illustrative augment having one or mom mounting members.
Figure 12:
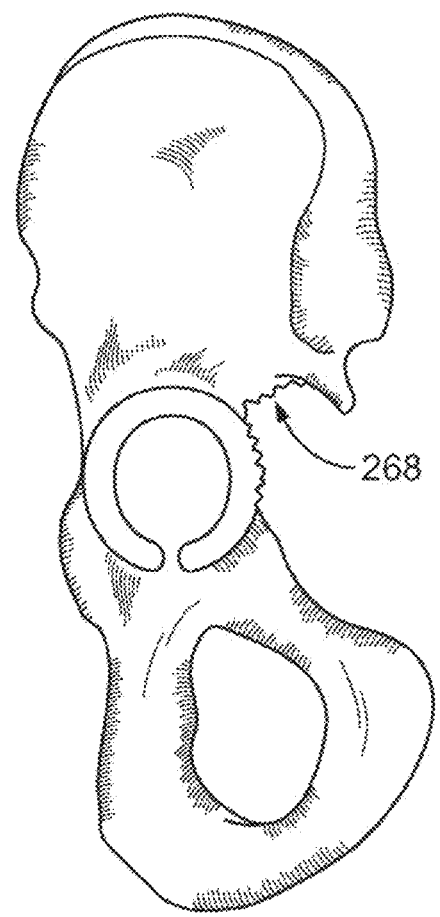
Figure 13:
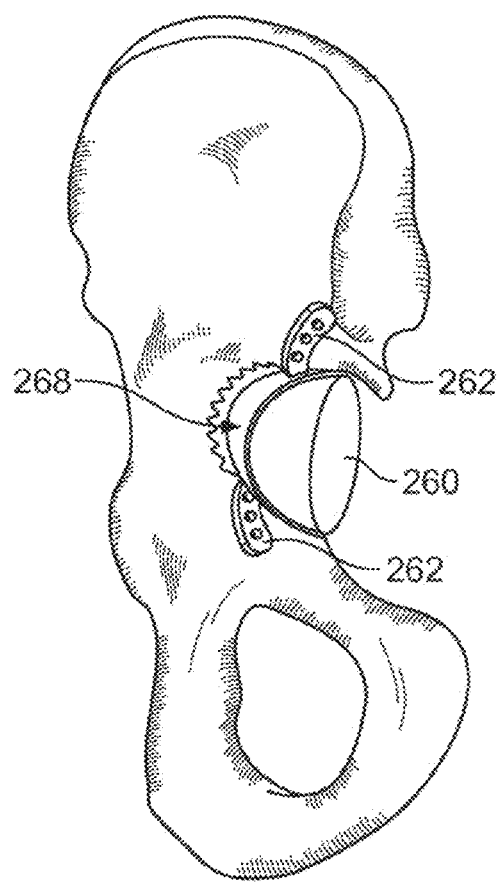

In the embodiments shown in FIGS. 11-13, one or more mounting members 262 (shown as flanges, but not limited thereto) are added to an acetabular augment 260. The mounting members 262 may be permanently fixed or detachable, and may be adjustably positionable about augment 260 as described above. Mounting members 262 may have frangible portions 264 between screw holes 266 or other structures for receiving fasteners. The frangible portions 264 may be provided, for example, as reduced cross-sections that allow bending or breaking or cutting of the mounting members 262 without disturbing the internal geometries of the screw holes 266. In certain embodiments, the frangible portions 264 may be prestressed or otherwise pretreated to make the frangible portions 264 weaker than other areas of the mounting members 262. Screw holes 266 may be smooth or provided with threads or other protrusions to be used with locking head screws or polyaxial screws. The screw holes 266 may be conventional holes, locking holes, or slots. The holes may be threaded, unthreaded, or partially threaded, and may be fixed or polyaxial. In some embodiments, screw holes 266 may include variable low-profile holes that allow for locking at a variety of angles. The augment 260 and mounting members 262 may be implanted proximate a patient's acetabulum. For example, as shown in FIGS. 12 and 13, augment 260 having mounting members 262 is implanted into an area having a posterior column defect region 268.

Figure 14:
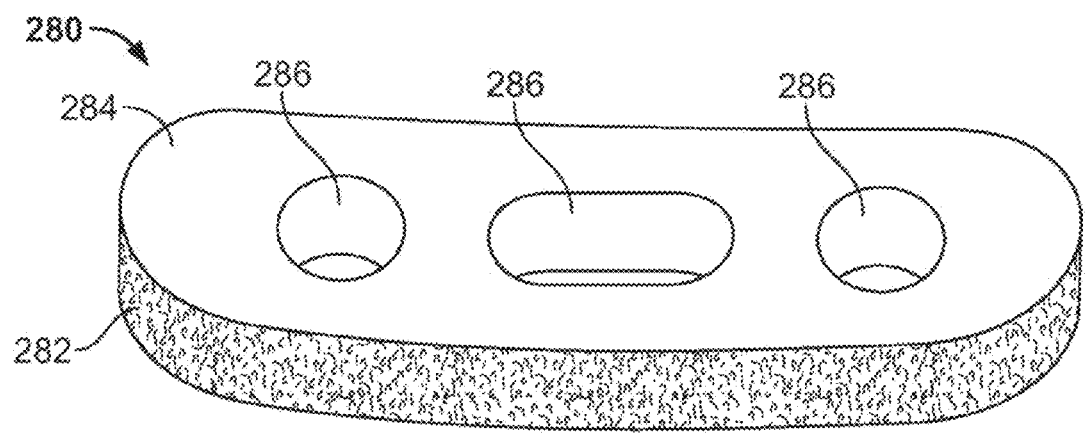
FIGS. 14-19 show one or more illustrative porous pieces or surfaces provided on bendable mounting members such as bendable flanges or plates.
Figure 15:
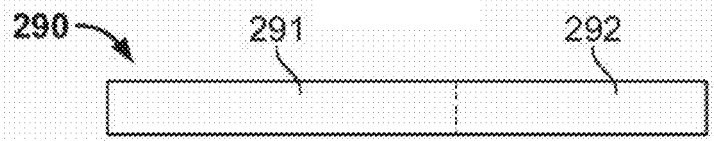
Figure 16:
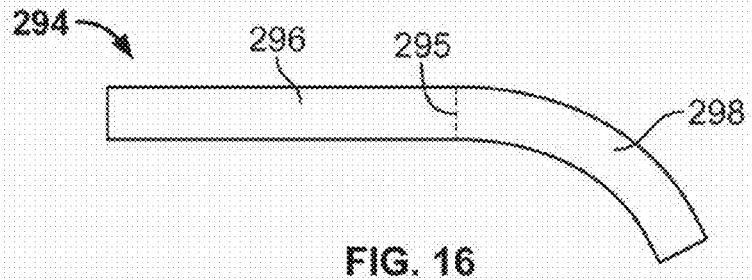
Figure 17:
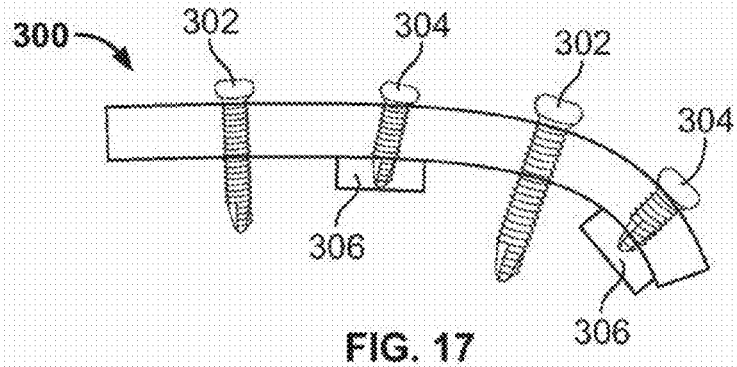
Figure 18:
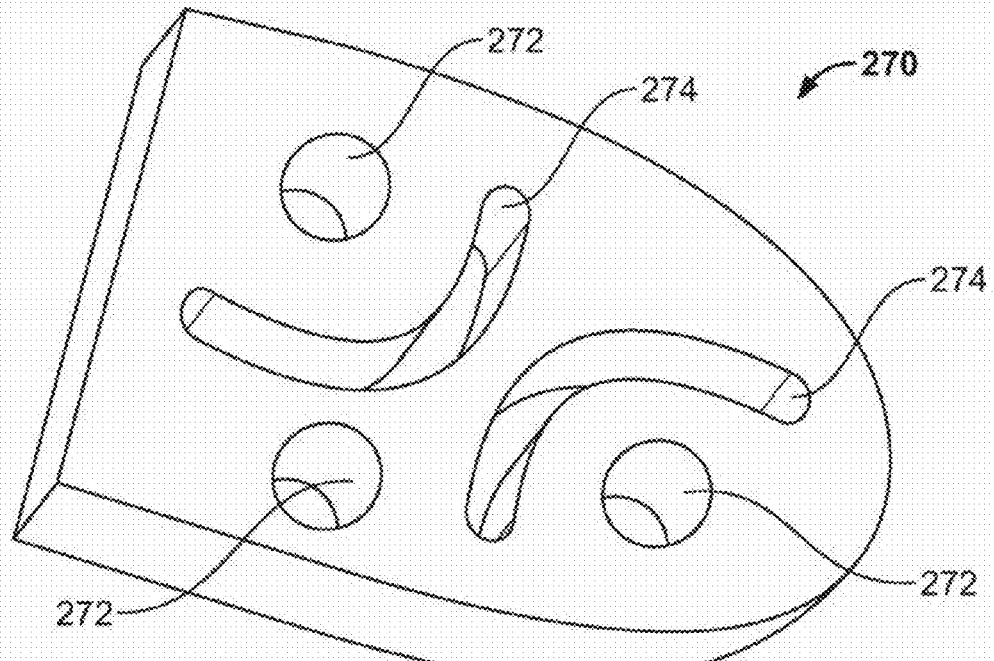
Figure 19:
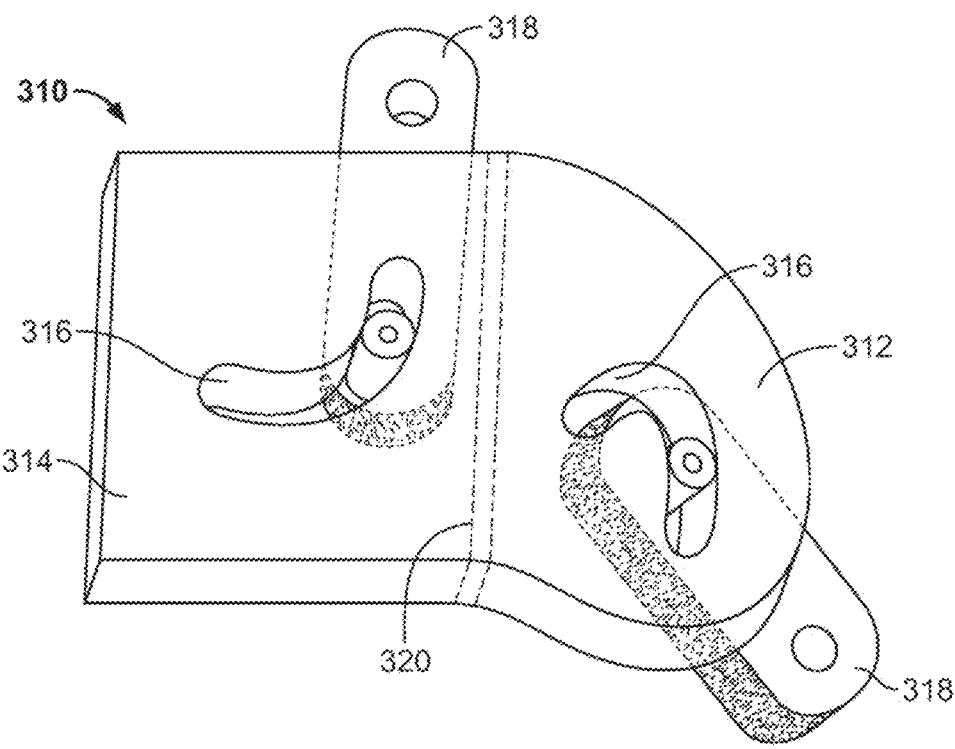

As shown in the embodiments depicted in FIGS. 14-19, one or more porous pieces or surfaces may be provided on bendable mounting members such as bendable flanges or plates, or any of the other mounting members. In some instances, solid or rigid augments may replace bendable mounting members. The mounting members may be modular, attachable, or integrally-provided on an acetabular implant structure such as an acetabular shell. As shown in FIG. 14, a mounting member 280 includes a porous coating 282 about a periphery while top portion 284 is substantially smooth and flat. Mounting member 280 also includes a plurality of fastening through-holes 286 for receiving screws or other fastening members. Through-holes 286 may include conventional holes, locking holes, or slots. The holes may be threaded, unthreaded, or partially threaded, and may be fixed or polyaxial. In some embodiments, through-holes 286 may include variable low-profile holes that allow for locking at a variety of angles. Exemplary bending motion of flanges is shown with respect to FIGS. 15 and 16. A mounting member such as flange 290 has a first portion 291 and a second portion 292 and is flat. Flange 294 may be bent in a first direction about bending axis 295 such that a second portion 298 is bent relative to a first portion 296. Because in some instances there may be a chance that porous structures integrally provided on mounting members (such as porous coating 282 of FIG. 14) may fracture, delaminate, or separate from the mounting members during or after bending, porous pieces may be provided separate from and/or spaced between securement devices such as screw holes, as shown in FIG. 17 and FIG. 19. In FIG. 17, a separate porous in-growth pad 306 is provided, which can be secured to a bendable mounting member 300 via screw 304, so that the bendable mounting member 300 may still be bent, while also featuring the desired in-growth advantages of the porous in-growth pads 306, without being subject to delamination or decoupling upon bending. This allows bending of the mounting members without stressing the struts of each porous piece. The porous piece may be positioned before or after bending. Screws 302 may be provided for securing the mounting member 300 to a patient's bone or soft tissue, an acetabular shell, augment, or other mounting member.

In lieu of screw holes, or in addition in screw holes, in some embodiments spikes, tacks, or other appropriate fasteners may be utilized. J-slots may be provided in the porous pieces or the mounting members to allow adjustability of the position of the porous piece relative to the augment or mounting member in both rotation and translation. For example, FIG. 18 shows a mounting member 270 having a plurality of screw holes 272 and J-slots 274. Screws or any appropriate fixation members may be used to rigidly fix the porous pieces to the augment or mounting member, or other members such as shape memory or deformable pegs (e.g., rivet structure) may be used to rigidly fix the porous pieces to the augment or mounting member. In some instances, members fixing the porous pieces to the augment or mounting member may be configured to allow the porous pieces to move during bending of the mounting members.

As shown in FIG. 19, a mounting member 310 includes a first portion 312 that is bent in a first direction about bending axis 320 relative to a second portion 314. The first portion 312 and second portion 314 of mounting member 310 each include J-slots 316 to allow adjustability of the position of the porous pieces 318 attached thereto relative to mounting member 310.

FIGS. 20-24 show various embodiments of adjustable and/or flexible mounting members. Stiff mounting members, such as stiff plates or flanges, or any other suitable stiff members that may be used to extend from a surgical implant for securing it into place, may be difficult to bend or position. It may thus be desirable in some instances to provide mounting members that are configured to bend or otherwise adjust.

Figure 20:
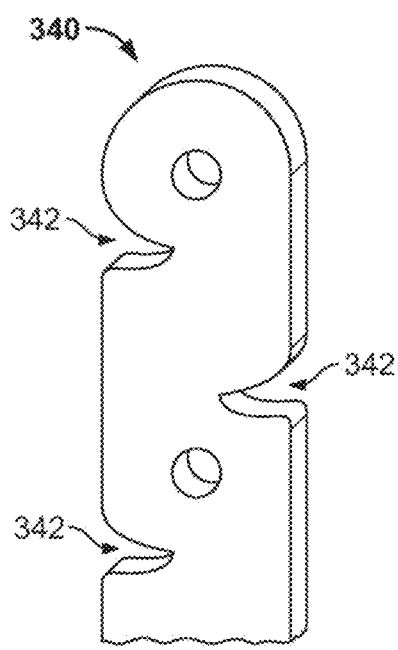
FIG. 20 shows an illustrative mounting member having peripheral notches or inlets.
Figure 21:
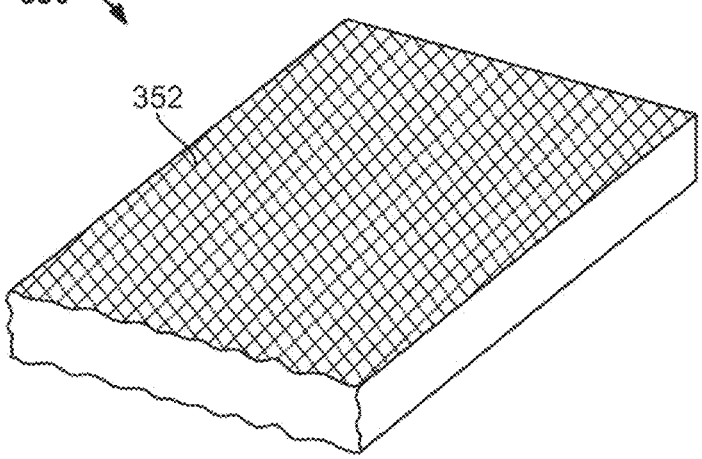
FIG. 21 shows an illustrative mounting member having cross-hatches or removed material from the surface.

FIG. 20 shows a mounting member 340 having peripheral notches or inlets 342 cut into the profile of the mounting member 340. In some embodiments, these features allow mounting member 340 to be flexed, bent, shaped, or otherwise contoured to bone or around other devices. In the embodiment shown, the notches 342 are Z-shaped, but it will be understood that any appropriate shape, such a J-slots, C-slots, V-slots, any other appropriate shapes, or any combinations thereof, may be used. FIG. 21 shows a mounting member 350 having cross-hatches or removed material 352 from the surface, thereby reducing the cross-sectional surface area of the member. These features may make it easier for mounting member 350 to flex, bend, shape, or contour.

Figure 22:
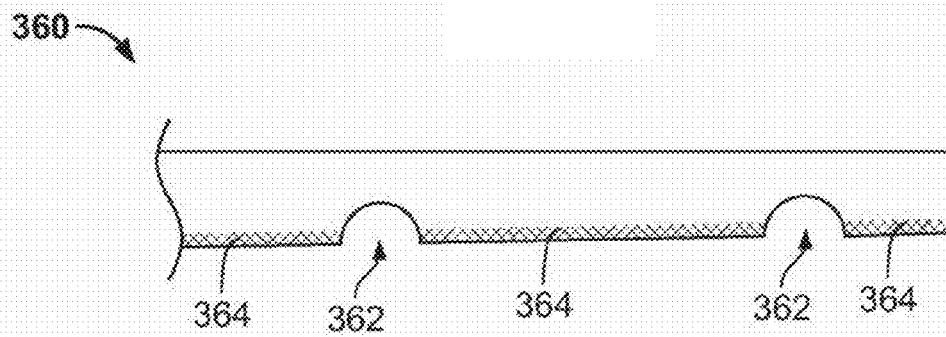
FIGS. 22 and 23 show illustrative mounting members having various reduced surface area portions.
Figure 23:
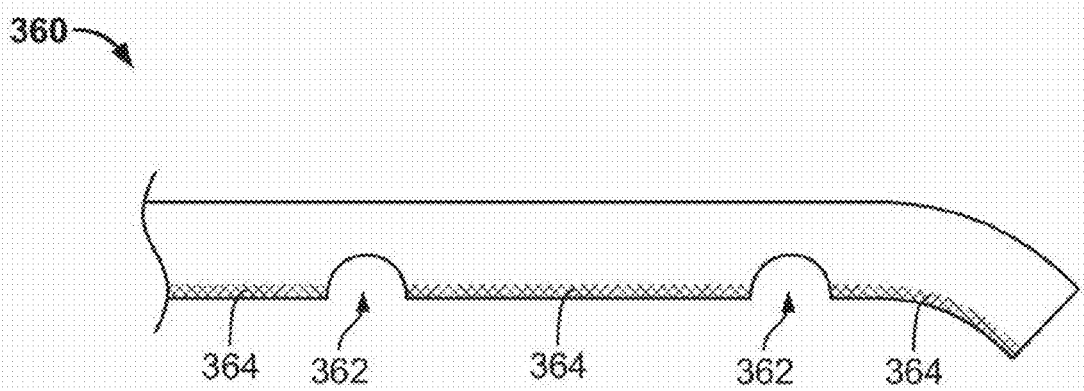

FIGS. 22 and 23 show further embodiments of mounting members that may have various reduced surface area portions, such as notches, indents, removed material, cut outs, or other portions of reduced surface area, or any combinations thereof. For example, mounting member 360 includes notches 362 and cross-hatches or removed material 364. These reduced surface area portions may have any appropriate profile or cross-sectional shape, examples of which may be circular, curved, triangular, irregularly-shaped or any other appropriate option. The reduced surface area portions may help enhance the flexibility or bendability of the member.

Figure 24:
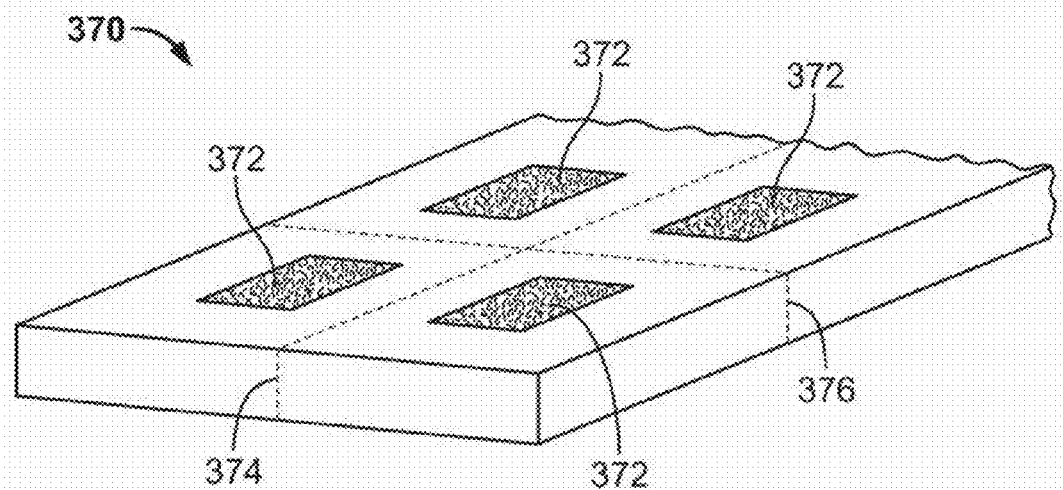
FIG. 24 shows an illustrative mounting member having one or more porous areas that are spaced out on the member.

FIG. 24 shows a mounting member 370 having one or more porous areas 372 that are spaced out on the member 370. In certain embodiments, the mounting member 370 may be bent or otherwise configured as desired, without being limited by the porous areas, as discussed above in connection with FIGS. 14-19. For example, mounting member 370 may be bent about region 374 or 376 without introducing bending stresses to the porous areas 372 or substantially limiting the bending stresses on porous areas 372. Mounting member 370 may have any of the above-discussed reduced surface area portions, or mounting member 370 may be provided as a typical, traditional mounting member.

Figure 25:
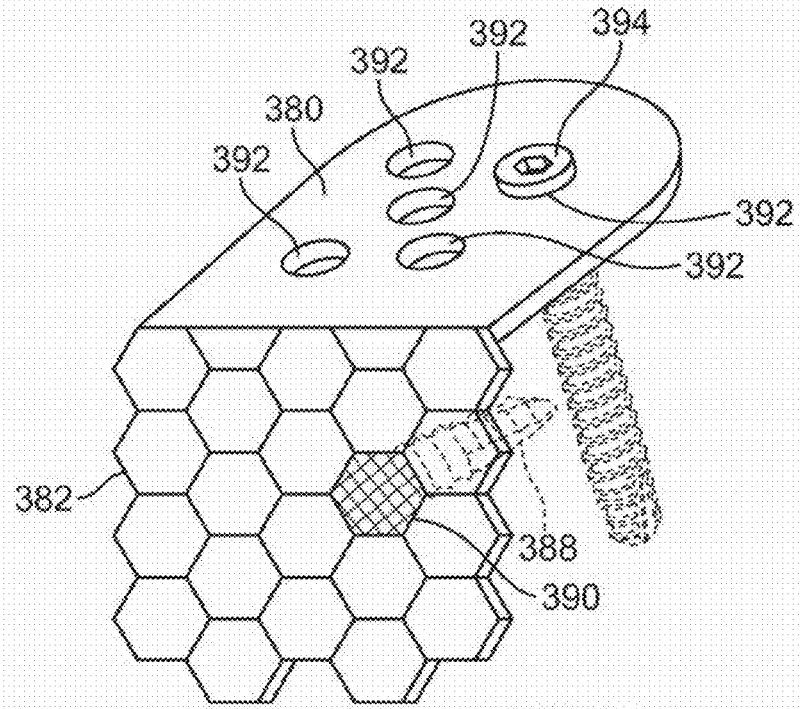
FIG. 25 shows a mounting member having an illustrative orthopedic mesh.
Figure 26:
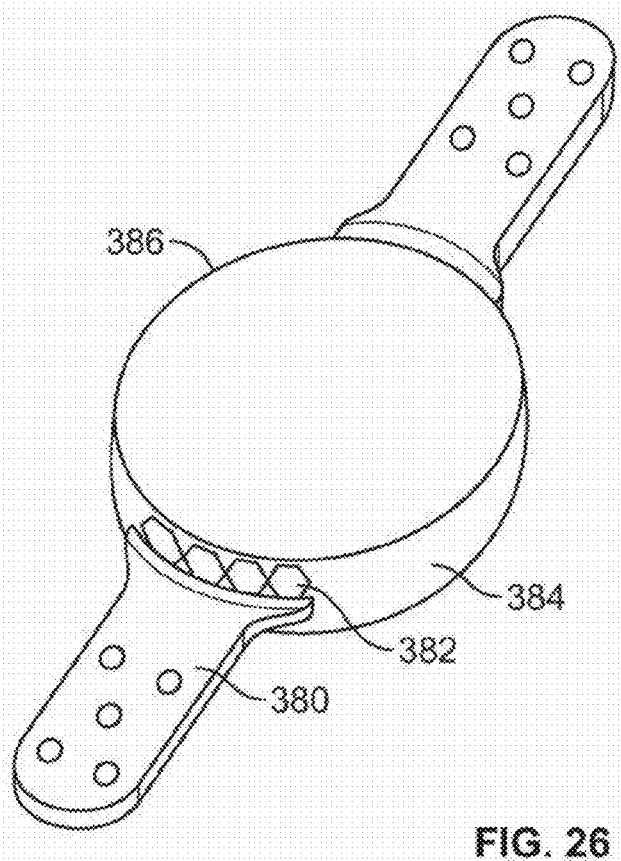
FIG. 26 shows an illustrative mesh portion placed on an outer portion of a shell.
Figure 27:
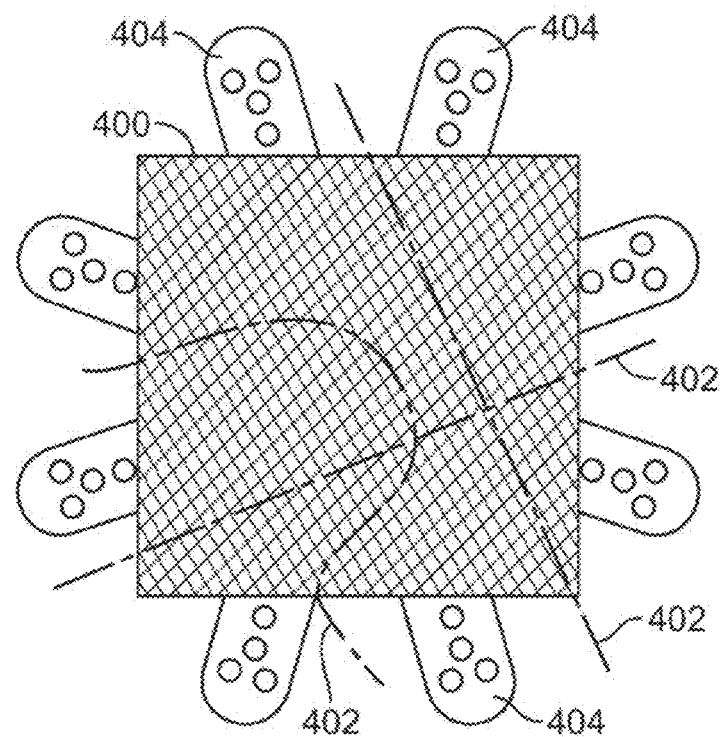
FIG. 27 shows an illustrative mesh that includes a plurality of trim lines that may be cut to separate the mounting members attached thereto.
Figure 28:
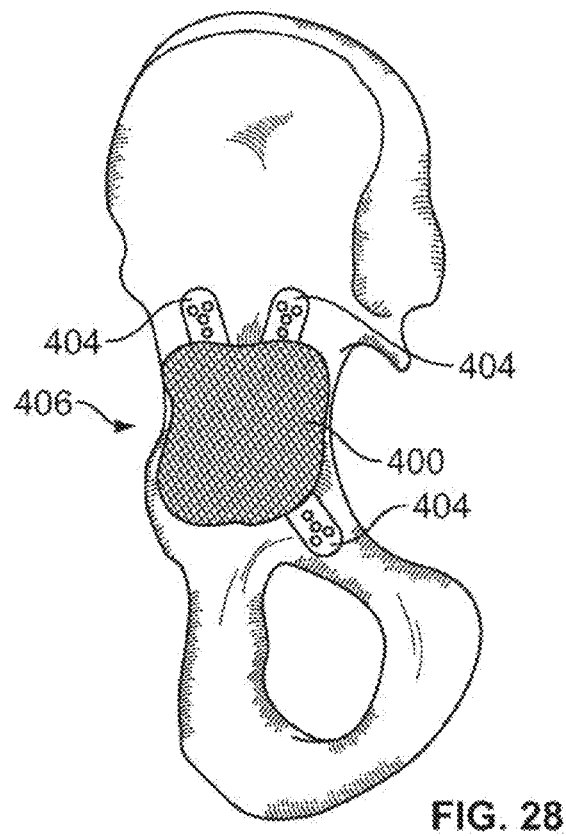
FIG. 28 shows illustrative separated mounting members from the mesh of FIG. 27 placed into a patient's hip region.

In the embodiments shown in FIGS. 25-28, one or more mounting members and/or augments may be integrally provided with orthopedic mesh to define one or more mesh mounts or void fillers. FIG. 25 shows a mounting member 380 having an orthopedic mesh 382. In FIG. 26, the orthopedic mesh portion 382 may be placed on an outer portion 384 of the shell 386 between bone, and a cement mantle can fill between the mesh 382. The cement mantle rigidly connects the mounting member 380 (or, in some embodiments, an augment) to the shell 386 via the surgical mesh 382. Rapid manufacturing techniques may be used to simultaneously create the mounting members or augments integrally with the orthopedic mesh portion. The mesh 382 may be honeycomb, diamond, or other weave pattern, or any combination thereof, and may come in multiple thicknesses. Mesh portion 382 may be oversized, customized for an individual patient, and/or standardized and trimmed by the surgeon to fit a particular patient's needs. Fasteners of all types may be inserted through one or more cells of the mesh 382, as well as through the one or more mounting members or augments to further secure the implant to bony anatomy. For example, as shown in FIG. 25, a first screw 388 may be inserted through cell 390, and a second screw 394 may be inserted through one of the plurality of screw holes 392 of mounting member 380. Screw holes 392 may include conventional holes, locking holes, or slots. The holes may be threaded, unthreaded, or partially threaded, and may be fixed or polyaxial. In some embodiments, screw holes 392 may include variable low-profile holes that allow for locking at a variety of angles. Soft tissues may be reattached, using the porosities of the mesh 382 as suture anchors, or simply as a bioscaffold. If desired, preformed trim lines may be provided by forming predetermined frangible portions in various areas of the mesh, in order to help configuration of the device for a particular patient. For example, as shown in FIG. 27, mesh 400 includes a plurality of trim lines 402 that may be cut to separate the mounting members attached thereto, such as mounting members 404. The separated mounting members 404 and the mesh 400 may then be placed into a patient's hip region 406 as shown in FIG. 28.

Figure 29:
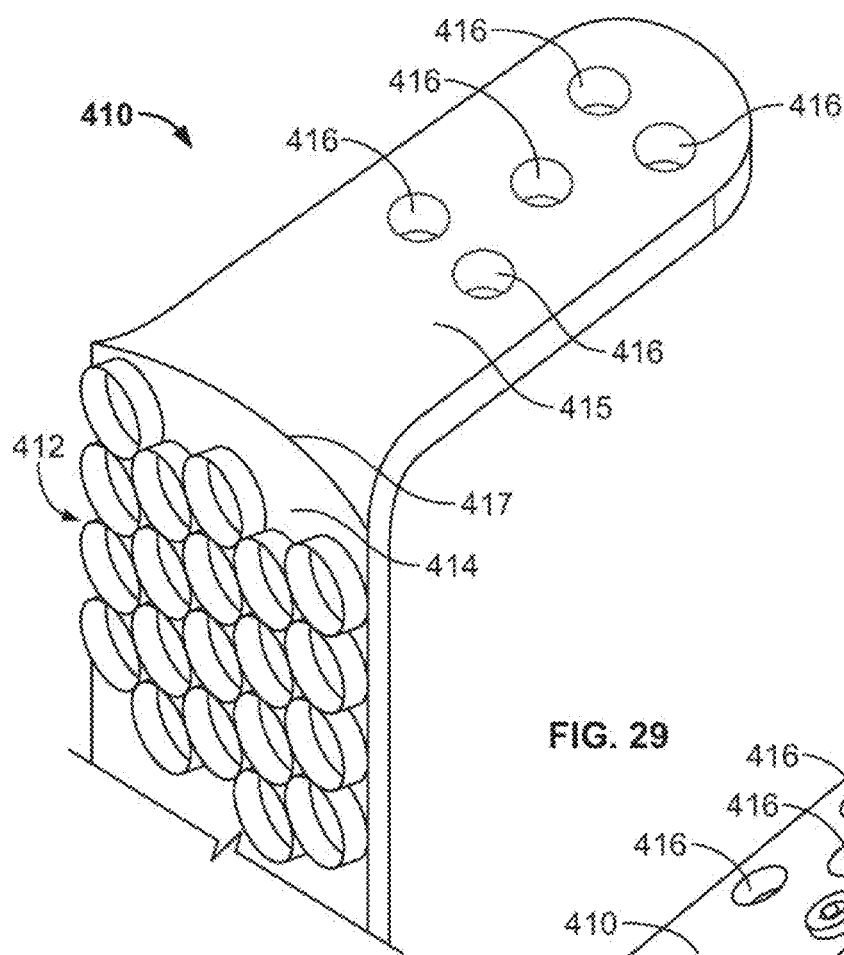
FIGS. 29 and 30 show an illustrative honeycomb design that may be provided on a mounting member or augment.
Figure 30:
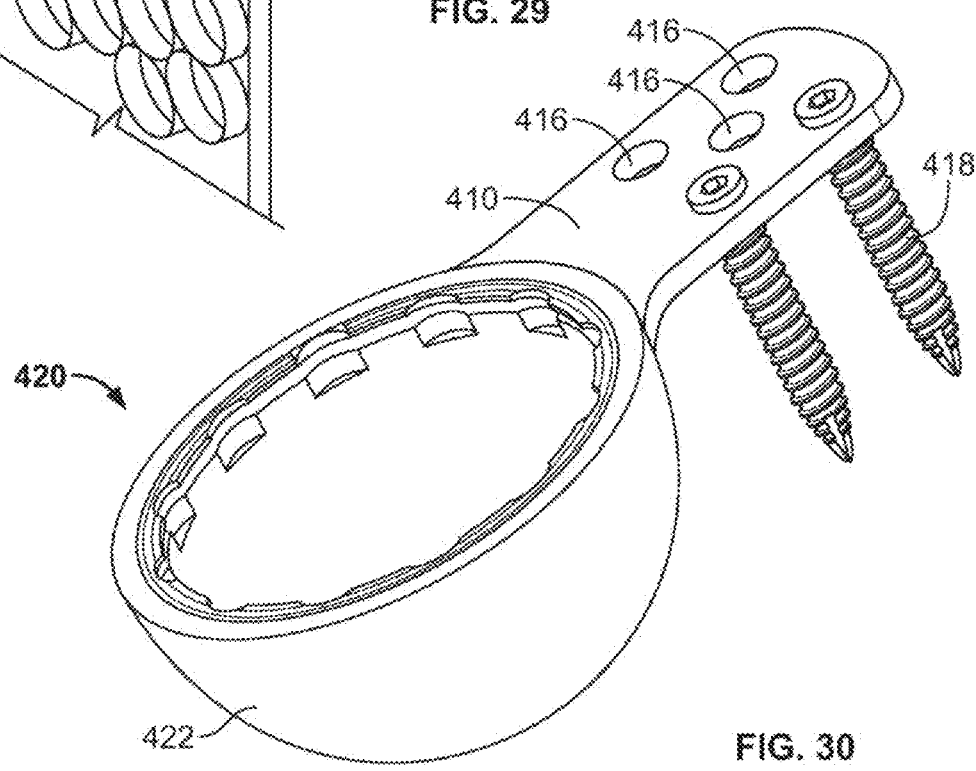

FIGS. 29 and 30 illustrate some embodiments of a honeycomb design that may be provided on a mounting member or augment in order to control cement mantle thickness and spacing between said mounting member or augment and an adjacent acetabular shell, augment, bone, or other implant. For example, mounting member 410 of FIG. 29 includes honeycomb portion 412 provided on an attachment surface portion 414 of the mounting member 410. The honeycomb feature 412 may be provided as any desired geometric shape. The mounting member 410 (or, in some embodiments, the augment) may comprise one or more securing holes 416 for receiving a surgical fastener 418 such as a polyaxial screw, cancellous screw, peg, or other securing device. The securing holes 416 may include conventional holes, locking holes, or slots. The holes may be threaded, unthreaded, or partially threaded, and may be fixed or polyaxial. In some embodiments, securing holes 416 may include variable low-profile holes that allow for locking at a variety of angles. The attachment portion 414 of the mounting member 410 may extend generally perpendicularly from another portion 415 of the mounting member 410, and may comprise one or more concave curved surfaces 417 configured to abut an outer portion 422 of an acetabular shell 420, or one or more convex surfaces (not shown) configured to abut an inner portion of a prepared acetabulum.

In the embodiments shown in FIGS. 86-89, cleats may be provided proximate to a rim of an acetabular shell, cage, mounting member, or augment. For example, in some embodiments, one or more cleats 780 and 781 may extend or project from a superior aspect of a rim portion 782 of an acetabular shell 784 as shown. Cleats 780 and 781 may be used to secure soft tissues to the acetabular shell 784 or may serve as a means to attach secondary augments or any type of mounting member 786 to the acetabular shell 784. In the particular instance shown in FIGS. 88 and 89, a "quarter-turn" fastener connector arrangement is utilized. The quarter-turn fastener arrangement may comprise, for instance, a generally T-shaped male member 790 located on one or more regions of an acetabular shell, cage, or augment, and one or more complementary female members 792 located on more secondary augments or mounting members. The one or more secondary augments or mounting members engage the one or more male members 790 on the acetabular shell, cage, or augment in one degree of rotation, and then are rotated by a specified or variable number of degrees (e.g., 90 degrees) to lock the one or more secondary augments or mounting members to the one or more male members 790. Of course, one of ordinary skill in the art would appreciate that the male and female members could be reversed to provide the same function. It should also be understood that other locking mechanisms may be used.

Figure 55:
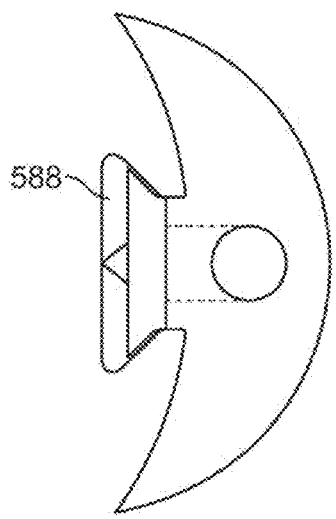
FIGS. 55 and 56 show an illustrative dovetail feature configured to receive a fastener.
Figure 90:
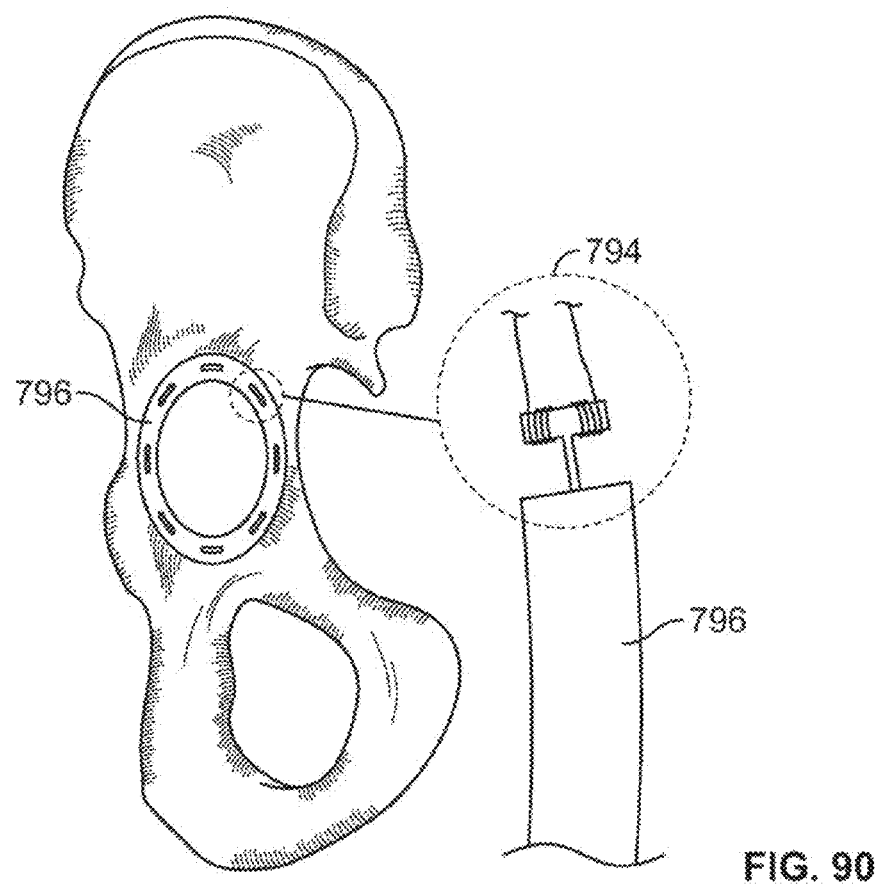
FIG. 90 shows illustrative cleat portions configured for securing soft tissues.

FIG. 90 further depicts one or more cleat portions 794 located at various portions of an acetabular shell or cage 796 (or, in some embodiments, an augment) configured for securing soft tissues. The one or more cleat portions 794 can be arranged in any particular fashion around the acetabular shell 796; however, it is preferred that the cleats 794 extend proximally from a rim portion or otherwise away from the acetabular shell 796 in order to provide clearance from liner-mating surfaces, cement mantle surfaces, bone contacting surfaces, and bony anatomy, for example. Cleat portions 794 may comprise suturing holes, roughened surfaces, clamps, hooks, or biologic coatings, or any other appropriate protrusions, or combinations thereof, to encourage fixation of the soft tissues to the implant (e.g., acetabular shell 796). For example, as shown in the inset of FIG. 55, sutures may be wrapped around cleat portion 794 and then secured to surrounding soft tissues.

FIGS. 91-95 illustrate embodiments wherein a mounting member 802 or an augment 804 may be attached peripherally to an acetabular shell or cage 806 via a recess 800 provided proximate a rim portion 808 of the acetabular shell or cage 806. The recess 800 is sized to accept a protruding insertion portion 810 of the mounting member 802 or a protruding insertion portion 812 of the augment 804, and the recess 800 may extend annularly circumferentially around the rim portion 808 to allow orbital placement of the mounting member 802 or augment 804 around a periphery of the shell or cage 806. The mounting member 802 or augment 804 may be inserted into the acetabular shell or cage 806 before or after shell/cage impaction or cementing into a prepared acetabulum. One or more screw holes in the mounting member (e.g., screw holes 814) or augment (e.g., screw holes 816) rigidly secure the mounting member 802 or augment 804 to the bone and prevent orbital movement of the mounting member 802 or augment 804 around the shell or cage 806. Screw holes 814 and 816 may include conventional holes, locking holes, or slots. The holes may be threaded, unthreaded, or partially threaded, and may be fixed or polyaxial. In some embodiments, screw holes 814 and 816 may include variable low-profile holes that allow for locking at a variety of angles. Once the mounting member 802 or augment 804 is positioned, the cantilever force pushes the rim 808 of the shell or cage 806 toward bone. The protruding insertion portion of the mounting member (e.g., portion 810) or augment (e.g., portion 812) provides a hold-down force to the shell or cage 806 after a screw is inserted through the mounting member 802 or augment 804 and into surrounding pelvic bone.

FIGS. 91 and 92 show an augment 804 being positioned with respect to an acetabular shell or cage 806. FIGS. 93 and 94 illustrate a mounting member 802 being positioned with respect to an acetabular shell or cage 806. The mounting member 802 is shown as having multiple securing holes 814 for use with fasteners. Securing holes 814 may be smooth, tapered, or threaded and may be used with any appropriate fastener, including but not limited to polyaxial screws. The securing holes 814 through the mounting member 802 (or securing holes 816 through the augment 804) may be positioned at any appropriate angle, as shown, such as parallel to the member, oblique through the member, or otherwise as desired. While not shown, a honeycomb feature may be placed on outer portions of the mounting member 802 or augment 804 to provide spacing for a cement mantle between the mounting member 802 or augment 804 and surrounding bone. Moreover, porous structures, textured surfaces, biologic coatings, or orthopedic meshes may be integrally provided on, or incorporated between outer surfaces of the mounting members 802 or augments 804 and surrounding bone.

In the embodiments of FIGS. 93 and 94, a recess 800 in the shell or cage 806 is defined by a proximally-extending lip 818 such that the mounting member 802 will sit on bone surrounding the acetabulum. In this way, the mounting members 802 will not interfere with the press-fit area between the shell 806 and prepared acetabulum adjacent the acetabular rim 808. Moreover, because the connection is configured to allow mounting members 802 to sit on surrounding bone, the surrounding bone does not need to be countersunk or otherwise prepared to receive mounting members 802.

Figure 95:
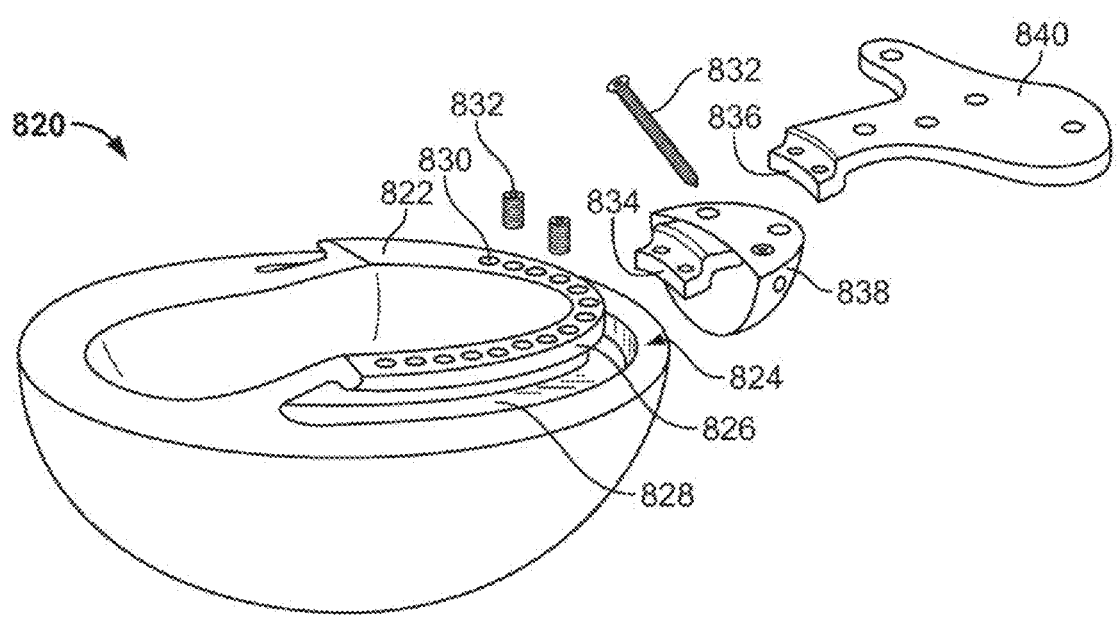
FIG. 95 shows an acetabular shell or cage having an illustrative annular protrusion.

FIG. 95 depicts an acetabular shell or cage 820 comprising an annular protrusion 822 along a rim portion 824 of the acetabular shell 820. The annular protrusion 822 may extend partially around (as shown) or entirely around the circumference of the acetabular shell 820, or one or more protrusions may be provided in any fashion around the acetabular shell 820. The annular protrusion 822 may comprise an annular lip 826 defining an annular undercut groove 828 running circumferentially around the acetabular shell 820 proximate the rim portion 824. The annular protrusion 822 may comprise one or more openings 830 for receiving sutures (e.g., for soft tissue or capsule re-attachment) or fasteners 832 such as set screws for contacting and frictionally engaging surfaces, (e.g., divots) provided on protruding insertion portions 834 and 836 of mounting members 840 or augments 838 alike.

Fasteners 832 may be inserted into openings 830 located circumferentially laterally of the insertion portions 834 and 836 to serve as stops for preventing or limiting rotational movement of the attached mounting members 840 or augments 838. The mounting members 840 or augments 838 may be secured down to surrounding bone after being inserted into the annular undercut groove 828 via long bone screws, thereby providing a hold-down force to the acetabular shell or cage 820. The hold-down forces provided may complement the press fit, threaded fit, or cemented fixation between the acetabular shell or cage and surrounding prepared acetabular bone. In the instance shown, shell 820 is provided as a "hooded" shell similar to a cage, and may act as a buttress for a cemented or pressed-in liner to support various liner inclinations in varying degrees of acetabular or pelvic degradation, although it will be understood that these features may be provided on any other type of shell or cage.

Figure 31:
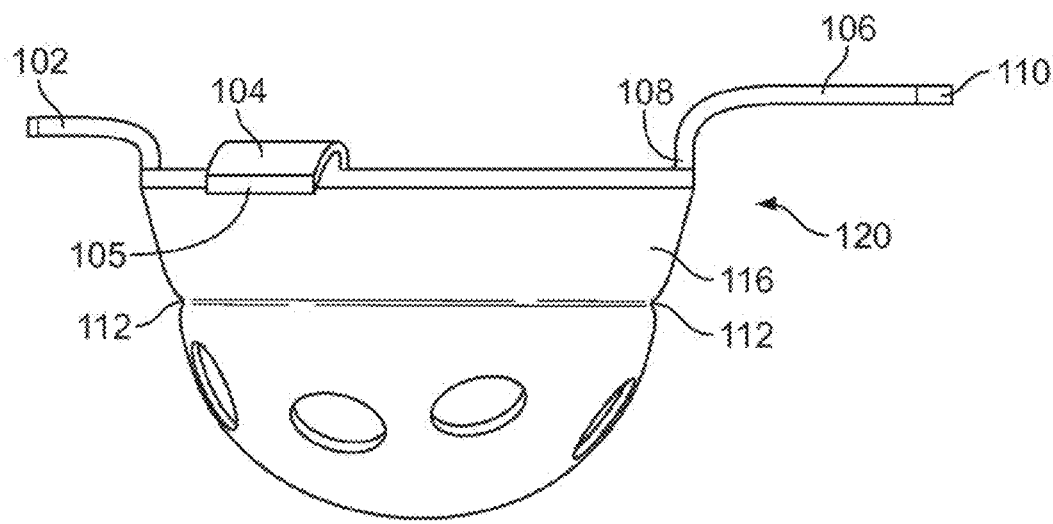
FIG. 31 shows a side elevation view of an illustrative cup member.
Figure 32:
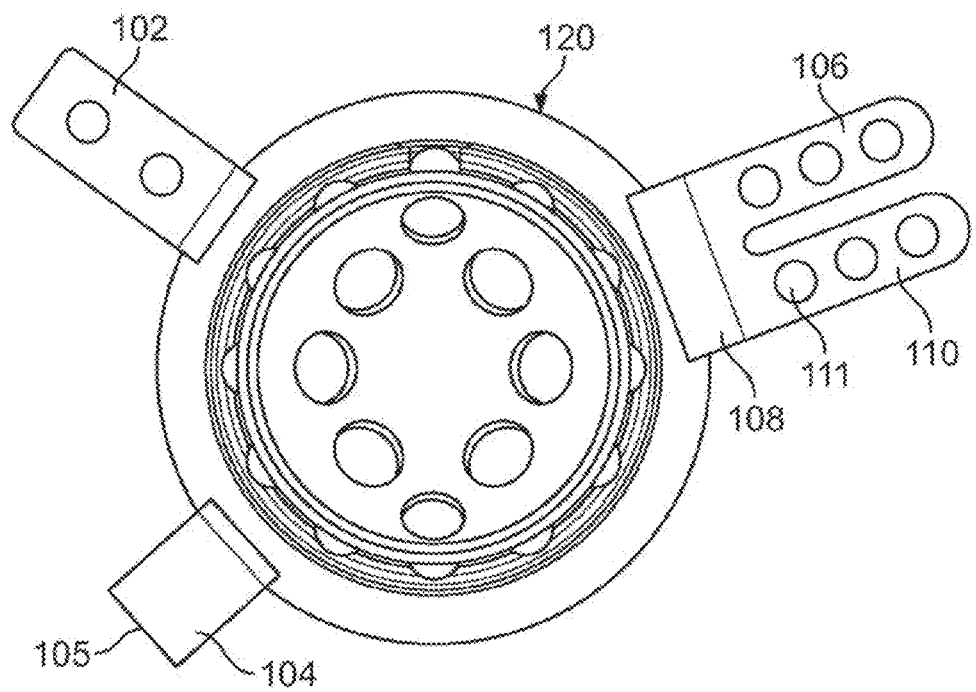
FIG. 32 shows a top plan view of the illustrative cup member of FIG. 31.

FIGS. 31-34 show a cup member 120 intended for insertion into an acetabular cup 140 (also referred to as an "acetabular shell," "shell," "cage," or "cup"), and in some embodiments, between the acetabular cup 140 and a liner 160 that may be disposed within the cup member 120. The cup member 120 is provided with various mounting members (also referred to as "attachment members"), such as flanges, blades, hooks, or plates, where each respective mounting member may be removably or integrally provided on the cup member. As shown in FIG. 31, for example, cup member 120 includes blade 102, hook 104, and flange 106. The mounting members such as blade 102, hook 104, and flange 106, may be adjustably positionable about the cup member (e.g., about the perimeter of the cup member or about any other suitable location on the cup member). For example, a removable mounting member may be attached to the cup member and then, while still attached, positioned from a first location to a second location along the cup member. Alternatively, the removable mounting member may be removed and then repositioned. As another example, an integral mounting member (e.g., a mounting member that is not removable) may nonetheless be adjustably positionable about the cup member. In some embodiments, an integral mounting member may be rigidly fixed in a first location and may not be adjustably positionable about the cup member.

The portion of the mounting members that is not attached to the cup member may be used to attach or anchor to a patient's bone. For example, as shown in FIG. 31, flange 106 includes a portion 108 attached to the cup member 120 and an attachment portion 110 that is attachable to a patient's bone to thereby anchor to the patient's bone. Attachment portion 110 includes a plurality of screw holes 111 for anchoring flange 106 to the patient's bone, although it will be understood that any suitable attachment mechanism may be used. For example, hook 104 includes a curved end 105 to thereby hook onto a patient's bone. Screw holes 111 may include conventional holes, locking holes, or slots. The holes may be threaded, unthreaded, or partially threaded, and may be fixed or polyaxial. In some embodiments, screw holes 111 may include variable low-profile holes that allow for locking at a variety of angles. Other suitable attachment mechanisms may include bone cement, shape-memory polymer fixation members, expanding screws, any other suitable mechanism for attaching a mounting member to a patient's bone or soft tissue, or any combinations thereof.

FIGS. 31-34 depict some embodiments of a cup member 120 suitable for receiving a polymer, ceramic, or metal line 160, the cup member 120 having mounting members that extend radially therefrom. The cup member 120 may be placed into an acetabular shell 140, and the mounting members such as blade 102, hook 104, and flange 106 may be disposed around the rim 142 of the shell 140 when the cup member 120 is inserted into and substantially fully seated in the shell 140. As shown in FIG. 31, in some embodiments, the outer portion 116 of the cup member 120 may have a conical taper 112 for frictional locking engagement with a complementary conical taper 114 in an acetabular shell 140. The taper 114 of acetabular shell may be contoured to receive the specific type of conical taper 112 of the cup member 120. In some embodiments, multiple cup members may be available, and each may have a profile similar to conical taper 112 such that they can be interchangeably placed into acetabular shell 140. The complementary conical taper 114 in the acetabular shell 140 may also be used to accept a ceramic liner 162 having a conical taper similar to that of the cup member 120, providing various options during surgery. The ceramic liner 162 may be utilized to allow a cup member 120 to be used with an acetabular shell 140 even when taper 112 of the cup member does not match the taper 114 of the acetabular shell. For example, the inner surface of ceramic liner 162 may be shaped to engage the taper 112 of the cup member 120 while the exterior surface of ceramic liner 162 has a different shape to engage the taper 114 of the acetabular shell 140. Mounting members may be provided as one or more flanges, blades, hooks, or plates which may be rigid or bendable, and which may have any other appropriate features described herein.

Figure 33:
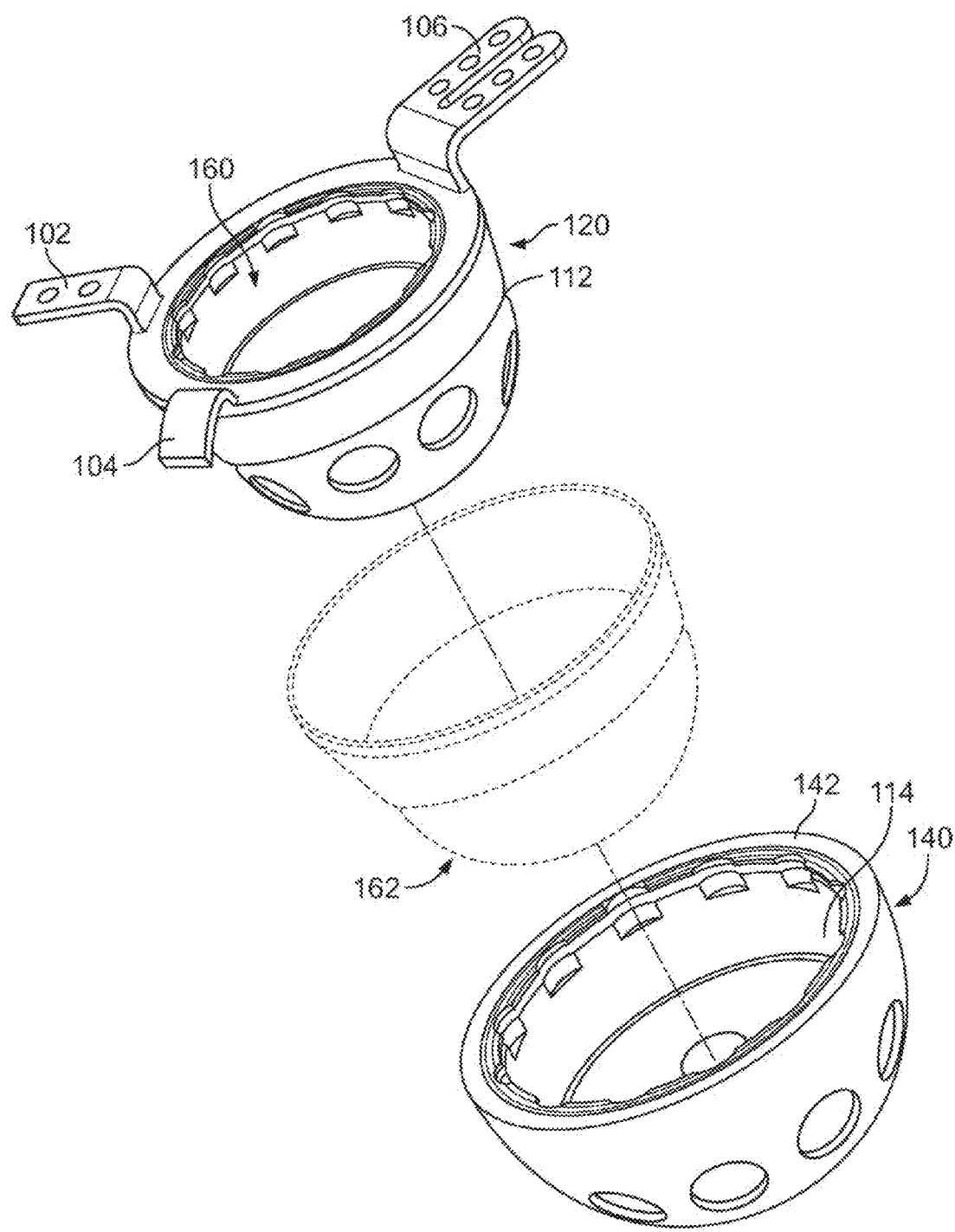
FIG. 33 shows an exploded view of an illustrative cup member and acetabular shell with an optional liner therebetween.
Figure 34:
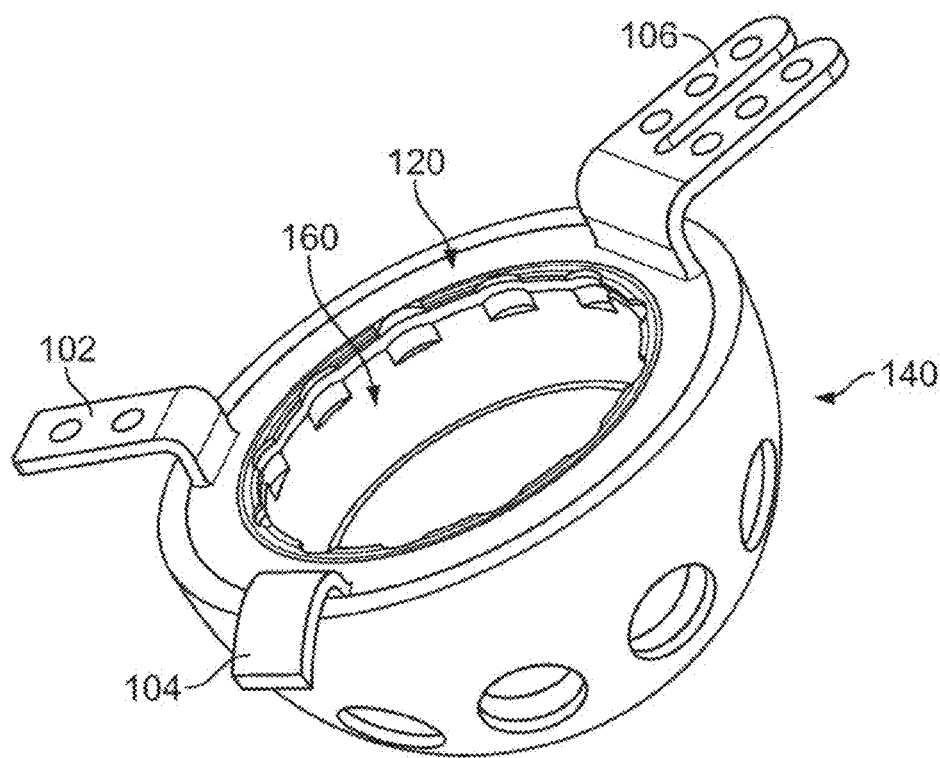
FIG. 34 shows a perspective view of an illustrative cup member and acetabular shell.

In certain embodiments, as shown in FIG. 33, a polyethylene or ceramic liner 160 is placed within the cup member 120 (which may also be referred to as a "flange cup") to line the inside of the cup member 120. The cup member 120 may comprise integral flanges that rest superiorly of the interior surface that accepts the liner. Alternatively, if metal on metal articulation is desired, a metal liner that incorporates integrally-formed flanges may be used. However, it will be understood that the modular options described herein may also be used. The cup member may contain internal scallops suitable for use with current polyethylene liners such that it may be used with the system, for example, disclosed in the '705 patent application.

When the described cup members 120 are used, the liners 160 may need to be provided slightly smaller than those typically provided within an acetabular shell that does not have a cup member therein in order to provide clearance between the liner and the cup for a taper lock. Alternatively or additionally, smaller femoral heads may be used.

Figure 35:
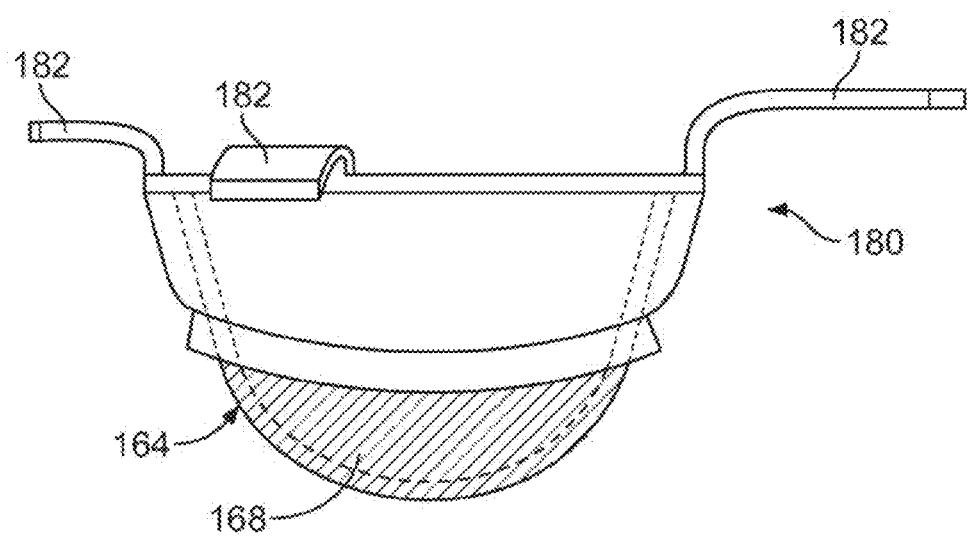
FIG. 35 shows a side elevation view of an illustrative band cup member.

In some embodiments, it may be desirable for a liner to sit in and be fully supported by a cup member such that the liner is not suspended. In some instances, suspended liners can creep or deform. As shown in FIG. 33, the cup member 120 is provided as a full cup rather than just a band with adjustable mounting members so that it can fully support a liner if used. However, in other embodiments, the cup member does not necessarily have to be a full cup, and may not necessarily even have a cup shape. For example, as shown in FIG. 35, a cup member 180 is provided as a band cup having mounting members 182. A liner 164 may be placed within the band cup member 180 such that a portion 168 of the liner 164 is suspended below the band cup.

In some embodiments, an advantage provided by the cup member is that the mounting or attachment members are provided on the separate cup member and not on the acetabular shell. This allows the acetabular shell to be positioned independently of the cup member, providing a greater range of modularity and adjustment options. Another advantage provided by the cup member may be seen during revision surgeries. Rather than having to remove the acetabular shell during revision surgery, a surgeon may remove the liner from within the acetabular shell, insert a cup member having one or more mounting members into the acetabular shell, and then insert a new liner into the cup member.

Figure 36:
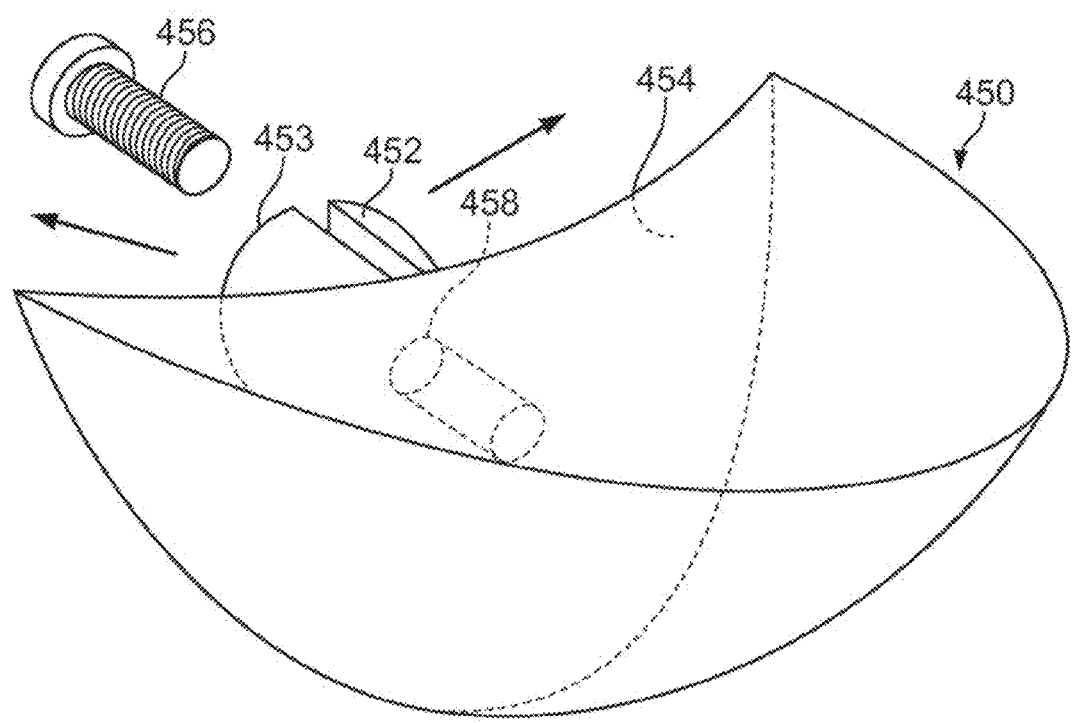
FIG. 36 shows an illustrative augment configured to attach to acetabular shells or cages, mounting members, or other augments.

The embodiments shown in FIGS. 36-50 provide augments that may be configured to attach to acetabular shells or cages, mounting members, or other augments without cement, and are also configured to allow fine positional adjustments for best bone fit, coverage, and stability. It will be understood that the features and components described in connection with the augments of FIGS. 36-50 may also be applied to mounting members, such as hooks, flanges, blades, or any other suitable mounting members, that may be configured to attach to acetabular shells or cages, augments, or other mounting members. FIG. 36 illustrates certain embodiments wherein an augment 450 may be placed on a periphery of a hemispherical acetabular shell, cages, or other augment. As shown in FIGS. 37 and 38, a shell or cage 460 may comprise a track 462 that is undercut so as to form a dovetail joint 461 with a mounting member or an augment. The track 462 may be provided as a J-shaped slot (as shown), T-shaped slot, H-shaped slot, or any other shape involving combinations of straight and/or curved segments. The track 462 preferably includes at least two portions or slots, at least one of which can receive a complementary connector or protrusion from the augment or mounting member. As shown in FIG. 37, for example, the first portion or slot 464 and second portion or slot 466 join about common region 468 but are separated out at distal ends 465 and 467 by angle Θ, which is less than 180° in the example. The at least two portions thereby permit the augment or mounting member to be adjustably positioned along the surface of the shell, cage, or other augment by sliding the augment (and its connector) along the track and securing it at the desired location. For example, the augment could be secured in one of the at least two portions (such as slot 464), or the other of the at least two portions (such as slot 466), or in between.

The mounting member or augment may have a protrusion that is flared outwardly, and may be generally frustoconical, bulbous, or otherwise forms a portion of a male portion of a dovetail joint. For example, as shown in FIG. 36, augment 450 includes protrusion 452 that is flared outwardly. The flared protrusion 452 may be expandable when used with a central mandrel or expanding fastener. Additionally or alternatively, it may be made from a deformable material and/or may be provided as a bifurcated member having one or more leg portions to facilitate expansion of the protrusion.

The outer peripheral surface portions 453 of the protrusion 452 may be rounded (e.g., a frustoconical shape), and the augment 450 (or, in some embodiments, mounting member) may not only be translated within and along the track 462 on the shell 460, but also rotated within the track 462 on the shell 460. A fastener 456 such as a screw, setscrew, mandrel, shank, rivet, or any other fastener having a low profile head which is accessible from the inside dome portion of the shell or cage 460 (or another augment) is configured to engage an inner bore or opening 458 located in the flared protrusion 452, thereby expanding the protrusion 452. The term "expansion member" is used herein to refer to any appropriate member, including but not limited to the fasteners listed above, that can be used to engage and/or otherwise expand another feature. One example of an expansion member that may be used in connection with this embodiment comprises a setscrew/mandrel/fastener that has a tapered outer portion or a surface having an outer diameter that is greater than the receiving portion of the protrusion, such that when the expansion member is threaded into the protrusion, the protrusion expands. The expansion of the flared protrusion causes the protrusion to frictionally engage the track in the shell/cage/augment, thereby forming a locked dovetail connection which secures the mounting member or augment to the shell. Once the expansion member is completely tightened, the mounting member or augment is locked to the shell/cage/augment in both translation and rotation with a strong dovetail locking joint. For example, augment 450 can be attached to the track 462 by the protrusion 452. Before tightening the protrusion 452, the augment 450 can be rotated with respect to the shell 460, such that the augment interior surface 454 and the shell exterior surface 469 remain generally interfaced while the augment 450 rotates about the shell 460 like a cam, until the augment 450 is in the desired position. The protrusion 452 is then tightened to secure the augment 450 in that position.

One advantage of such a mechanism is that the assembly of the shell/cage/augment and the mounting member or augment may be loosely assembled, then placed info a bone void such as an irregularly shaped bone void. Once generally positioned, the assembly components may be adjusted with respect to each other to best fit an existing or prepared bone void. The assembly components may then be tightened together such that the assembly closely approximates the size, shape, and orientation of the existing or prepared bone void.

While the particular embodiment shown in FIG. 36 illustrates an expansion member 456 seated in a "blind" interior opening or bore 458 in augment 450, an augment may alternatively or additionally comprise a through hole such as through hole 478 of augment 470 in FIG. 39, configured to receive an expansion or tightening member 476, for example a long bone screw, long fastener, or other long expansion member (such a tightening configuration will be referred to throughout as a "long bone screw," but it will be understood that any appropriate fastener that can secure two components together, while also potentially gain purchase into bone is considered appropriate for use in connection with the described embodiment). The tightening member 476 may be configured to gain purchase in the augment 470 and/or surrounding bone as illustrated in FIG. 30. The opening 487 in the flared protrusion 472 that receives the bone screw 476 may generally continue through the augment 470 and out a hole 470 in a side of the augment 470 opposite the protrusion 472. In such embodiments, the bone screw 476 enters the augment 470 through an opening in the track 462 on the inside surface 463 of the shell/cage 460 (or, in some embodiments, another augment), and protrudes through the entire augment 470, including the flared protrusion 472 which, during insertion of the bone screw 476, will expand into the undercut track 461 on the shell/cage 460. Essentially, the bone screw 476 locks the augment 470 to the shell/cage 460 and secures the entire assembly to surrounding bone, thereby stabilizing the assembly with respect to hip anatomy. In this sense, not only does the bone screw 476 serve to rigidly secure the augment 470 to the shell/cage 460 before necessarily securing purchase of the bone screw 476 into surrounding bone, the bone screw 476 further provides secondary fixation of the assembly to surrounding bone by then subsequently securing purchase with surrounding bone.

The embodiment shown in FIG. 39 allows a surgeon to lock the augment 470 to a second component from an inside portion (e.g., an inside portion 463 of a shell 460), after the loose assembly is placed into the prepared bone void. In other words, the augment 470 may be loosely coupled to the shell 460 or other second component in the patient's bone void, and a fastener is used to secure the augment to the second component (not shown, but which may be the shell, cage, or a second augment) and to the patient's bone. The head is arranged within the slot of track 462 so that it is aligned with the interior opening 478 of the augment 470 and extends radially within the shell 460. The surgeon can then insert a tightening rod through the interior opening 478, from inside the shell 460, to access and tighten the screw 476.

Figure 40:
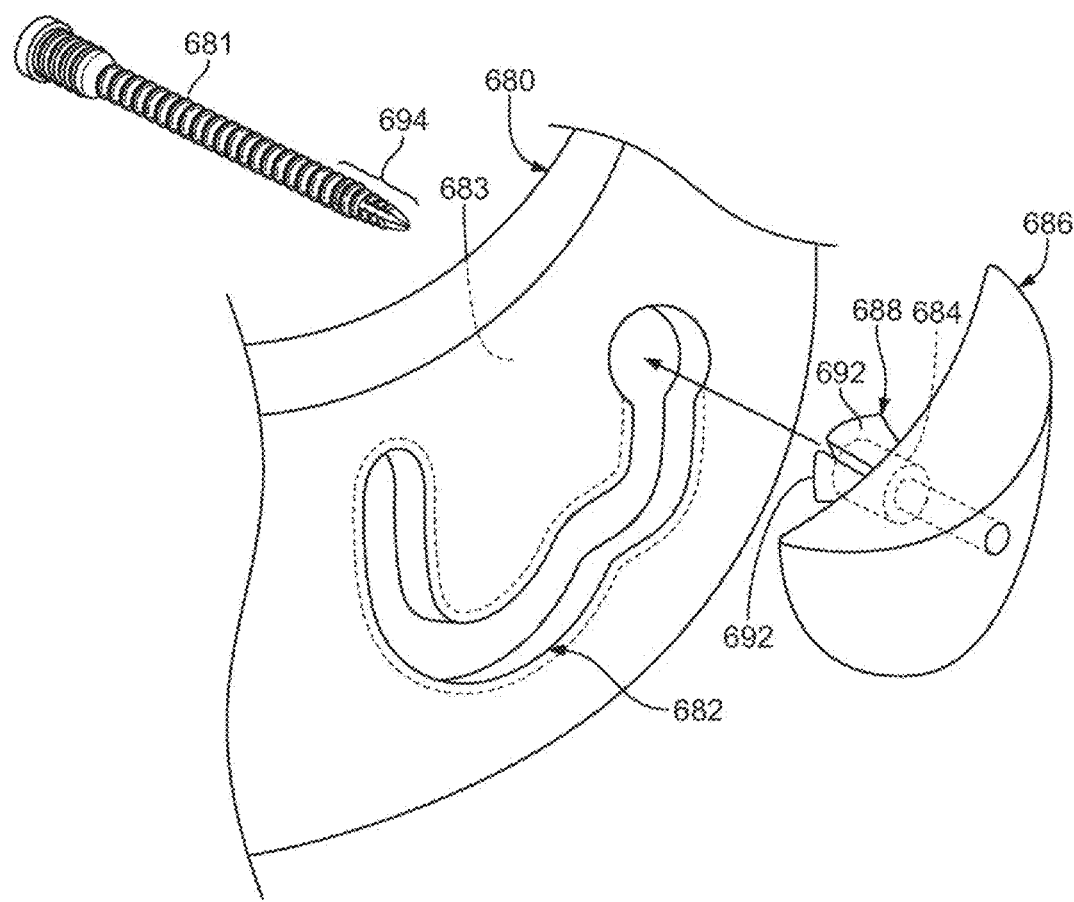
FIG. 40 shows an illustrative fastener having an expanding portion configured to be inserted through a track on an acetabular shell and into an augment.

FIG. 40 illustrates some embodiments related to those shown in FIG. 39. A bone screw 681 or other fastener having both an expanding portion 694 and a bone engaging portion is inserted through an undercut recess, groove, or track 682 provided on an acetabular shell or cage 680 (or, in some embodiments, provided on an augment). The bone screw 681 or other fastener may be inserted from an accessible inside portion 683 of said shell/cage 680. The bone screw 681 or other fastener protrudes into and through an opening 684 within an adjacent augment 686 (or, in some embodiments, a mounting member) having a male connection member 688. The male connection member 688 may be generally cylindrical or flared, (e.g., frustoconical) and is configured to be inserted into and move within (translate, rotate, etc.) the undercut recess, groove, or track 682.

In use, as the bone screw 681 begins to make purchase with bone, the expanding portion 694 of the bone screw 681 engages a complementary expanding portion 692 of the augment 686 adjacent the male connection member 688, thereby expanding a portion of the male connection member 688 inside the undercut recess, groove, or track 682 and locking the augment 686 to the shell/cage 680 (or other augment). In some embodiments, one or more of the expanding portions of the bone screw and mounting member or augment may not be threaded. For example, the expanding portion 694 of the bone screw 681 may be threaded, and the expanding portion 692 of augment 686 may be a smooth tapered recess. Alternatively, the expanding portion 694 of the bone screw 681 may be a smooth tapered surface that seats within and wedges against a smooth tapered expanding portion bore 684 in the augment 686. The taper angle of the bone screw 681 expanding portion 694 may differ from the taper angle of the expanding portion bore 684. Furthermore, the expanding portion 694 of the bone screw 681 may be an enlarged threaded section that engages with a smooth undersized bore 684 in expanding portion 692 of the augment 686.

Figure 41:
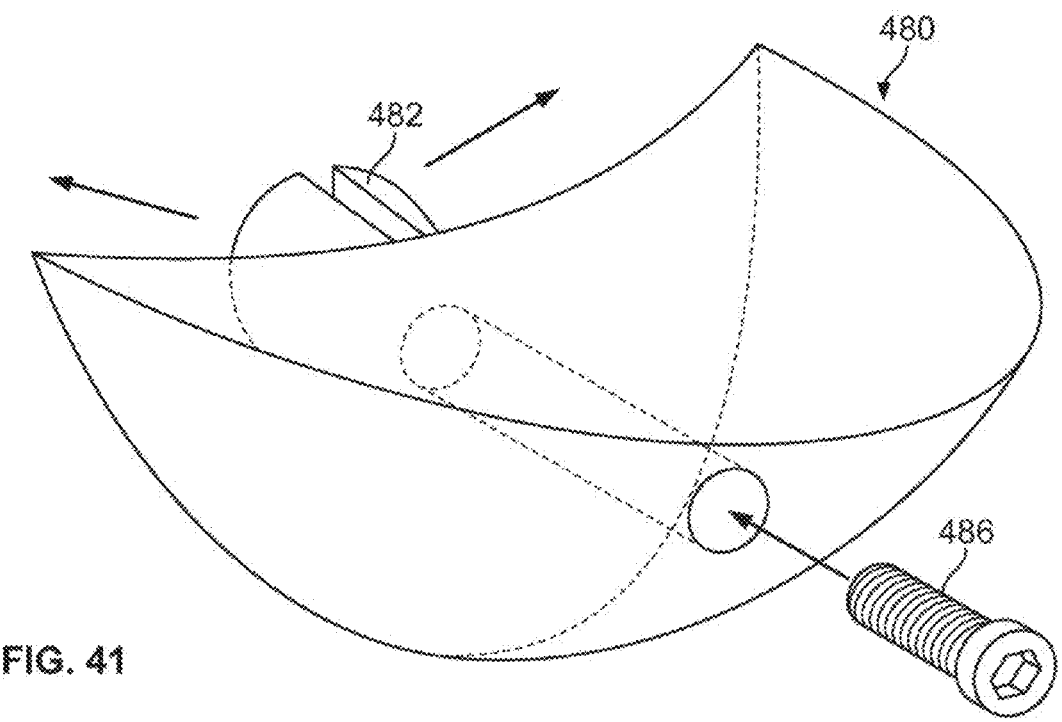
FIGS. 41 and 42 show illustrative augments configured to secure to an acetabular shell or cage, mounting member, or other augment prior to insertion into a prepared bone void.
Figure 42:
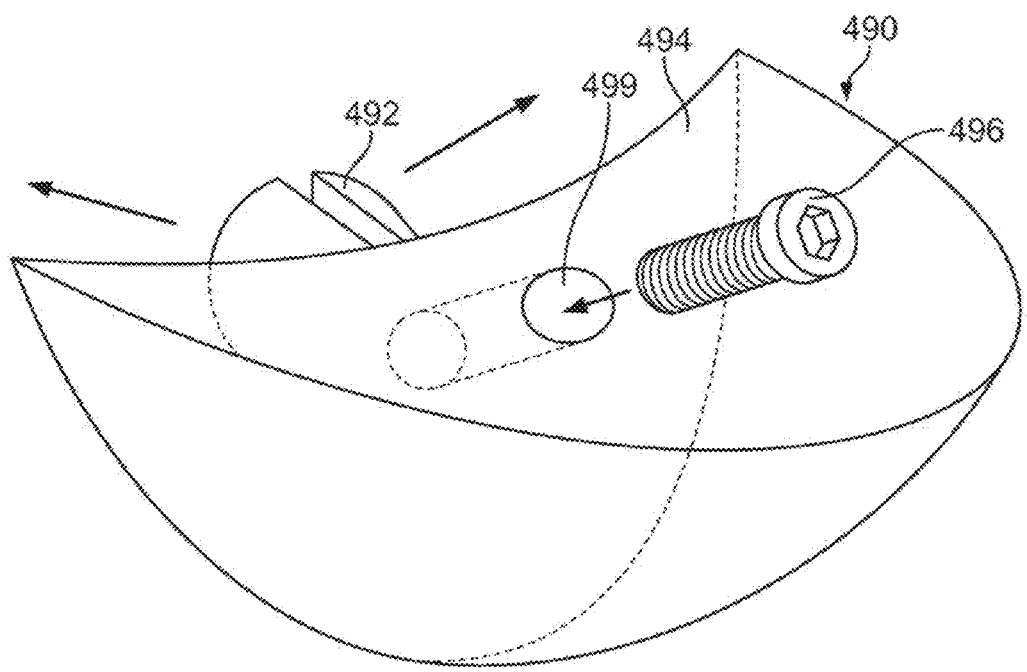

In further embodiments, as shown in FIGS. 41 and 42, it may be desirable to secure a mounting member or augment to an acetabular shell or cage, or other augment or mounting member prior to insertion into a prepared acetabular bone void. In such instances, the expansion member used to expand the protrusion may be made relatively shorter, so as to be partially or completely encased by the mounting member or augment. For example, expansion member 486 of augment 480 and expansion member 496 of augment 490 may be relatively shorter than bone screw 476 of augment 470. The insertion direction of the expansion member may be reversed with respect to the aforementioned embodiments, and move in a securing direction which is towards the acetabular shell/cage or other augment. In this way, the mounting member or augment may be attached to the shell/cage or other augment in a predetermined configuration, prior to insertion of the assembly into the prepared bone cavity.

The embodiment shown in FIG. 41 allows a surgeon to lock the augment 480 to the shell 460 prior to insertion into the prepared bone void, outside of the body cavity. The attachment prior to insertion may be a tight securement or a loose coupling. If a loose coupling is desired, such that complete securement can be completed once the assembly has been fully positioned, an opening 499 on an upper surface 494 of the augment 490, as shown in FIG. 42 allows tightening once the completed assembly is positioned in the bone cavity. In other words, this embodiment allows a surgeon to lock the augment 490 to the shell 460 from an outside portion on exterior surface 469 of the shell 460, after the loose assembly is placed into the prepared bone void.

Figure 43:
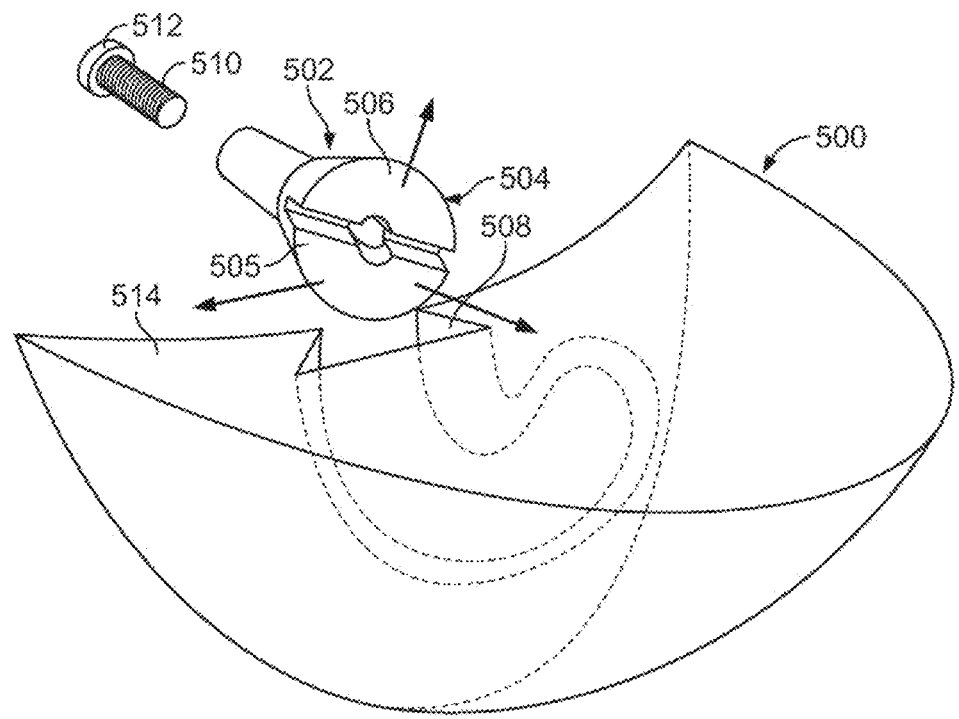
FIG. 43 shows in augment having an illustrative intermediate adapter member.

In use, the surgeon may place a frustoconical or otherwise flared protrusion of the mounting member or augment into an insertion clearance opening in the shell/cage or other augment, and then may move the augment within a track extending from and connected to the opening (as shown in FIG. 43) to a desired rotational angle and/or location along the track. The surgeon may rotate, translate, or otherwise position or move the mounting member or augment as desired within the track. When the augment is positioned and located in a desired spatial orientation relative to the shell/cage or other augment, the expansion member can be inserted into and through the augment, and tightened within a threaded bore located in the protrusion.

It will be appreciated by one having ordinary skill in the art that, while not shown, the expansion member may be internally threaded and engageable with a male thread located within an opening in the protrusion. It will also be appreciated that, while not shown, the expansion member may only threadingly engage the bulk body of the mounting member or augment and may have a distal wedge portion provided thereon which engages a smooth tapered opening in the protrusion. In this embodiment, when the expansion member moves toward the protrusion in threaded engagement with the bulk body of the mounting member or augment, its distal wedge portion wedges open the flared projection via inclined surfaces without actually "threadably" engaging in inner surface of the protrusion. It should also be noted that the use of other fasteners such as the rivet-type, or any other suitable fastener, or combinations thereof is envisioned.

When the expansion member is tightened or otherwise adjusted, the arms of the bifurcated protrusion expand and move away from each other, and therefore, the outer flared portions of the protrusion engage the undercut walls of the track provided on the shell/cage/augment. For example, when expansion member 456 of FIG. 36 is tightened or otherwise adjusted, the arms of protrusion 452 may expand and engage the undercut walls 461 of the track 462 provided on shell 460 of FIG. 37. The arms of protrusions 472, 482, and 492 may similarly be expanded when an expansion member is tightened or otherwise adjusted. Friction between the walls of the track and the expanded bifurcated protrusion maintain the mounting member or augment in fixed relationship relative to the shell/cage/augment, and the assembly may be inserted into the prepared bony site.

As shown in FIG. 43 and for potential use in connection with or interchangeably with the embodiments shown in FIGS. 79-82, an intermediate adapter member may be used to secure a mounting member or augment to an acetabular shell, cage, or other augment. For example, adapter 502 comprises a portion that is received in an opening (e.g., tapered hole or undercut track) in the shell/cage/augment, and sits flush or recessed with respect to an inner surface of the shell/cage/augment, so as to not protrude into the inside portion of the shell/cage/augment where a liner might be seated. The adapter 502 may have an expanding tapered or flared head 504 (e.g., frustoconical) that protrudes outwardly from the shell and engages an undercut slot, blind or through-slot, or a tapered aperture in the mounting member or augment. For example, adapter 502 includes an expanding tapered or flared head 504 that engages undercut slot 508 of augment 500. The adapter 502 may be entirely or partially cannulated and may be non-threaded, threaded partially, or threaded all the way through its length. The expanding tapered or flared head 504 of the adapter 502 may be made bifurcated so as to have two or more arm portions 505 and 506 that are configured to move away from each other to expand the head 504 and create a locking interference between the expanding head 504 and the undercut slot or tapered aperture 508. A small expansion member 510, a long bone screw (not shown), or any other suitable fastening member may be threadably received in the adapter 502 such that when the expansion member 510, long bone screw, or other fastening member threads into the bifurcated head portion 504, the arms 505 and 506 of the head portion 504 expand and frictionally engage the wads of the slot or aperture 508 to lock augment 500 to the shell/cage 600 or other augment. A mounting member may similarly locked to an acetabular shell or cage 606 or an augment. The head 512 of the expansion member 510, long bone screw, or other fastening member may lie flush with, or slightly recessed from the inside (e.g., concave) surfaces of the shell/cage/augment, so that a liner may be properly seated.

Figures 44, 45:
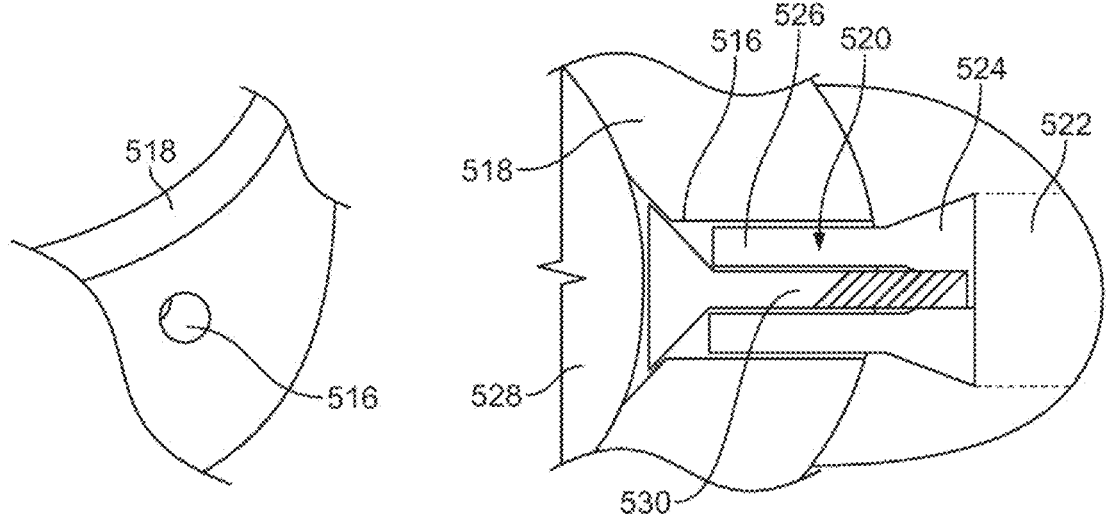
FIG. 44 shows an illustrative insertion opening in a shell adapted to receive features of the intermediate adapter system of FIG. 43.
FIG. 45 shows an illustrative expansion member inserted into an intermediate adapter member to secure the adapter in a desired location.

FIG. 44 shows an insertion opening 516 in a shell 518 adapted to receive features of the adapter system of FIG. 43 according to some embodiments. FIG. 45 shows a side cross-sectional view of an adapter 520 in place within the shell 518 and an augment 522, used to secure the two components to one another. As shown, the adapter 520 may have a frustoconical head 524, and specifically, may have a head 524 that is bifurcated and expandable. The head 524 of the adapter 520 may be received in an augment 522 or any other first component (e.g., a mounting member) that is desired to be coupled or otherwise secured to a second component (e.g., an acetabular shell or cage). The augment 522 may have a J-slot (e.g., as shown in more detail in FIG. 43), a dovetail configuration, or may have any other appropriate shape, such as an undercut design, or another appropriate track-type slot or groove. This feature may extend to the upper edge of augment 522 or first component (e.g., as shown in FIG. 43 where slot 508 extends to upper surface 514 of augment 500) or it may be positioned in the side wall only of the augment 522 or first component (e.g., as shown in FIG. 37 where track 462 is provided through surfaces 463 and 469 of shell 460).

In use, the adapter head 524 slides into or is otherwise positioned in the slot/track/undercut. The adapter tail end 526 may extend slightly from the augment 522 or first component and extend toward and slightly into an insertion opening in the shell 518 or second component. As discussed above and shown clearly in FIG. 45, if is preferable that the adapter tail 526 not extend completely into the internal cavity of the shell 518 or second component so that a liner 528 may be used without having the liner 528 directly abut or otherwise contact the adapter 520. Once positioned, an expansion member 530 is inserted into the adapter 520 to cause the bifurcated head 524 to expand and lock, plug, or otherwise securely lodge the adapter 520 in the desired location.

Figure 46:
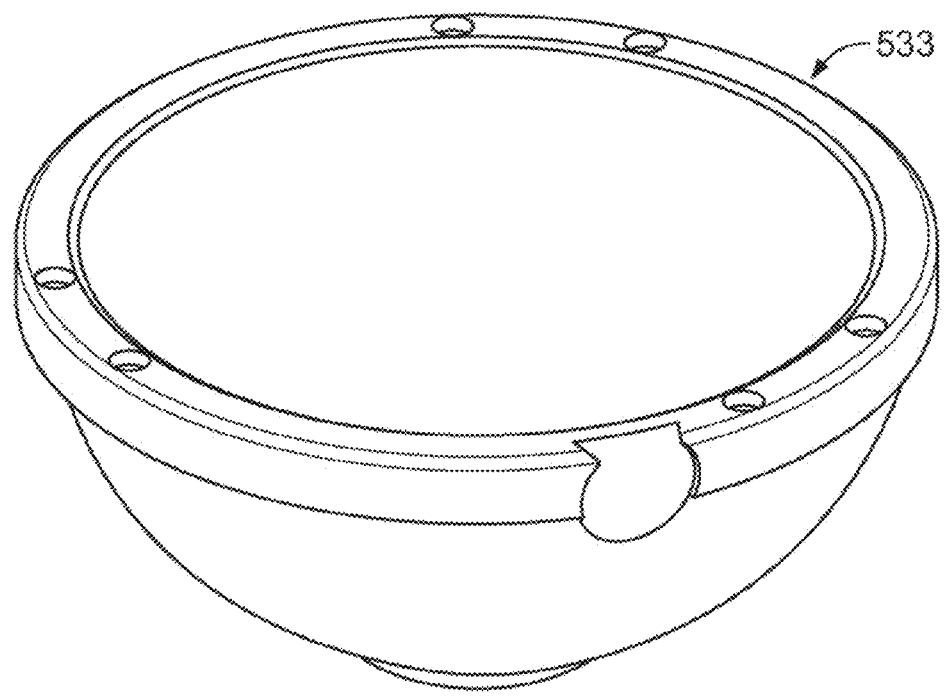
FIGS. 46 and 47 show examples of a prior mounting member or augment adapted for securement to a shell.
Figure 47:
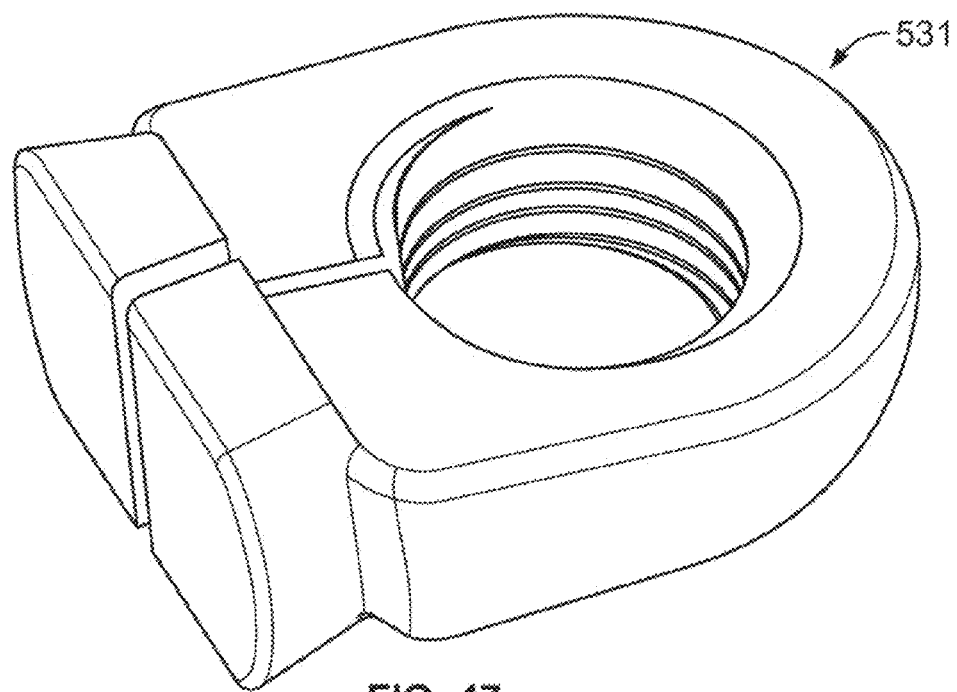

FIGS. 46 and 47 illustrate an example of a prior mounting member or augment 531 adapted for securement to a shell 533 as disclosed in U.S. Patent Application Publication No. 2007/0093133, entitled "Fixing Assembly," which is incorporated by reference herein in its entirety.

Figure 48:
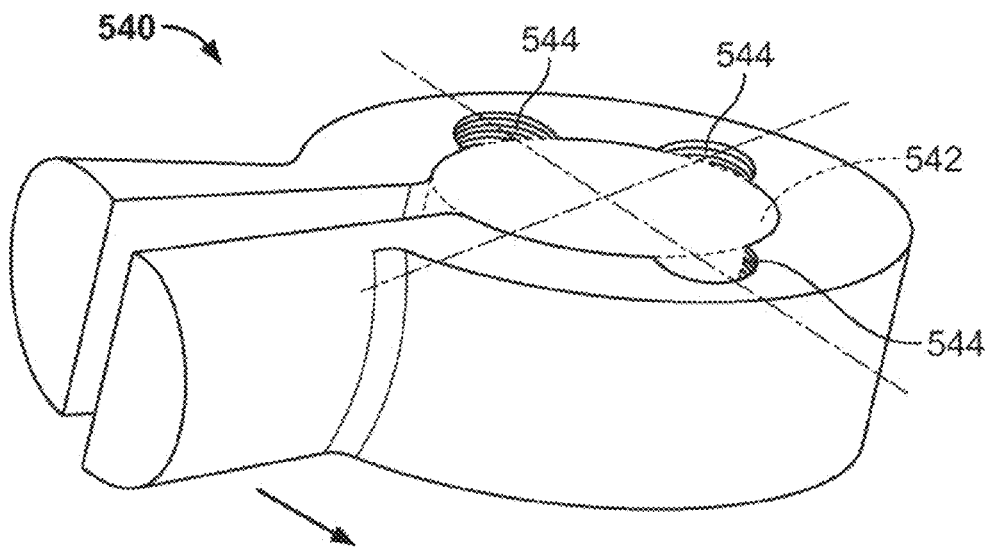
FIGS. 48-50 show an illustrative mounting member or augment provided with an opening having multiple fixed directional threaded screw holes.
Figure 49:
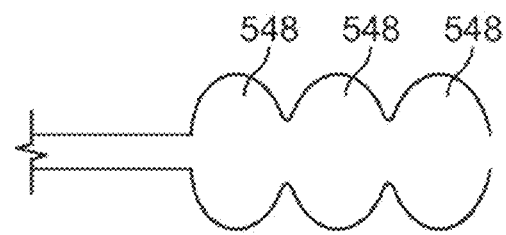
Figure 50:
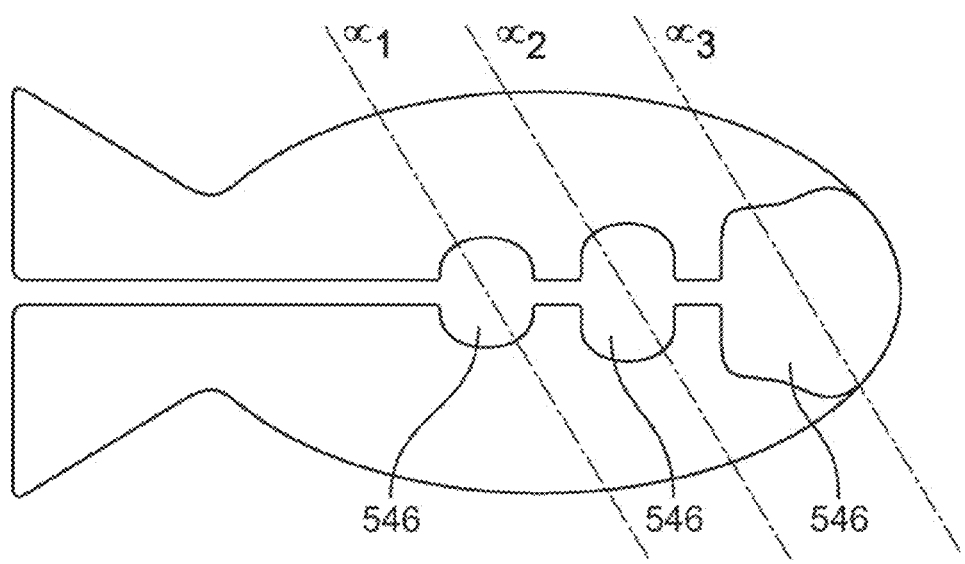

FIGS. 48-50 illustrate various embodiments of an improvement of the devices shown in FIGS. 46 and 47. A mounting member or augment may be provided with an opening having multiple fixed directional threaded screw holes. For example, Mounting member or augment 540 of FIG. 48 includes an opening 542 having a plurality of fixed directional threaded screw holes 544. In the specific embodiments shown, there are three fixed directional threaded screw holes (e.g., screw holes 544), but it will be understood that more or fewer holes may be provided. The holes may be fixed in various orientations in space with respect to each other. The holes may be spaced apart from each other as shown by holes 546 in FIG. 50. The holes may intersect radially as shown by holes 544 in FIG. 48. The holes may be positioned linearly as shown by holes 548 in FIG. 49. In use, a protrusion member that extends from a mounting member or augment is received in rotating engagement by a round blind undercut recess on an acetabular shell, cage, or augment as shown in FIG. 46. Alternatively, the protrusion member may be received in an undercut track (e.g., as shown in FIGS. 37 and 38) provided on an acetabular shell, cage, or augment. As shown, the projection may be bi-forked in configuration to facilitate its expansion when one or more screws or other fastening members are inserted through one or more of the threaded screw holes in the mounting member or augment. The protrusion on the mounting member or augment is generally configured to expand upon partial screw insertion and is also generally configured to secure and lock the mounting member or augment to the shell/cage/augment in a desired relative spatial orientation, regardless of whether or not the screw secures purchase within the bone.

Figure 51:
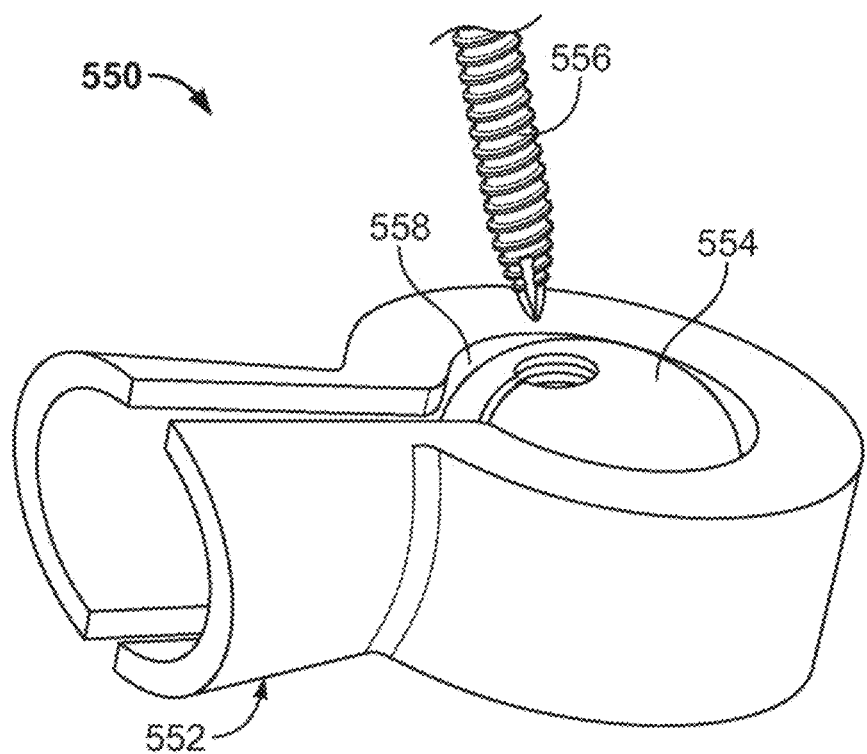
FIG. 51 shows an illustrative mounting member or augment having an expandable or deformable spherical ball member.

FIG. 51 illustrates a mounting member or augment 550 according to certain embodiments that may be used for coupling to an acetabular shell, cage, or other augment having a round blind undercut on the shell, one example of which is shown in FIG. 46. Alternatively, as previously mentioned, the protrusion member 552 may be received in an undercut track (e.g., as shown in FIGS. 37 and 38) provided on an acetabular shell, cage, or augment. As shown in FIG. 51, an expandable or deformable spherical ball member 554 is adapted to be positioned within, located inside, or otherwise captured within an opening 558 in a split or bifurcated mounting member augment 550 and captured therewithin. The ball member 554 may be undersized so as to expand when an expansion member (e.g., screw 556) or other fastener is inserted therein. Alternatively, the ball member 554 may be formed of a deformable material to allow the ball 554 to expand upon insertion of an expansion member (e.g., screw 556) or other fastener. Moreover, the ball member 554 may be split to facilitate expansion of the ball member 554. The ball member 554 is generally captured within, secured to, or otherwise operable with the mounting member or augment 550 so as to form a ball joint.

The ball member 554 may have a deformable smooth bore which is ultimately deformed to be threaded by the screw fastener during insertion. Alternatively, the ball member 554 may comprise a threaded bore which is slightly undersized in inner diameter with respect to the inserted screw. Alternatively, the bore in the ball member 554 may be smooth and the ball member 554 expanded when engaged by an expansion member or other fastener. In some instances, as shown, a screw 556 or other fastener may be provisionally positioned adjacent an aperture of the cannulated ball member 554, and then oriented to a desired spatial location and angulation with respect to a patient's anatomy for insertion into adjacent pelvic or other bone. The expansion member (e.g., screw 556), long bone screw, or other fastener may be used as a lever to move the ball 554 at any angle relative to the mounting member or augment 550 and then inserted to secure bone purchase.

When the screw or fastener 556 passes through the aperture in the ball 554, the ball 554 spreads open or deforms via the aforementioned undersized, deformable, or expandable means. In this instance, the ball 554 expands, and in turn, also further expands the mounting member or augment 550, which may be bifurcated, one example of which is described above. When the mounting member or augment 550 is expanded, the protrusion member 552, shown here as a generally flared and bifurcated frustoconical projection, expands within and may lock into a round, blind undercut recess or undercut groove in the shell/cage/augment in the desired angular spatial orientation. The mounting member or augment 550 is generally configured to allow fixing of itself to the shell/cage/other augment regardless of whether or not the screw 556 secures purchase within the bone. Moreover, the ball member 554 captured within the mounting member or augment 550 also allows the screw 556 to be inserted in any orientation relative to both the mounting member or augment 550 and the shell/cage/other augment.

Figure 52:
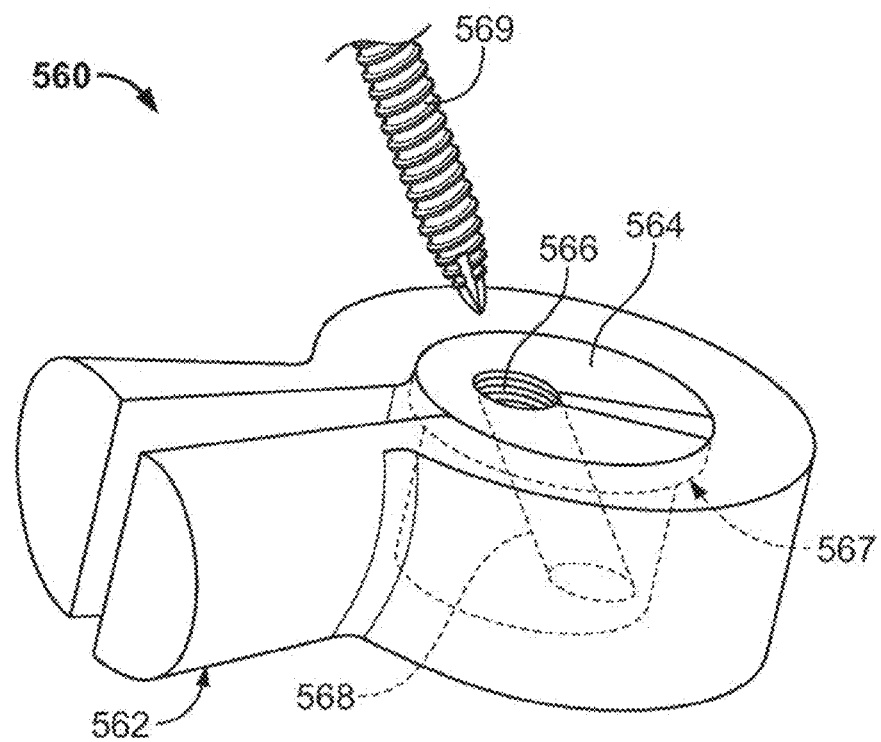
FIG. 52 shows an illustrative mounting member or augment having a rotatable inner cylinder insert member.
Figure 53:
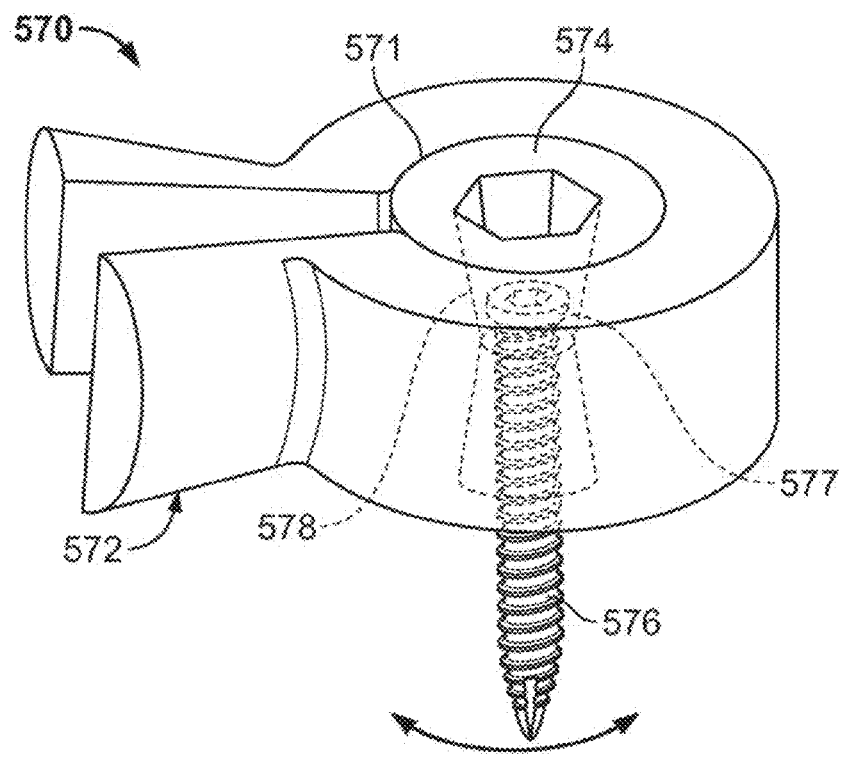
FIG. 53 shows an illustrative mounting member or augment similar to FIG. 52 that is configured for use with a polyaxial fastener.

In some embodiments, such as those shown in FIGS. 52 and 53, an optional rotatable inner cylinder insert member may be used. The cylinder may be split along its length and may have one or more threaded bores extending along its length at one or more various angles, offsets, and eccentricities for engagement with a long bone screw or other fastener. For example, as shown in FIG. 52, a single bore 566 may be provided in a cylindrical insert 564, the bore 566 having a smooth outer bearing surface 568 that is angled and offset. The insert 564 shown is captured within the mounting member or augment 564 by a knurl, step, flange, or lip 567 so as to be rotatable with respect to the mounting member or augment 560, but not axially displaceable from the mounting member or augment 560. When the screw or fastener 569 is inserted into the bore 566, the insert 564 expands, and in turn, expands a projection member 562 on the mounting member or augment 560 or alternatively or additionally expands the entire mounting member or augment 560. The projection member 562 may expand within the round blind undercut on the shell, cage, or other augment shown in FIG. 46, or alternatively may expand within an undercut groove within said shell, cage, or other augment as shown in FIGS. 37 and 38.

FIG. 53 depicts a mounting member or augment 570 that is similar to the embodiment shown in FIG. 52, but instead, is configured for use with a polyaxial screw or fastener 576 having a smooth rounded head 577. In this exemplary embodiment, the inner cylindrical insert 574 is not split, but is instead provided as a larger diameter, externally-threaded body configured to be received in a smaller diameter threaded bore 571 in the mounting member or augment 570. The inside of the cylindrical insert 574 has one or more "hourglass"-shaped bores 578, for instance, those that can be used with polyaxial screw heads having rounded or spherical screw heads. Various examples of polyaxial locking systems and methods are shown and described in U.S. Patent Application Publication No. 2002/0147499, entitled "Locking Systems for Implants," U.S. Patent Application Publication No. 2008/0300637, entitled "Systems and Methods for Using Polyaxial Plates," and U.S. Provisional Patent Application No. 61/178,633, entitled "Polyaxial Fastener Systems and Methods," all of which are intended for potential use in connection with the described systems and are incorporated by reference herein in their entireties.

The bore 578 may comprise portions engageable with threads of the polyaxial screw 576, or may contain deformable tabs in regions proximate the head 577 for use with threaded heads. The angle of the screw or fastener 576 can be varied within the bore 578 of the cylindrical insert 574. Regardless of whether or not the polyaxial screw 576 is inserted into the bore 578, the mounting member or augment 570 is positively secured and locked to the shell/cage/augment in a desired spatial orientation and angulation due to the expansion of the projection member 572 or the mounting member or augment 570 as a whole. This occurs, for example, after inserting and threadably engaging the cylindrical insert 574 with an undersized threaded recess (e.g., bore 571) provided in the mounting member or augment 570.

FIGS. 54-70 show certain embodiments for attaching mounting members or augments to an acetabular shell, acetabular cage, or other augment. Disclosed is an apparatus and method for attaching the acetabular mounting members or augments to shells, cages, and other augments with an amount of adjustability. A kit of different augments may be provided for use with the same acetabular shell, cage, or augment. Relative spatial adjustments between the mounting member or augment position and the shell/cage/augment may be made with multiple degrees of freedom. The mounting members and/or augments may be attached and subsequently permanently and irremovably secured and locked to the shell/cage/augment prior to or after its insertion into a prepared acetabulum and/or surrounding bone voids.

Figure 54:
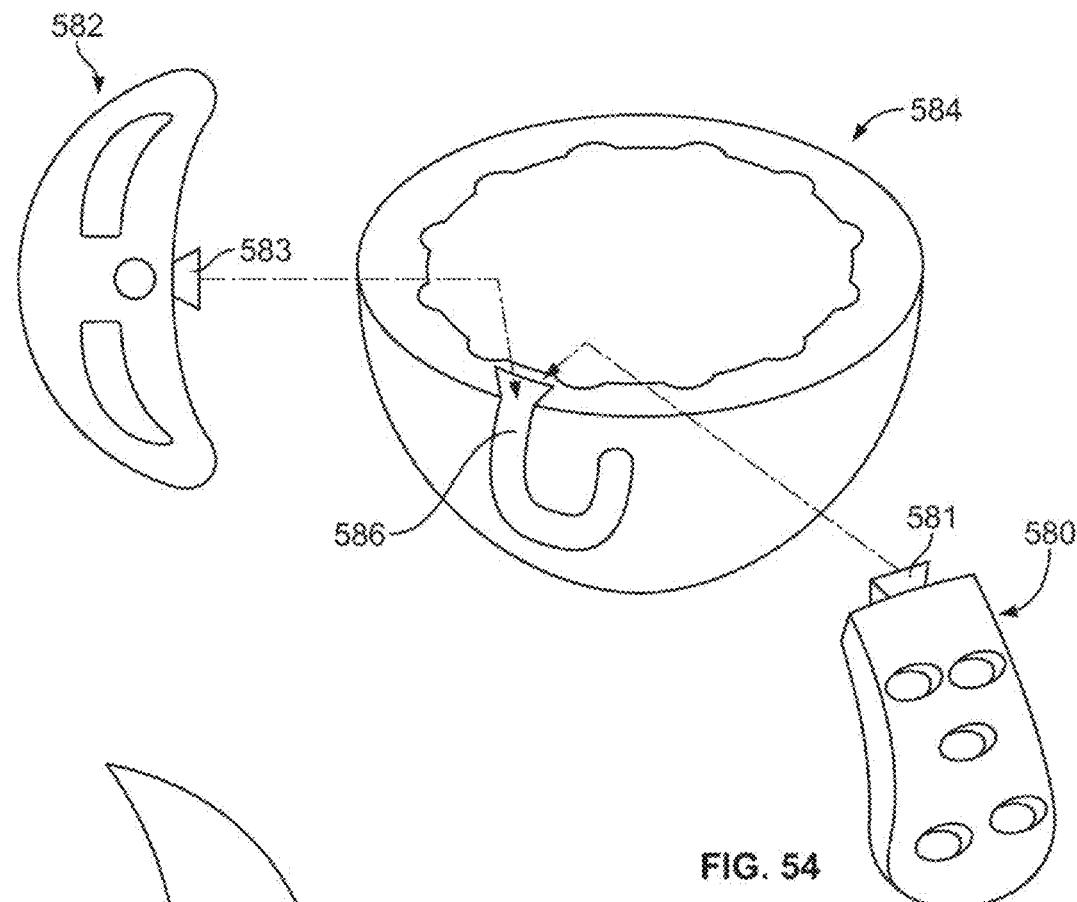
FIG. 54 shows an illustrative mounting member and an illustrative augment member provided with a dovetail feature.

In certain embodiments shown in FIG. 54, a mounting member 580 or augment member 582 is provided with a dovetail feature 581 and 583 (that may be male or female), respectively, to connect it to an acetabular shell or cage 584 (or, in some embodiments another augment) having the other complementary mating female or male dovetail feature 586. In the embodiment shown, the complementary feature 586 on the shell 584 is a J-shaped track or J-slot, but it will be understood that any mating features or configurations may be used. In the specific embodiment described, the dovetail feature 586 is configured to allow the mounting member 580 or augment member 582 to rotate and/or translate with respect to the shell 584 in a semi-locked state. The semi-locked state generally allows some independence of movement between the two pieces, which can be desirable to allow a surgeon to toggle between relative positions or otherwise continue to position and adjust the members. Such a semi-locked or loose connection can be particularly useful for revision surgeries.

The mounting member 580 or augment member 582 may be provided in a number of various shapes, sizes, textures, and configurations configured to fill bone defects and voids of varying degrees and locations with respect to a patient's anatomy. For instance, an implant may comprise a flange member that does not necessarily serve to fill a bone void/defect, but is instead configured to couple with a bone surface. Dovetail features according to FIGS. 54-70 generally mate by providing a flared male member (e.g., member 581 or 583) that is configured to slidingly engage one or more complementary female members such as one or more separated or intersecting undercut grooves or recesses (e.g., member 586). The undercut grooves or recesses may be provided on either component or vise versa, without limitation. A third member, for example an expansion member (e.g., setscrew, fastener, rivet, wedge, pin, cam, long bone screw, or any other fastener), may further be provided and used to securely lock the two pieces together to form a locked assembly. In some instances, the third member will engage one or more portions of the dovetail features to cause the male member to expand in the female member.

Figure 56:
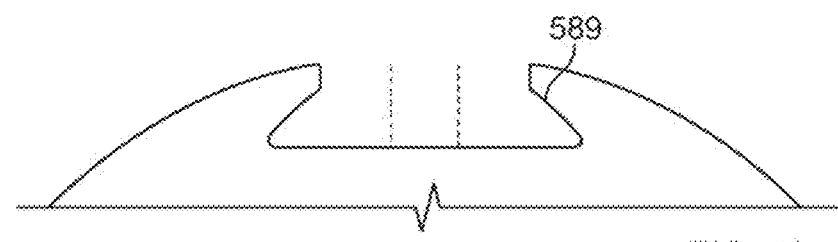

In other instances, for example, as shown in FIGS. 55 and 56, a fastener such as a setscrew may be inserted through a male portion 588 of the dovetail features to move the male member 588 away from a blind portion of the female member 589, thereby spreading the two pieces such that tapered surfaces of the dovetail features frictionally engage each other.

Figure 57:
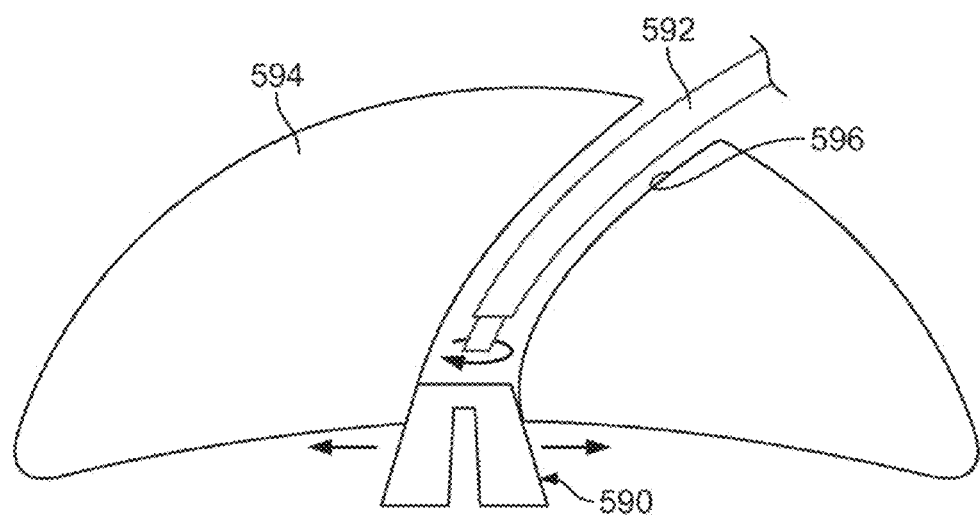
FIGS. 57 and 58 show an illustrative chock distally-connected to a surgical cable and positioned within a portion of an augment.
Figure 58:
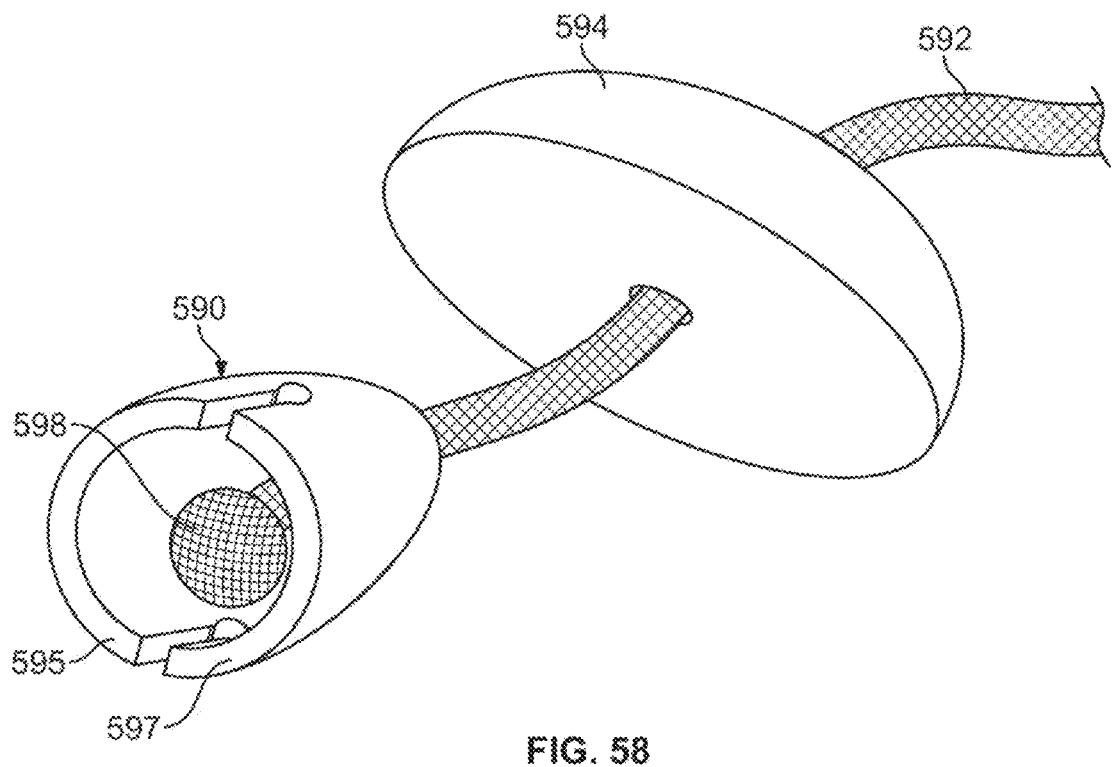
Figure 59:
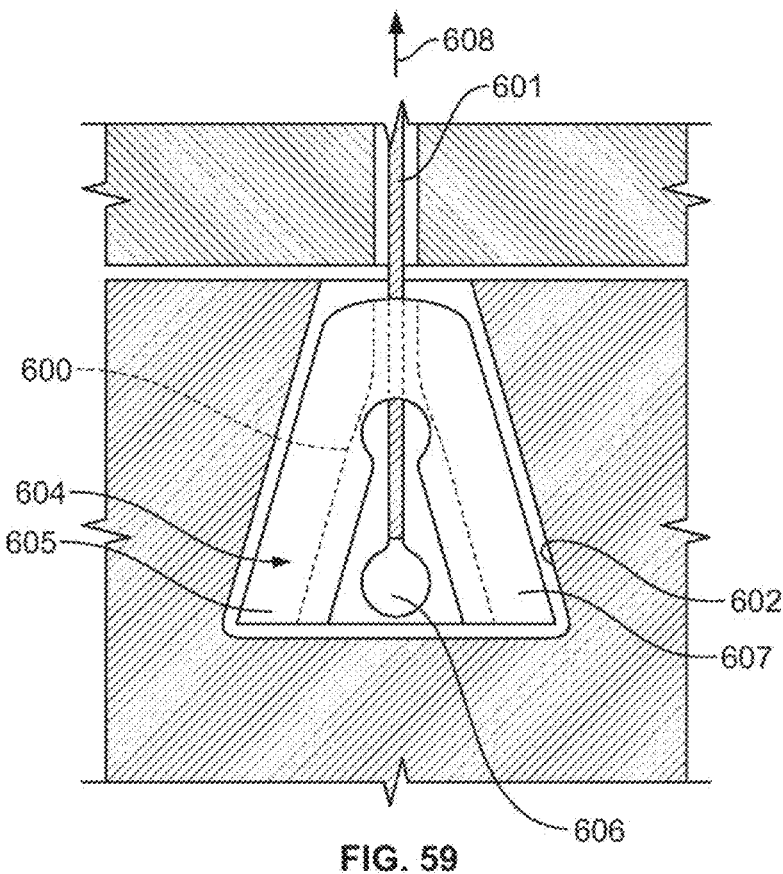
FIGS. 59 and 60 show an illustrative chock having an angled or inclined surface configured to receive an expansion member.
Figure 60:
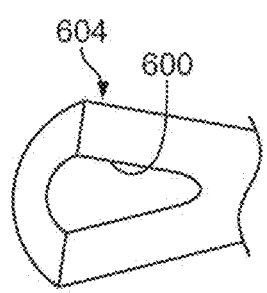

FIGS. 57-61 illustrate some embodiments wherein one or more locking chocks are distally-connected to a surgical cable and are configured to be received and/or captured within a portion of a mounting member or augment. For example, FIGS. 57 and 58 show a locking chock 590 distally-connected to a surgical cable 592 and positioned within a portion of augment 594. The cable 592 may be introduced through a through-bore in a mounting member or augment (e.g., bore 596 of augment 594) and tightened via a clamping device. The chock 590 is shaped to complement a tapered hole or an undercut groove or recess provided in an acetabular shell, cage, or other augment (e.g., undercut recess or groove 602 of FIG. 59). When the surgical cable 592 is tightened around the mounting member or augment adjacent bone or to any other plating structures, the chock 592 is pulled toward the undercut surfaces of the tapered hole undercut groove/recess and is expanded by an expansion member 598, for example, by a ball crimped to a distal portion of the surgical cable or any of the other expansion members described herein. The chock 590 may engage the undercut groove or recess. As shown in FIGS. 59 and 60, an internal portion of a chock 604 may have an angled or inclined surface 600, which is adapted to receive an expansion member 606.

In use, the chock rides along the cable and once positioning is desired, the wings of the chock may be forced apart for securement. For example, wings 595 and 597 of chock 590 shown in FIG. 58 may be forced apart for securement. When the cable is tightened, this can (a) pull the augment towards the shell/cage/other augment and (b) pull the ball or other expansion member at the end of the cable inside the chock so that the wings will expand and the chock will be secured in place. For example, when cable 601 of FIG. 59 is pulled in the direction of arrow 608, this can pull expansion member 606 inside the chock 604 so that the wings 605 and 607 of chock 604 expand, thereby securing the chock 604 in place.

Alternatively, while not shown, the chocks may be separate pieces attached to the surgical cable at different portions and provided with inclined surfaces that ride together to facilitate expansion and frictional engagement with the tapered hole or undercut groove/recess. The one or more locking chocks may be oblong for easy insertion into the undercut groove or recess. Once the cable is pulled tight, it may be used as cerclage cable or K-wire and tightened around bone or other anatomical structures, keeping the mounting member or augment attached to the shell, cage, or other augment.

Figure 61:
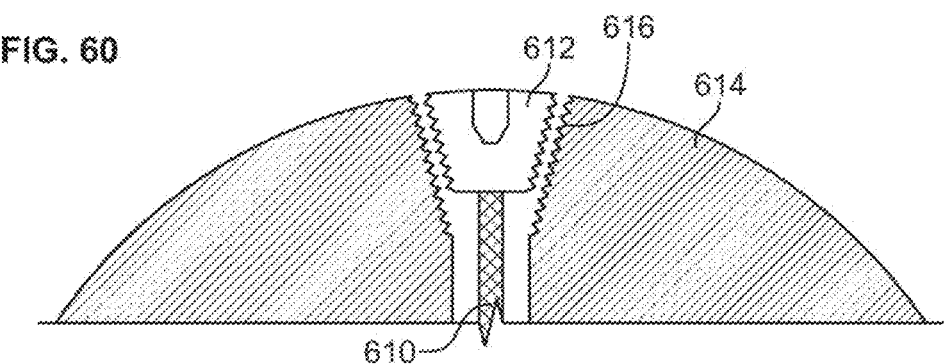
FIG. 61 shows an illustrative cable tensioning device provided on a mounting member or augment.

Alternatively, as shown in FIG. 61, the cable 610 may be tensioned using a cable tensioning device provided on the mounting member or augment 614. For instance, as shown, a tensioning screw member 612 may threadingly engage a female thread 616 located in the mounting member or augment 614. As the tensioning screw member 612 is turned, the cable 610 is pulled into tension, thereby moving an expansion member (e.g., a crimped ball) against inner inclined surfaces located on the one or more locking chocks such as inclined surface 600 of chock 604. When the expansion member (e.g., expansion member 606) reaches a point of interference with the one or more locking chocks, the tensioning screw member may be turned further to spread the chocks apart and lock the mounting member or augment to the shell, cage, or other augment via a tightened dovetail joint.

Figure 62:
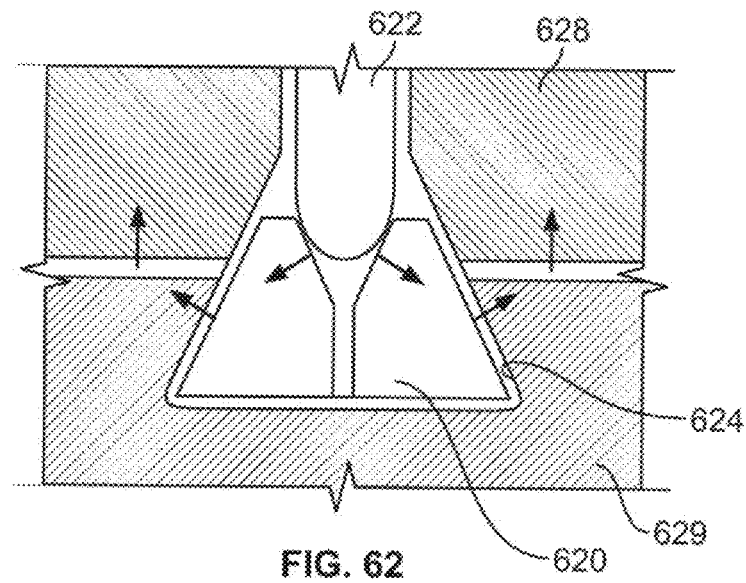
FIGS. 62-64 show an illustrative mounting member or augment that may be attached to an acetabular shell, cage or other augment using a separate expandable chock member and an intermediate connecting member.
Figure 63:
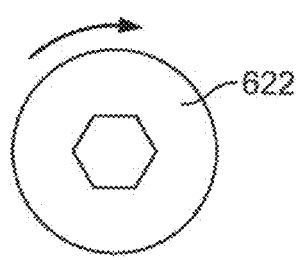
Figure 64:
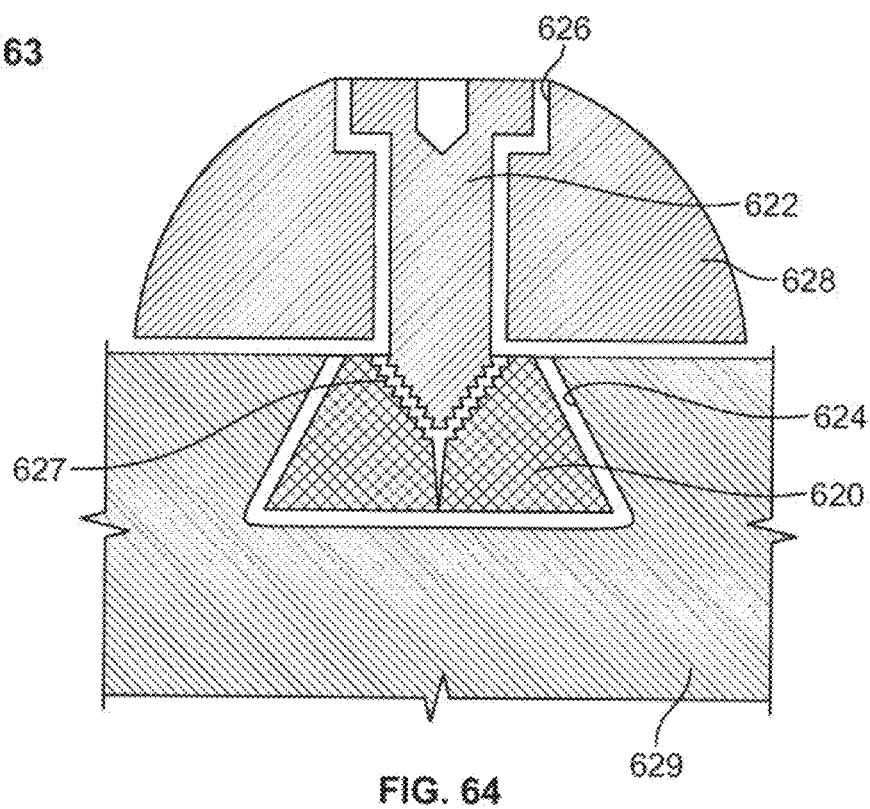

FIGS. 62-64 illustrate some embodiments wherein a mounting member or augment 628 may be attached to an acetabular shell, cage, or other augment 629 using a separate expandable chock member 620 and an intermediate connecting member 622. The intermediate connecting member 622 serves to temporarily loosely couple the mounting member or augment 628 to the shell/cage/augment 629, and also serves to expand the separate chock member 620 and lock the two components together. In some embodiments, it is preferred that the separate expandable chock member 620 is provided as a generally frustoconical portion or a male portion of a dovetail connection. The separate expandable chock member 620 may be inserted into and captured within an undercut recess, groove, or track (e.g., undercut recess, groove, or track 624) in an acetabular shell, cage, or other augment 629. In some embodiments, the separate expandable chock member 620 is movably captured and may be positioned at various locations and orientations within said undercut recess, groove, or track.

The mounting member or augment 628 is then placed adjacent to the shell/cage/other augment 629, and the intermediate connecting member 622 inserted through an aperture, opening, or recess 626 in the mounting member or augment 628 to engage an undersized or tapered female thread 627 in the separate expandable chock member 620. The mounting member or augment 628 may be moved to a desired position relative to the shell/cage/augment 629 by virtue of the loose connection and undercut recess, groove, or track, and then locked in a desired relative spatial orientation by engaging the intermediate connecting member.

In the embodiment shown, the intermediate member 622 is provided as a headed bolt that threadingly engages the separate expandable chock member 620 to expand the separate expandable chock member 620. When the separate expandable chock member 620 is fully expanded, a frictional dovetail locking connection is achieved, which locks the mounting member or augment 628 to the shell/cage/other augment 629 in the desired relative spatial orientation.

Figure 65:
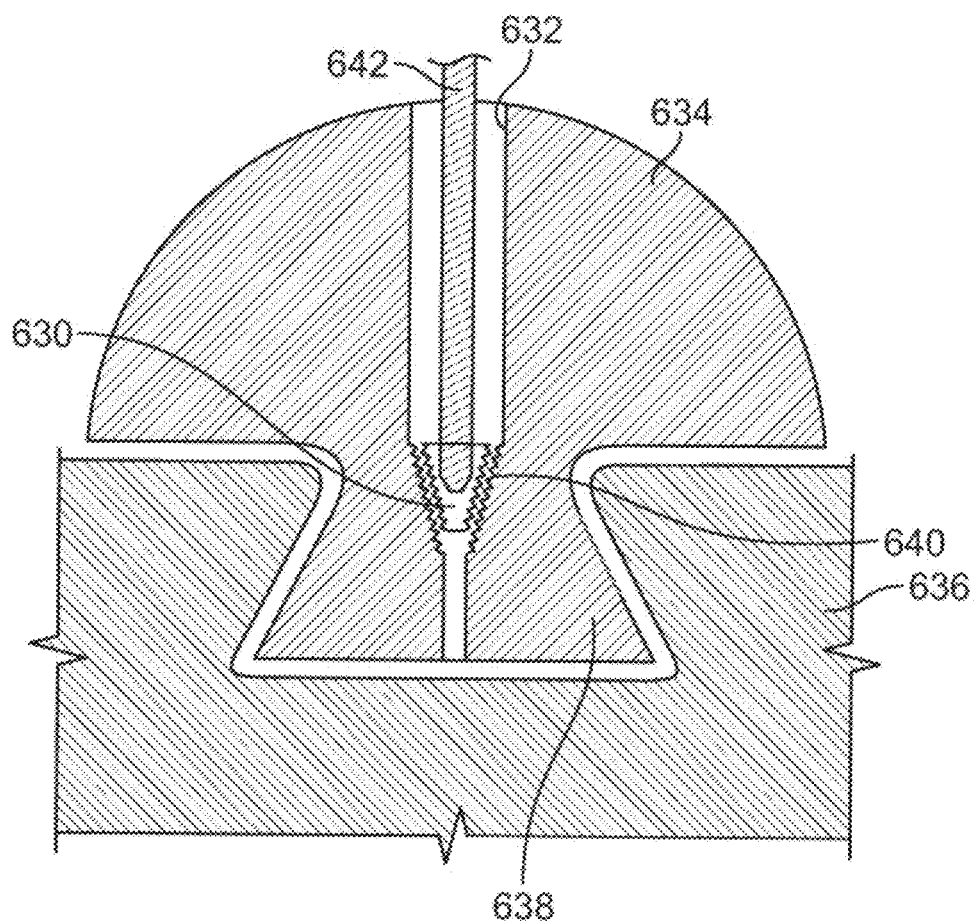
FIG. 65 shows an illustrative expanding element that may be provided in an aperture of a mounting member or augment.

FIG. 65 illustrates an alternative embodiment to FIGS. 62-64, which is similar to the embodiment shown in FIGS. 41 and 42. A small expanding element 630 is provided within an aperture, opening, or recess 632 in a mounting member or augment 634 configured to be loosely attached and locked to an acetabular shell, cage, or other augment 636. The mounting member or augment 634 includes a male portion of a dovetail. The male portion of a dovetail may be formed by a deformable or expandable protrusion 638 which may be bifurcated and/or initially flared outwardly in an un-deformed/unstressed state. Alternatively, while not shown, in some embodiments, the expandable protrusion 638 may be provided as a generally cylindrical member which can be first introduced into an undercut recess, groove, or track, and then expanded within said undercut recess, groove, or track, by the expanding element in order to provide a locking function between the mounting member or augment and the shell/cage/augment. As shown in FIG. 65, the expanding element 630 may be provided as a small tapered setscrew which engages a complementary tapered or otherwise undersized thread 640 inside the male portion of a dovetail. A flexible driver 642 may be used to access the small expanding element 630. Upon torsional engagement with the expanding element 630, a dovetail locking connection is formed, thereby securing the mounting member or augment 634 to the acetabular shell, cage, or other augment 638 in a desired configuration and relative spatial orientation.

Figure 66:
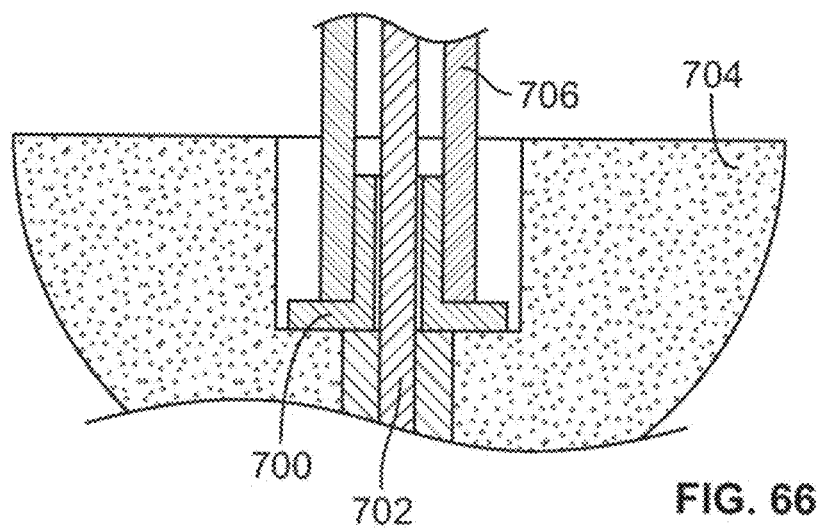
FIG. 66 shows an illustrative ferrule on a cable that may be positioned against an augment.

FIG. 66 shows in alternate and additional feature relating to the cable and chock embodiments of FIGS. 57-65. FIG. 66 shows a ferrule 700 on a cable 702 that may be positioned against an augment 704. A tensioning tool 706 may be used to hold the cable 702 tight and the ferrule 700 can be crimped onto the cable 702. When the cable 702 is pulled tight, the chock (e.g., chock 590 of FIG. 57) engages the dovetail slot and the tension pushes the chock towards or into the augment 704, held in place by the ferrule 700.

Figure 67:
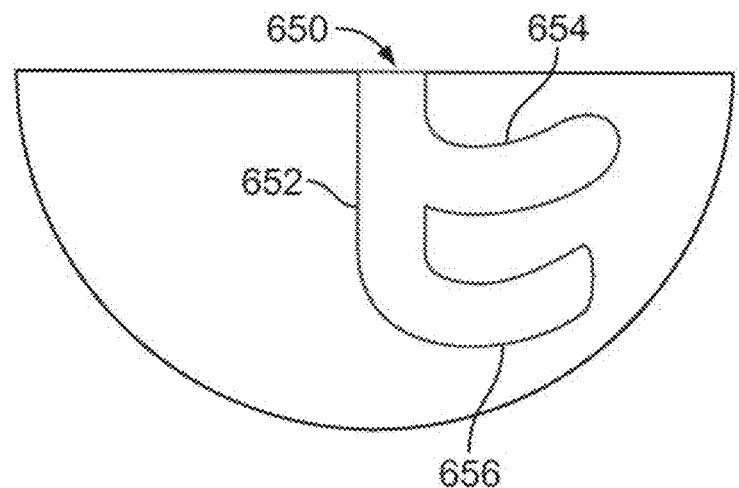
FIGS. 67 and 68 show illustrative geometries for a receiving portion of a shell, cage, or augment.
Figure 68:
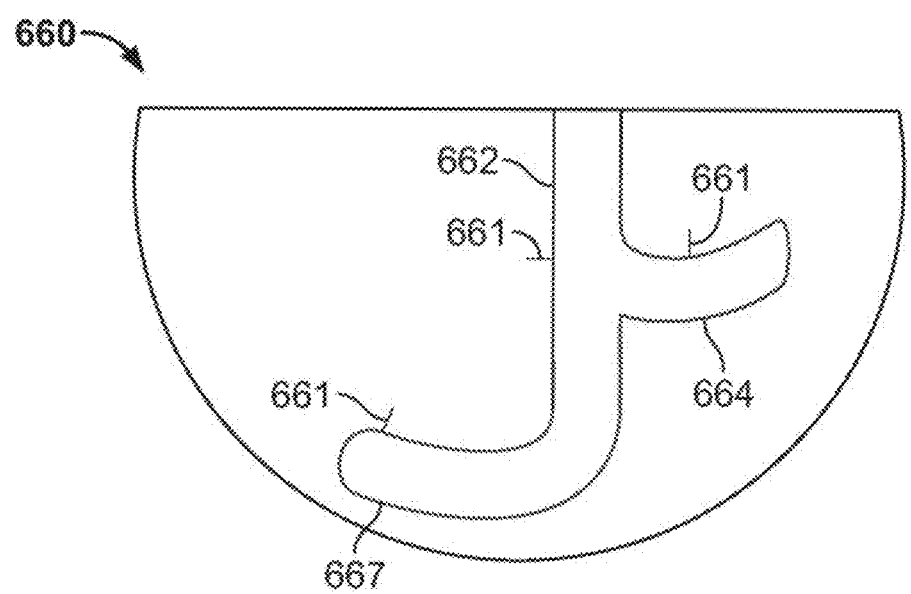

FIG. 67 shows one potential geometry for a receiving portion 650 (such as an undercut recess, groove, or track) in a shell, cage, or augment according to some embodiments. In this example, the receiving portion is a double J-slot formed by slots 652, 654, and 656. FIG. 68 shows a further optional geometry, where J-slots are provided in opposing directions formed by slots 662, 664, and 667.

Figure 69:
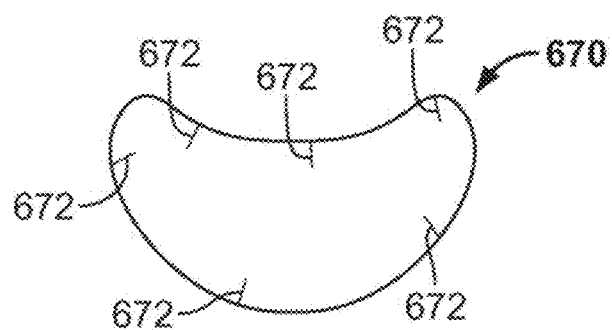
FIG. 69 shows illustrative indicia for indicating a positional relationship between the mounting member or augment and the implant to which it is to be attached.

As shown in FIGS. 68 and 69, any of the mounting members or augments shown and described herein may comprise tick marks or other indicia for indicating a positional relationship between itself and the implant to which it is to be attached. For example, an augment 670 may comprise a plurality of peripheral markings 672 or central markings 661 (not shown) for alignment with markings 661 provided in an acetabular shell or cage 660 (or, in some embodiments, another augment). In use, a surgeon may loosely insert the mounting member or augment (e.g., augment 670) and the shell/cage/augment (e.g., shell 660) into a patient's bone void, prior to assembling the two. The surgeon may then position both components and possibly other components to determine the best relative spatial orientation to best fill a volume of the void. The surgeon may then observe, compare, and note the relative positions of the markings or indicia between the bodies, thereby receiving repeatable and reproducible information about the desired spatial orientation. The surgeon may then remove both bodies from the surgical environment, realign them in the desired spatial orientations (facilitated by the markings or indicia), and then cement or otherwise secure the two bodies together in said desired spatial orientation. Subsequently, the assembled implant may be introduced into the void and the surgery completed in a normal fashion.

Figure 70:
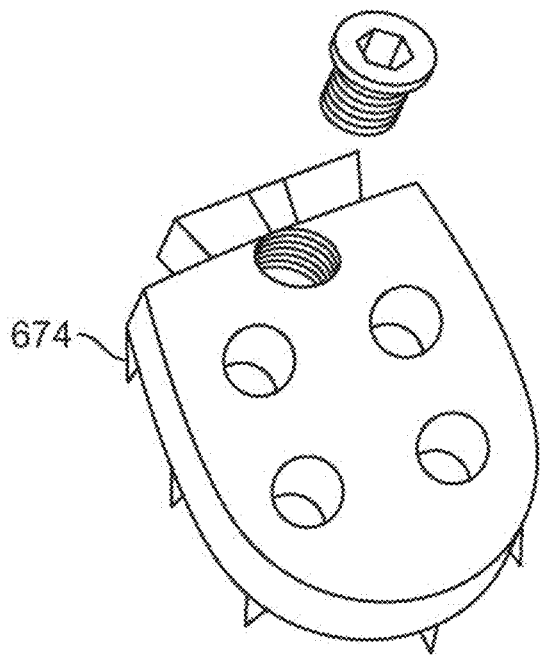
FIG. 70 shows illustrative spikes that may be provided on mounting members or augments for improving fixation.

Moreover, as shown in FIG. 70, mounting members or augments shown and described in the figures contained herein may comprise tacks, spikes, coatings, or textured surfaces 674 so as to improve initial fixation. The geographic locations of said tack, spike, coatings, or textured surface structures 674 may be strategically placed on select portions so as to evenly load the implant assembly and obtain the best biologic response initially, and over an extended period of time.

FIG. 71 shows a bi-lobe cup or shell 710, which is a shell 710 having a lobe 712 extending therefrom. Typical bi-lobe shells are made of solid material, but this embodiment shows a bi-lobe shell 710 having a lobe 712 of porous material. The lobe 712 may have some solid portions for receiving screws other fastening members. As shown, additional augment members 714 may be attached to the lobe 712 of porous material or to the solid shell 710. Areas of the porous lobe 712 may be provided with areas of solid, non-porous material having apertures or other structures for receiving and locking to screws, such as polyaxial bone screws. Moreover, the porous lobe 712 may comprise holes 716 extending through fully porous sections for insertion of bone screws.

FIG. 72 shows two augments 720 and 722 attached together via a fastening device 724 such as a screw or a shape-memory polymer peg according to some embodiments. It will be understood that although augments are shown, the securement mechanisms described herein may also be used with any type of mounting member, shell, or cage as well. In some embodiments, a peg of shape memory material may extend from one or more augments and into a prepared hole in bony anatomy. The shape memory peg may then be activated (via thermal changes or an applied electric current) and expanded within the prepared hole so fix an augment or mounting member to the patient's bone. Non-limiting examples of further features for such shape memory plugs are that they may comprise outer textured surfaces, may be porous, and may comprise barbs, flutes, ridges, grooves, spines, any other suitable features, or combinations thereof.

FIG. 73 shows an augment 726 with integral spikes 728 according to some embodiments. The spikes 728 may allow the augment 726 to be positioned initially in bone, without the augment 726 having to be first secured to a shell, cage, mounting member, or other augment or without the use of bone cement. The augment 762 may be positioned and then impacted or otherwise pressed into a bone void to achieve instant fixation.

Figure 74:
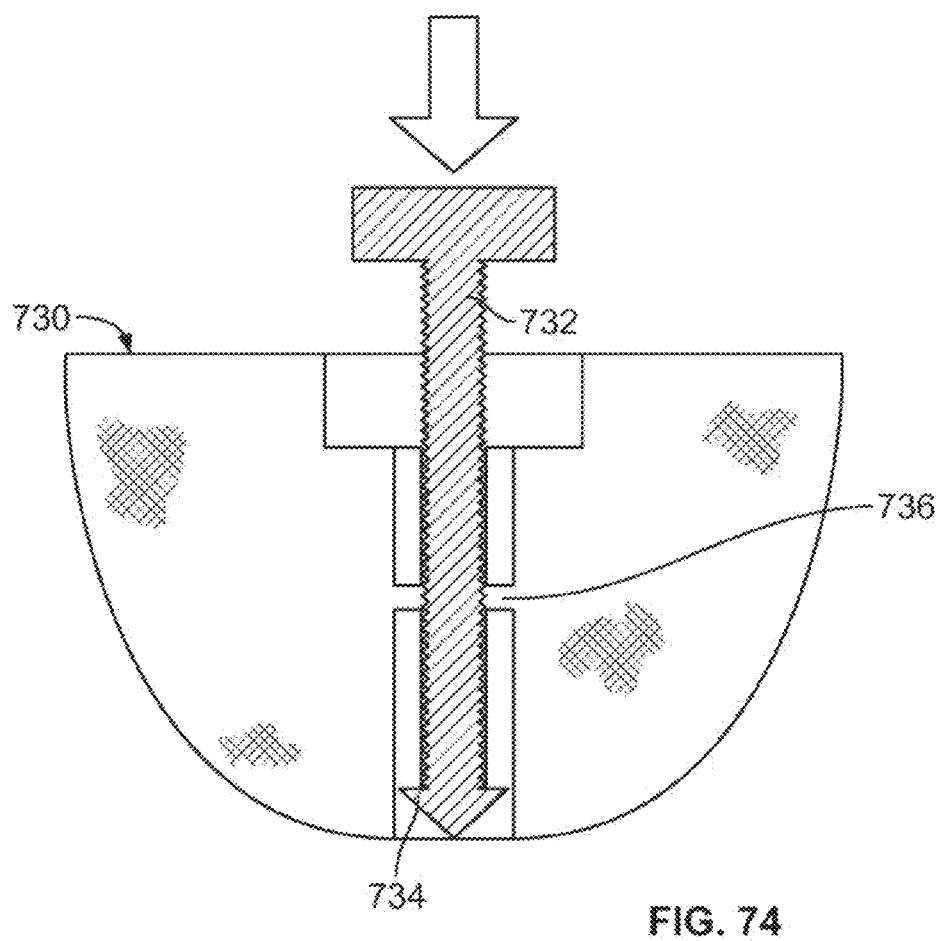
FIG. 74 shows an illustrative augment with built-in securement features.

FIG. 74 shows other embodiments of an augment 730 having built-in securement features. Embodiments of this augment may have one or more integral spikes, barbs, screws, or other fasteners pre-positioned therein. For example, augment 730 includes integral fastener 732 which may be a spike having barbs 734. When the augment 730 is positioned as desired, the surgeon may screw, impact or tack the augment 730 in place, causing the integral fastener 732 to extend and secure bone purchase. One advantage of this embodiment is that is can prevent the surgeon from having to locate and insert separate fasteners. In some embodiments, there is provided a breakable or frangible connector 736 that is sheared once the fastener 732 has been impacted, twisted, or otherwise activated by a force or moment. A further advantage of the described embodiments is that the augment 730 is a one-piece component that can be positioned without additional fasteners or other components attached thereto, simplifying some aspects of insertion. Moreover, the surgeon may desire to place the augment 730 first, and then quickly secure it to the other implant portions to be used. Integral fasteners which are not utilized may be removed by a pulling out force, and breaking the connector. Fasteners such as integral fastener 732 may be configured to connect the augment to bone or to other implant devices such as other augments, acetabular shells, acetabular cages, and/or bone plates.

Figure 75:
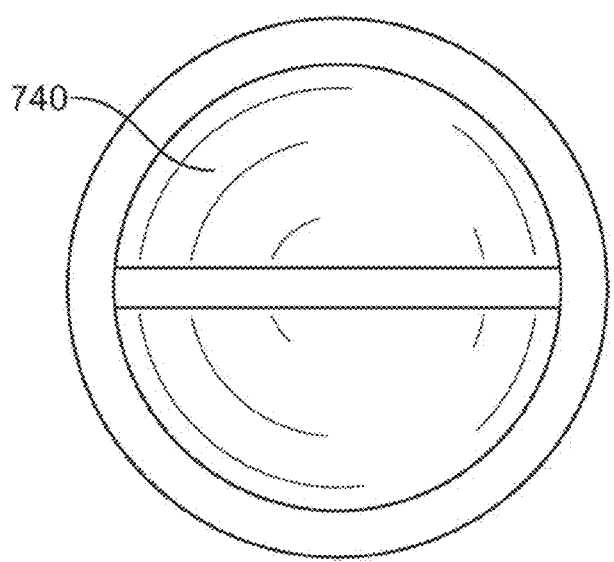
FIGS. 75-77 show various illustrative augments or porous coating portions having one or more cross-sectional areas of reduced material.
Figure 76:
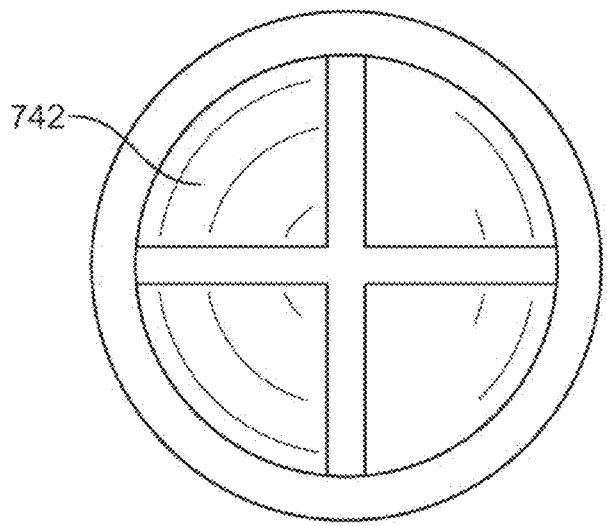
Figure 77:
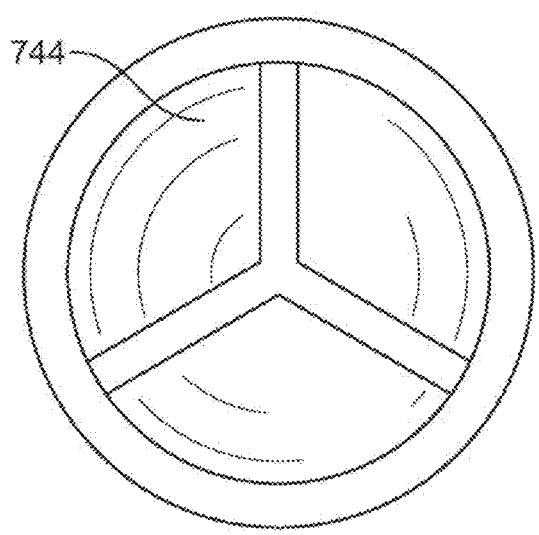
Figure 78:
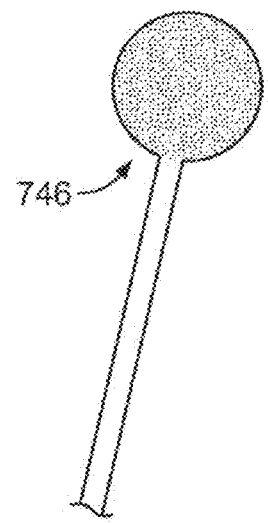
FIG. 78 shows an illustrative rotary tool.

FIGS. 75-77 illustrate various augments or porous coating portions comprising one or more cross-sectional areas 740, 742, and 744 of reduced material which are "designed" for easy drilling, shaping, and screw insertion. In some embodiments, a bulk porous structure is provided with waffle patterns of recesses defined therein. The recesses may be externally provided, internally provided, or combinations thereof. External recesses may be created using rapid manufacturing, wire EDM, milling, or other processes. Internal recesses may be created using rapid manufacturing (e.g., selective laser sintering with an EOS machine or EBM process using an Arcam machine), cross-drilling processes, any other suitable processes, or any combinations thereof. The areas of reduced cross-section 740, 742, and 744 make it easier for a surgeon to drill through the augments or porous coating portions, orient screws, and burr, mill, cut, break, bend or otherwise shape with a rotary tool 746 such as the one shown in FIG. 78. Other modification tools such as reciprocating saws or oscillating saws may be utilized to shape the augments or porous coating portions. Recesses may extend in various patterns in two-dimensional or three-dimensional space, and may vary in width, depth, aperture, thickness, density, and length.

FIGS. 79-82 illustrate some embodiments of a connection device for securing a mounting member or an augment to an acetabular shell or acetabular cage. Certain embodiments of the connection device comprise an intermediate locking member 750 that may be placed between an acetabular shell or cage and a mounding member or augment, the intermediate locking member 750 configured to provide initial loose and adjustable attachment of the mounting member or augment to the acetabular shell or cage. After or before impaction, the mounting member or augment position relative to the shell or cage may be adjusted and then fixed with respect to the shell or cage by engaging a portion of the intermediate locking member 730. After the intermediate locking member 750 is engaged to lock the adjacent components together against relative movement, a liner may be inserted into the shell or cage. The intermediate locking member 750 may either be a separate portion or integral to one of the shell, cage, mounting member or augment.

Portions of the intermediate locking member 750 may be low profile and configured to be received in and locked within an acetabular shell (e.g., via a threaded, smooth, or tapered screw hole). In the embodiment shown, the intermediate locking member 750 is provided within an acetabular shell as disclosed in the '705 application. Intermediate locking member 750 may comprise, as shown, a cam locking pin 752 and a locking head screw 734. The mounting member or augment may comprise an undercut recess 750 which has an opening of any appropriate shape, such as oblong, scalloped, triangular, dovetail, or any other option. A distal end 756 of the cam locking pin 752 has a complementary shape (oblong, scalloped, triangular, dovetail, or any other appropriate complementary shape) and is flared or tapered radially outwardly to engage one or more undercut surfaces forming the undercut recess 759.

Figure 80:
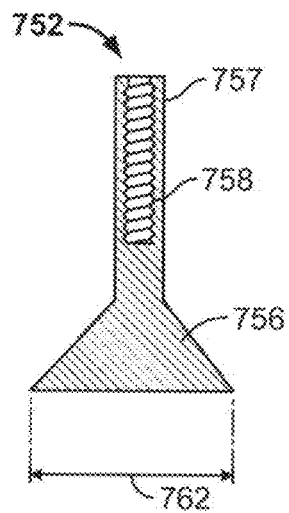
Figure 81:
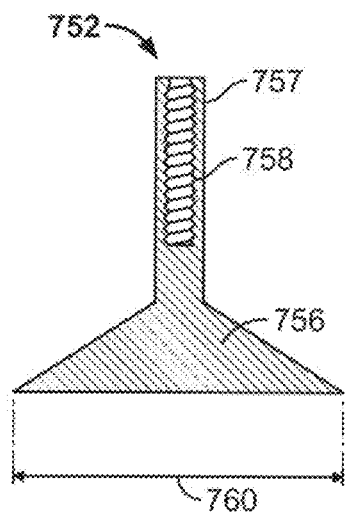
Figure 82:
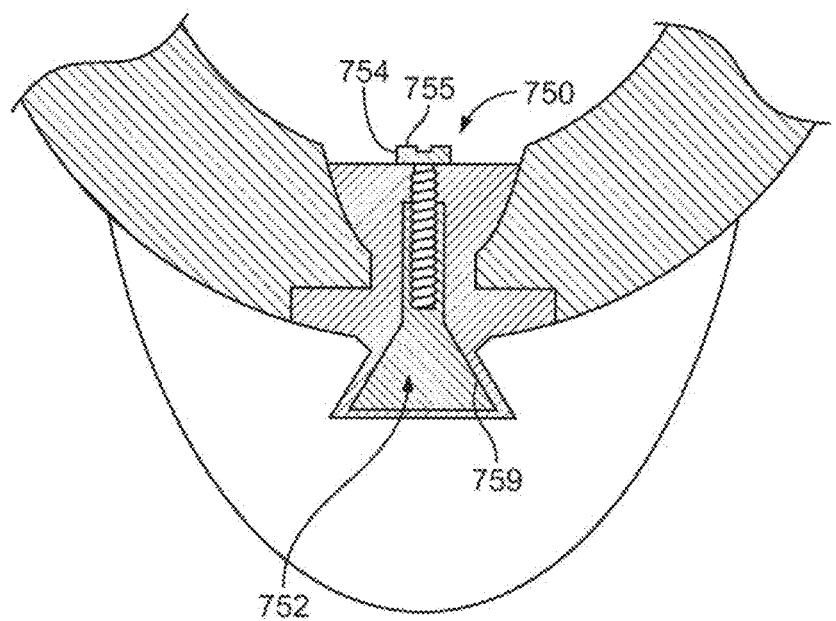

As shown in FIGS. 80 and 81, a proximal end 757 of the cam locking pin 752 may have a shaft 758 with engageable threads axially-disposed therein. A locking head screw (shown for example, as locking head screw 754 of FIG. 82) is configured to engage the threads on the shaft 758 of the cam locking pin 752. The threads of the locking head screw may be female or male, and the threads of the cam locking pin 752 may be the other of male or female. Locking screws prevent the cam locking pin 752 from backing out once properly positioned. During use, the cam locking pin 752 is positioned within a receiving groove or recess and rotated to lock the cam locking pin 752 in place. The complementary shapes of the distal end 756 of cam locking pin 752 and a receiving groove or recess allow the cam locking pin 752 to be inserted into the groove or recess in a first orientation and then rotated to a second orientation in which it cannot be removed from the groove or recess.

The shaft portion 758 of the cam locking pin 752 may be provided with one or more flats on the outside (e.g., a hexagonal outer cross section for the shaft) to allow turning of the cam. Alternatively, a cruciform recess or hexagonal recess or other driving structure may be provided on the cam locking pin 752. In some embodiments, the female thread in the cam locking pin 752 may be substituted for threads on the outside of the shaft 758 of the cam locking pin 752 which engage a partially cannulated locking screw having an internally-threaded aperture extending axially through the shaft of the locking screw. In such latter embodiments, outer portions of the locking screw play be smooth. The head 755 of the locking head screw 752 may alternatively be rounded for polyaxial movement (exemplary polyaxial locking options are provided in more detail below) within the hole in the acetabular shell or cage. It will be understood by those of ordinary skill in the art that the connection shown in the figures may also be used to connect augments or mounting members together, without limitation.

Figure 83:
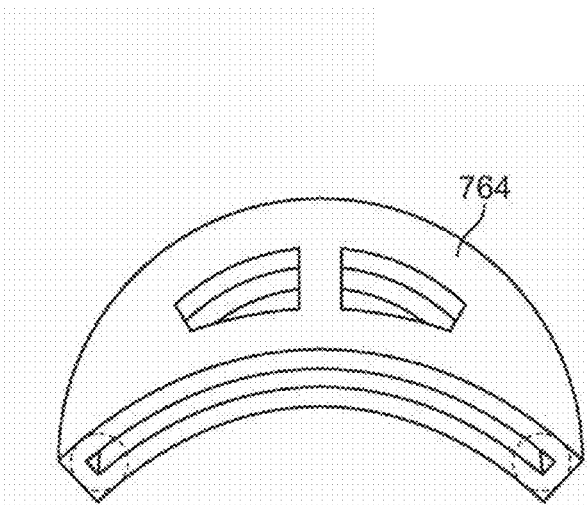
FIGS. 83-85 show illustrative augments provided with an elongated undercut groove configured to receive a cam locking pin.
Figure 84:
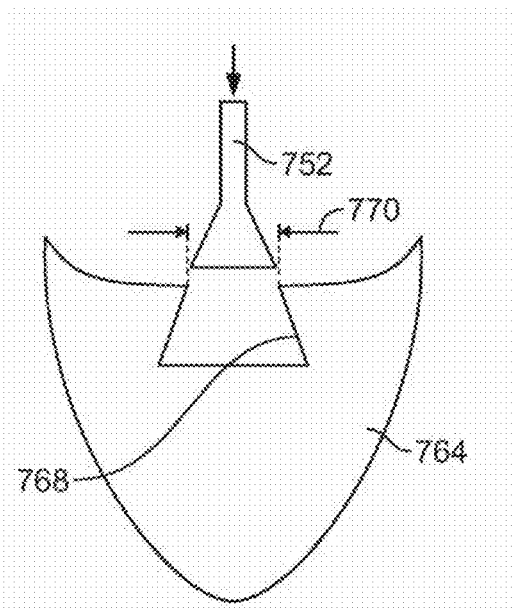
Figure 85:
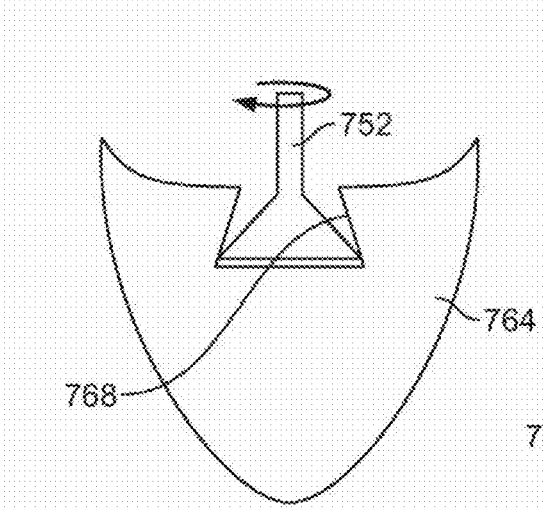
Figure 86:
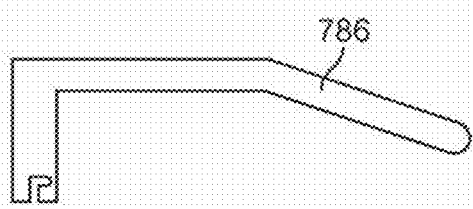
FIGS. 86-89 show illustrative cleats provided proximate to a rim of an acetabular shell or cage, mounting member, or augment.
Figure 87:
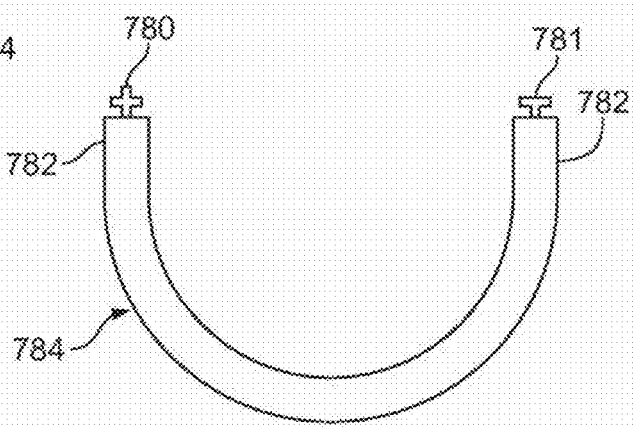
Figure 88:
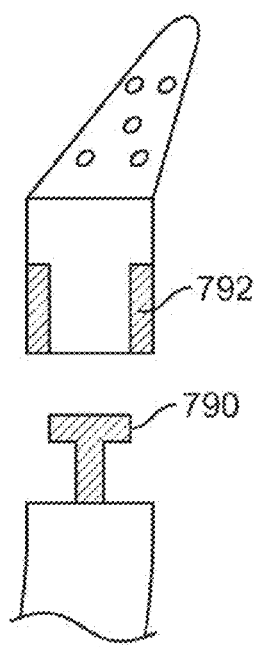
Figure 89:
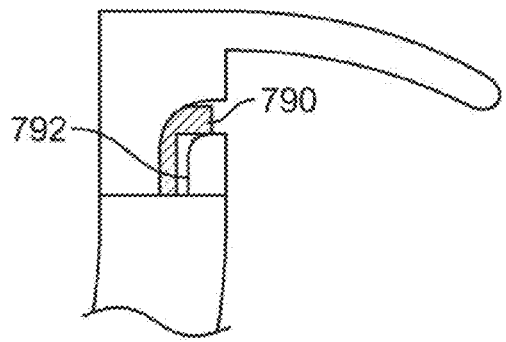

FIGS. 83-85 illustrate some embodiments wherein a mounting member or augment, for example, as disclosed in FIGS. 79-82, is provided with an elongated undercut groove which is configured to receive a cam locking pin. The elongated undercut groove allows the mounting member or augment to be radially adjusted in space and locked in an orbital position around a corresponding acetabular shell or cage. In some embodiments, portions of the mounting member or augment proximate the elongated groove may be made solid, rather than porous for strength, and outer regions of the mounting member or augment may be smooth, textured, coated (e.g., hydroxyapatite), porous, or combinations thereof in order to encourage biologic fixation and ingrowth in select regions.

Figure 79:
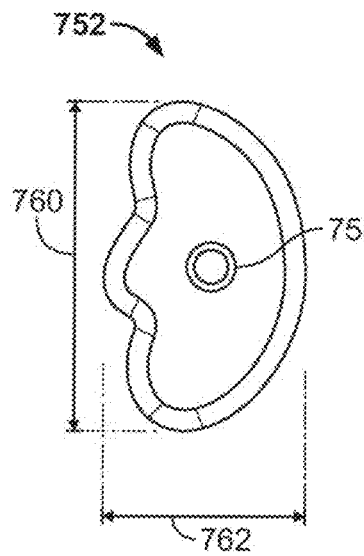
FIGS. 79-82 shows various connection devices for securing a mounting member or an augment to an acetabular shell or cage.

FIG. 84 illustrates a cross-sectional view of an augment 764 and a cam locking pin 752 being inserted into an elongated undercut groove 768 of the augment 764 in an insertion position. The cam locking pin 752 is positioned into the groove 768 by rotating the cam locking pin 752 along its axis such that the insert width 762 of the distal end 756 of the cam locking pin 752 (as shown in FIGS. 79-81) fits through the insert width 770 of the elongated undercut groove 768. FIG. 85 illustrates a cross-sectional view of the augment 764 with the cam locking pin 752 locked into the elongated undercut groove 768 of the augment 764 in a locking position. In the locking position, the cam locking pin 752 may generally be rotated along its axis between 50 and 130 degrees, preferably around 90 degrees (i.e., a "quarter-turn"). The locking width 760 prevents the distal end 756 of the cam locking pin 752 from fitting through the insert width 770 of the elongated undercut groove 768. In some embodiments, cam locking pin 752 may be symmetrical and may have a flared end (e.g., distal end 756) comprising a generally frustoconical surface, and the undercut groove 768 in the augment 764 (or, in some embodiments, an undercut groove in a mounting member) may have one or more enlarged openings to receive the flared end of the cam locking pin 752. In such alternative embodiments, a locking screw (e.g., locking head screw 754 of FIG. 82) may threadingly engage the cam locking pin 752 to apply a tensile force to the cam locking pin 752 against another implant such as a mounting member, augment, shell, or cage.

In the embodiments shown in FIGS. 86-89, cleats may be provided proximate to a rim of an acetabular shell, cage, mounting member, or augment. For example, in some embodiments, one or more cleats 780 and 781 may extend or project from a superior aspect of a rim portion 782 of an acetabular shell 784 as shown. Cleats 780 and 781 may be used to secure soft tissues to the acetabular shell 784 or may serve as a means to attach secondary augments or any type of mounting member 786 to the acetabular shell 784. In the particular instance shown in FIGS. 88 and 89, a "quarter-turn" fastener connector arrangement is utilized. The quarter-turn fastener arrangement may comprise, for instance, a generally T-shaped male member 790 located on one or more regions of an acetabular shell, cage, or augment, and one or more complementary female members 792 located on more secondary augments or mounting members. The one or more secondary augments or mounting members engage the one or more male members 790 on the acetabular shell, cage, or augment in one degree of rotation, and then are rotated by a specified or variable number of degrees (e.g., 90 degrees) to lock the one or more secondary augments or mounting members to the one or more male members 790. Of course, one of ordinary skill in the art would appreciate that the male and female members could be reversed to provide the same function. It should also be understood that other locking mechanisms may be used.

FIG. 90 further depicts one or more cleat portions 794 located at various portions of an acetabular shell or cage 796 (or, in some embodiments, an augment) configured for securing soft tissues. The one or more cleat portions 794 can be arranged in any particular fashion around the acetabular shell 796; however, it is preferred that the cleats 794 extend proximally from a rim portion or otherwise away from the acetabular shell 796 in order to provide clearance from liner-mating surfaces, cement mantle surfaces, bone contacting surfaces, and bony anatomy, for example. Cleat portions 744 may comprise suturing holes, roughened surfaces, clamps, hooks, or biologic coatings, or any other appropriate protrusions, or combinations thereof, to encourage fixation of the soft tissues to the implant (e.g., acetabular shell 796). For example, as shown in the inset of FIG. 55, sutures may be wrapped around cleat portion 794 and then secured to surrounding soft tissues.

FIGS. 91-95 illustrate embodiments wherein a mounting member 802 or an augment 804 may be attached peripherally to an acetabular shell or cage 806 via a recess 800 provided proximate a rim portion 808 of the acetabular shell or cage 806. The recess 800 is sized to accept a protruding insertion portion 810 of the mounting member 802 or a protruding insertion portion 812 of the augment 804, and the recess 800 may extend annularly circumferentially around the rim portion 808 to allow orbital placement of the mounting member 802 or augment 804 around a periphery of the shell or cage 806. The mounting member 802 or augment 804 may be inserted into the acetabular shell or cage 806 before or after shell/cage impaction or cementing into a prepared acetabulum. One or more screw holes in the mounting member (e.g., screw holes 814) or augment (e.g., screw holes 816) rigidly secure the mounting member 802 or augment 804 to the bone and prevent orbital movement of the mounting member 802 or augment 804 around the shell or cage 806. Screw holes 814 and 816 may include conventional holes, locking holes, or slots. The holes may be threaded, unthreaded, or partially threaded, and may be fixed or polyaxial. In some embodiments, screw holes 814 and 816 may include variable low-profile holes that allow for locking at a variety of angles. Once the mounting member 802 or augment 804 is positioned, the cantilever force pushes the rim 808 of the shell or cage 806 toward bone. The protruding insertion portion of the mounting member (e.g., portion 810) or augment (e.g., portion 812) provides a hold-down force to the shell or cage 806 after a screw is inserted through the mounting member 802 or augment 804 and into surrounding pelvic bone.

FIGS. 91 and 92 show an augment 804 being positioned with respect to an acetabular shell or cage 806. FIGS. 93 and 94 illustrate a mounting member 802 being positioned with respect to an acetabular shell or cage 806. The mounting member 802 is shown as having multiple securing holes 814 for use with fasteners. Securing holes 814 may be smooth, tapered, or threaded and may be used with any appropriate fastener, including but not limited to polyaxial screws. The securing holes 814 through the mounting member 802 (or securing holes 816 through the augment 804) may be positioned at any appropriate angle, as shown, such as parallel to the member, oblique through the member, or otherwise as desired. While not shown, a honeycomb feature may be placed on outer portions of the mounting member 802 or augment 804 to provide spacing for a cement mantle between the mounting member 802 or augment 804 and surrounding bond. Moreover, porous structures, textured surfaces, biologic coatings, or orthopedic meshes may be integrally provided on, or incorporated between outer surfaces of the mounting members 802 or augments 804 and surrounding bone.

In the embodiments of FIGS. 93 and 94, a recess 800 in the shell or cage 806 is defined by a proximally-extending lip 818 such that the mounting member 802 will sit on bone surrounding the acetabulum. In this way, the mounting members 802 will not interfere with the press-fit area between the shell 806 and prepared acetabulum adjacent the acetabular rim 808. Moreover, because the connection is configured to allow the mounting members 802 to sit on surrounding bone, the surrounding bone does not need to be countersunk or otherwise prepared to receive mounting members 802.

FIG. 95 depicts an acetabular shell or cage 820 comprising an annular protrusion 822 along a rim portion 824 of the acetabular shell 820. The annular protrusion 822 may extend partially around (as shown) or entirely around the circumference of the acetabular shell 820, or one or more protrusions may be provided in any fashion around the acetabular shell 820. The annular protrusion 822 may comprise an annular lip 826 defining an annular undercut groove 828 running circumferentially around the acetabular shell 820 proximate the rim portion 824. The annular protrusion 822 may comprise one or more openings 830 for receiving sutures (e.g., for soft tissue or capsule re-attachment) or fasteners 832 such as set screws for contacting and frictionally engaging surfaces (e.g., divots) provided on protruding insertion portions 834 and 836 of mounting members 840 or augments 838 alike.

Fasteners 832 may be inserted into openings 830 located circumferentially laterally of the insertion portions 834 and 836 to serve as stops for preventing or limiting rotational movement of the attached mounting members 840 or augments 838. The mounting members 840 or augments 838 may be secured down to surrounding bone after being inserted into the annular undercut groove 828 via long bone screws, thereby providing a hold-down force to the acetabular shell or cage 820. The hold-down forces provided may complement the press fit, threaded fit, or cemented fixation between the acetabular shell or cage and surrounding prepared acetabular bone. In the instance shown, shell 820 is provided as a "hooded" shell similar to a cage, and may act as a buttress for a cemented or pressed-in liner to support various liner inclinations in varying degrees of acetabular or pelvic degradation, although it will be understood that these features may be provided on any other type of shell or cage.

In the embodiments shown in FIGS. 25-28, one or more mounting members and/or augments may be integrally provided with orthopedic mesh to define one or more mesh mounts or void fillers. FIG. 25 shows a mounting member 380 having an orthopedic mesh 382. In FIG. 26, the orthopedic mesh portion 382 may be placed on an outer portion 384 of the shell 386 between bone, and a cement mantle can fill between the mesh 382. The cement mantle rigidly connects the mounting member 380 (or, in some embodiments, an augment) to the shell 386 via the surgical mesh 382. Rapid manufacturing techniques may be used to simultaneously create the mounting members or augments integrally with the orthopedic mesh portion. The mesh 382 may be honeycomb, diamond, or other weave pattern, or any combination thereof, and may come in multiple thicknesses. Mesh portion 382 may be oversized, customized for an individual patient, and/or standardized and trimmed by the surgeon to fit a particular patient's needs. Fasteners of all types may be inserted through one or more cells of the mesh 382, as well as through the one or more mounting members or augments to further secure the implant to bony anatomy. For example, as shown in FIG. 25, a first screw 388 may be inserted through/cell 390, and a second screw 394 may be inserted through one of the plurality of screw holes 392 of mounting member 380. Screw holes 392 may include conventional holes, locking holes, or slots. The holes may be threaded, unthreaded, or partially threaded, and may be fixed or polyaxial. In some embodiments, screw holes 392 may include variable low-profile holes that allow for locking at a variety of angles. Soft tissues may be reattached using the porosities of the mesh 382 as suture anchors, or simply as a bioscaffold. If desired, preformed trim lines may be provided by forming predetermined frangible portions in various areas of the mesh, in order to help configuration of the device for a particular patient. For example, as shown in FIG. 27, mesh 400 includes a plurality of trim lines 402 that may be cut to separate the mounting members attached thereto, such as mounting members 404. The separated mounting members 404 and the mesh 400 may then be placed into a patient's hip region 406 as shown in FIG. 28.

FIGS. 29 and 30 illustrate some embodiments of a honeycomb design that may be provided on a mounting member or augment in order to control cement mantle thickness and spacing between said mounting member or augment and an adjacent acetabular shell, augment, bone, or other implant. For example, mounting member 410 of FIG. 29 includes honeycomb portion 412 provided on an attachment surface portion 414 of the mounting member 410. The honeycomb feature 412 may be provided as any desired geometric shape. The mounting member 410 (or, in some embodiments, the augment) may comprise one or more securing holes 416 for receiving a surgical fastener 418 such as a polyaxial screw, cancellous screw, peg, or other securing device. The securing holes 416 may include conventional holes, locking holes, or slots. The holes may be threaded, unthreaded, or partially threaded, and may be fixed or polyaxial. In some embodiments, securing holes 416 may include variable low-profile holes that allow for locking at a variety of angles. The attachment portion 414 of the mounting member 410 may extend generally perpendicularly from another portion 415 of the mounting member 410, and may comprise one or more concave curved surfaces 417 configured to abut an outer portion 422 of an acetabular shell 420, or one or more convex surfaces (not shown) configured to abut an inner portion of a prepared acetabulum.

Referring now to FIGS. 96-102, certain embodiments provide components having porous beaded coatings and methods for their manufacture. Because implants and natural bone usually have different degrees of flexibility, uneven stress distributions may occur. Consequently, when an implant is loaded, there is generally some relative movement at the interface between the bone (more compliant) and the implant (more rigid). Many implants thus employ an intermediate material such as bone cement to reduce the amount of relative movement; however, cementless implants may rely on relative roughness to achieve the same goals.

Historically, small spherical beads, bundles of thin wires, and thermal-sprayed metal have been used to produce the friction necessary to reduce the amount of relative movement. Optionally, screws and/or press-fit features may improve the fixation of implant to bone. Such technologies are generally accepted by the orthopedic surgeon community. However, the geometric nature of these coatings limits the location and size of their porosity. Newer technologies, such as those that employ asymmetric beads or metallic foams have improved the location and size of porosity, but they are difficult to manufacture with favorable surface textures. Remedies have included placing hatch lines into the surface of an already porous coating (e.g., via machining). Other porous surfaces have been manufactured having sharp protrusions at a microscopic level. These protrusions can cause problems when there is even a small amount of relative movement between the bone and implant. The sharper protrusions can dig into the bone and create bone particles or can break off from the implant and create wear particles at the implant-bone interface. In addition to loosening the attachment between the implant and bone, these loose particles can cause harmful complications.

The shortcomings of previous porous surfaces are addressed by providing an implant having a surface that is textured with numerous blunt protrusions on a macroscopic level and has a porous structure an a microscopic level. The blunt protrusions create friction that reduces the amount of relative movement between an implanted component and surrounding bone. The porosity allows the surrounding bone to grow into the implant, and the lack of relative movement between implant and bone facilitates this ingrowth.

A consideration in designing and creating a porous implant having blunt protrusions is the size and density of the protrusions. The protrusions create an area on which the bone initially contacts an implant. If the protrusions are too large or spaced too far apart, the majority of the implant's surface area between the protrusions will be too far from the bone for the bone to grow into the implant, and the bone may be unable to create a solid interface with the implant. In contrast, if the protrusions are too small or located too close together, their effect will be minimal and an implant may encounter the same problems as prior implants with smoother surfaces or surfaces composed of many concentrated sharp protrusions. An ideal surface contains protrusions that are large enough to create the needed friction between the bone and implant and still small enough to still allow for a high degree of bone ingrowth into the porous surface. The protrusions may be any suitable height, and preferably are between about 50 μm and about 2000 μm. For certain applications, it may be preferable to limit the protrusion heights to between 200 μm and 400 μm to achieve the desired level of friction and ingrowth with surrounding bone.

Protrusions on a surface of an implantable component may be any suitable shape or profile desired for a general or specific application of the component. In certain embodiments, each surface protrusion may be a bump shaped as a portion of a sphere above the surface of the implant. Protrusions may also be shaped like wires or any other suitable features, including features common to cementless implants.

Figure 96:
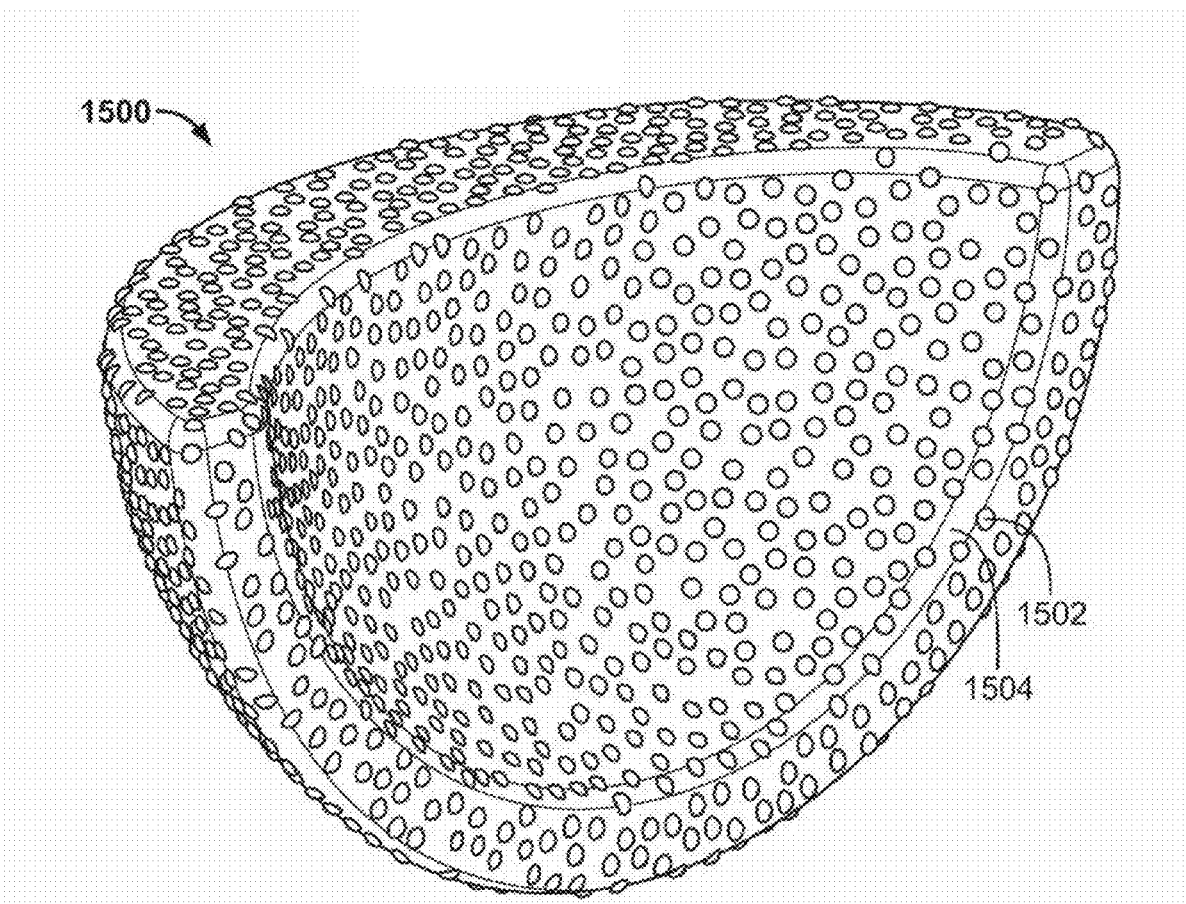
FIG. 96 shows a first view of an illustrative implant component.
Figure 97:
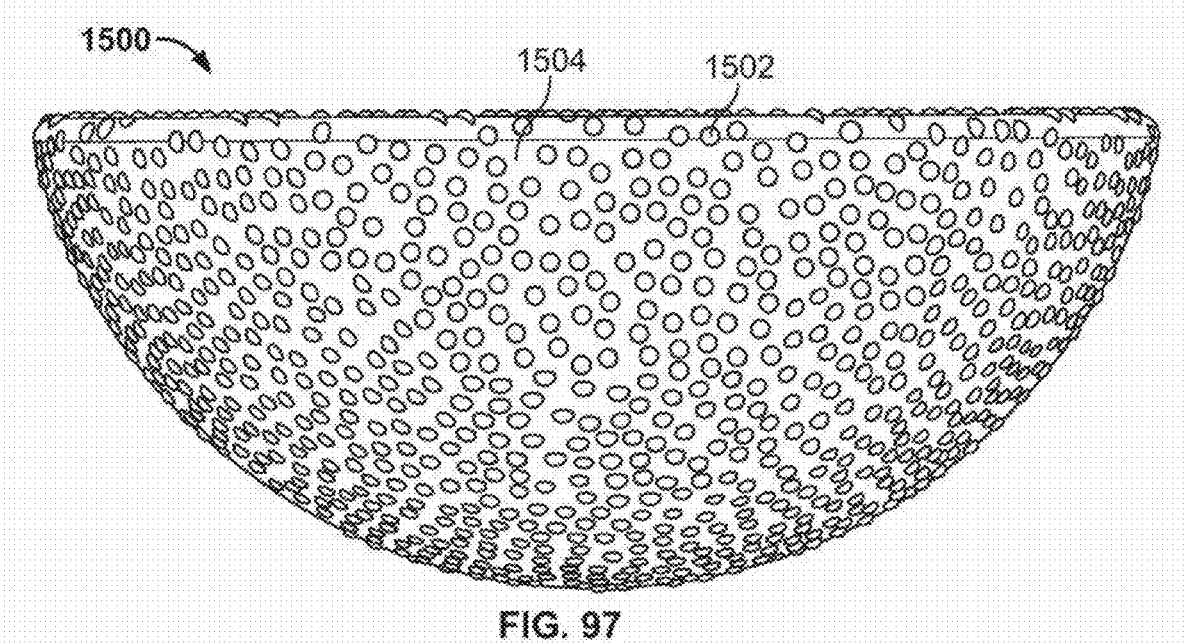
FIG. 97 shows a second view of an illustrative implant component.

FIGS. 96 and 97 show some embodiments of an improved acetabular implant 1500 which may be a whole augment, a portion of an augment, a flange, a plate, other mounting member, a shell, or a cage. The improved acetabular implant 1500 mimics the bumpy outer surface geometries and profiles of clinically-successful porous beads, with the roughness and porosity of a desired ingrowth interface. The surface of implant 1500 is textured by blunt protrusions 1502, which are shaped substantially as hemispherical bumps on the surface of implant 1500. The protrusions 1502 are sized and spaced to create desirable friction that reduces movement of the implant 1500 relative to surrounding bone while allowing the surrounding bone to grow substantially into the porous protrusions 1502 and porous surface area 1504 between the protrusions. In addition to the protrusion heights discussed above, the spacing and density of protrusions 1502 affect the amount of friction and bone ingrowth created. Any suitable density of protrusions 1502 may be used for an implant, and the protrusions preferably occupy between about 10% and about 60% of the surface. The protrusions may be concentrated to a density of between about 0.25 beads/mm$^2$ and about 6 beads/mm$^2$.

Improved acetabular implants, such as the implant 1500 of FIGS. 96 and 97, may be formed by any suitable approach, and may be formed using one of the following four methods.

A first method includes the steps of: 1) providing a mold having a negative impression of a porous beaded surface, 2) providing an implant substrate, which may be solid or porous, to be coated, 3) interposing small asymmetric particles between the implant substrate and said mold, and 4) applying a pressure and/or an elevated temperature to the mold, implant substrate, and small asymmetric particles to create a "green-state" implant (i.e., ready for full sintering) or a final implant (sintered), the implant having a roughened porous coating with an outer surface geometries and profiles mimicking a clinically-proven porous beaded structure with the roughness and porosity of a desired trabecular structure.

A second method includes the steps of: 1) creating a 3D model simulating an outer surface profile of a porous beaded implant, 2) creating a model of an implant substrate volume, 3) applying the 3D model simulating an outer surface profile of a porous beaded implant to the 3D model of the implant substrate volume to create a bumpy pre-form volume, 4) applying an algorithm to fill the bumpy pre-form volume with a desired interconnected porous or otherwise reticulated structure to create a porous implant model, and 5) creating an implant having a roughened porous texture with an outer surface profile geometry mimicking a clinically-proven porous beaded structure using the implant model in a rapid-manufacturing process.

A third method includes the steps of: 1) providing a mold of an implant having an inner surface mimicking a negative image of an outer surface profile geometry of a porous beaded surface, 2) providing a plurality of small asymmetric particles, 3) placing the plurality of small asymmetric particles into the mold, and 4) applying a pressure and/or an elevated temperature to the mold and/or small asymmetric particles to create a "green-state" implant (i.e., ready for full sintering) or a final implant (sintered), the implant having a roughened porous texture with an outer surface profile geometry mimicking a clinically-proven porous beaded structure.

A fourth method includes the creation of a beaded surface on a foam component during the precursor step of making a metallic foam, the method comprising the steps of: 1) providing a mold of an implant having an inner surface mimicking a negative image of an outer surface profile geometry of a porous beaded surface, 2) loading one or more foaming agents into the mold, 3) creating a porous foam component (e.g., polymeric, polyurethane) in the general shape and/or size of said implant, which has an outer surface geometry mimicking an outer surface profile geometry of a porous beaded surface, 4) removing the porous foam component from the mold, 5) applying a binder or binding agent to the porous foam component, 6) applying a plurality of small symmetric or asymmetric particles (or a combination thereof) to the porous foam component having a binder or binding agent thereon, 7) subjecting the porous foam component having binder or binding agent and particles thereon to an elevated temperature to sinter the particles together and/or burn out the foam component to form a "green-state" implant (i.e., ready for full sintering) or a final implant (sintered), the implant having a roughened porous texture with an outer surface profile geometry mimicking a clinically-proven porous beaded structure. Implant has a bumpy outer surface profile and geometries mimicking a clinically-proven porous-beaded structure.

The substrate forming at least an outer portion of the implant may be a bulk porous, reticulated structure resembling a trabecular structure. One or more core portions or outer surface portions of the implant may be solid (e.g., a portion of the implant may be configured for articulation with another implant component). The implant may also include one or more solid internal portions. For example, implant 1500 shown in FIG. 96 may include a solid structural portion on the interior of the implant. The structural portion may be a single solid area or multiple solid areas on the interior of implant 1500 that provide a series of structural ribs to add support to the implant. The solid internal structure may have any suitable shape and configuration, such as a structural lattice similar to rebar in concrete. Illustrative but non-limiting examples areas where the internal structure may be desired include areas around screw holes, the equator region of an augment, or any other suitable area. In some embodiments, a polymer foam could be melted or burned to have the shape of beads—or the foam could be polymerized on a bead-shaped subsurface resulting in the end-product having a bead-shaped surface. In addition to solid internal components, implant 1500 may be coupled with external flanges or other mounting members to provide additional support to the implant. For example, implant 1500 may be implanted along with a flange that is attached to the implant at a first end of the flange and attached to a patient's bone at a second end, for example, with a bone screw secured into a through-hole in the flange. Implant 1500 may also include external solid reinforcements, similar to common strut and brace structures, to provide support to porous sections of the implant.

For rapid-manufacturing technologies, the bead surface geometries and profile could be created virtually and subtracted out from a bulk porous entity or virtual beads could be created and combined with a porous entity. It is the general intent, in some, but not necessarily all, embodiments that the end-product be homogenous. Alternate embodiments of implants may include surface profiles that mimic metallic wire bundles or the peaks and valleys of a thermal sprayed coating. Once a virtual model of the desired geometry is created using modeling software, an implant component having the desired surface profile can be created using any suitable rapid manufacturing techniques. For example, the porous implant can be created using 3D printing technology that uses powdered metal to "print" the modeled implant. In such an approach, a foam may be created having a surface profile that includes protrusions, such as protrusions 1502 in FIGS. 96 and 97, and the profiled foam may then be filled in with powdered metal to create a porous microstructure with the profiled surface. A foam that does not contain the protrusions may also be used to create the porous microstructure with powdered metal, and the desired surface profile with protrusions can then be stamped into the surface of the porous metal implant.

Advantages of implants manufactured this way are that they contain integral porosity with the initially bone-engaging surface profile of clinically-proven porous beads. In other words, the same features providing the traction needed between bone and implant are the same features providing a surface for bone to grow into and around for a rigid and enduring fixation surface. As non-limiting examples, Tables A and B show some examples of potentially suitable bead density (spacing), and diameter.

TABLE A

Chart of number of beads in selected area and average and standard deviation of bead diameter of 50 beads on a shell used with the Birmingham Hip ® Resurfacing system available from Smith & Nephew, Inc. in at least 3 fields of view (SEM, Jeol, Japan)

| Beads in 6.4 × 4.8 mm area | Bead Diamter (mm) | |
| --- | --- | --- |
| 11 | Average D | 1.24 |
| 20 | Std D | 0.12 |
| 20 | | |

TABLE B

Percent solid for typical beaded product for bone ingrowth.

| Product | Company | Implant Type | Percent Solid |
| --- | --- | --- | --- |
| CoCr ROUGHCOAT (2-layer) | Smith and Nephew | Profix ® Femoral | 46.3% |
| CoCr Porocoat (3-layer) | DePuy | LCS ® Knee Femoral | 46.5% |
| CoCr Porocoat (3-layer) | DePuy | AML ® Stem | 50.2% |
| Ti ROUGHCOAT (2-layer) | Smith and Nephew | Synergy ™ Stem | 51.9% |

Wherein, "percent solid" is a 2D measurement of bead density produced by typical metallographic techniques based on the test method disclosed in ASTM F1854, entitled "Standard Test Method for Stereological Evaluation of Porous Coatings on Medical Implants," which is incorporated by reference herein in its entirety.

Figure 98:
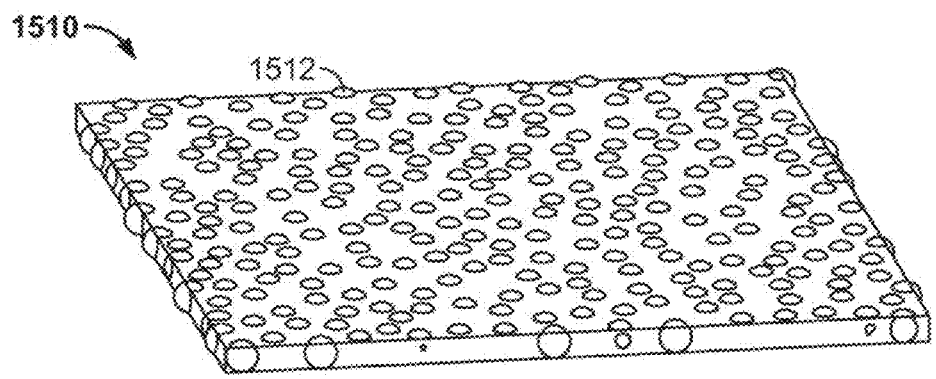
FIG. 98 shows an illustrative implant coating volume having a spherical bead surface profile.

FIG. 98 shows a coating volume 1510 having spherical bead volumes 1512 placed therein, such that the spherical bead volumes 1512 protrude from the coating volume 1510 to form a second coating volume mimicking a spherical bead profile. Alternatively, solid spherical beads may be combined into a porous coating. To create the coating volume 1510, two software models can be created and then merged to form the final model of the porous volume with the profiled protrusion surface. A first model of a macroscopic structure of the volume, including the plurality of bead volumes 1512, can be created in modeling software, and may look substantially the same as the volume shown in FIG. 98.

Figure 99:
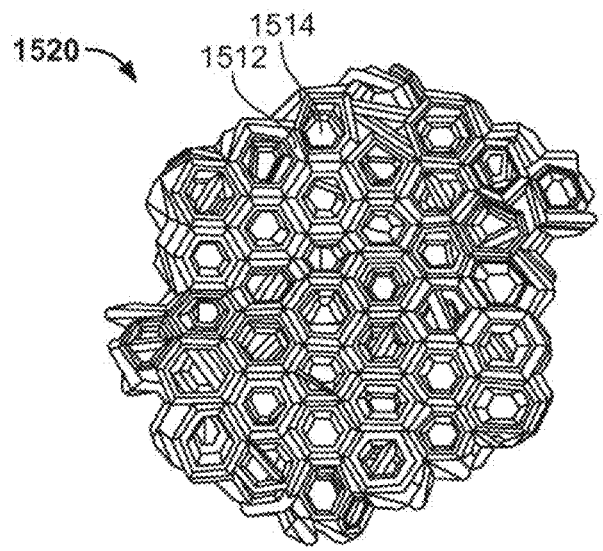
FIG. 99 shows an illustrative unit cell having a porous structure.

A second software model can be created to produce the porous microscopic structure desired for a macroscopic volume, such as the volume shown in FIG. 98. FIG. 99 shows a unit cell 1520 of an exemplary porous reticulated structure, which may configured to fill the coating volume mimicking a spherical bead profile. The unit cell 1520 is made up of a complex structure of struts 1512. The arrangement of struts 1512 creates voids 1514 within unit cell 1520, thus making the desired porous microstructure. The size and arrangement of struts 1512 can be varied to control the number and size of voids 1514. By controlling the size and arrangement of the struts 1512, a desired amount and profile of the porous structure is achieved.

Figure 100:
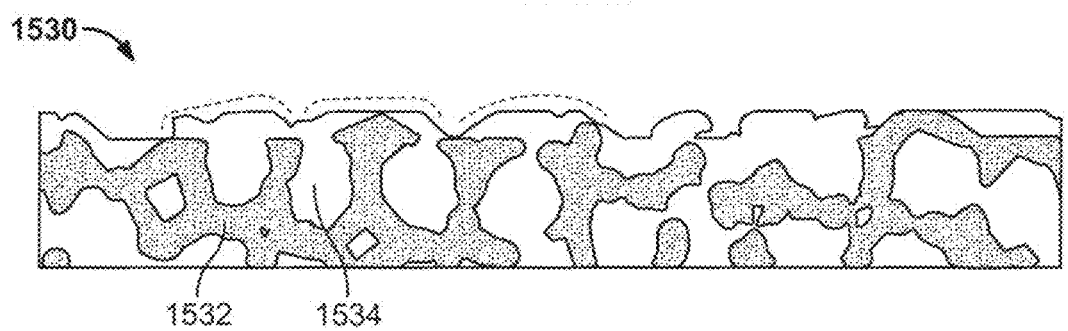
FIG. 100 shows a cross-section of an illustrative coating volume with a spherical bead profile and a porous structure.

FIG. 100 shows a cross section of a coating volume 1530, which may correspond to coating volume 1510 of FIG. 98, mimicking a spherical bead profile after the volume has been replaced with a reticulated structure (e.g., via a repeating unit cell such as unit cell 1520 in FIG. 99 in CAS software, or using any of the 4 methods described above). The finished coating volume 1530 exhibits both the profiled macrostructure and porous microstructure. The dotted lines in FIG. 100 outline the surface profile of coating volume 1530 and shows the protrusions that create a bumpy surface that produces friction with bone when implanted. The microstructure of coating volume 1530, made up of a combination of solid structure 1532 and voids 1534, creates a porous implant into which surrounding bone can grow to fill in voids 1534 and create a solid mating of implant and bone.

Figure 101:
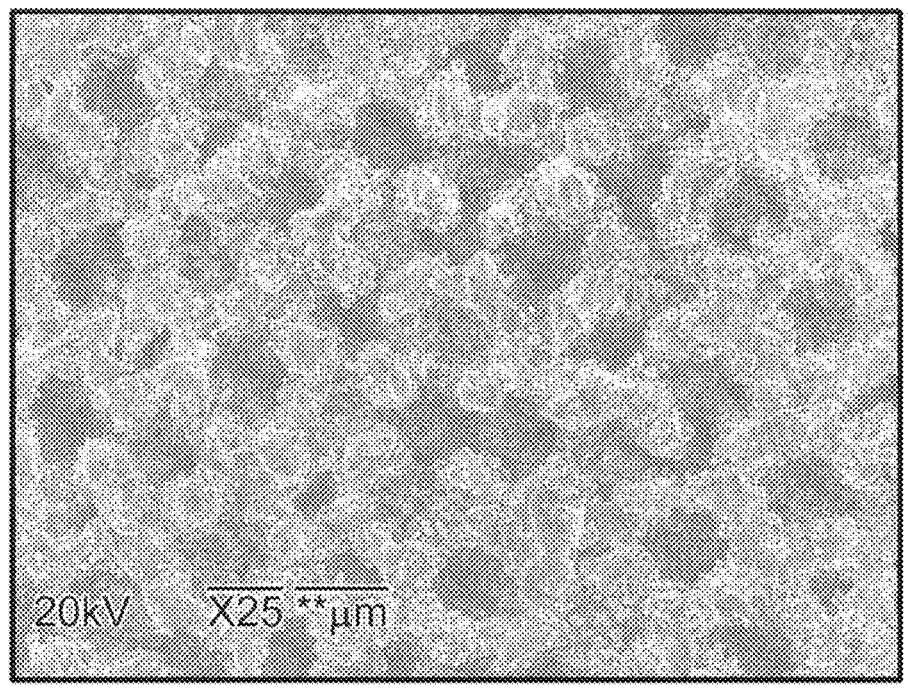
FIG. 101 shows a first illustrative SEM image of a porous surface.
Figure 102:
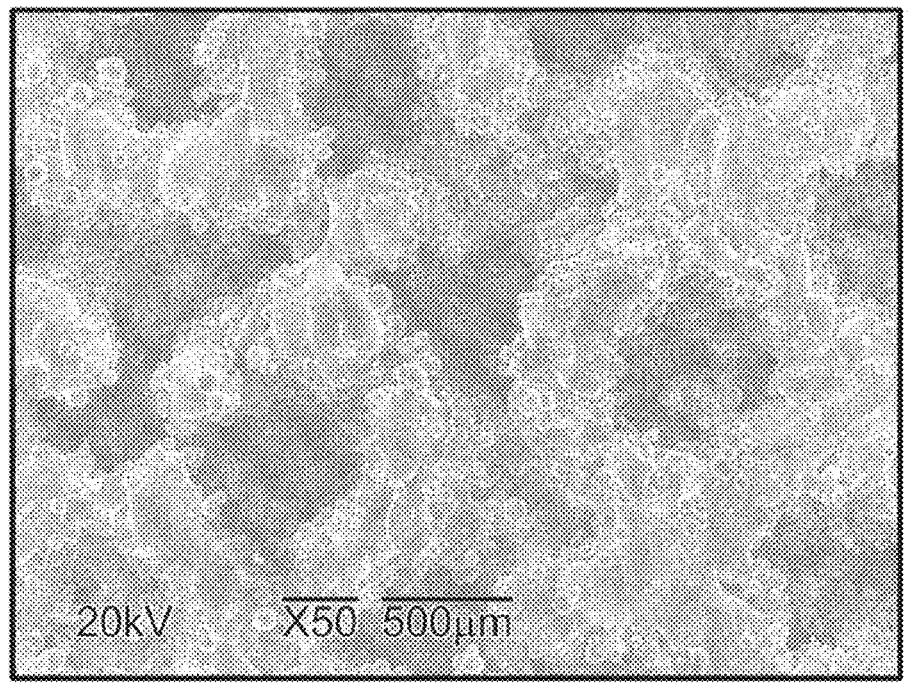
FIG. 102 shows a second illustrative SEM image of a porous surface.

FIG. 101 shows an SEM image 1540 taken at 25× magnification of the surface of a part made by the disclosed method. Surface topography is not apparent with this view. FIG. 102 is an SEM image taken 1550 at 50× magnification of the structure made with the disclosed method. The structures shown in FIGS. 101 and 102 exhibit the porous microstructure discussed above with respect to coating volumes 1510 and 1530, and can be created by merging a solid macrostructure with a porous microstructure model, such as the unit cell 1520 in FIG. 99.

As a further non-limiting example, the following chart shows some additional exemplary parameters that have proven to be useful for various embodiments. In the chart below, MVIL refers to Mean Void Intercept Length, which is another way of characterizing the average pore size, particularly in structures where the pore shapes and sizes are not uniform. On generally known definition of MVIL is "measurement grid lines are oriented parallel to the substrate interface. The number of times the lines intercept voids is used with the volume percent void to calculate the mean void intercept length."

|  |  | Electron beam melting (EBM) | Direct metal laser sintering (SLS) Eurocoating EOS | Landon Structure (FIG. 99) |
| --- | --- | --- | --- | --- |
| Avg. Strut Thickness (μm) |  | — | 275-450 (360) | 275-400 (340) |
| Avg. Pore Size: MVIL |  | 300-920* (565) | 450-690 (560) | — |
| Average Pore Size: (μm) | Pore | 900-1300* | 1310 ± 280 | 1970 ± 40 |
|  | Window | — | 370 ± 100 | 830 ± 150 |
|  | Not Specified | 670-1340 | 600 ± 100 | — |

*(fine, medium, and coarse structures)

It is generally desirable to provide between about 60-85% porosity. Pore sizes may generally range between about 50-1000 microns. In the above example, the smallest pore size provided was about 300 microns, and the smallest window was about 595 microns across at its largest diameter. It will be understood that this example is intended to be non-limiting and provided for illustrative purposes only.

The systems, methods, and devices described herein to create implants having both a profiled macrostructure and a porous microstructure can allow a medical professional to utilize customizable, patient-specific implants. A customized implant can be efficiently created using the rapid manufacturing techniques discussed herein by merging two or more models of an implant and then printing the modeled component. This could allow a medical professional, such as an orthopedic surgeon, to order an implant specific to a single patient, including modeling the size and shape of the implant to fit defects or other unique features of the patient's anatomy. This process can also be automated by taking bone scans of the patient's anatomy or using other available medical imaging and modeling techniques to automatically create a 3D model to use for rapid manufacturing.

The ability to customize an individual implant also allows a medical professional to adjust the detailed macrostructure and microstructure of the implant to fit the needs of a particular application. For example, an orthopedic surgeon can adjust the macrostructure of the implant by selecting the shape, height, density, or other characteristics of protrusions on the surface of the implant. The surgeon can also customize the number and size of voids within the implant to achieve a desired porosity for the implant. In some embodiments, the surgeon may also select the configuration of the macrostructure of the implant. For implants that include internal solid portions for strength and structure, the surgeon can customize the size and location of the internal solid portions to provide the structure in certain non-uniform areas of the implant where increased strength is needed. Illustrative but non-limiting examples areas where increased strength may be desired include areas around screw holes, the equator region of an augment, connection sites of augments, augment areas that are thinner than others, or any other suitable area. The surface profile of the implant can also be non-uniform if different areas of the implant require different levels of friction or surface area for a bone interface. A surgeon may want a higher concentration of surface protrusions in certain areas of the implant, such as areas that experience higher levels of stress, and a lower concentration of protrusions, or no protrusions at all, in other areas.

Porous implants described herein allow for an implant to provide good contact surface area and friction regardless of the quality of bone into which an implant is implanted. For example, patients who have soft spongy bone may need features that are longer, and a lower number of those features. Patients with hard dense bone may require features that are shorter, but a higher number of those features to create the same fixation in the bone. The specific requirements of a patient's anatomy and bone quality can be accommodated by the individualized design options provided by the porous implants described herein.

Referring now to FIGS. 103-115, there are some instances during hip arthroplasty when an expandable augment or expandable shell implant may be desired. Initial fixation during hip arthroplasty is important, but the shapes of conventional augments may not be ideal and conventional bone preparation for receiving shaped augments and shells may not be precise. For example, hand-reaming is typically used to prepare an affected area of bone and create a shaped void for receiving an augment or shell. Although surgeons try not to remove more bone than necessary, in some instances, the surgeon may unintentionally create a slightly larger opening or an oblong void that does not precisely fit the shape of outer surfaces of an augment or shell to be implanted. Moreover, poor bone quality may affect the press fit and/or total interference between bone and an augment or shell even if the bone is well-shaped to fit external geometries of the augment or shell. Cement, allograft, and bone pastes have been used in the past to fill in the gaps between augments, bone, and implants. However, FIGS. 103-115 show several embodiments of augments, shells, and/or mounting members that may be expanded to compensate for poor bone quality or non-precise bone preparation (e.g., over-reaming). The augments, shells, and/or mounting members are preferably manufactured by a rapid manufacturing method (e.g., stereolithography, 3D-printing, selective laser sintering (SLS), electron beam welding (EBM), etc.). The augments, shells, and/or mounting members may also be machined or casted from a bulk material and then plasma-sprayed or otherwise coated with a surface texture or porous ingrowth structure. They may have a generally porous outside for contact with bone, and may have one or more non-porous external or internal surfaces and volumes for attaching to implants or improving strength and flexibility of the augments, shells, and/or mounting members.

The expandable augments, mounting members, or other implants, including shells and cages, have at least first and second portions that are connected, for example, by a soil or adjustable hinge portion or by a wire fixation or other suitable means, and the connections allow for separation of the portions. The separation is controlled by actuating an expansion member disposed between the at least two portions. As shown in FIGS. 103-107, an expansion member 1602, non-limiting examples of which may include a wedge, fastener, mandrel, screw, or other component, is inserted into an augment in order to expand the augment once it is placed inside or adjacent to a prepared bone cavity. The expansion member 1602 is actuatable, for example, by a surgical tightening rod or driver. A torque wrench can be utilized to ensure that the augment, shell, or mounting member has a proper interference or "press-fit" with surrounding bone, without fracturing the bone. Alternatively, as shown in the expansion member 1630 in FIG. 108, an expansion member itself may comprise torque-limiting means such as a frangible-driver portion 1632 with a calibrated circumferential notch or groove 1634 that is designed to shear off after a specified torque is reached. By controlling the amount of torque applied to an expansion member, a proper press fit and interference with surrounding bone is achieved.

As shown in augments 1600, 1610, and 1620 in FIGS. 103-107, the outer geometries, shape, or size of an augment may be initially biased inwardly or undersized, and then expanded with an expansion number, which may alternatively comprise or be provided by a shape memory polymer or wedging action from a setscrew. For example, two portions 1604 and 1606 of augment 1600 in FIG. 103 are initially biased toward each other but are displaced away from each other upon actuation of the expansion member 1602. An augment, shell, or mounting member may have one or more flexible hinge portions, such as hinge area 1608 of augment 1600 to create a fulcrum for two or more other augment, shell, or mounting member portions to move in relation with each other. The geometries or portions of the augment, shell, or mounting member may also or alternatively be connected by a wire, screw, staple, threaded expansion rod or other structure, which holds the portions together but still allows them to expand under actuation of the expansion member. Additionally or alternatively, the augment or mounting member may have one or more slit portions, such as slit 1609 of augment 1600, to allow for even radial expansion. In certain embodiments, there may be a slit portion, a cruciform, or any other appropriately shaped cut or division in the augment, shell, or mounting member positioned a set desired distance or a set angle from one another so that the augment, shell, or mounting member portions expand evenly when one or more expansion members are positioned.

In FIGS. 104 and 105, an augment is provided that has two augment portions 1612 and 1614 separated by a slit 1616 and hinged together by a flexible binge portion 1618. It will be understood that additional or fewer augment portions may be provided, and that the portions may also be provided on one or more mounting members and that the following description would be related thereto. The flexible hinge portion 1618 allows the augment portions 1612 and 1614 to move away from each other upon insertion of an expansion member 1602, which is shown as an expansion screw, but may be any other type of expansion member, such as a wedge, a plug, a bone screw, a set screw, a member having a smooth bore with a taper, a shape memory plug, or any other component, which, in turn, expands the entire augment. While not shown, one or more additional slits and/or flexible hinge portions may be added to allow a more uniform radial expansion.

The augment 1610 shown in FIGS. 104 and 105 may include one or more porous portions to facilitate bone ingrowth into the augment. For example, each of augment portions 1612 and 1614 may be porous. All of augment 1610 may be porous for bone ingrowth, or some portions of augment 1610 may be porous and some may be solid to provide strength to augment 1610. It may be desirable to provide a solid core in augment 1610 surrounded by porous outer portions to provide needed strength at the interface between augment 1610 and expansion member 1602 while still providing porous portions 1612 and 1614 for bone in growth. For example, the inner core of augment 1610 outlined by the dotted line in FIGS. 104 and 105 may be solid to provide needed strength around expansion member 1602 while augment portions 1612 and 1614 may be porous for ingrowth.

FIGS. 106 and 107 show an expandable augment 1620 that may be implanted and expanded similar to augments 1600 and 1610 discussed above in FIGS. 103-105. In particular, Augment 1620 includes two portions 1622 and 1624 that move radially outward when expansion member 1602 is inserted into augment 1620. Augment 1620 may be made of a solid material with surface treatment, a porous material, or may be a combination of solid and porous sections to provide both strength and bone ingrowth for the augment. The dotted line in FIGS. 106 and 107 may separate a solid core of augment 1620 that surrounds the threaded hole for expansion member 1602 from a porous peripheral portion of the augment, as discussed above with respect to FIGS. 104 and 105. The solid and porous portions may be located and separated within the augment in any suitable geometry, as shown in the different solid and porous geometries in augment 1610 of FIGS. 104 and 105 and augment 1620 of FIGS. 106 and 107.

During replacement or revision surgery, a surgeon may use any of the augments shown in FIGS. 103-107 to fill bone voids surrounding an implant. Depending on the anatomy of a certain patient and the surgical procedure, the augment may be placed into a bone void either before or after an implant shell is inserted. The augment may also be attached to the shell before Implantation, before expansion begins, or after the augment is expanded to its final size. The surgeon positions the augment within the bone void in a contracted state such that there is space in the bone void that is not initially filled by the augment. The surgeon then activates an expanding component of the augment, for example, by turning a set screw with a surgical tool, to cause two or more portions of the augment to expand. The surgeon expands the augment until the augment fills substantially the entire bone void and abuts both the implanted shell and the patient's bone. The augment is then fixed in place, either by mechanical fasteners such as screws or by allowing surrounding bone to grow into ingrowth surfaces on the augment.

Because the augments, shells or mounting members shown and disclosed in FIGS. 103-115 are slowly expanded in-situ within the prepared bone void, impaction forces are avoided, but bone interference and press-fit is still achieved. Moreover, the risks of bone fracture, sitting too proud from a bone surface, and too much bone interference/press-fit (all generally being associated with impaction techniques) are mitigated or eliminated. It should be noted that one advantage of the devices shown in FIGS. 103-115 is that augments, shells, or mounting members may be more easily removed during revision surgeries due to the slits and flexible hinge portions provided thereon.

For example, in a revision hip surgery, a surgeon may first remove the expansion member and then simply impact the augment, shell, or mounting member radially-inwardly from a side portion to fold the augment or mounting member, urging the augment or mounting member portions towards each other and away front outer areas of bone ingrowth. In another example, the one or more slits generally "compartmentalize" the augment, shell, or mounting member into several smaller outer ingrowth surface areas. Therefore, each augment, shell, or mounting member portion may be removed individually from well-fixed bone with greater ease than for a well-fixed non-adjustable/expandable implant that may have an entire outer solid surface that is well-fixed with bone ingrowth. Lastly, slits may facilitate the entry of a saw blade, osteotome, or other cutting tool (e.g., a Midas Rex® pneumatic tool by Medtronic) for removing the augment, shell, or mounting member from well-fixed bone. The threaded openings provided in the augment, shell, or mounting member may be engaged by a threaded distal end of a slap hammer tool for removal from well-fixed bone in a manner similar to that used for hip stem removal during revision total hip arthroplasty (THA).

Figure 109:
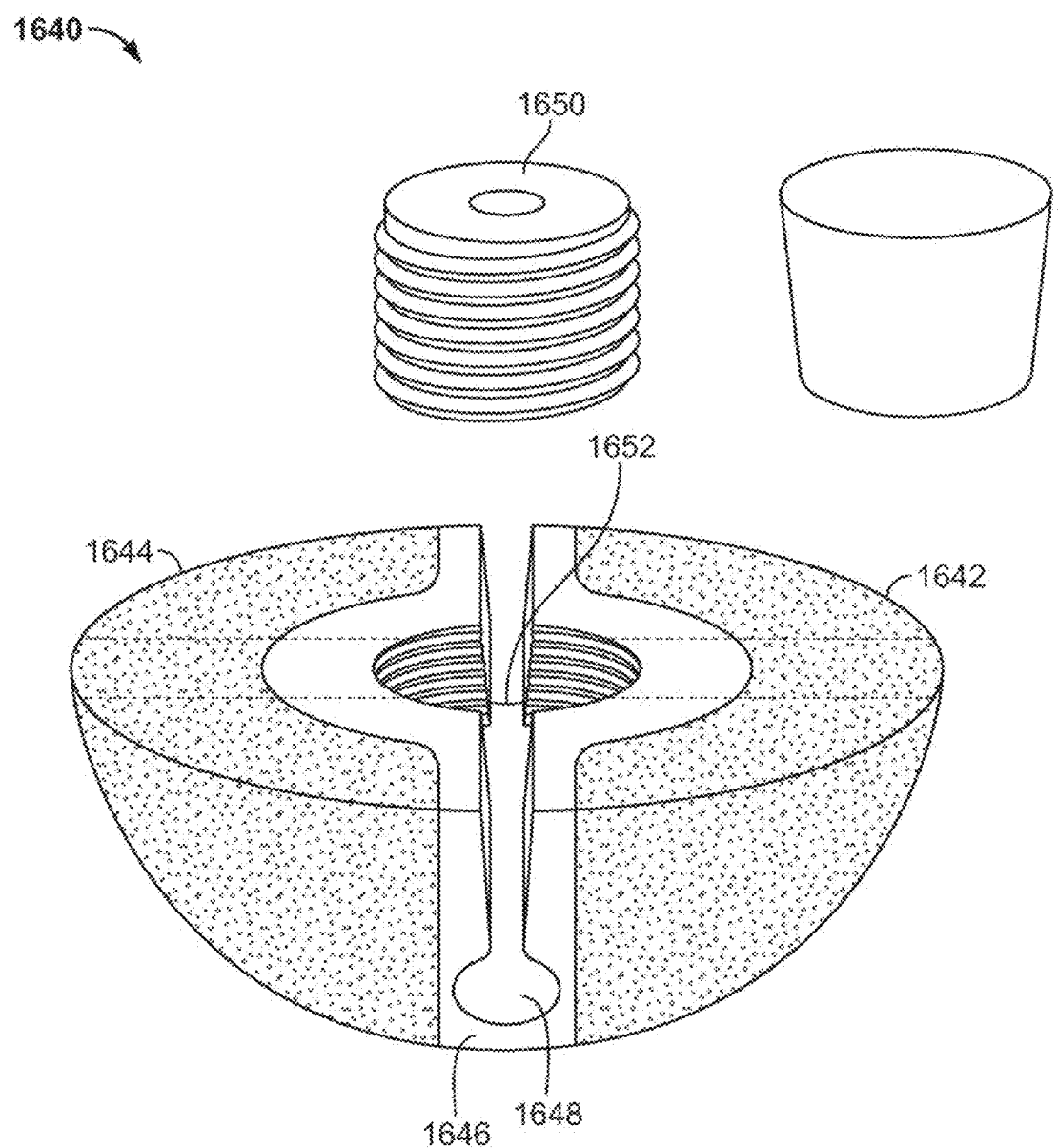
FIGS. 109-113 show illustrative expandable/adjustable augments.

FIG. 109 shows an expandable/adjustable augment 1640 related to the embodiments described above and shown in FIGS. 103-108. The augment 1640 may have any outer peripheral shape to accommodate various bone voids and defects. While the entire augment 1640 may be solid and simply surface textured to improve bone ingrowth properties, volume portions of the expandable/adjustable augment 1640 may be fully porous. In FIG. 109, the augment 1640 comprises at least two fully-porous volume portions 1642 and 1644 separated by a solid portion 1646. The fully-porous volume portions 1642 and 1644 are movable with respect to each other. The solid portion 1646 may extend all the way to an outer periphery of the augment 1640 proximate a hinge region 1648 as shown in order to better distribute stresses and maintain the integrity of the struts and nodes of the ingrowth structures contained within the fully-porous volume portions 1642 and 1644. This design may help reduce cracks and fatigue failure. As shown in dotted lines in FIG. 109, the expandable/adjustable augments disclosed herein may comprise additional intersecting slits to separate portions of the augment into multiple portions, such as thirds, quarters, or any other appropriate division.

Figure 110:
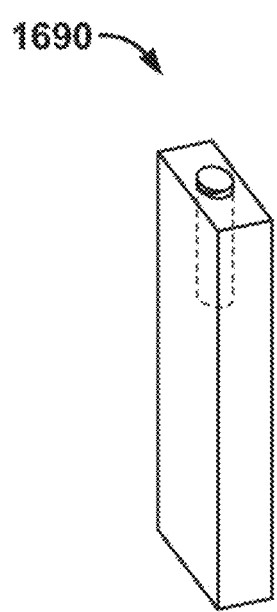
Figure 111:
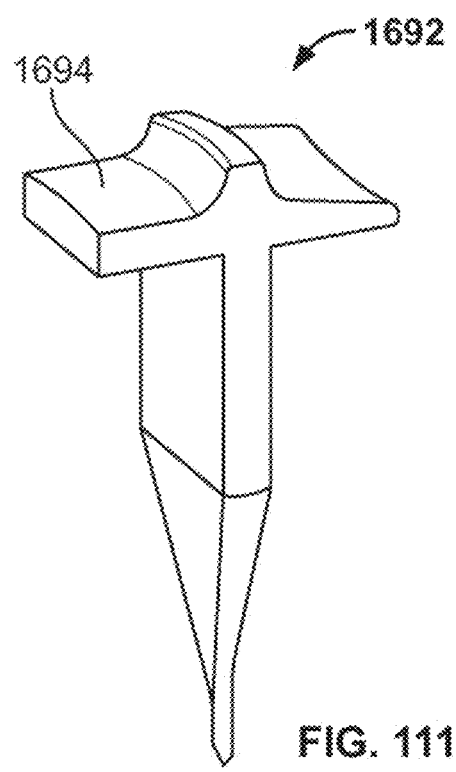

An expansion member 1650, which may be any of the above-described expansion members such as a screw, wedge, or plug, may be inserted into the augment 1640 to expand the augment 1640 in at least one direction, such as in a radial, direction, or a width. A receiving portion 1652 may be provided on the expandable/adjustable augment 1640 which receives the expansion member 1650, and is generally complementary to the shape of the expansion member 1650. For example while it may not be shown, either the expansion member 1650 or the receiving portion 1652 may be tapered, undersized, oversized, threaded, shim or wedge-shaped, threaded, smooth, symmetrical, non-symmetrical, corneal, cylindrical, concentric, eccentric, and may be provided with various cross-sectional geometries, non-limiting examples of which are shown in FIGS. 110 and 111. In some non-limiting examples, the expansion member 1650 may comprise a screw, a quarter-turn fastener, a shape-memory plug, a wedge, or a settable or injectable material such as an injectable polyurethane, or packed graft material.

FIGS. 110 and 111 show non-limiting examples of a wedge expansion member for use with expandable/adjustable augments and mounting members disclosed herein. FIG. 110 shows a locking wedge 1690, and FIG. 111 shows a locking pin 1692 with a removal head 1694, which, when inserted into a recess of an expandable/adjustable augment or mounting member, may keep the augment or mounting member in a desired expanded state. The wedge expansion member shown in either FIG. 110 or 111 may be inserted at different depths within the expandable/adjustable augment to expand or contract the expandable/adjustable augment or flange to different diameters or peripheral shapes.

Figure 112:
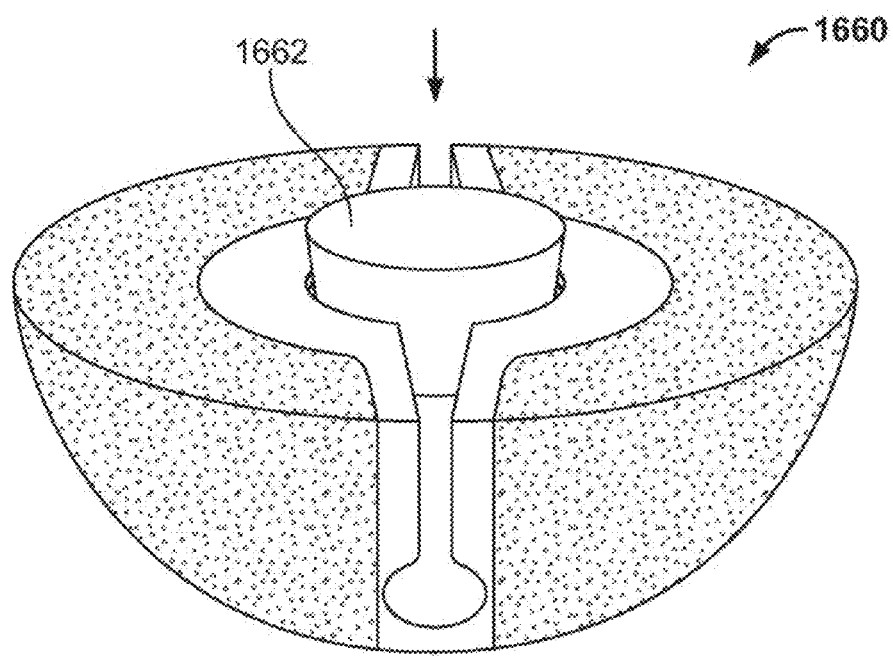

FIG. 112 shows an expandable/adjustable augment 1660 that is similar to the ones shown in FIGS. 103-109, incorporating a tapered plug expansion member 1662. The tapered plug expansion member 1662 may have an inclined or otherwise tapered outer surface that wedges against a complementary inclined or otherwise tapered inner surface provided within the body of the expandable/adjustable augment 1660.

Figure 113:
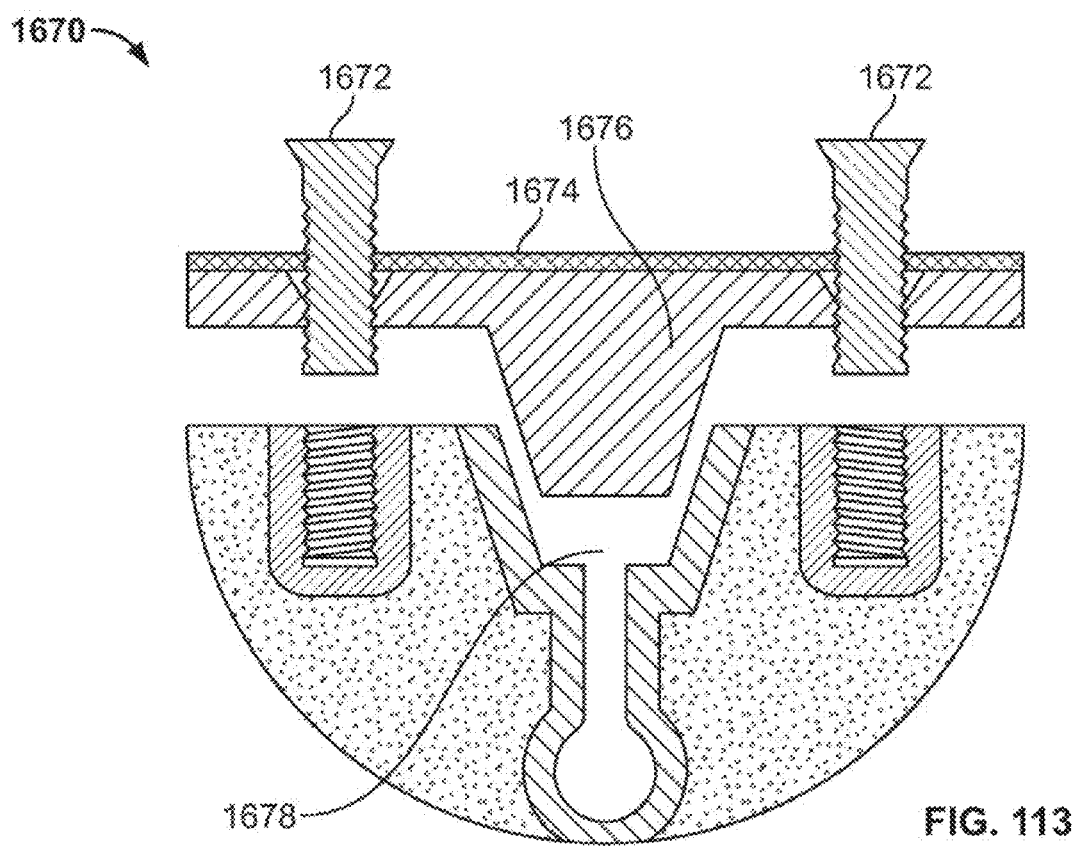

FIG. 113 shows an expandable augment 1670 similar to the one shown in FIG. 112, wherein expansion of the augment 1670 is controlled by the turning of one or more positioning screws 1672. An upper plate member 1674 having an expansion member 1676 provided thereon is placed on top of an expandable augment portion. As the positioning screws 1672 are introduced and tightened, the upper plate member 1674 moves closer to the augment 1670, and the expansion member 1676 moves into a receiving portion 1678 located adjacent an expandable region in the augment 1670 to bulge the augment 1670 radially-outwardly.

Figure 114:
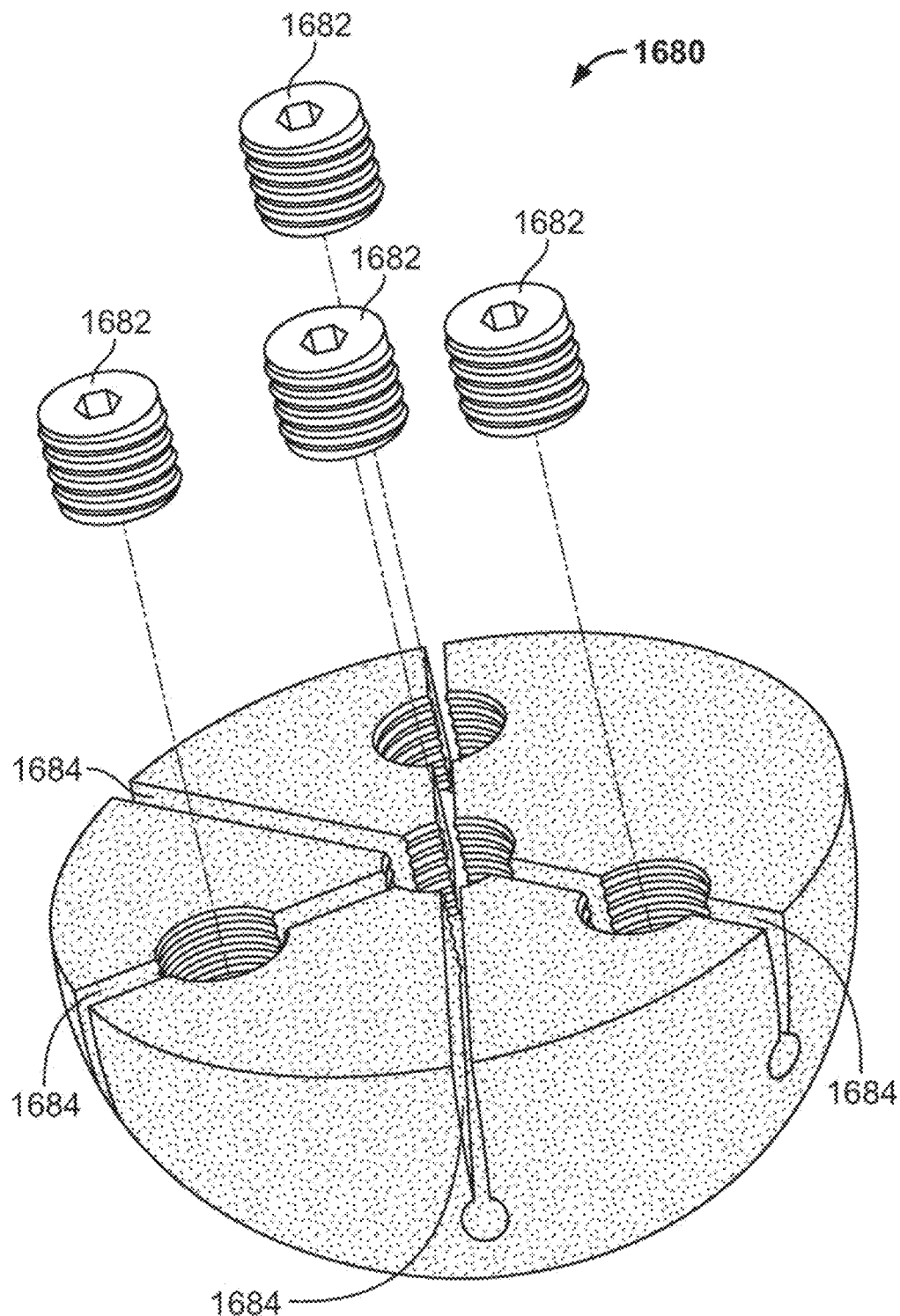
FIG. 114 shows an illustrative expandable/adjustable augment with multiple expansion screws.

FIG. 114 illustrates an expandable/adjustable augment 1680 similar to the ones shown in FIGS. 103-113, wherein expansion of the augment 1680 is controlled by the turning of multiple expansion screws 1682. The augment 1680 may be configured to expand by different amounts in different regions of the augment 1680. A plurality of slots 1684 may split the augment 1680 into several portions that are moveable relative to each other. The expandable/adjustable augment 1680 may be used to secure a press fit around its entire perimeter even if a surgeon wobbles a reamer, or if the bone void is prepared with a slightly different shape and/or size than the undeformed expandable/adjustable augment 1680.

Figure 115:
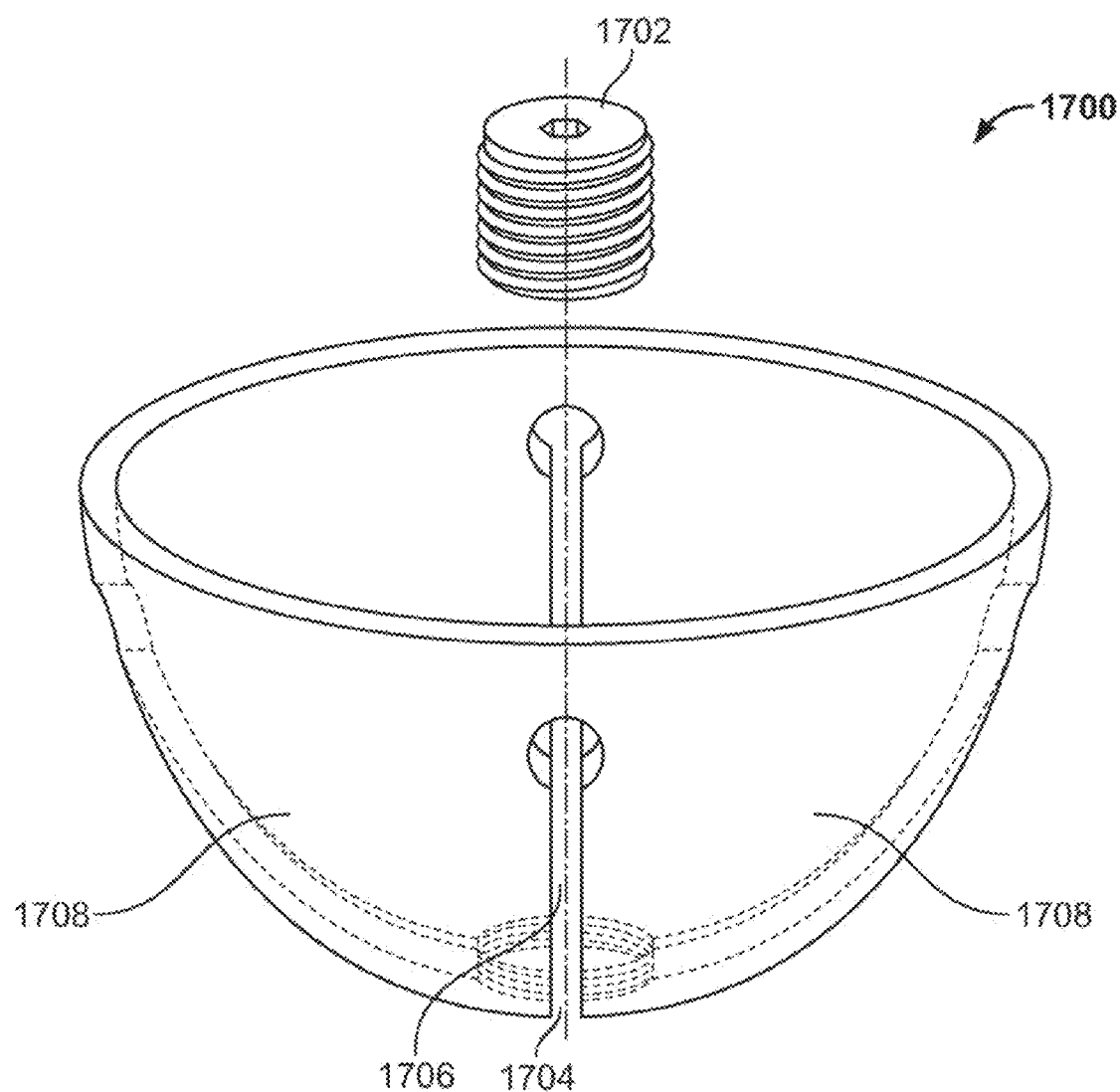
FIG. 115 shows an illustrative expandable/adjustable implant shell.

FIG. 115 shows an expandable/adjustable implant shell 1700 that provides an implant having an adjustable size to allow for precise fit to a reamed bone void, similar to the expandable and adjustable augments discussed with respect to FIGS. 103-114. The shell 1700 has a threaded hole 1704 that receives an expansion member 1702. Expansion member 1702 may be a mandrel, screw, wedge, plug, or any other suitable expanding component. Depending on the expansion member used, threaded hole 1704 may be replaced by a non-threaded hole and may have any shape or contour needed to receive expansion member 1702 and cause the shell 1700 to expand. The shell 1700 has slits 1706 cut into shell 1700 to allow for flexibility needed to expand the shell. The slits 1706 create multiple segments 1708 around the shell that can be forced outward for expansion. Any number of slits 1706 and segments 1708 may be used to provide the desired amount of flexibility and expansion. As expansion member 1702 is placed into the shell 1700, for example, by a surgeon manually screwing expansion member 1702 into threaded hole 1704, the shell 1700 expands as segments 1708 are forced radially outwards, increasing the profile of the shell 1700 and allowing the shell 1700 to fill surrounding bone voids.

Expandable and adjustable augments may also be used to facilitate removal of the augments in revision surgeries. Implant shells occasionally require revision surgery due to wear of the implant or changes in a patient's anatomy, and revision surgeries to improve the implants may involve removing augments as well as implanted shells. An expanding augment that is used to fill a patient's bone void can make the removal process easier by allowing a surgeon to reverse the expansion and return the augment to its contracted state for quick removal. A modified expandable augment that provides for convenient removal is shown in FIG. 166.

Figure 166:
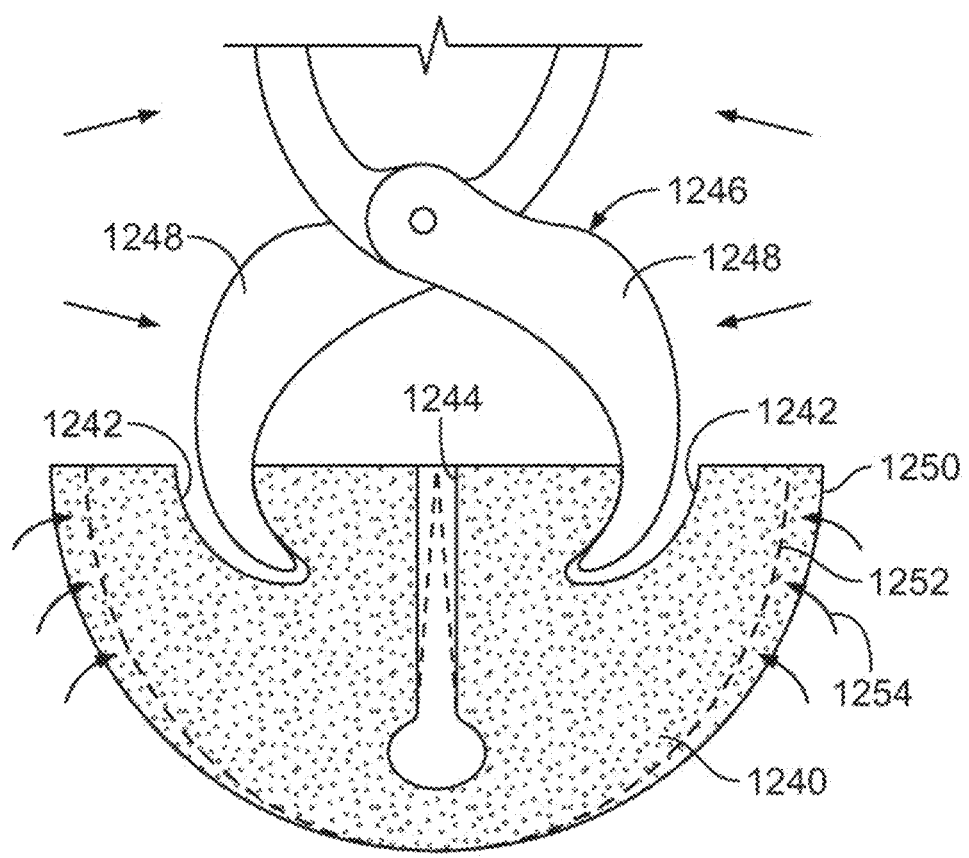
FIG. 166 shown an illustrative augment having recess portions alongside a split portion.

FIG. 166 shows an augment 1240 that may be provided with recess portions 1242, which, in this embodiment, are shown alongside a split portion 1244, but which can be provided anywhere on the augment 1240, or even on augments not having a split portion. Recess portions 1242 are configured to receive a clamp or other instrument 1246. Recess portions 1242 may be curved or otherwise shaped to correspond to the instrument to be used. For removal of the augment 1240, arms 1248 of the instrument 1246 may be inserted into recess portions 1242 in order to securely grasp the augment 1240, squeeze the augment 1240, and pull the augment 1240 from bone. The mechanical advantage of the clamp 1246 causes the augment 1240 to squeeze or shut slightly or otherwise flex inwardly, particularly in split augment embodiments, so that the augment 1240 may be removed, even if well fixed in bone.

The split augment 1240 shown may move from a first position, shown as the outer boundary 1250 in solid lines, to a second compressed position, shown in dotted lines 1252 in a direction shown by inward arrows 1254. This compression allows removal of the augment 1240 in a relatively easier and more efficient manner than chipping away at the augment 1240 or cutting the augment 1240 out in separate portions with a blade.

Recess portions 1242 and instrument 1246 may also be used to initially position or introduce the augment 1240 into a bone void. Once positioned, an expansion member, such as any of the expansion members shown and described herein, may be used to expand and lock the augment 1240 into place. Although not shown, it may be desirable to insert plugs or any other appropriate recess portion cover to prevent bone ingrowth therein. Alternatively, bone graft material or injectable polymers or other filler material may be inserted into recess portions, particularly if recess portions are to be used solely for insertion and are not envisioned for use in subsequent removal.

FIGS. 116 and 117 are a front perspective view and a back view, respectively, of an augment according to certain embodiments. In FIGS. 116 and 117, augment 910 is in the shape of a staple and is provided with a number of projections and optional fixation elements. For example, augment 910 includes two projections 920 extending from a base portion or member 970, although it is possible that the augment 910 may have three or more projections that extend from a base member as described below. As shown, the projections 920 may be disposed in substantially the same direction from the augment 910 defined by the respective axis of each projection, with a gap 925 between the two projections 920. In certain embodiments the projections 920 may be angled or otherwise offset such that the projections 920 are not disposed in the same direction from the augment 910; however, there may still preferably be a gap disposed between the two projections 920. Furthermore, although the length of the projections 920 is shown as being substantially the same, it will be understood that the length of one of the projections 920 may be different than the respective length of the other projection. The base member 970, or the projections 920, or both, may have a surface that is substantially arcuate, for example, in order to complement an outer curved surface of an acetabular shell or other implant.

Other fixation elements include screw holes 930 and cement troughs 960. The fixation elements fix the augment 910 in place when implanted. Each fixation element may connect the augment 910 to a patient's bone, an acetabular shell, or both. The augment 910 may also include a connection element 940 on base member 970, for example, at the center top of the augment 910. In certain embodiments, connection element 940 is a threaded opening that may be attached to the end of a drive handle (e.g., driver handle 1060 of FIG. 122) for assisting with the implantation of the augment 910. However, the connection element 940 may be a tapered connection, a quick-connect, or any other type of fitting. The augment 910 may further include timing marks 950 to allow the augment 910 to be properly placed within the hip bone. Installation of the augment 910 is described in further detail below.

FIG. 118 is a top view of an augment installed on an acetabular shell. Augment 860 may be similar to augment 910. As shown, augment 860 is positioned next to acetabular shell 862 such that timing marks 864 disposed on the augment 860 are aligned with timing marks 866 disposed on the acetabular shell 862. The base member of augment 860 has an arcuate surface that contacts the complementary curved outer surface of the acetabular shell 862. As described above, an augment such as augment 860 may be fixed to the acetabular shell 862, a patient's bone, or both, via optional fixation elements such as screw holes and cement troughs.

FIGS. 119-122 illustrate exemplary methods for installing an augment 910 into a patient's joint according to certain embodiments.

Figure 119:
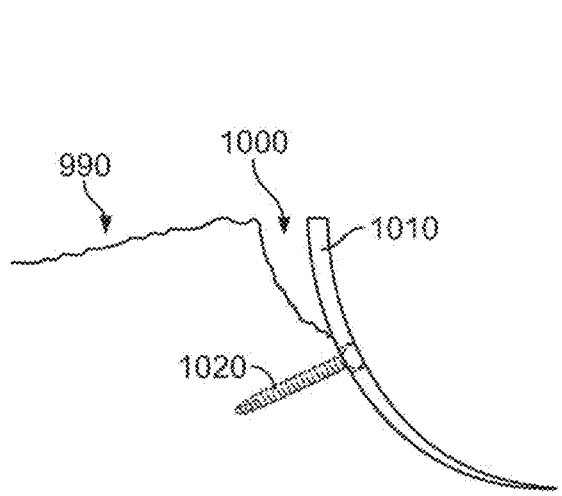
FIGS. 119-122 illustrate exemplary methods for installing an augment into a patient's joint.

FIG. 119 is a cross-sectional elevation drawing of an acetabulum 990 and an acetabular shell 1010. The acetabulum 990 would have been prepared to receive the shell 1010 by reaming, rasping or the like. Bone screws 1020 or other appropriate fixation devices have also been installed to secure shell 1010. Also shown is bone deficient area 1000. This area 1000 is a void space extending from the outer wall of the acetabular shell 1010 to the acetabulum 990.

Figure 120:
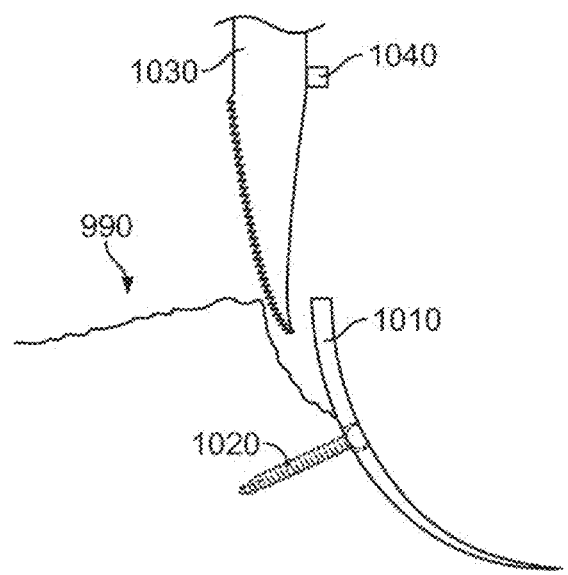

In FIG. 120, the acetabulum 990 is prepared for the augment 910 by use of broach 1030. The broach 1030 can be of any kind useful for rasping or reaming bone. For use with the augments described herein, the broach 1030 is typically provided with a depth stop 1040. Depth stop 1040 prevents the broach 1030 from removing too much bone by catching, for example, on the rim of acetabular shell 1010. The broach 1030 may have roughly the same cross-sectional profile and overall shape as the augment 910 and is typically sized to allow the augment 910 to be wedge-fitted into bone deficient area 1000. The broach 1030 may also have a slot provided therein to allow the broach 1030 to slide on either side of the installed screw 1020 to clear away bone on both sides of the screw 1020.

Figure 121:
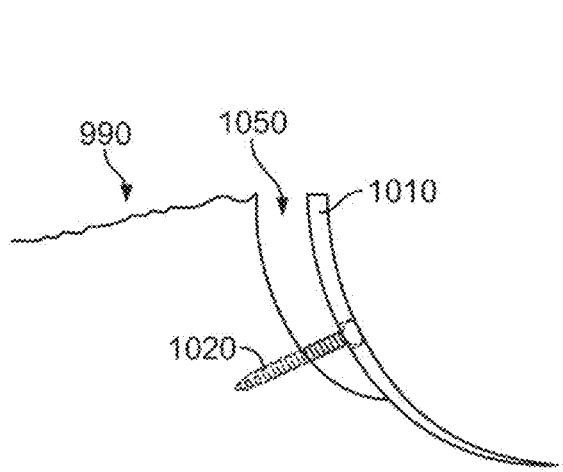

In FIG. 121, the acetabulum 990 has been prepared for the augment 910. Bone deficient area 1000 has been replaced with prepared space 1050 between the acetabulum 990 and the acetabular shell 1010, the prepared space including screw 1020.

Figure 122:
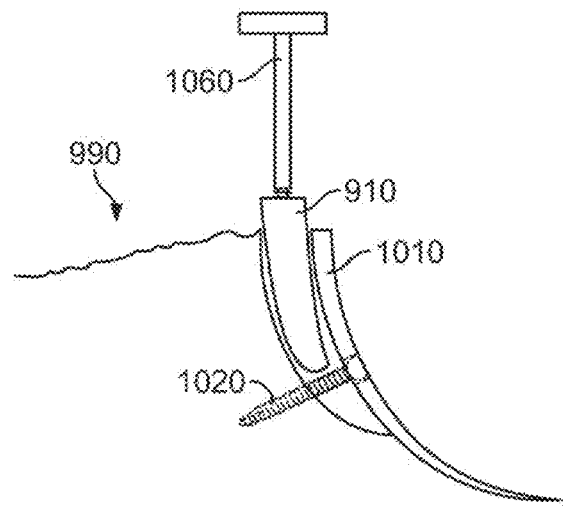

The next step in the procedure is illustrated in FIG. 122. The augment 910 is attached to driver handle 1060 and inserted into prepared space 1050. During insertion, the surgeon matches the timing marks 950 on the top of the augment 910 to timing marks (e.g., timing marks 886) on the acetabular shell 1010 to ensure that bone screw 1020 is avoided. The augment 910 is inserted into the prepared space by positioning the augment around the screw 1020 (or any other fixation member) such that the screw 1020 extends through the gap 925 between projections 920 of augment 910. Once the augment 910 has been pushed into place by hand, it may be tapped into its final position with a hammer. If the surgeon desires, the surgeon may then fix the augment 910 even further by using augment screws placed into screw holes 930 and then into the patient's bone. Alternatively or additionally, the surgeon can pour bone cement down the troughs 960 illustrated in FIG. 116. The cement may bind the augment 910 to the acetabular shell 1010, the patient's bone, or both.

In some embodiments, the augment 910 is held in place solely by a friction fit. In some embodiments, fixation devices like bone screws or cement may be used to secure augment 910 in place, for example, via screw holes 930 or cement troughs 960, respectively. Any kind of bone screw or cement familiar to one of ordinary skill in the art may be used.

FIG. 123 shows a front perspective view of an augment having three projections extending from a top or base member according to certain embodiments. For example, augment 910' may be similar to augment 910 of FIG. 116, but augment 910' includes three projections 920' extending from the top member 970'. It will be understood that in certain embodiments an augment may include more than three projections.

In some embodiments, the augments described above may be provided with flanges, blades, plates, hooks, any other suitable mounting members, or any combinations thereof. For example, FIG. 124 shows a top plan view of an augment 1080 with flange 1090. Flange 1090 may provide additional support for the augment 1080 on the outside of the acetabulum (e.g., acetabulum 1092 of FIG. 125). FIG. 125 illustrates a partial cross-section elevation view of an augment 1080 installed in acetabulum 1002 with flange 1090 having bone screw 1094 provided therethrough.

The augments described herein may be made of a number of materials, including Titanium, Cobalt-Chromium, Zirconium oxide, any other biocompatible materials or alloys that have the appropriate strength, resistance to wear, etc., or any combinations thereof. The augments may also be made fully porous or partially porous to allow for greater bone in-growth, for example, and the augments may be coated with hydroxyapatite or any other bone-promoting agents or combinations thereof.

The embodiments described preferably above allow a surgeon to implant the acetabular shell or cup first and gain desired screw fixation and then prepare the bone minimally to fit a desired augment. This enables the surgeon to get the desired fixation for the acetabular shell without compromising the surgeon's ability to use an augment. An additional advantage is that the surgeon removes no more bone than is necessary.

Figure 126:
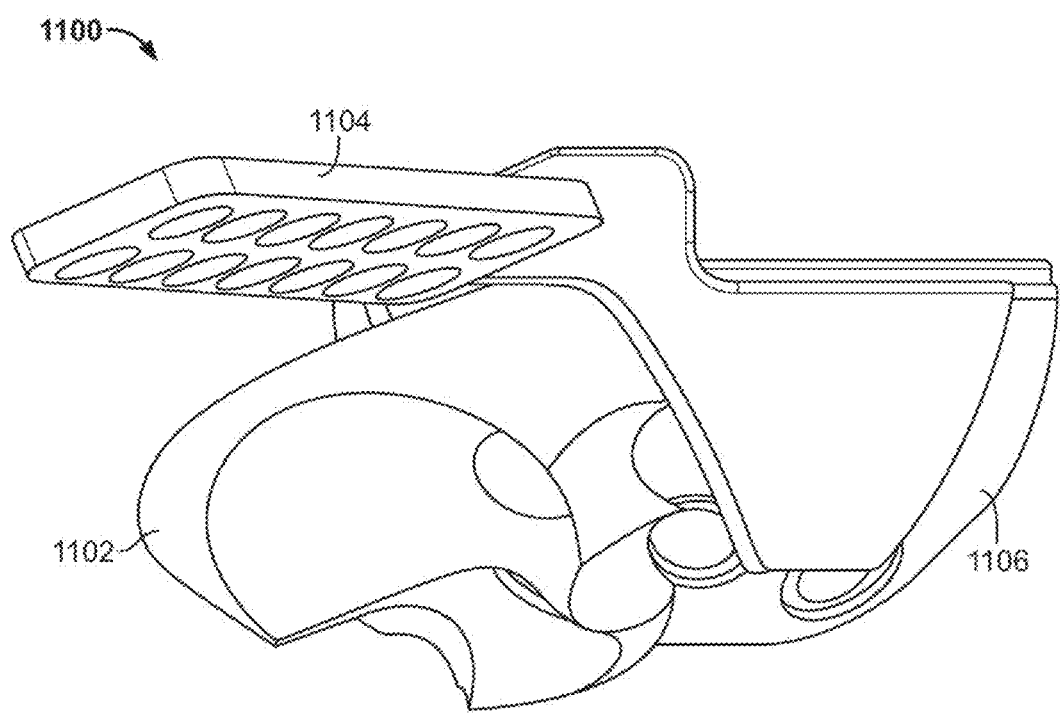
FIGS. 126 and 127 show an illustrative augment and flange combination.
Figure 127:
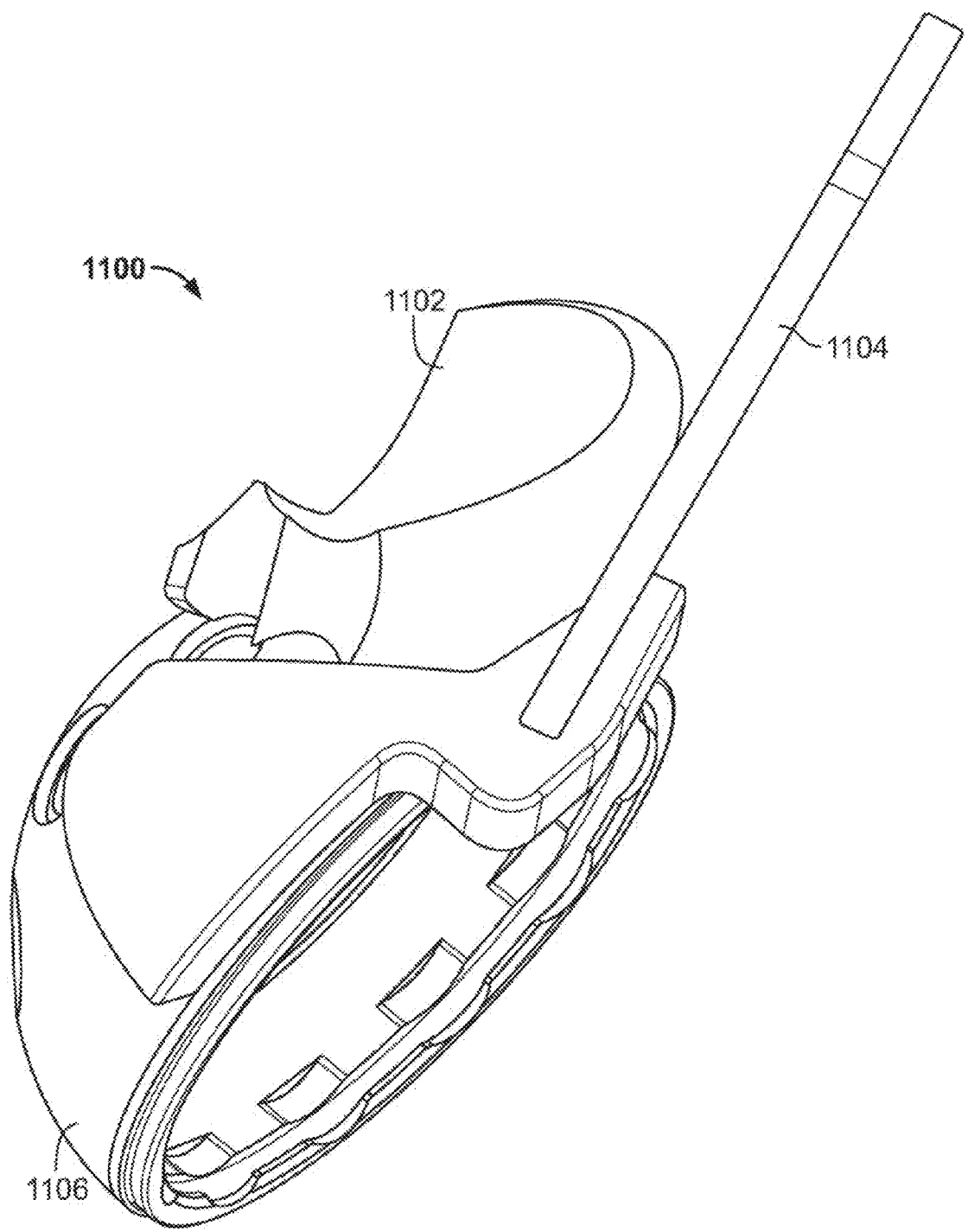

FIGS. 126 and 127 illustrate an augment and flange combination 1100 for attachment to an acetabular cup (also referred to as an "acetabular shell," "shell," "cage," or "cup") or other partially-spherical augment. Combination 1100 includes augment 1102 and flange 1104 coupled to acetabular cup 1106. It will be understood that in place of, or in addition to, flange 1104, other mounting members may be used, including but not limited to various blades, hooks, plates, any other suitable mounting member, or any combinations thereof. In some embodiments, the augment and flange combination 1100 may be configured to provide up to approximately 45° of circumferential coverage around acetabular shell 1106. The augment and flange combination 1100 may be provided in multiple sizes to fit multiple cup sizes, for example, cap outer diameter sizes ranging between approximately 30 mm to approximately 90 mm. The augment and flange combination 1100 generally utilizes a modular plate member (e.g., flange 1104) which is configured to be fixed to the acetabulum. The flange 1104 may be bent, shaped, or otherwise contoured to the anatomy of the patient, and may be adapted to be cut or otherwise provided in various lengths to allow an end user to select from a long or short plate member.

The augment and flange combination 1100 may be positioned in a superior position (as shown in the FIGS. 126 and 127). In such instances, it is likely that a longer plate member may be used. The augment and flange combination 1100 may offer anterior coverage (as shown), or, while not shown, may be positioned inferiorly to provide posterior coverage. In the latter instance, a shorter plate member may be desirable.

Figure 128:
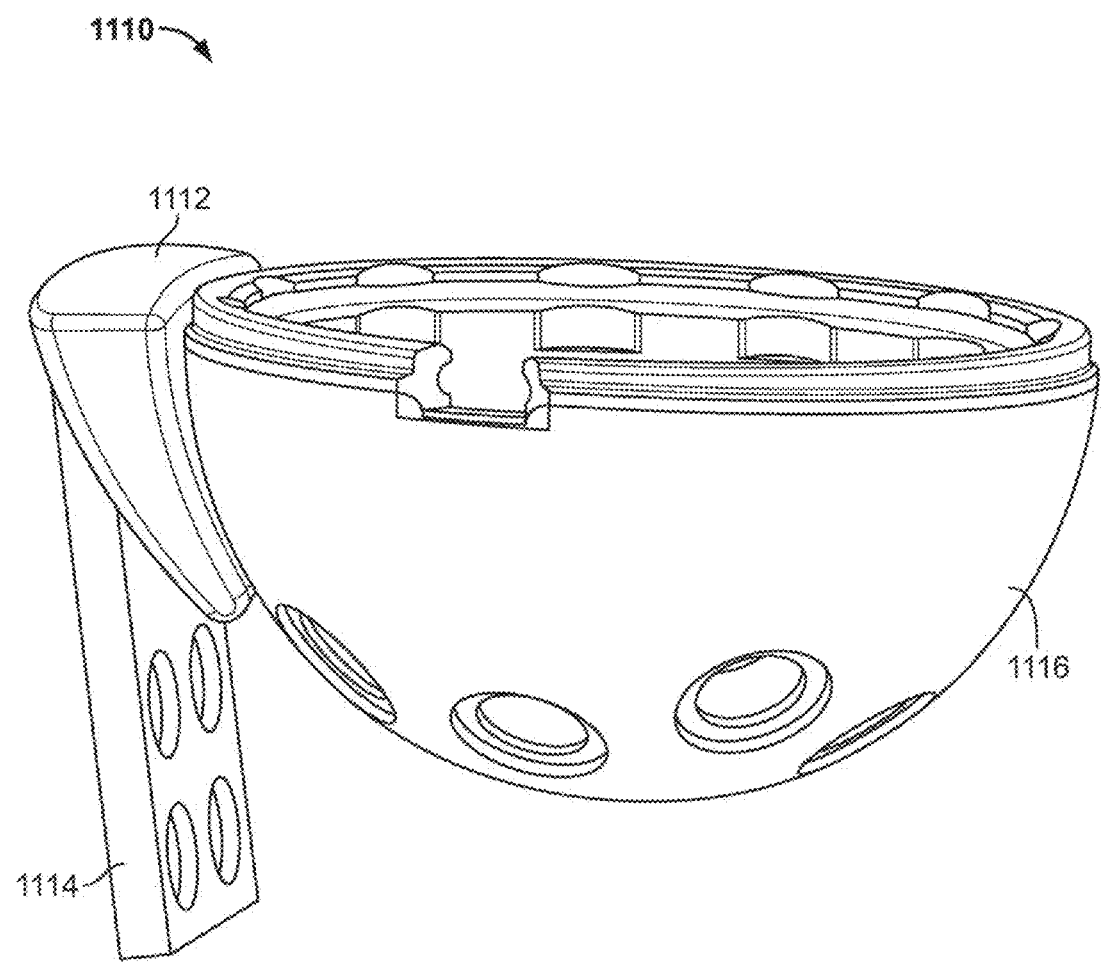
FIGS. 128 and 129 show an illustrative posterior wall augment and mounting member combination.
Figure 129:
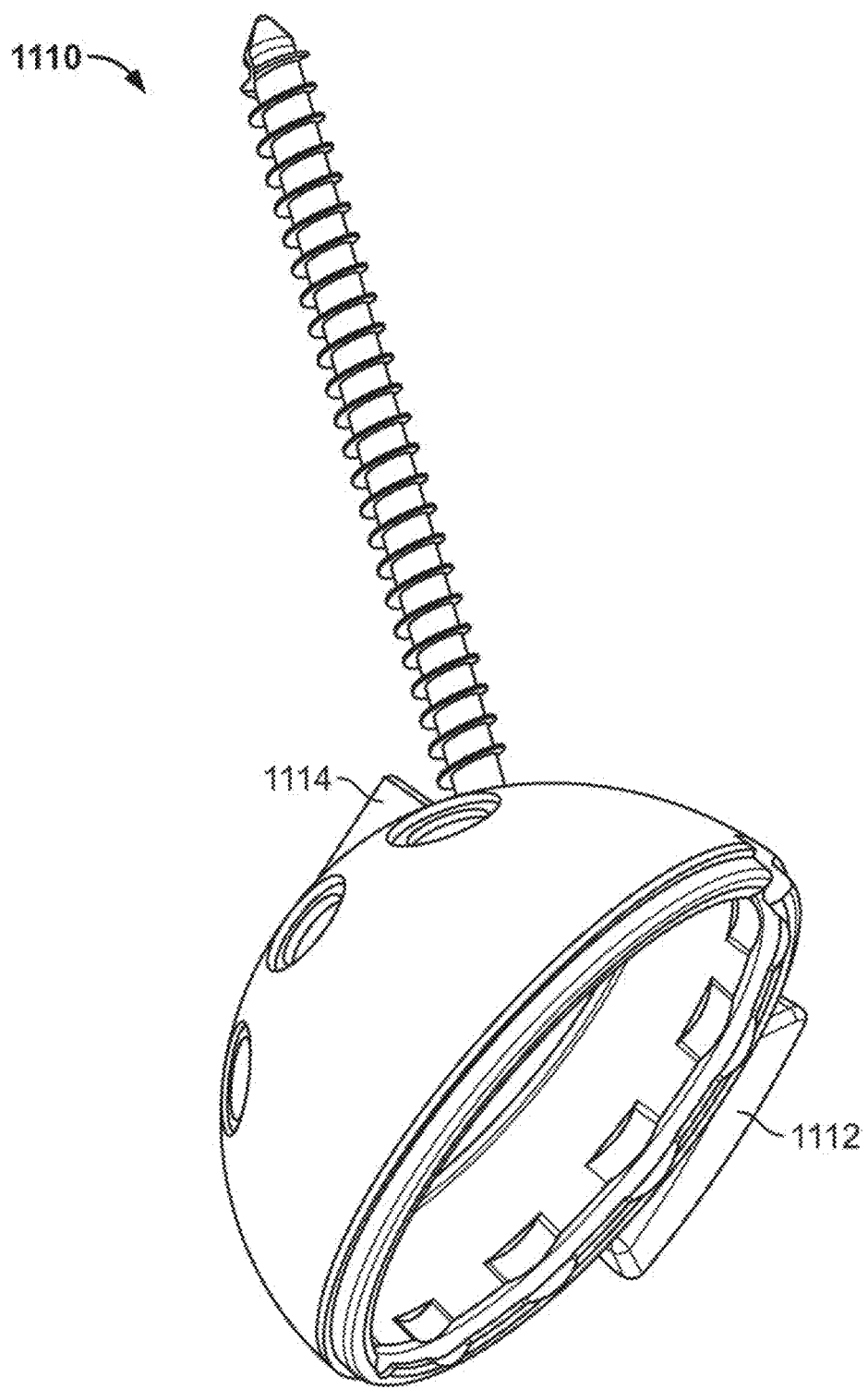

FIGS. 128 and 129 show some embodiments of a posterior wall augment and mounting member combination 1110. Combination 1110 includes augment 1112 and mounting member 1114 coupled to one another and to acetabular shell 1116. A kit of posterior wall augments and mounting members may be provided in multiple sizes, shapes, and lengths to accommodate different patients and to fit multiple cup sizes, wherein the cup may be an acetabular shell, cage, or other augment. The multiple cup sizes may be, for example, cups having outer diameters ranging from approximately 30 mm to approximately 90 mm. In some embodiments, the posterior wall mounting members or augments may be configured to provide approximately 45° of circumferential coverage circumferentially about an acetabular shell, cage, or other augment. In some instances, the mounting member or augment may be universally used on either right and left hips.

Figure 130:
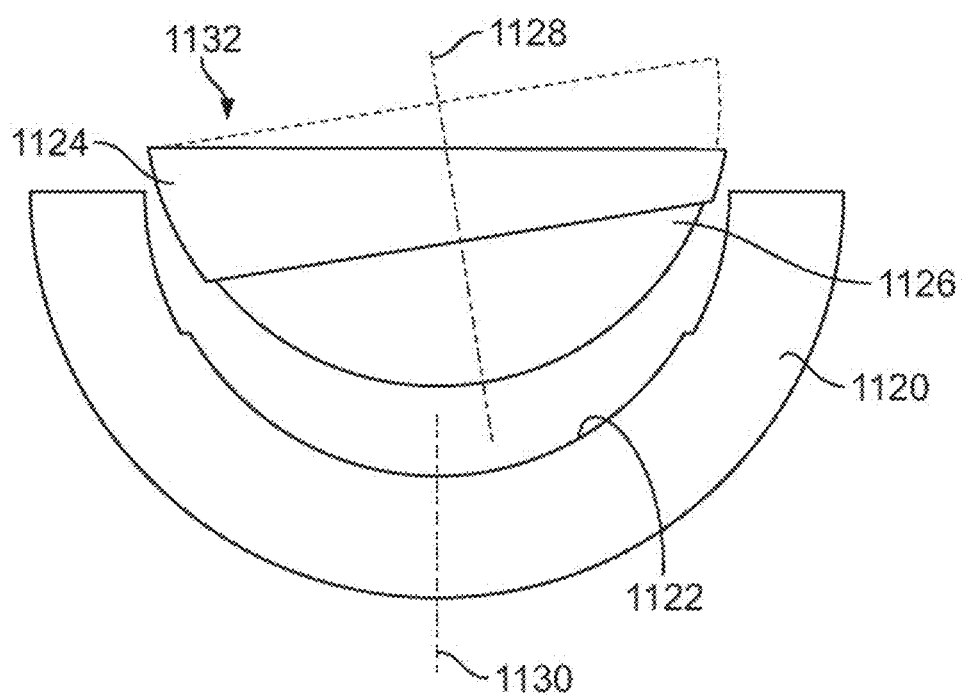
FIGS. 130 and 131 show an acetabular shell of cage with an illustrative concentric frustoconical tapered inner surface.
Figure 131:
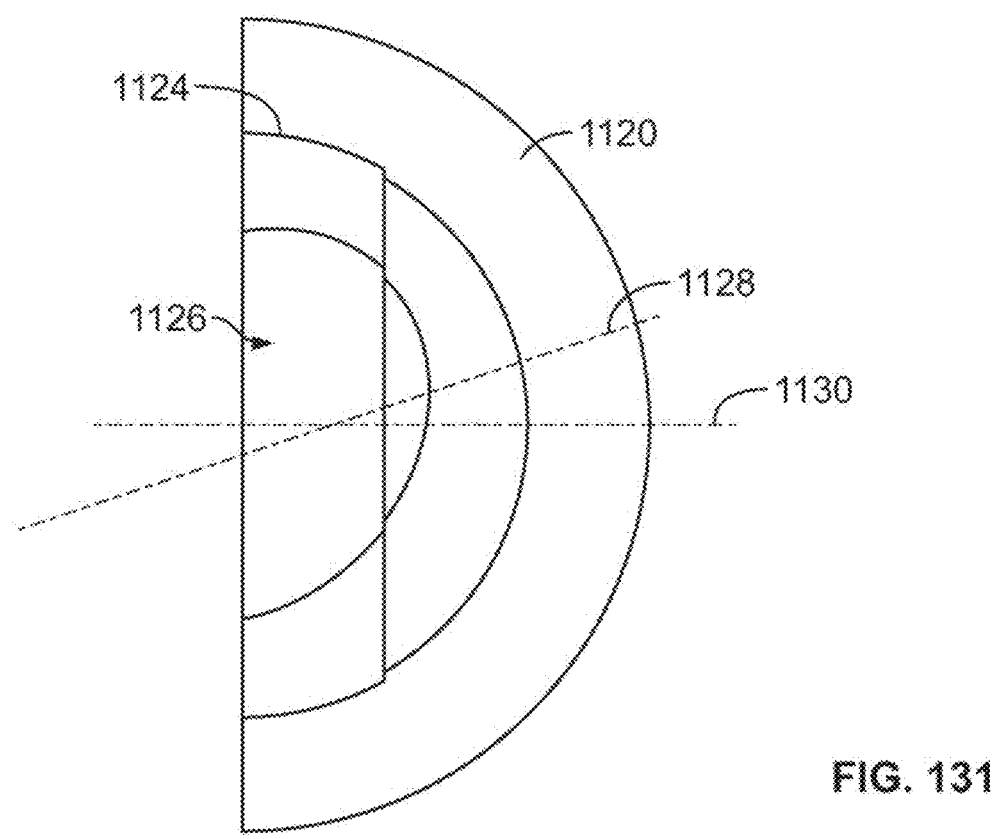

FIGS. 130 and 131 illustrate some embodiments where an acetabular shell or cage 1120 (or, in some embodiments, an augment) has a concentric frustoconical tapered inner surface 1122 configured to taper lock with a complementary frustoconical tapered outer surface of a band 1124. The band 1124 is pressed onto or otherwise provided on a separate liner 1126 adjacent a rim portion of the liner 1126. The liner 1126 may be metallic, polymeric, or ceramic. The liner 1126 has a central axis 1128 which is angled with respect to the axis 1130 of both the acetabular shell/cage 1120 and the frustoconical tapered outer surface of the band 1124 (e.g., the liner axis 1128 is not parallel or co-linear with the shell/cage axis 1130). The liner and band assembly 1132 may be placed at any angular orientation with respect to the acetabular shell/cage 1120 before engaging the tapered outer surface of the band 1124 with the frustoconical tapered inner surface 1122 of the shell/cage 1120. By allowing some degree of angularity between the liner axis 1128 and the axis 1130 of the shell/cage 1120, a surgeon can independently compensate for inadequate "cup angle" after the shell/cage 1120 is already secured to bone for best coverage, void fill, and fixation. In other words, the devices shown in FIGS. 130 and 131 allow a surgeon to decouple two surgical steps, without making a compromise between optimal fit/coverage, and liner angle/joint stability/range-of-motion.

With hard-on-hard bearings, fluid film lubrication is important to preserving the wear benefits of the bearing couple. Any deformation of the acetabular shell 1120 and liner 1126 due to the geometry of the patient's pelvic bones may cause the effective clearance to be reduced, which can disrupt fluid film lubrication. Alternatively, the band 1124 may be "integrally-provided" with the liner 1126 as a single unitary machined piece instead of pressed on as a separate member. In some embodiments, the frustoconical tapered outer surface provided to the liner 1126 may not be orthogonal to the equatorial face or rim surface of the liner 1126 (e.g., a "lipped liner" may be provided, wherein the lip is skewed with respect to the taper lock). In some alternative embodiments, the mating tapered surfaces may allow insertion of the liner 1126 in either a coaxially-aligned relationship with respect to the shell/cage 1120 (or, in some embodiments, an augment), or in a non-coaxially-aligned relationship. Changing the amount of mating taper surface area between the frustoconically-tapered outer surface and the frustoconically-tapered inner surface at different circumferential locations around a periphery of the connection may actually cause a non-uniform taper lock. In other words, the frustoconically-tapered outer surface may only contact the frustoconically-tapered inner surface band at a few discrete points, and may help reduce deformation of the liner by counteracting rim impingement forces on the shell/cage/augment from surrounding acetabular bone.

Figure 132:
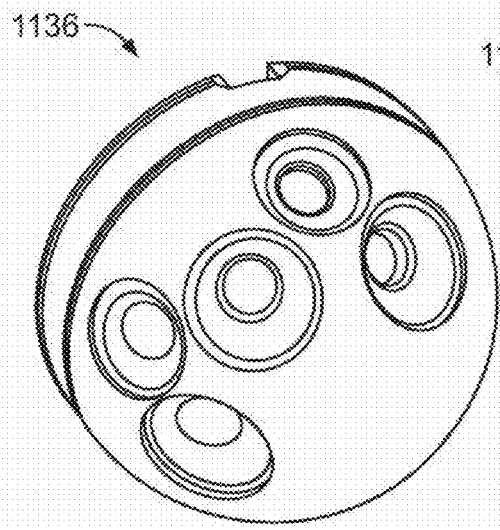
FIGS. 132-134 show an illustrative deep profile acetabular augment.
Figure 133:
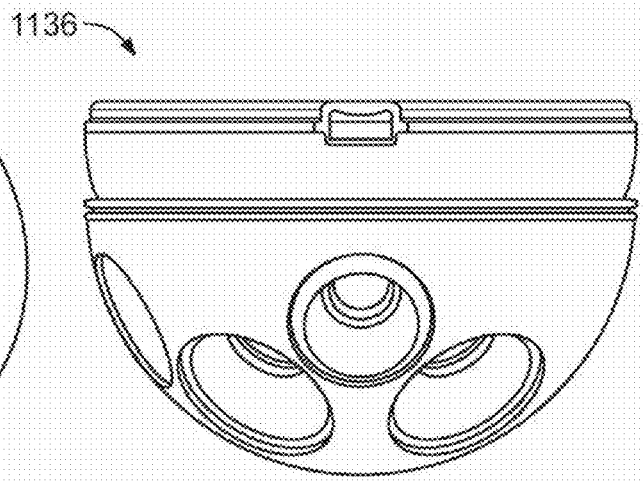
Figure 134:
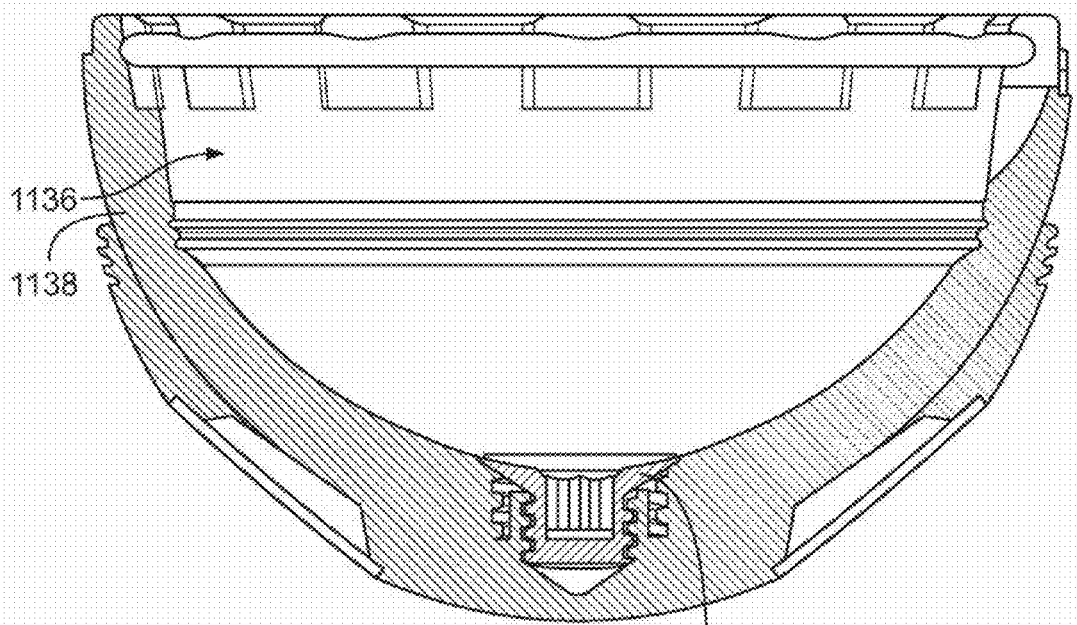
Figure 135:
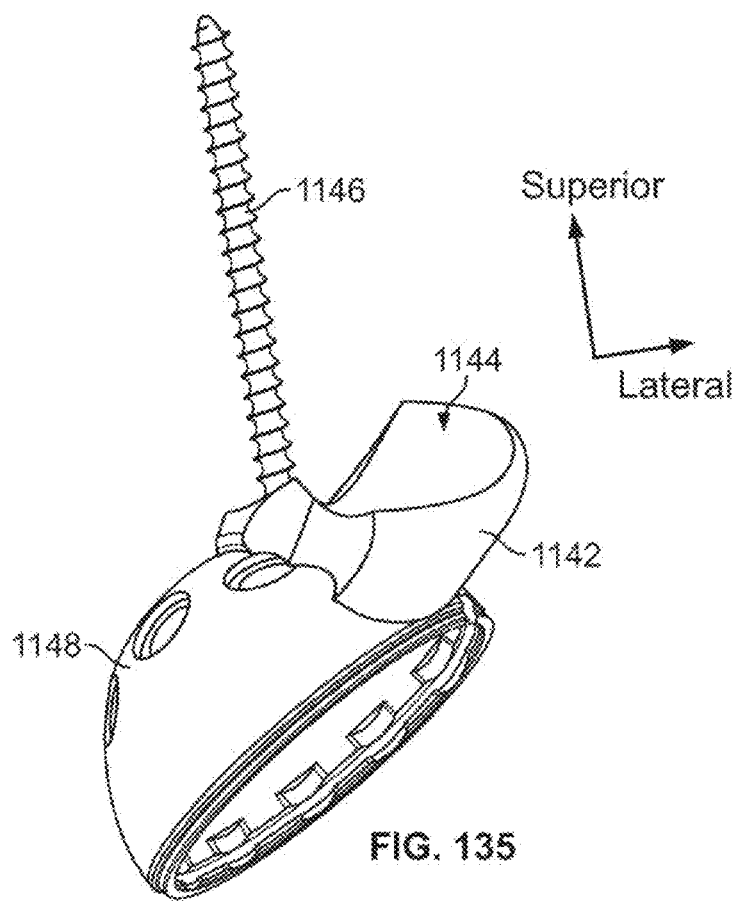
FIGS. 135-140 show an illustrative superolateral augment or flange member.
Figure 136:
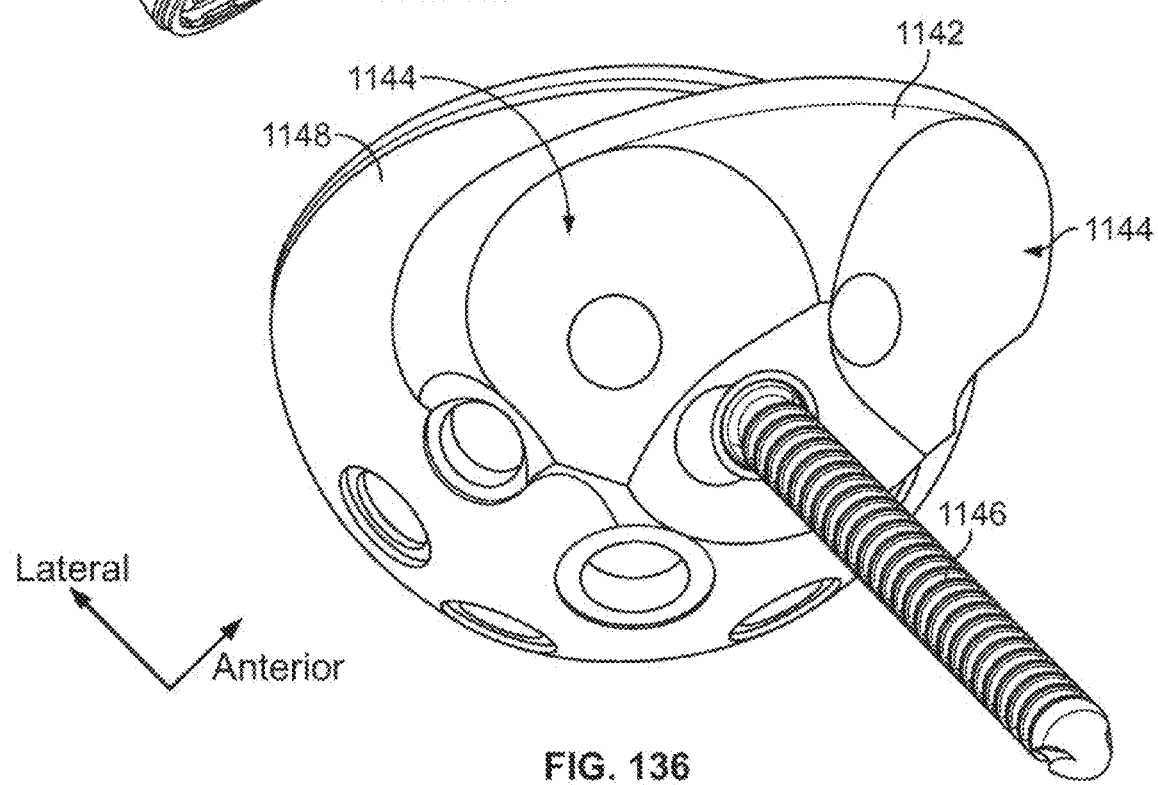
Figure 137:
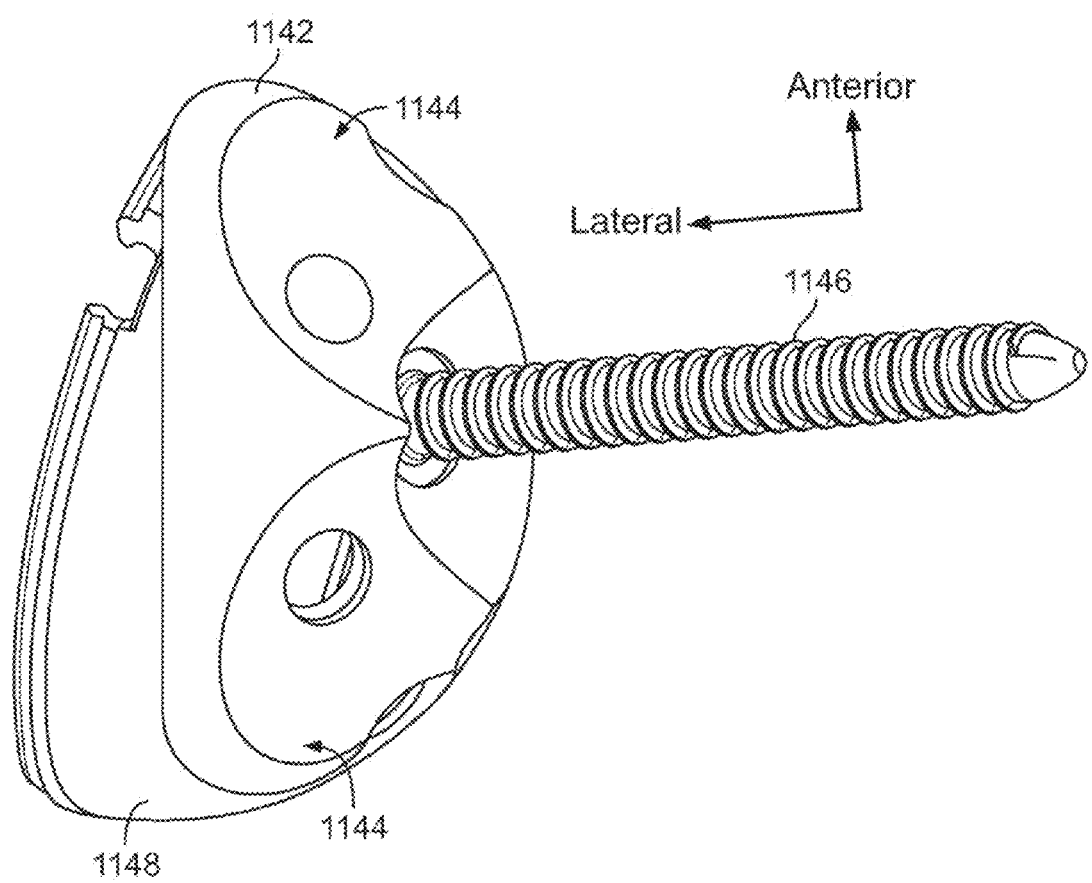
Figure 138:
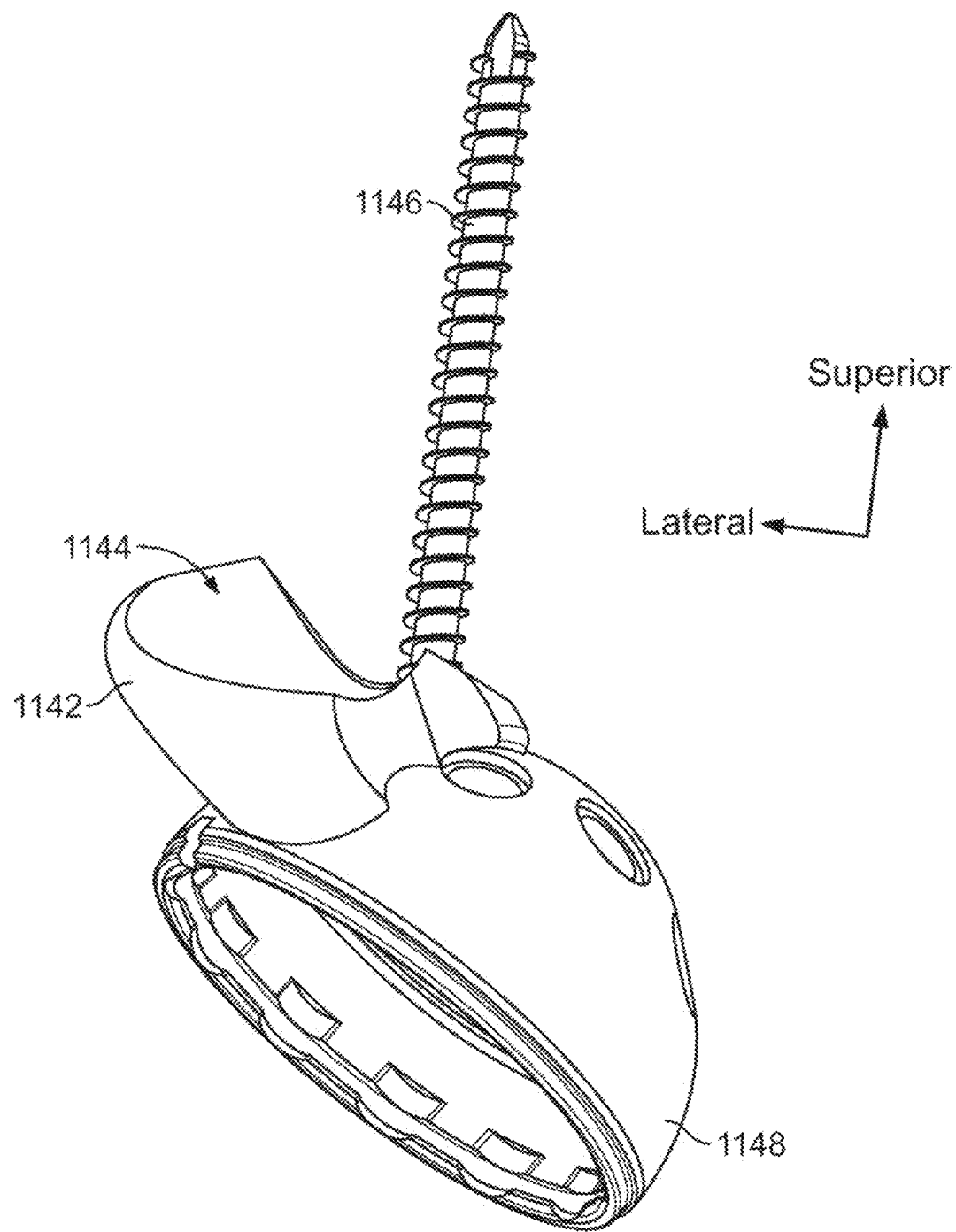
Figure 139:
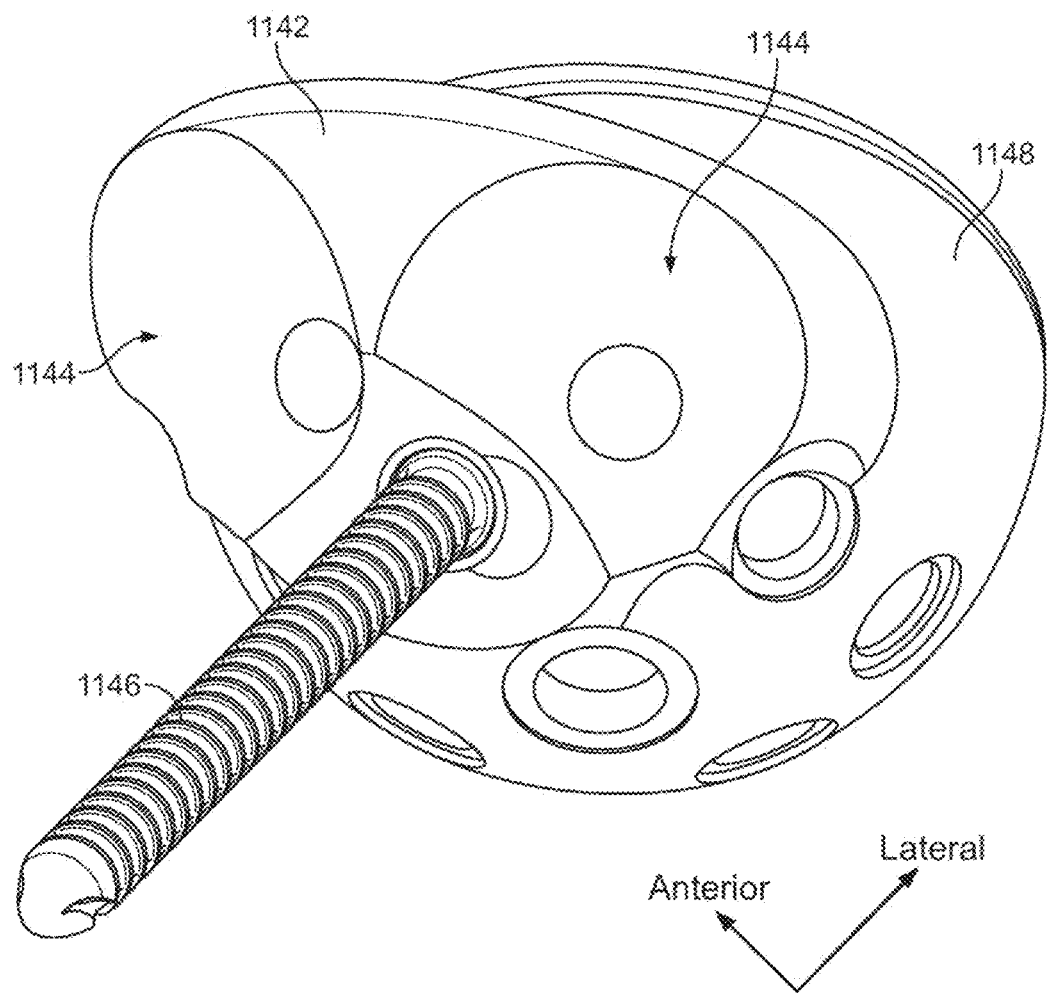
Figure 140:
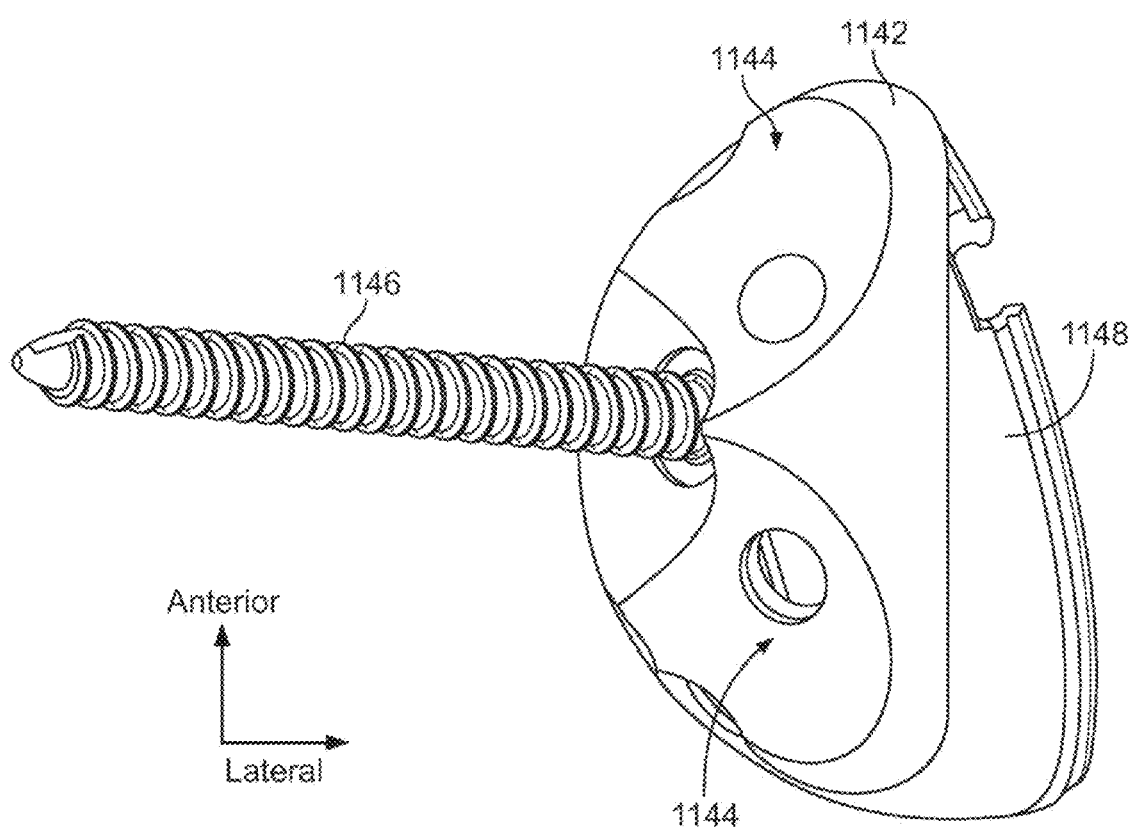

FIGS. 132-134 show a deep profile acetabular augment 1136 according to some embodiments, which fills in deep defects without offsetting the center of the joint. In other words, the deep profile acetabular augment 1136 can convert an existing standard cup implant to a cup implant having an increased offset. The deep profile acetabular augment 1136 is configured to attach to an acetabular shell, cage, or other augment via a fastener such as a bolt or screw. As shown in FIG. 134, for example, deep profile acetabular augment 1136 is attached to an acetabular shell 1138. In the particular embodiment shown, the fastener is a screw 1140 which is inserted through a screw hole located in the acetabular shell 1138 (e.g., an R3™ acetabular shell by Smith & Nephew, Inc.), adjacent to the apex of the shell 1138. The screw 1140 passes through the shell 1138 and connects the acetabular shell 1138 to the deep profile augment 1136. The deep profile augment 1136 may come in multiple depths/thicknesses/offsets. For example, the augment 1136 may increase the depth of an acetabular shell, cage, or other augment by approximately 1 mm to about 20 mm without limitation. The deep profile acetabular augment 1136 shown in the figures represents a +8 mm depth.

Internal geometries (e.g., internal diameter or radius) of the deep profile acetabular augment 1136 may range to accommodate the outer geometries (e.g., outer diameter or radius) of multiple acetabular shell sizes. For instance, a kit of deep profile acetabular augments may be provided, the kit comprising a set of deep profile acetabular augments for each acetabular shell size, each set of deep profile acetabular augments comprising multiple depths, thicknesses, or offsets. Such deep profile acetabular augments may be particularly advantageous for use with protrusion acetabulums or acetabulums having Paprosky type IIC acetabular defects.

FIGS. 135-140 show a superolateral augment or flange member. As shown, the superolateral augment/flange member 1142 may be fully symmetrical, thus allowing it to be universally used in both left and right hips. The superolateral augment/flange member 1142 may come in multiple depths, for instance, approximately 0.01 mm to approximately 40 mm (shown in FIGS. 135-140 as a +20 mm depth) and multiple sizes to fit multiple cup sizes, for instance, cup outer diameters ranging between approximately 30 mm and 90 mm. The augment/flange member 1142 may be provided with one or more widened or tapered holes 1144 that do not restrict screw angulation or placement. In this manner, polyaxial screws may be used, and the surgeon may insert the screws into a patient's bone at a desired angulation to obtain bone purchase in select areas. The augment/flange member 1142 may be of particular use for acetabulums with Paprosky type IIIA acetabular defects.

The superolateral augment/flange member 1142 may be configured to allow screws such as screw 1146 to pass from the inside of a 3-hole or multi-hole cup 1148 through a cup wall, and subsequently through a wall of the superolateral augment/flange member 1142 to engage the acetabulum and surrounding bone, while maintaining or enabling full screw angulation. Alternatively, the superolateral augment/flange member 1142 may be configured to be initially directly attached to acetabular bone by one or more screws. In this instance, a no-hole cup may then be cemented over the augment/flange member 1142 (in-situ) at an inner surface of the augment/flange member 1142 that faces away from bone. Such embodiments configured for use with a no-hole cup may be desirable, because no-hole cups provide an uninterrupted barrier between the liner and cup and help prevent articulation wear debris from reaching the backside of the liner (i.e., between the cup and liner).

In either of the embodiments described above, benefits are realized when compared to prior designs. For example, some currently-available designs need to be cemented and do not allow screws originating from the inner cup diameter to engage the augment before engaging the acetabulum. Moreover, other currently-available augments do not allow for full screw angulation.

FIGS. 141-159 show an acetabular mounting member or augment comprising a polyaxial screw hole. As shown, the mounting member or augment 1150 may comprise a solid substrate 1152 adjacent an aperture 1154 having an engagement structure 1156, which may be machined, for complementarily engaging a polyaxial screw head 1158. The polyaxial screw head 1158 may be rounded or threaded, and the engagement structure 1156 may comprise smooth rounded surfaces, threads, partial threads, tabs, or deformable structures that are complementary to the polyaxial screw. Various examples of polyaxial locking systems and methods are shown and described in U.S. Patent Application Publication No. 2002/0147499, entitled "Locking Systems for Implants," U.S. Patent Application Publication No. 2008/0300637, entitled "Systems and Methods for Using Polyaxial Plates," and U.S. Provisional Patent Application No. 61/178,633, entitled "Polyaxial Fastener Systems and Methods," all of which are intended for potential use in connection with the systems described herein and are incorporated by reference herein in their entireties.

Figure 141:
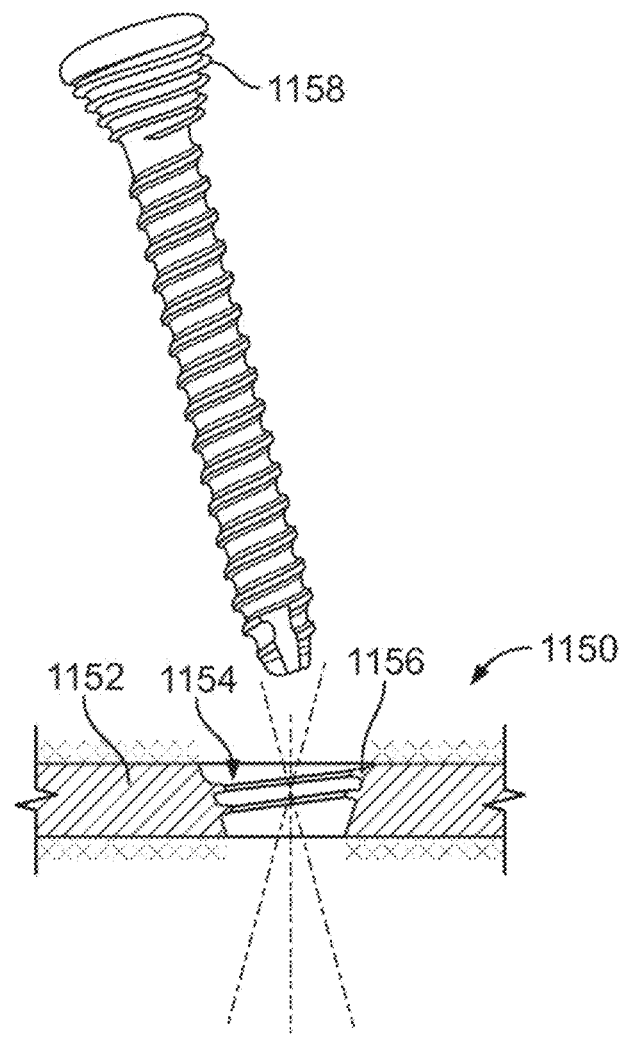
FIGS. 141-143 show an augment or mounting member incorporating variable locking angle screw geometry.
Figure 142:
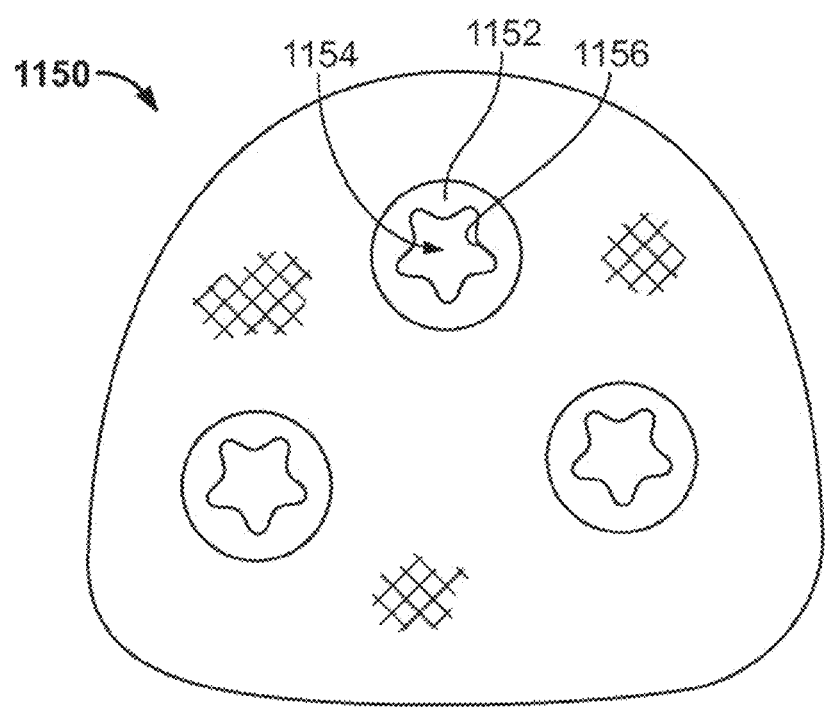
Figure 143:
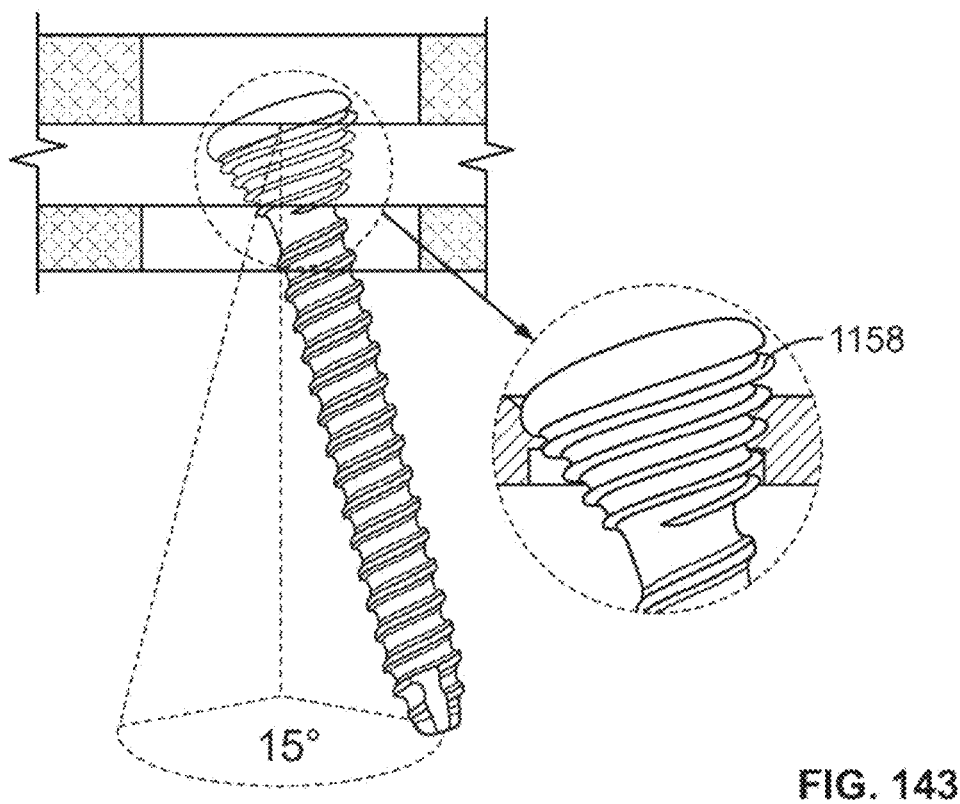
Figure 144:
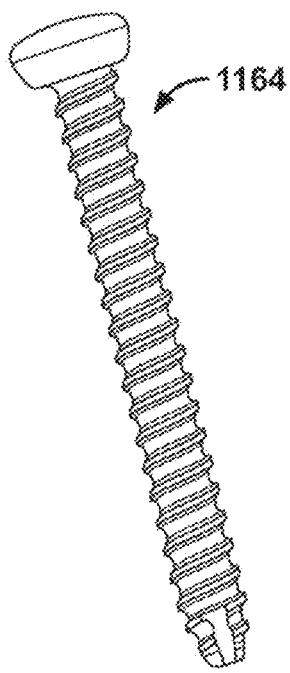
FIGS. 144-148 show various examples of screws that may be used with augments or mounting members.
Figure 145:
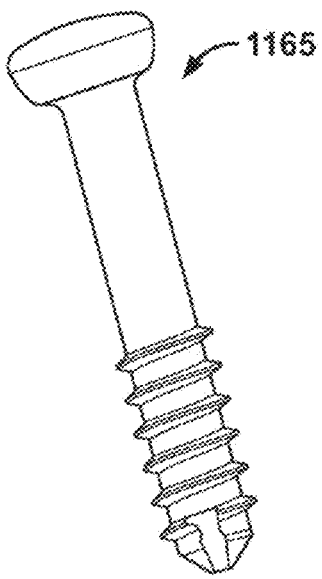
Figure 146:
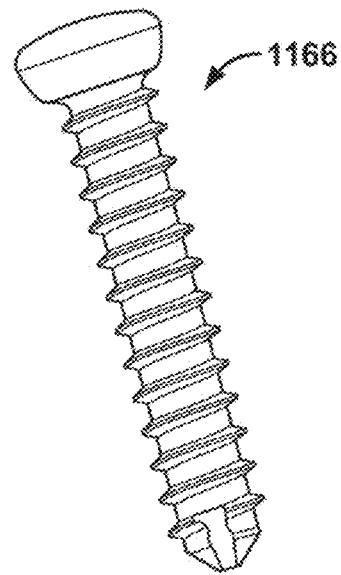
Figure 147:
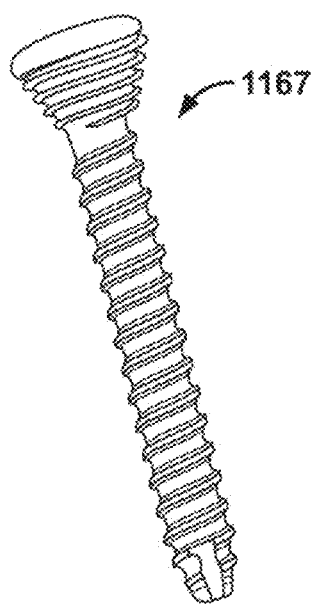
Figure 148:
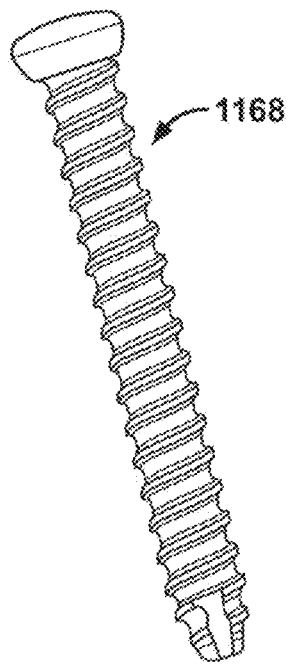
Figure 149:
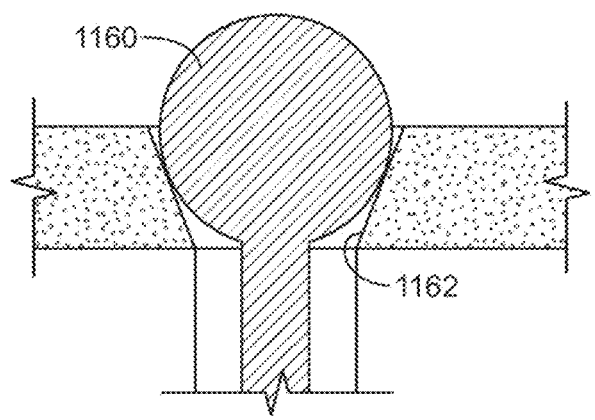
FIG. 149 shows an illustrative screw having a rounded, tapered, or spherical head.

Any of the screws or fixation members used in connection with any of the embodiments described herein may be locking screws, polyaxial screws, or screws that are generic in nature. They may have a threaded head as shown in FIGS. 141, 143, and 147, or may, alternatively, comprise a rounded, tapered, or spherical head 1160 that mates and forms a locking connection with a tapered recess or aperture 1162 as shown in FIG. 149. In some embodiments, polyaxial screws may be utilized. FIGS. 144-148 show some non-limiting examples of screws 1164-1168 that may be used with the augments and/or mounting members described herein, including but not limited to 2.7 mm cortex screws, 5.0 mm partially-threaded osteopenia screws, 5.0 mm osteopenia screws, fully-threaded 3.5 mm locking screws, and 3.5 mm cortex screws, respectively. FIGS. 141-143 and 150-155 illustrate various embodiments of an augment or mounting member 1150 incorporating a variable locking angle screw geometry. One specific embodiment of a variable locking angle screw geometry is provided by the Peri-lock™ system, but it will be understood that various embodiments described herein may be used with any appropriate variable locking angle fixation systems.

Figure 150:
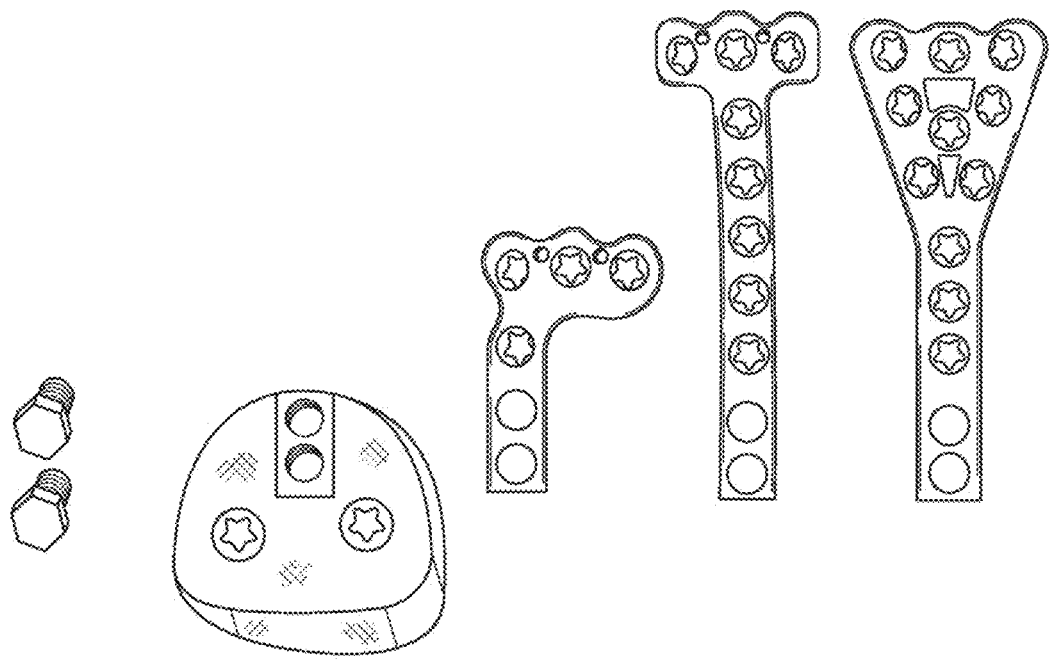
FIGS. 150-155 show an augment or mounting member incorporating variable locking angle screw geometry.
Figure 151:
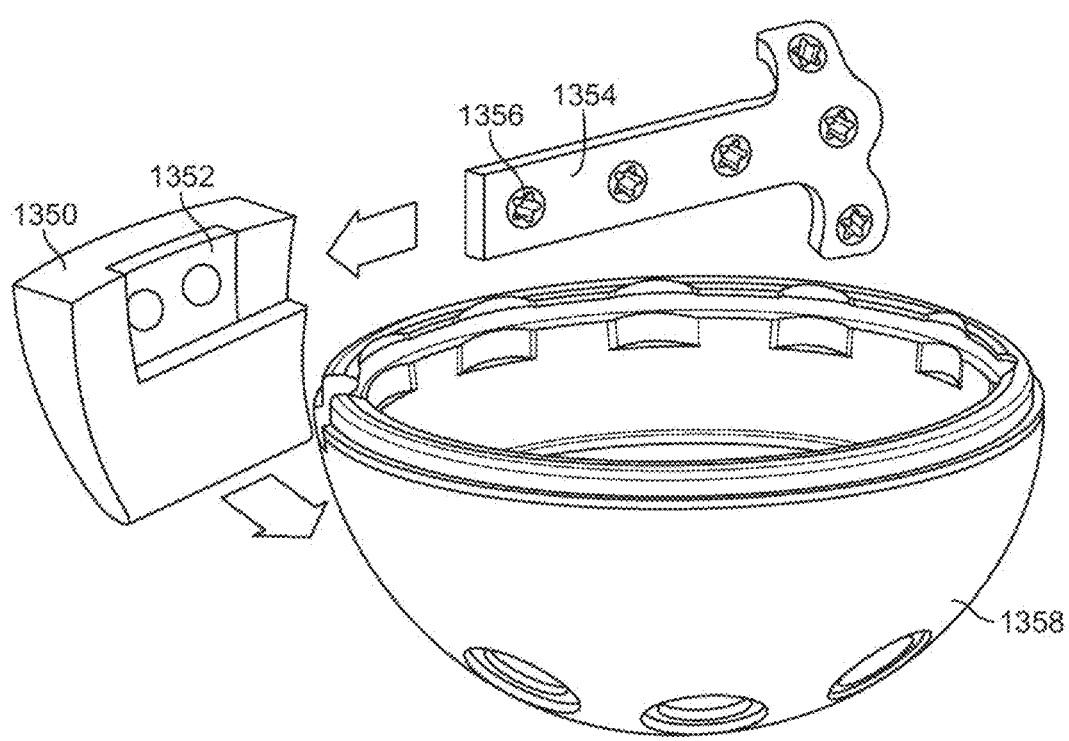
Figure 152:
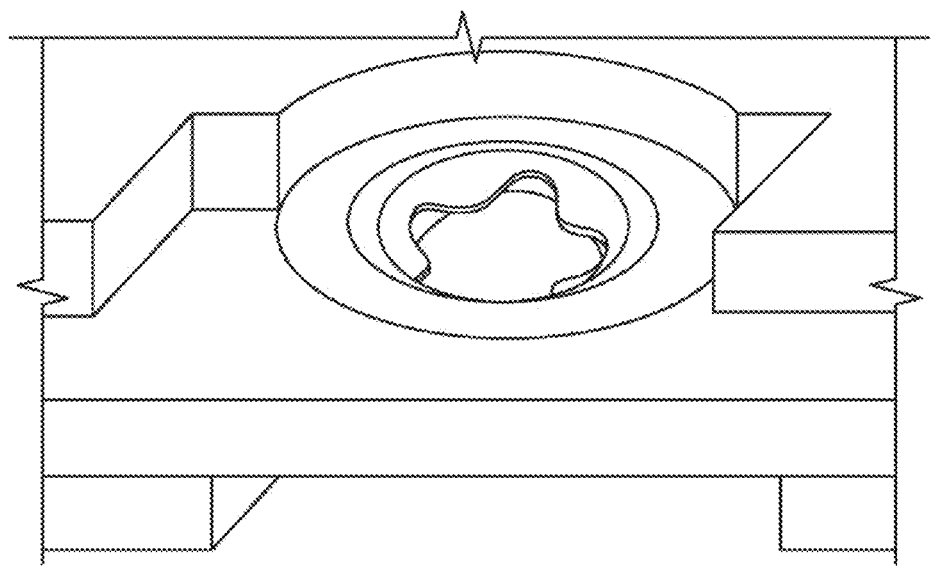
Figure 153:
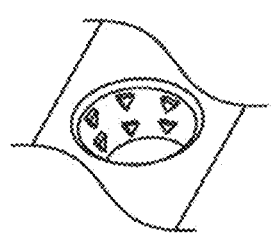
Figure 154:
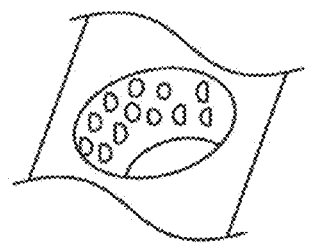
Figure 155:
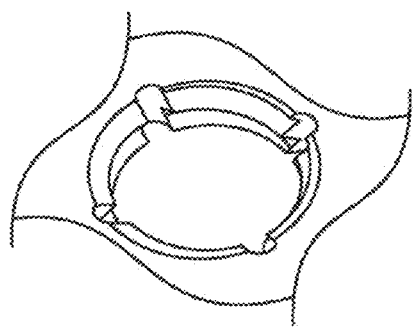

FIG. 151 shows some embodiments similar to those shown in FIG. 150, wherein an augment and a mounting member is attached or positioned proximate an acetabular shell, cage, or other augment. For example, augment 1350 is positioned proximate shell 1358 and comprises a mounting structure 1352 thereon for accepting an optional fracture reduction plate 1354. The fracture reduction plate 1354 may come in various configurations and may be adapted to be shaped, bent, or cut to fit an area of pelvic bone surrounding the acetabulum. The fracture reduction plate 1354 may comprise screw holes 1356 and/or other mounting structures such as spikes protruding therefrom for instant securing to the bone. Screw holes 1356 are variable low-profile holes that allow for locking at a variety of angles, but may also be threaded, unthreaded, or partially threaded, and may be fixed or polyaxial. The spikes may comprise barbed structures to increase pull-out strength and/or temporarily position and secure the fracture reduction plate to the bone while bone screws are subsequently introduced. One or more outer portions of the augment 1350 may have recesses for introducing a cutting member to facilitate removal of the augment 1350 using any of the methods described above.

Figure 156:
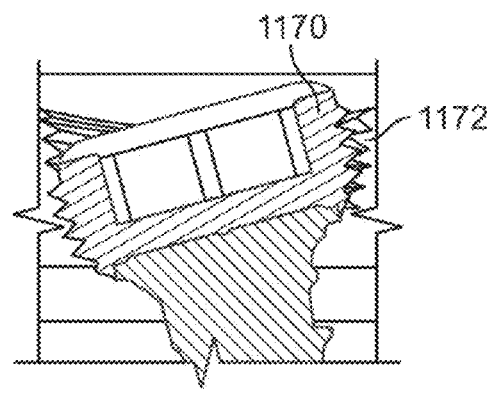
FIG. 156 shows an illustrative screw head including a polymer that is deformed by an engagement structure provided on an augment or mounting member.

In some embodiments, screws or fixation members used in connection with any of the embodiments described herein may comprise fully or partially polymeric heads. In some embodiments, the polymeric heads may be comprised of PEEK material, which deforms when inserted into screw holes having engagement features such as tabs, projections, partial threads, full threads, tapers, splines, ridges, steps, or any other mechanical locking structures or combinations thereof provided in the screw holes. Portions of the screws, such as heads or shank portions, or the entire screw itself may comprise a polymer, for example, a bioresorbable polymer material or a shape-memory polymer material. One example of such material is provided by PolyNovo Biomaterials Limited. FIG. 156 shows a portion of a screw head 1170 according to some embodiments that comprises a polymer that is deformed by an engagement structure 1172 provided on an augment or mounting member.

Additionally or alternatively, screws or fixation members used in connection with any of the embodiments described herein may be cannulated or otherwise provided with one or more holes, apertures, recesses, grooves, or channels adapted for injection a material therein. For example, the screws or fixation members may be configured for placement of a reinforcement cement or polymer, such as for example, injectable polyurethane, within the screw and to surrounding adjacent areas of bone. See, for example, U.S. Pat. No. 7,338,493, U.S. Patent Application Publication No. 2009/0157078, and International Publication No. WO/2010040573, all of which are incorporated by reference in their entireties.

Many different locking configurations may be used between screw or fixation members and the augments and mounting members described herein. Non-limiting examples of potential locking mechanism connections are shown and described in U.S. Patent Application Publication No. 2002/0147499 and U.S. patent application Ser. No. 12/069,331, all of which are incorporated by reference herein in their entireties. See also, FIGS. 141-156.

Figure 157:
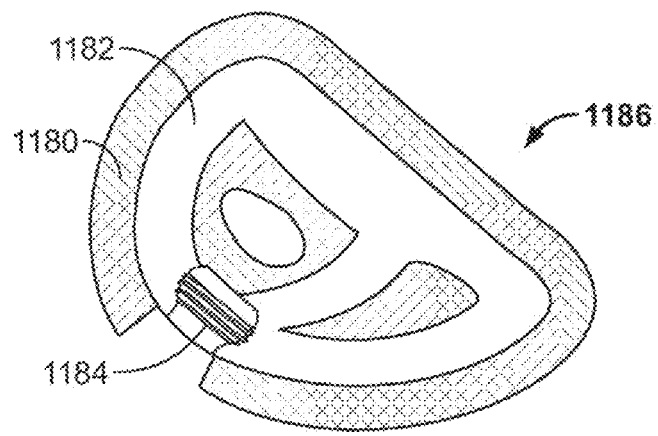
FIG. 157 shows an illustrative porous outer layer applied to a solid substrate.
Figure 158:
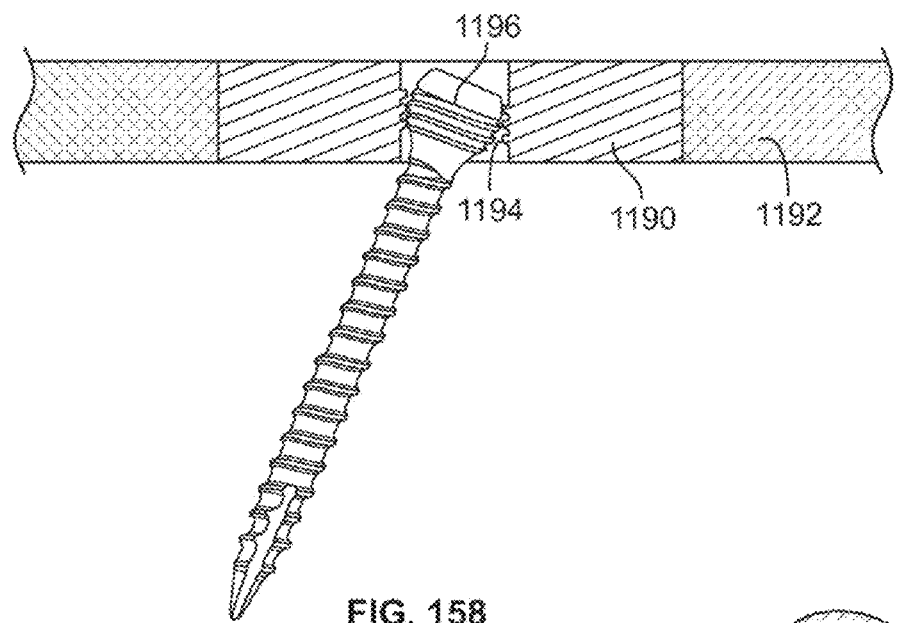
FIG. 158 shows an illustrative solid insert pressed into a porous mounting member or augment.

As shown in FIG. 157, in some embodiments, a porous outer layer 1180 comprising symmetric particles, asymmetric particles, beads, hydroxyapatite, plasma-sprayed chemically-etched surface textures, combinations thereof, or the like is applied to the solid substrate 1182. This porous outer layer 1180 is intended to allow bone ingrowth in order to help achieve better fixation of the component. A solid substrate 1182 beneath the porous coating provides relatively better strength to the engagement structure 1184 than if the engagement structure 1184 was formed directly in a porous substrate or the porous outer layer 1180. FIG. 157 shows a crescent-shaped augment 1186 with large windows. FIG. 158 shows a solid insert 1190 pressed into a fully-porous mounting member or augment 1192 according to some embodiments. The insert 1190 comprises an engagement structure 1194 that cooperates and forms a locking engagement with a polyaxial screw head 1196.

Figure 159:
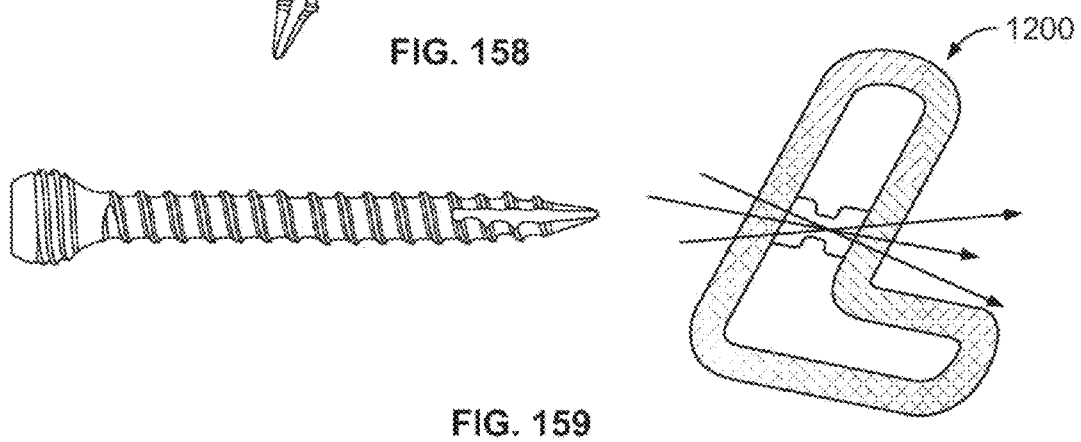
FIG. 159 shows an illustrative augment shaped in the form of an "L"

In some embodiments, the insert such as insert 1190 may be integrally formed with a porous structure (e.g., porous structure 1192) using a rapid manufacturing process, for example, selective laser sintering. In some embodiments, the insert may be formed as a separate component that is pressed into the body of the augment or mounting member. In such cases, the insert may be formed of a material that is dissimilar with the body of the mounting member or augment. For example, the insert may comprise a soft material, such as for example, UHMWPE, PEEK, any other suitable polymer, or combinations thereof, which is configured to deform and lock with a threaded screw head to prevent screw "back-out." FIG. 159 schematically illustrates an augment 1200 shaped in the form of an "L" according to some embodiments.

Figures 160, 161:
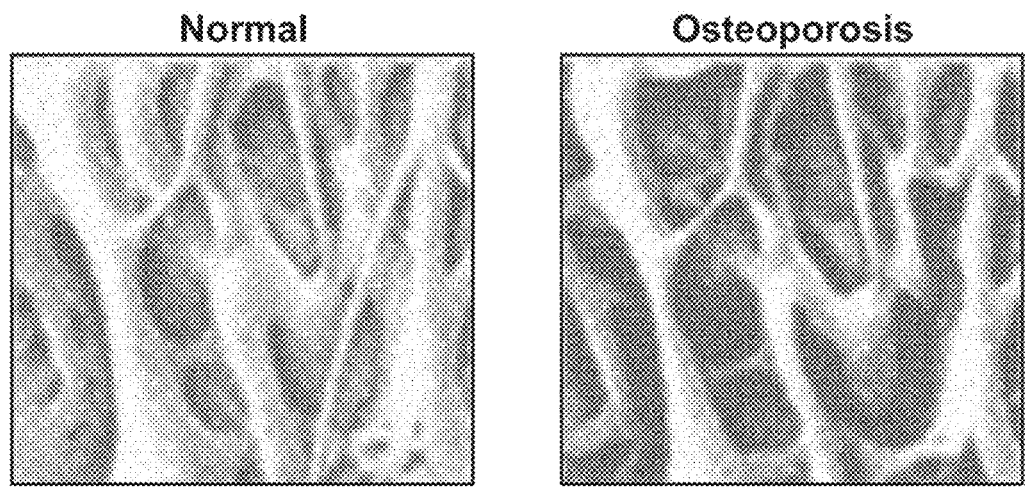
FIGS. 160 and 161 schematically illustrate the difference in bone density and strength between normal bone (FIG. 160) and osteoporotic bone (FIG. 161)
Figures 162, 163, 164, 165:
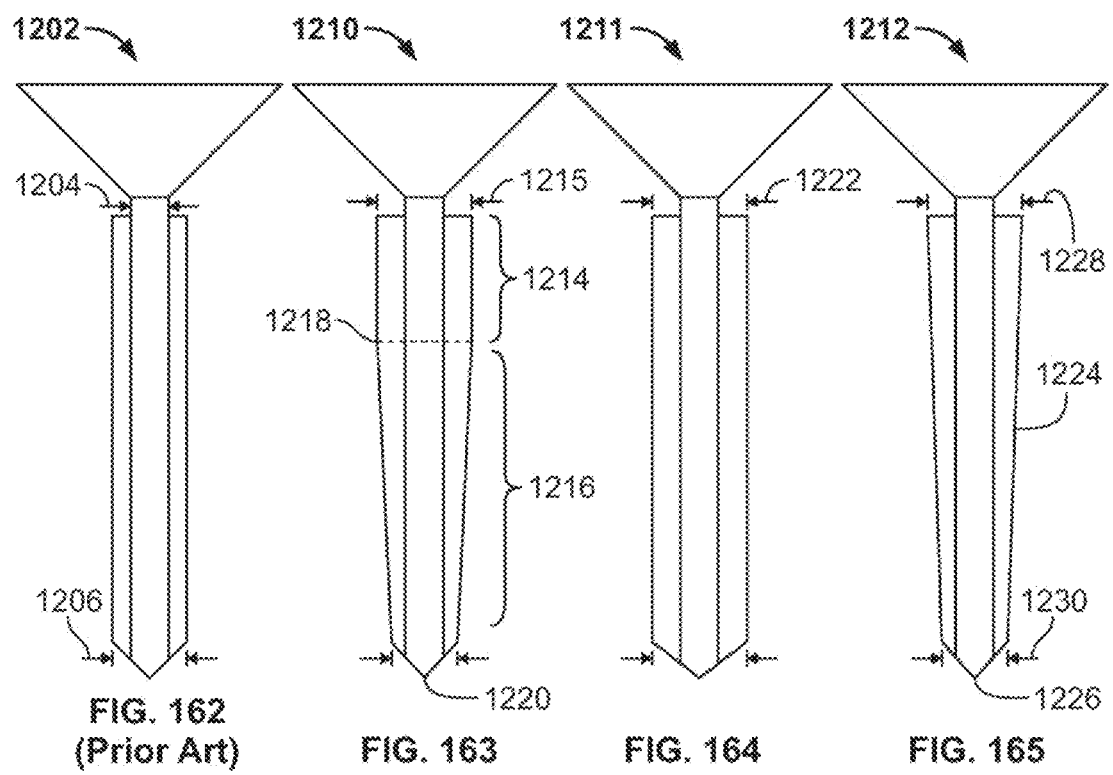
FIG. 162 shows a conventional cancellous bone screw.
FIG. 163 shows an illustrative bone screw having a proximal outer straight thread portion and a distal tapering thread portion.
FIG. 164 shows an illustrative bone screw having a larger outer crest thread diameter than the bone screw of FIG. 162.
FIG. 165 shows an illustrative bone screw having a fully tapered thread.

FIGS. 163-165 illustrate various bone screws or other attachment mechanisms or fasteners that may be used to secure the various embodiments described herein. As background, FIGS. 160 and 161 schematically demonstrates the difference in bone density and strength between normal bone (FIG. 160) and osteoporotic bone (FIG. 161), which may be present in the acetabular or pelvic bone of a patient undergoing revision hip surgery. FIG. 162 schematically illustrates a conventional 6.5 mm cancellous bone screw 1202 having an inner root thread diameter 1204 and an outer crest thread diameter 1206 of 6.5 mm.

FIGS. 163-165 show several embodiments of improved cancellous bone screws 1210-1212 that may be used with the various mounting members or augments described herein and shown in the drawings, and which are optimally-configured for use in revision surgeries, particular acetabular and pelvic reconstruction. FIG. 163 schematically illustrates an improved cancellous bone screw 1210 comprising a proximal outer straight thread portion 1214 and a distal tapering thread portion 1216 with a transition region 1218 therebetween. The proximal outer straight thread portion 1214 comprises an outer crest thread diameter 1215 between approximately 6.5 mm and 10 mm, for instance, 8.5 mm. The thread then tapers down to 6.5 mm as the thread approaches the distal tip 1220 of the screw. FIG. 164 schematically illustrates an improved cancellous bone screw 1211, according to some embodiments having a similar inner root thread diameter as prior cancellous bone screws (e.g., inner root thread diameter 1204) and an outer crest thread diameter 1222 that is between approximately 6.5 mm and 10 mm, for instance, 8.5 mm. The larger outer diameter 1222 secures better purchase in osteoporotic bone. Moreover, in revision hip surgery, previous screw holes may create large bone voids which may reduce the pullout or holding strength of conventional 6.5 mm cancellous bone screws.

FIG. 165 schematically illustrates an improved cancellous bone screw 1212, according to some embodiments, comprising a fully tapered thread 1224 that reduces in diameter as the thread approaches a distal tip 1226 of the screw. Proximally, the thread has an outer crest thread diameter 1228 between approximately 6.5 mm and 10 mm, for instance, 8.5 mm. The thread tapers distally to a lesser outer crest thread diameter 1230, for instance, 7.5 mm. The taper angle may vary and may be non-linear, however, in certain embodiments, it is preferable that the outer crest thread diameter remains greater than 6.5 mm.

FIGS. 166-175 show various embodiments of augments that provide features to improve removal of an augment that has been previously positioned in a patient's bone. For example, during revision surgery, a surgeon may need to remove an augment positioned during an earlier surgery, which can be particularly difficult in instances where there is bone-ingrowth in, around, and/or through the augment. Surrounding bone ingrowth can render augments difficult to remove in subsequent surgeries; thus, providing augments with one or more removal features can be beneficial.

FIG. 166 shows an augment 1240 that may be provided with recess portions 1242, which, in this embodiment, are shown alongside a split portion 1244, but which can be provided anywhere on the augment 1240, or even on augments not having a split portion. Recess portions 1242 are configured to receive a clamp or other instrument 1246. Recess portions 1242 may be curved or otherwise shaped to correspond to the instrument to be used. For removal of the augment 1240, arms 1248 of the instrument 1246 may be inserted into recess portions 1242 in order to securely grasp the augment 1240, squeeze the augment 1240, and pull the augment 1240 from bone. The mechanical advantage of the clamp 1246 causes the augment 1240 to squeeze or shut slightly or otherwise flex inwardly, particularly in split augment embodiments, so that the augment 1240 may be removed, even if well fixed in bone.

The split augment 1240 shown may move from a first position, shown as the outer boundary 1250 in solid lines, to a second compressed position, shown in dotted lines 1252 in a direction shown by inward arrows 1254. This compression allows removal of the augment 1240 in a relatively easier and more efficient manner than chipping away at the augment 1240 or cutting the augment 1240 out in separate portions with a blade.

Recess portions 1242 and instrument 1246 may also be used to initially position or introduce the augment 1240 into a bone void. Once positioned, an expansion member, such as any of the expansion members shown and described herein, may be used to expand and lock the augment 1240 into place. Although not shown, it may be desirable to insert plugs or any other appropriate recess portion cover to prevent bone ingrowth therein. Alternatively, bone graft material or injectable polymers or any other filler material may be inserted into recess portions, particularly if recess portions are to be used solely for insertion and are not envisioned for use in subsequent removal.

Figure 167:
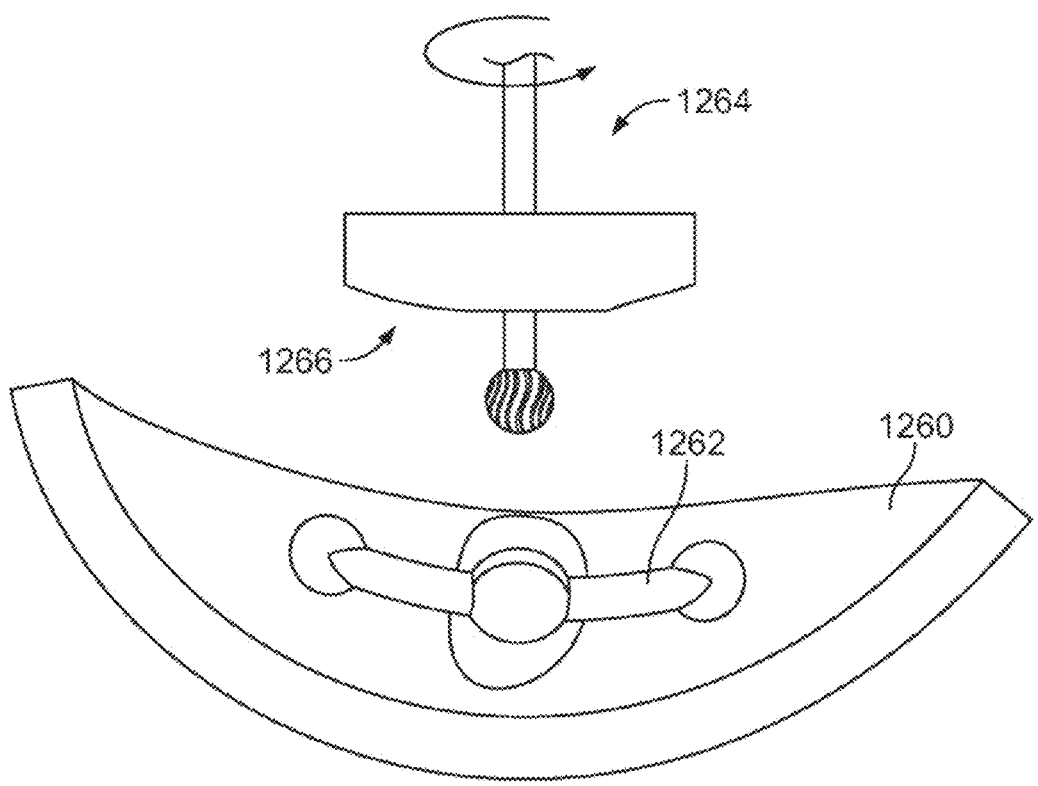
FIG. 167 shows an illustrative augment having a slot that is shaped to correspond to an appropriate removal tool.

FIGS. 167-170 show alternate augment removal options. In FIG. 167, the augment 1260 is shown as provided with a slot 1262 that is shaped to correspond to an appropriate removal tool. In this embodiment, the slot 1262 is built into the augment 1260 which can be used with a burr tool 1264. The burr removal tool 1264 is shown having a fixed stop 1266 that corresponds to the curvature or contour of the augment 1260. The augment 1260 of this embodiment provides surface area for bone ingrowth, but also provides room for a removal tool, which can be used to mill out areas of the augment 1260 that are well fixed into bone.

Figure 168:
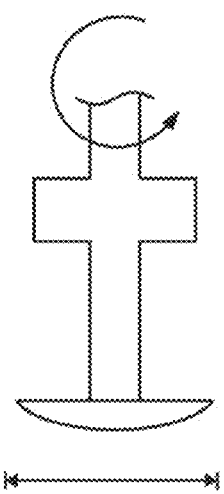
FIGS. 168-170 show illustrative crescent blades or two-sided blades that can rotate into a slot to affect removal of an augment.
Figure 169:
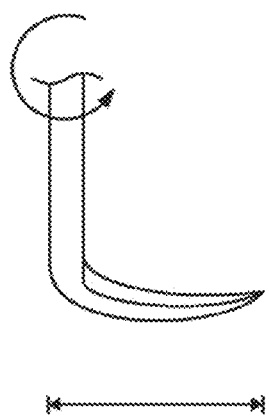
Figure 170:
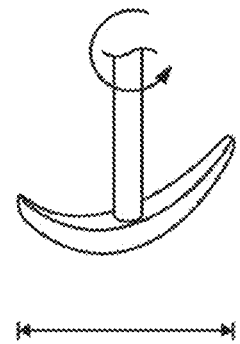
Figure 171:
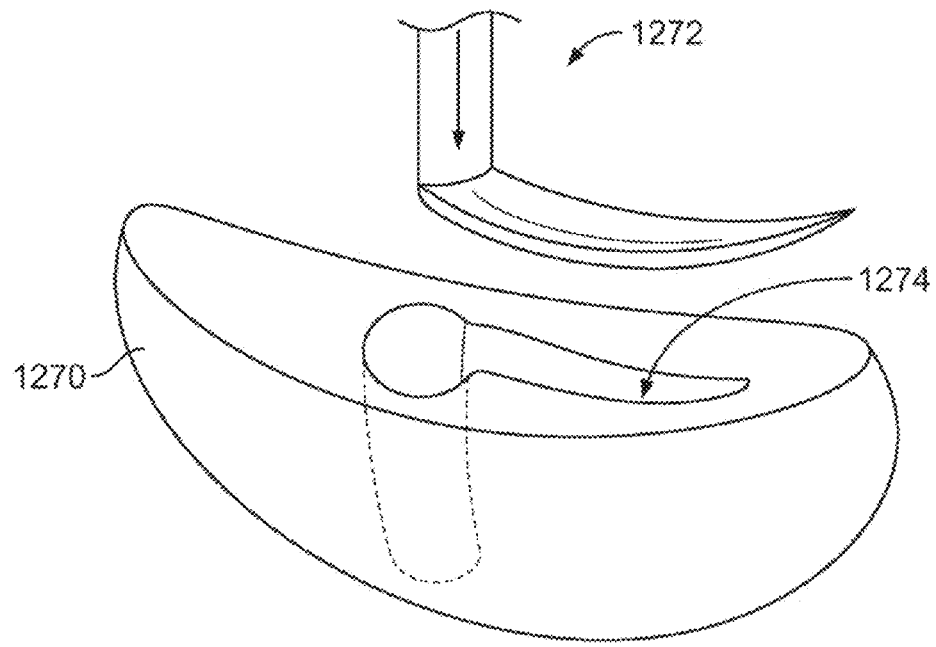
FIG. 171 shows an illustrative augment for use with a blade removal tool.
Figure 172:
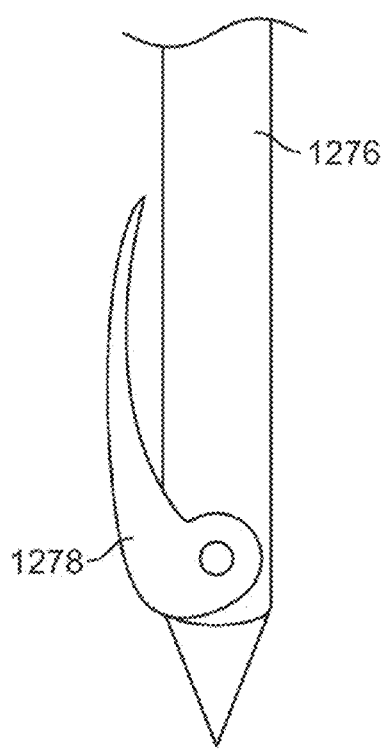
FIGS. 172 and 173 show an illustrative removal tool that may include a collapsible blade.
Figure 173:
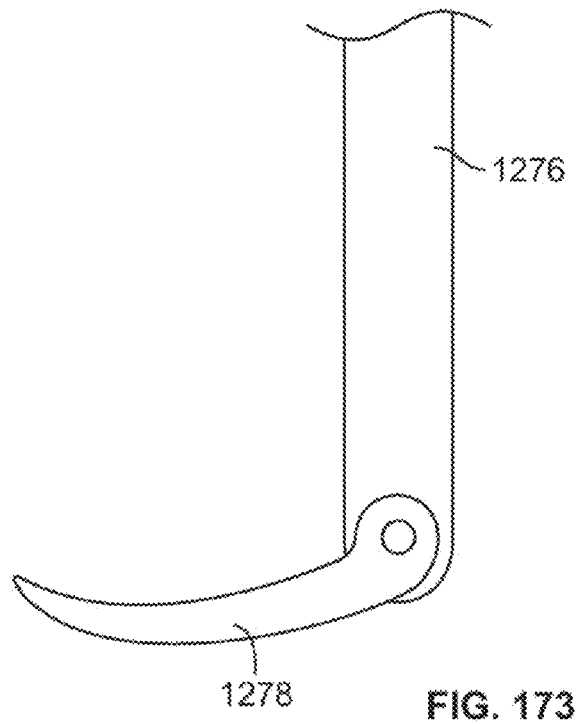

FIGS. 168-170 show some embodiments that may be used with a crescent blade or a two-sided blade that can rotate in the slot in order to affect removal. The blade is inserted into an augment and then turned or rotated, which allows the blade cut away adjacent ingrown bone and/or to securely "grab" the augment for removal. FIG. 171 shows an augment 1270 for use with a blade removal tool 1272. The opening or slot 1274 of the augment 1270 of this embodiment is shaped to correspond to removal tool 1272. The removal tool 1272 may be inserted completely into and through the augment 1270 such that it extends out the other end of the augment 1270. Alternatively, the removal tool 1272 may be inserted into an opening that also has a quarter-shaped or other shaped turn configured. Inside the opening that allows the removal tool to be inserted, rotated inside the opening, for example 15° or 20°, and then removed to pull the augment out. FIGS. 172 and 173 show a removal tool 1276 that may comprise a collapsible blade.

Figure 174:
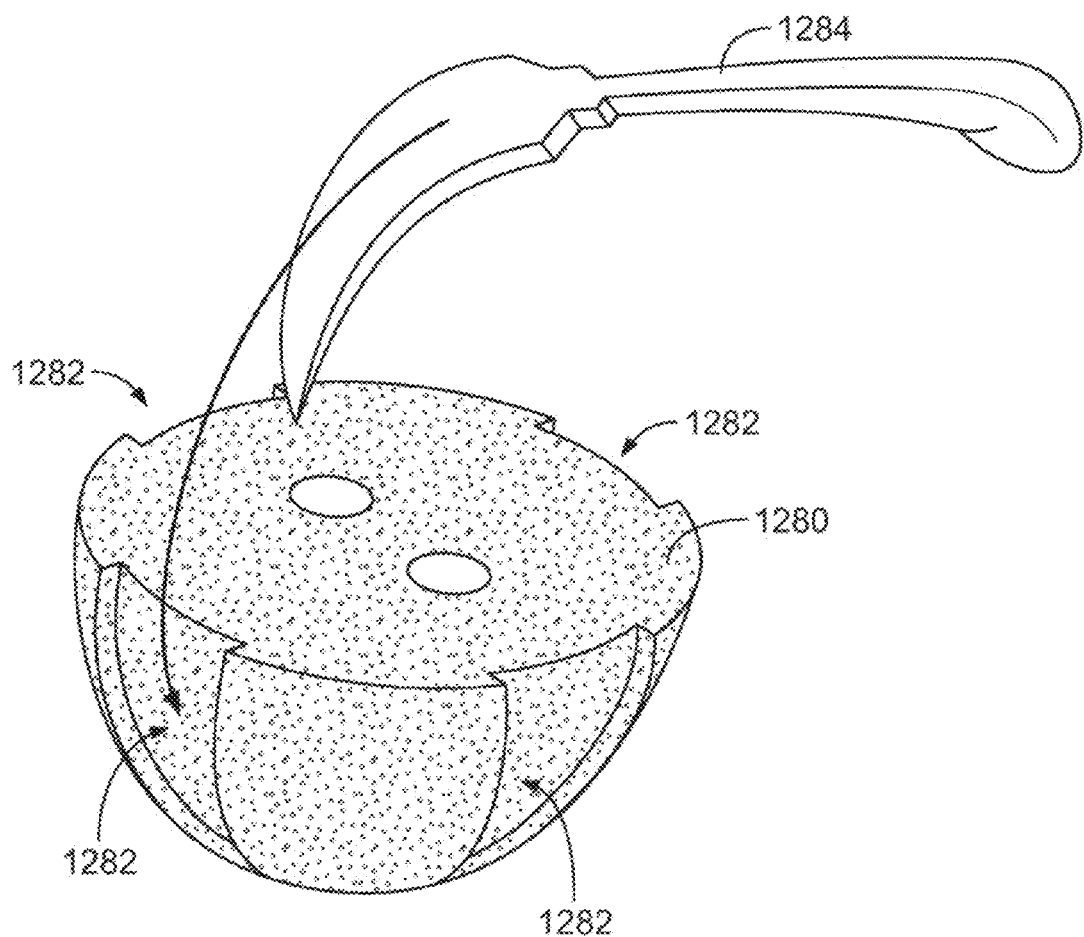
FIGS. 174 and 175 show illustrative augments predesigned for removal.

FIG. 174 shows certain embodiments of an augment pre-designed for removal. The augment is provided with one or more removal features comprising recesses, channels, or grooves on the outside of the augment. For example, augment 1280 includes channels 1282 on the outside of the augment 1280. It will be understood that removal features may also be positioned in and through the augment as desired. The removal features shown allow a blade, scalpel, or other removal instrument to be positioned alongside the augment 1280 or otherwise in the one or more removal portions. The removal tool (e.g., tool 1284) may be used to pull or lever the augment 1280 out of its initial position. In some embodiments, the removal features may be provided with any type of bone ingrowth prevention surface, in order to prevent bone ingrowth in those particular areas such that they can more easily accept a removal tool.

Figure 175:
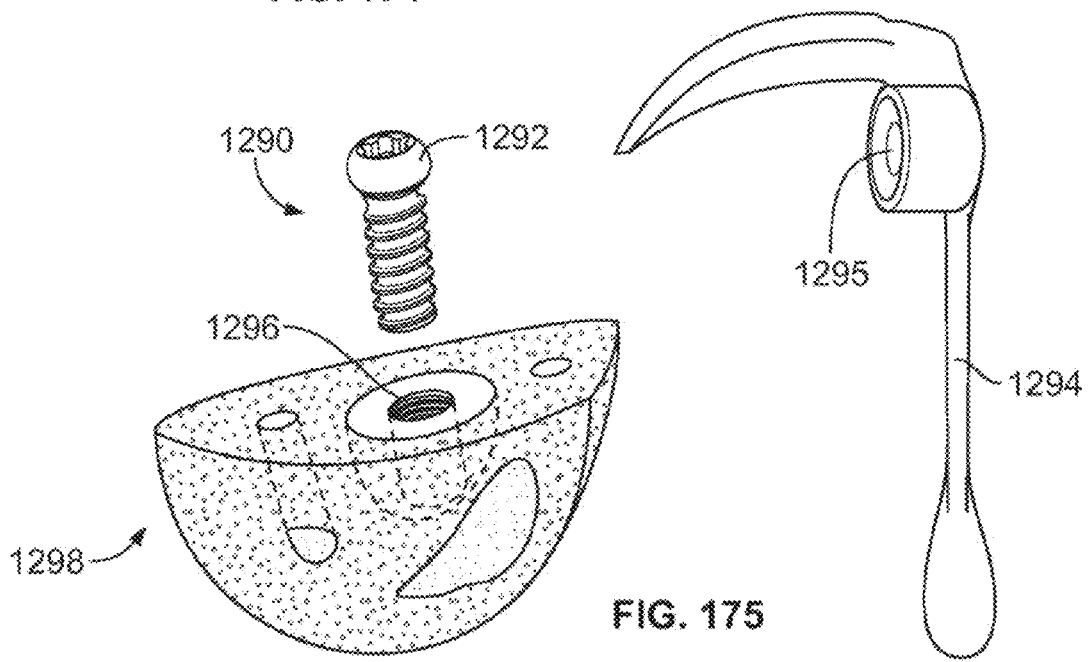

FIG. 175 shows certain embodiments of an augment pre-designed for removal. The augment is configured to receive a removable pivot member 1290. In some embodiments, the removable pivot member 1290 has a threaded shank and a convex or ball-shaped head 1292 that acts as a pivot point for a removal instrument 1294. When the removable pivot member 1290 is inserted into an opening 1296 in the augment 1298, the ball-shaped head 1292 provides a fulcrum or pivot point for removal instrument 1294, which, in some embodiments, is configured with a concave receiving portion 1295. In use, concave receiving portion 1295 articulates against convex head 1292, providing a removal force. The surgeon may move the instrument 1294 around the augment 1298, using a can opener-type action, in order to lever the augment 1298 out of the bone.

Figure 176:
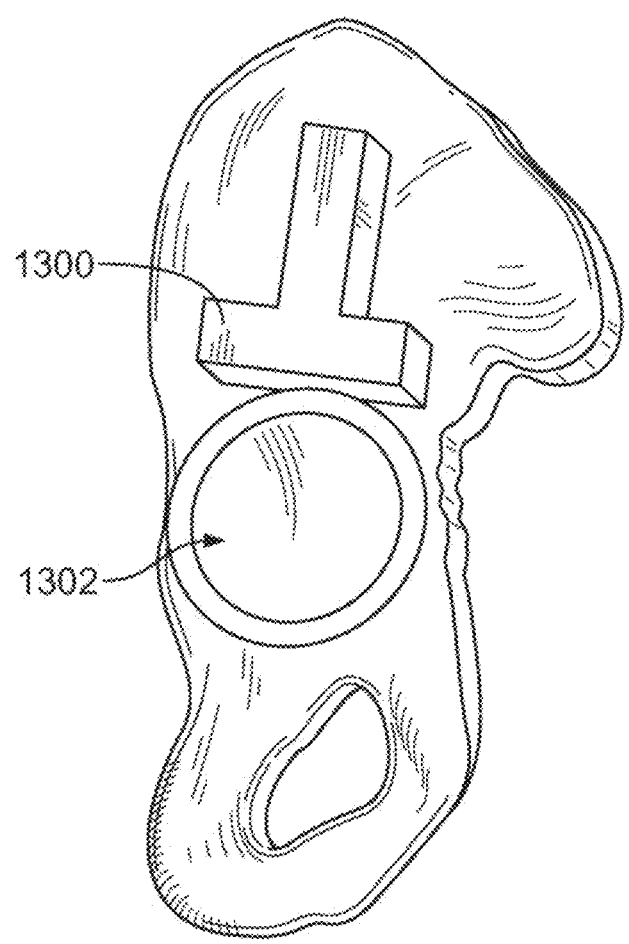
FIG. 176 shows an illustrative contact-reducing augment.

FIG. 176 shows a contact-reducing augment according to some embodiments. In some surgeries, it may be desirable to limit the amount of contact that metal has with bone, for example, if a patient has metal sensitivity or allergy. The T-shaped augment 1300 shown in FIG. 176 provides a reduced number of contact points with a patient's natural bone. The augment 1300 may be secured to a shell/cage or other augment disposed in acetabulum 1302 in any way, including those currently known as well as those described herein. However, this augment 1300 has open spaces between bone-contacting points. Once positioned, open spaces may be filled with bone graft material, such as allograft, bone paste, putty, or cements, with polyurethane graft materials, such as an injectable material, or any other specific material or combination thereof mat the particular surgeon uses to pack bone voids. Filler materials may include, for example, calcium phosphate and/or bone morphogenic proteins (BMPs).

One benefit provided by this design is that it provides a support to keep a shell/cup/augment in place or otherwise stable at points within the bone void without providing full contact with metal along the entire bone void. The embodiment shown is a T-shaped augment 1300, but it will be understood that any appropriate augment having one or more contact points but providing a reduced contact surface in general should be considered within the scope of the embodiment. For example, a "jacks"-shaped augment having a plurality of offshoots from a central region may be utilized.

Figure 177:
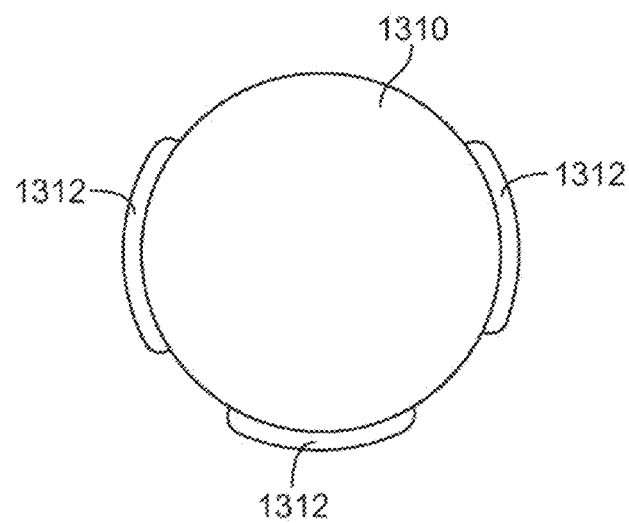
FIG. 177 shows an illustrative augment having one or more coated portions.

FIG. 177 shows an augment having one or more coated portions 1312 according to some embodiments. The augment 1310 may be fully coated or may have only strips or patches or select areas that are coated. This embodiment may be useful for patients having a metal allergy or reaction or any other time a surgeon wishes to fill a space with a material other than with completely metal augment. The coating 1312 may be overmolded polyurethane, hydroxyapatite, any other appropriate coating, or any combination thereof.

Figure 178:
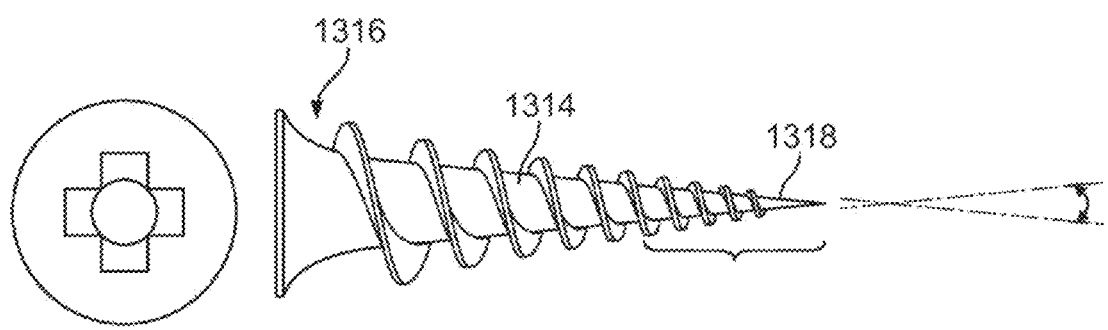
FIGS. 178 and 179 show illustrative anchor screws adapted for securement of an implant to surrounding bone.
Figure 179:
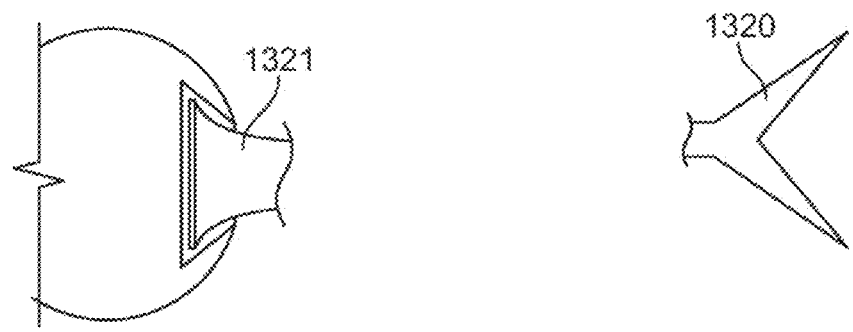

FIGS. 178 and 179 illustrate some embodiments of anchor screws adapted for securing an augment, mounting member, or acetabular shell or cage to surrounding bone. The screw 1314 has a flared head 1316 which is adapted for being received in a complementary undercut groove or recess in an augment, mounting member, or acetabular shell or cage. The anchor screw 1314 may be placed into the bone prior, and then connected to the augment, mounting member, or acetabular shell or cage in-situ, or the anchor screw 1314 may be loosely attached to the augment, mounting member, or acetabular shell or cage, and the augment/mounting member/shell/anchor screw assembly simultaneously inserted into the bone as one unit. The tip 1318 of the anchor screw 1314 may be sharp and self-starting/tapping/drilling. In some embodiments, as shown, the anchor screw 1314 may be tapered along one or more portions of its length. Large diameter threads may be employed to engage more bone and to prevent the anchor screw from stripping or pulling out. In some embodiments, one or more portions of the thread pattern, for example in some embodiments, regions proximal to the head, may be finer than other thread portions as desired to better engage cortical bone portions.

Figure 181:
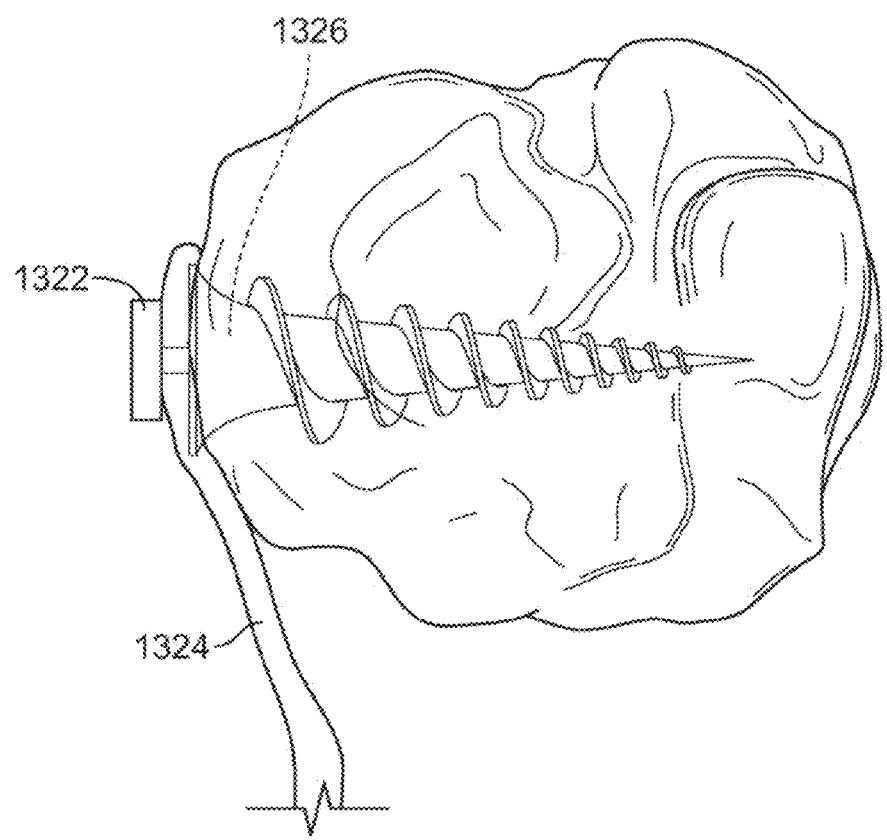

The screw anchor 1314 may be formed of a solid or porous material, such that it provides stability when it is anchored in place, and also provides long-term fixation because bone will be encouraged to grow into any portions of porous material. Moreover, by making one or more portions of the anchor screw 1314 porous, the modulus of elasticity may be more closely matched with surrounding bone as compared to a solid material, and the anchor screw 1314 may provide better initial fixation and overall stability of an adjoining or integral augment, for example. In some embodiments, the anchoring screw 1314 may be provided as an integral portion of an augment. In other words, a larger augment body may form a portion of the head or shank of the anchor screw. The anchor screw may also be configured for reconnecting soft tissues to bone, as shown in FIG. 181.

Figure 180:
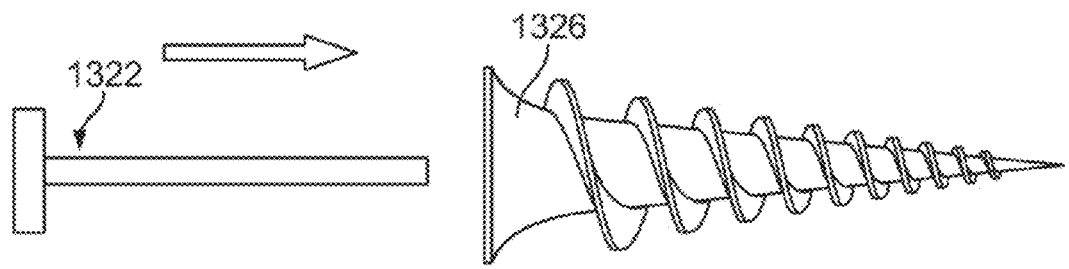
FIGS. 180 and 181 show an illustrative anchor screw screwed into place and a smaller screw that may be inserted into a cannulated portion of the anchor screw.

FIG. 179 illustrates an alternative embodiment of an anchor screw 1321 comprising a split tip 1320, which is configured to deform radially-outwardly to resist pull-out and/or prevent stripping out of the bone. FIGS. 180 and 181 schematically illustrate that once an anchor screw 1326 is screwed into place, another smaller nail or screw 1322 may then be inserted in a cannulated portion of the anchor screw 1326. The use of the smaller nail 1322 can be two fold, for example, to (1) split open the end of the anchor screw 1326 and/or (2) help secure soft tissues (e.g., soft tissue 1324). In certain embodiments, an anchor screw may generally resemble a dry wall anchor screw.

Figure 182:
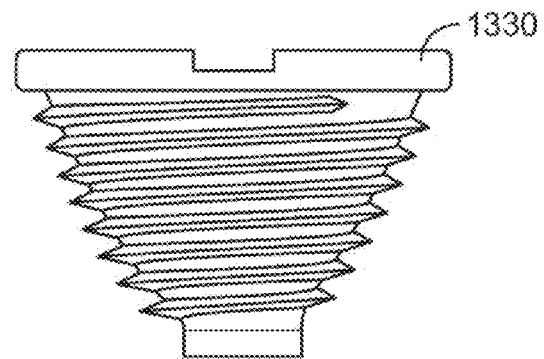
FIGS. 182 and 183 show an illustrative anchor screw configured to be used to secure a graft material.
Figure 183:
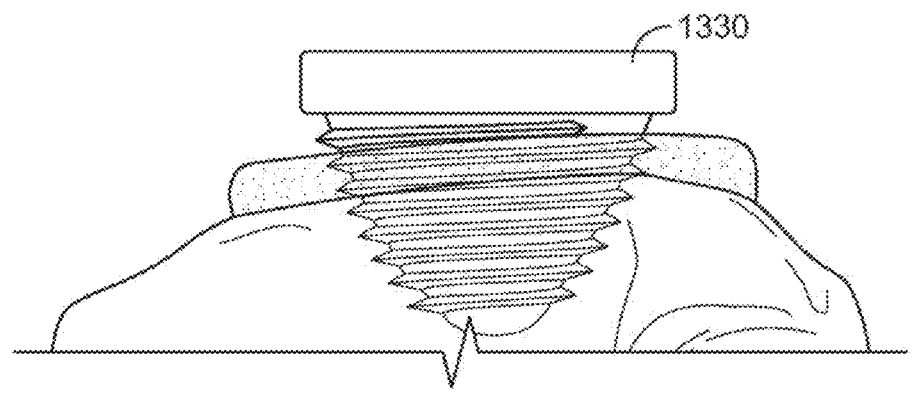

FIGS. 182 and 183 illustrate certain embodiments of an anchor screw 1330 that is configured to be used to secure a graft material, such as bone graft, allograft, or resorbable mesh, to a bone defect.

Figure 184:
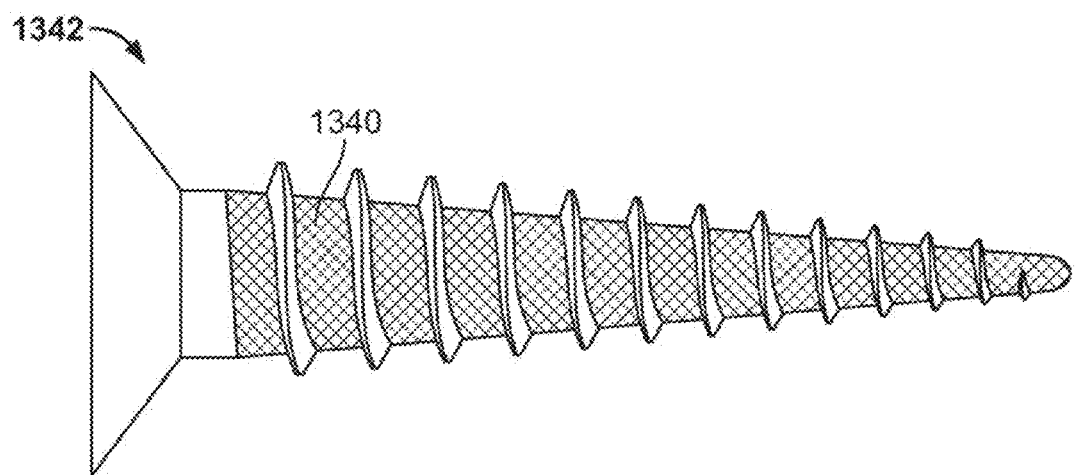
FIG. 184 shows an illustrative fastener that includes a porous shaft.

FIG. 184 shows a fastener 1342 that provides a porous shaft 1340 according to some embodiments. The porous shaft 1340 may encourage bone ingrowth into the fastener 1342. The fastener itself may serve as a porous augment or it may be used to secure any of the embodiments described herein.

Figure 185:
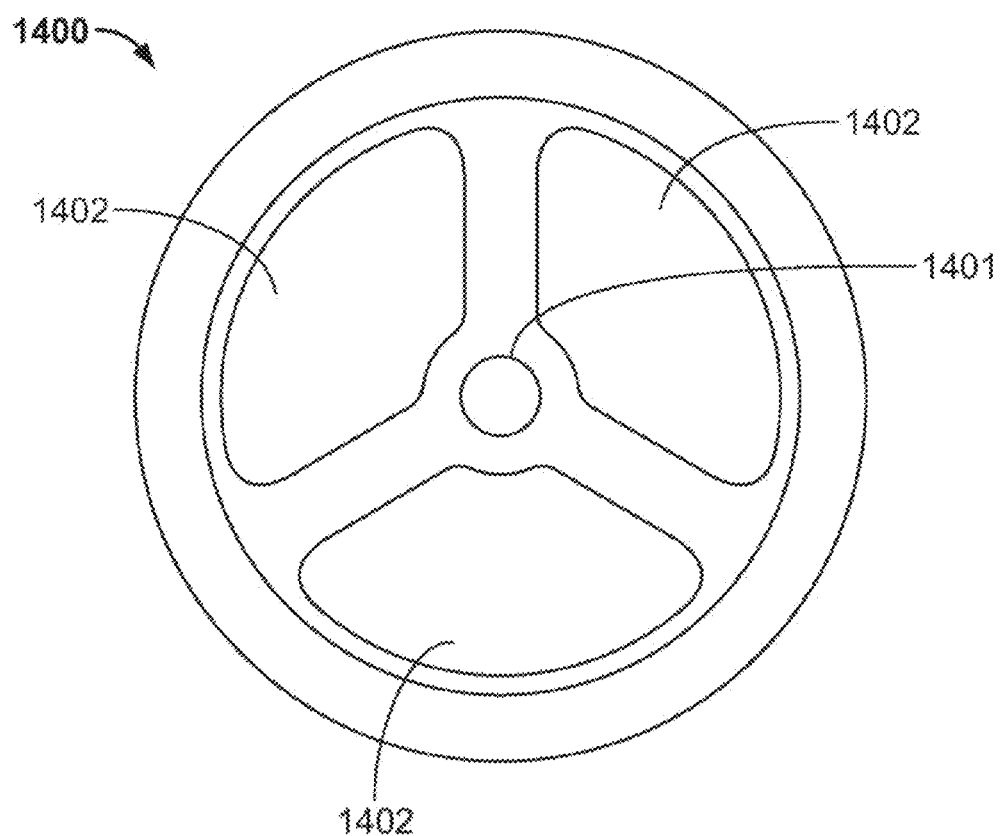
Figure 186:
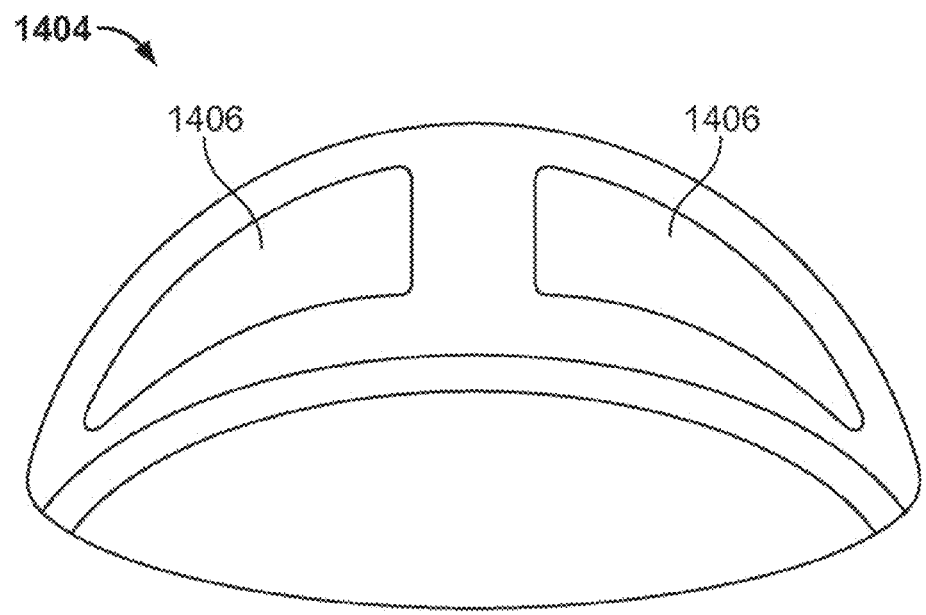

FIGS. 185-187 show certain embodiments of augments in the shape of an acetabular cup (also referred to as an "acetabular shell," "cage," or "cup") provided with a number of openings disposed circumferentially around the augment. For example, augment 1400 has openings 1402, augment 1404 has openings 1406, and augment 1408 has opening 1410. Any number of openings may be provided in the augment, and the openings may be of any shape or size. The embodiments of FIGS. 185 and 186 include multiple openings 1402 and 1406, while embodiments according to FIG. 187 may have a single opening 1410, which as shown is relatively larger than openings 1402 and 1406. The openings receive complementary-shaped inserts which serve to secure the augment in the acetabulum. The openings and inserts may be of any complementary shape (e.g., circular, rectilinear, semi-hemispherical, wedge-shaped, etc.) and are not limited to those shapes shown in the Figures.

Figure 190:
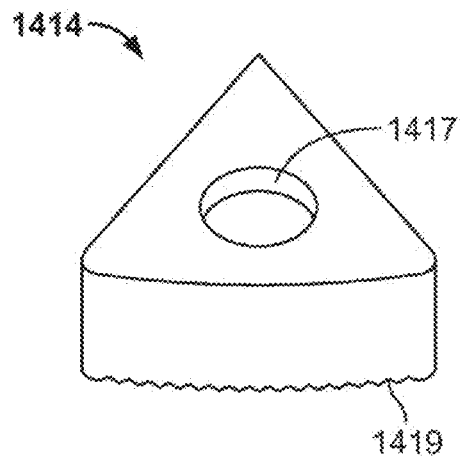
Figure 191:
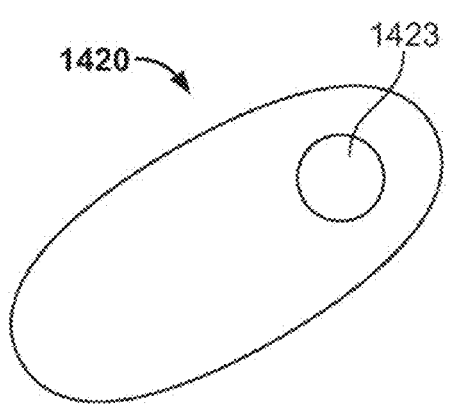
FIGS. 191-193 show illustrative curved inserts that may be positioned in the openings of the augments of FIGS. 185-187.
Figure 192:
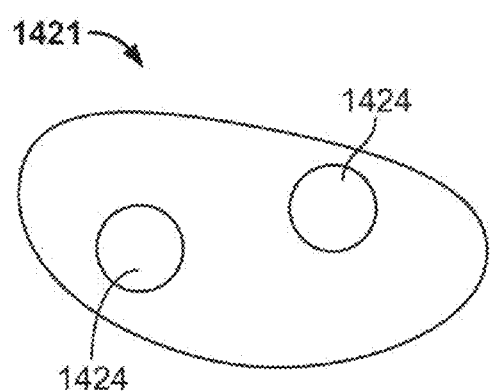
Figure 193:
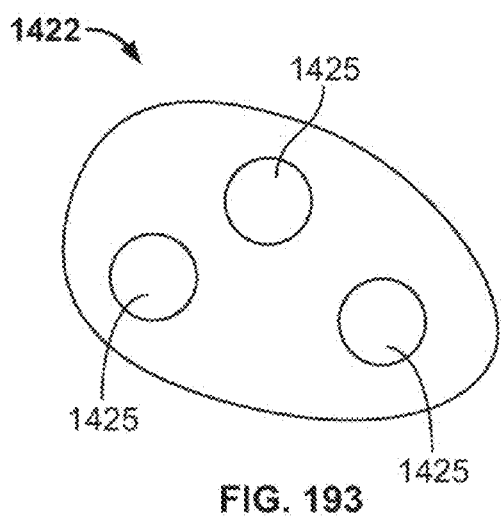

FIGS. 188-198 illustrate various embodiments of inserts that may be positioned in the openings of the augments of FIGS. 185-187. FIGS. 188-190 and FIGS. 191-193 illustrate embodiments of triangular-shaped inserts 1412-1414 and curved inserts 1420-1422, respectively, provided with screw holes to receive screws. Any number of screw holes may be provided on inserts and such holes may be provided in any location on the insert to have any trajectory. In FIGS. 188 and 193, three screw holes 1415 are provided on insert 1412 and three screw holes 1425 are provided on insert 1422. In FIG. 192, two screw holes 1424 are provided on insert 1421. In FIGS. 189-191 a single screw hole is provided (e.g., screw hole 1416, 1417, and 1423), which can be, but does not have to be, located asymmetrically on the insert as shown in FIGS. 189 and 191. The screw holes may be smooth, tapered, or threaded and may extend through the insert at any appropriate angle.

Figure 194:
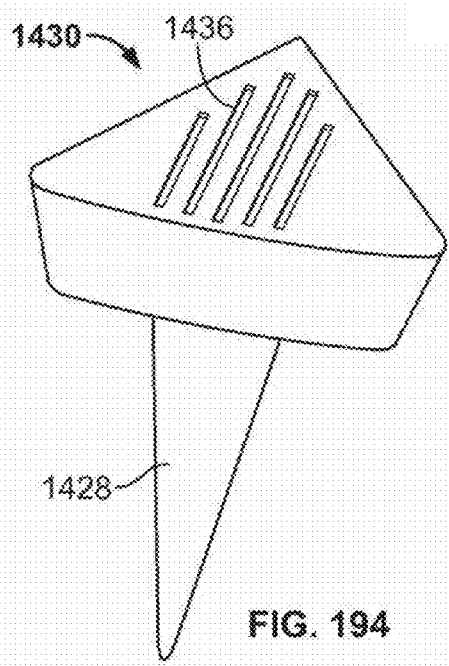
FIGS. 194 and 195 show an illustrative insert having a spike extending therefrom.
Figure 195:
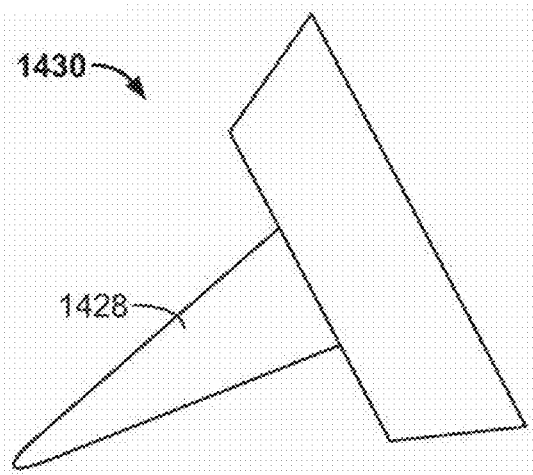
Figure 196:
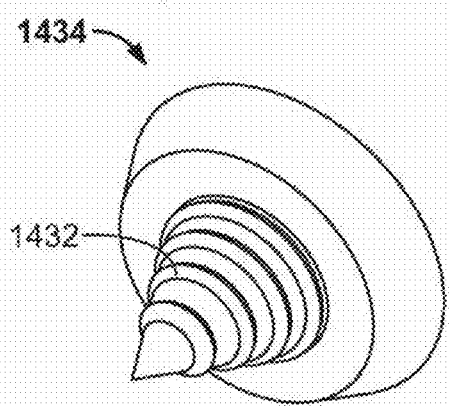
FIGS. 196 and 197 show an illustrative insert having screw threads extending from a surface thereof.
Figure 197:
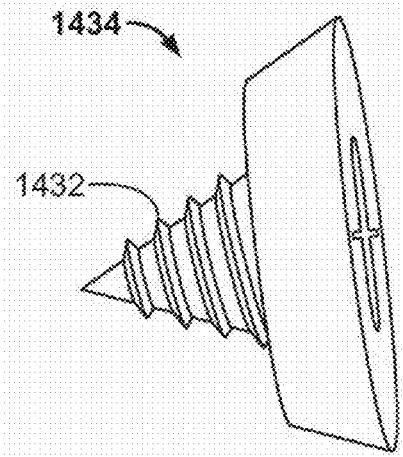

In FIGS. 194 and 195, a spike 1428 extends from the insert 1430. Alternatively or additionally, as shown in FIGS. 196 and 197, various types of screw threads 1432 may be formed integrally with, or be otherwise fixed to, an insert 1434 and extend from a surface thereof. Surfaces of the inserts may be grooved or etched to increase the surface area for cement fixation (e.g., as illustrated by surface 1436 of FIG. 194) or may be porous to facilitate bone ingrowth (e.g., as illustrated by surface 1419 FIG. 190).

Figure 198:
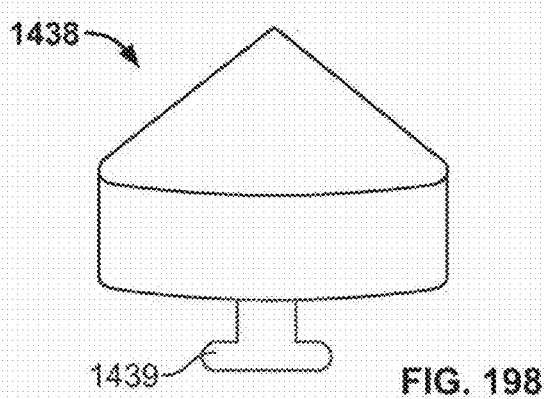
FIG. 198 shows an illustrative insert having a back portion provided with a mounting feature onto which supplemental augments or mounting members may be mounted.
Figure 199:
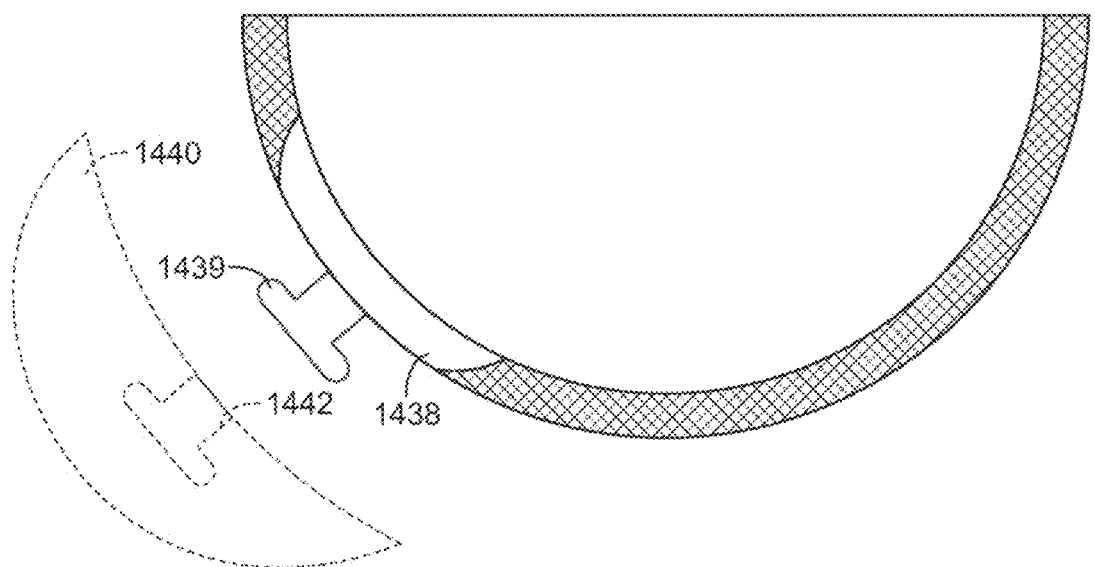
FIG. 199 shows an illustrative supplemental augment having a complementary track to the mounting feature provided in FIG. 198.

FIG. 198 shows the back of an insert 1438 provided with a mounting feature 1439 onto which supplemental augments or mounting members (e.g., flanges, blades, hooks, plates, etc.) may be mounted according to some embodiments. The mounting feature 1439 of insert 1438 may be provided, for example, as a male dovetail or other shape and the supplemental augment may have a complementary track. For example, as shown in FIG. 199, supplemental augment 1440 has complementary track 1442. The male mounting feature 1439 of insert 1438 is positioned in the track 1442 and the supplemental augment 1440 positioned relative to the insert 1438 by translating the male mounting feature 1439 of the insert 1438 in the track 1442. In some embodiments, a supplemental augment may be provided with an opening (rather than a track) that corresponds to the shape of the mounting feature extending from the insert, such as mounting feature 1439. The supplemental augment may be mounted on the insert by inserting the mounting feature of the insert into the opening on the supplemental augment and retained thereon such as via taper lock or other mechanical retention methods.

Figure 200:
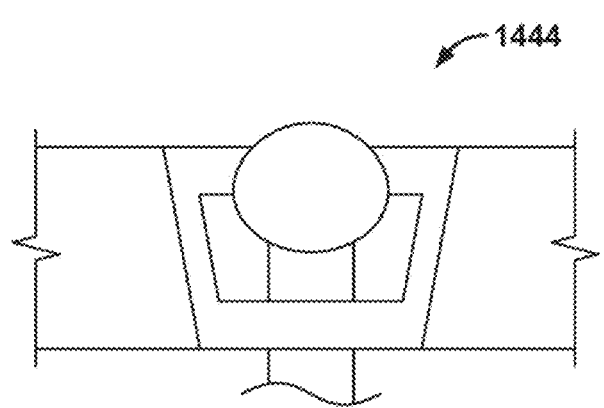
FIG. 200 shows an illustrative taper lock.
Figure 201:
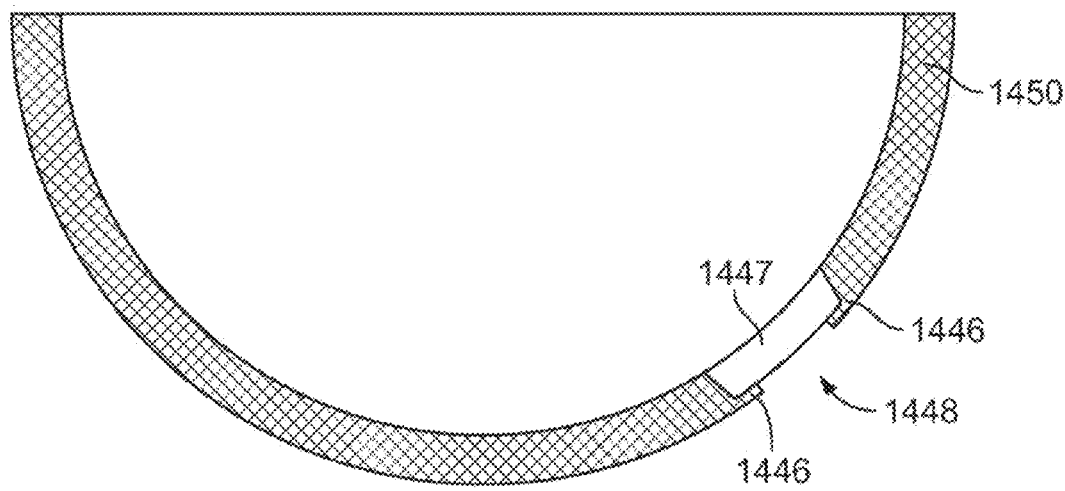
FIG. 201 shows an illustrative ledge that may be provided around at least a portion of an opening on the outer wall of an augment.

In use, an appropriate insert (which is selected in part to suit the anomalies and defects of a particular anatomy) is positioned and retained in an opening such as one of openings 1402, 1406, and 1410 of FIGS. 185-187, and the augment/insert assembly is positioned in the acetabulum. In some embodiments, an insert and an opening may form a taper lock (e.g., as illustrated by taper lock 1444 of FIG. 200) or friction fit to lock the insert in the opening. In some embodiments, as shown in FIG. 201, for example, a ledge 1446 may be provided around at least a portion of an opening 1448 on the outer wall of the augment 1450 so as to extend partially into the opening 1448. An insert 1447 is positioned in the opening 1448 and the ledge 1446 prevents the insert 1447 from passing through the opening 1448 and retains the insert 1447 within the opening 1448. Inserts need not be provided in every opening of the augment but rather may be strategically placed during surgery. If the inserts of FIGS. 188-193 are used, screws are positioned in the screw hole(s) of the insert and engage surrounding bone to secure the augment in place. The screws can be any appropriate fastener, including but not limited to polyaxial screws. If the inserts of FIGS. 194-197 are used, the spike (e.g., spike 1428) or screws (e.g., screw 1432) penetrate bone to secure the augment in place. The augment itself may include at least one screw hole (e.g., center hole 1401 in FIG. 185) through which a screw may extend to further secure the augment in place. Cement may be provided over or within the augment to fill the openings of the augment not provided with an insert for fixation of the augment to backside bone voids, and a shell or liner may be cemented into the augment in a desired orientation.

Figure 202:
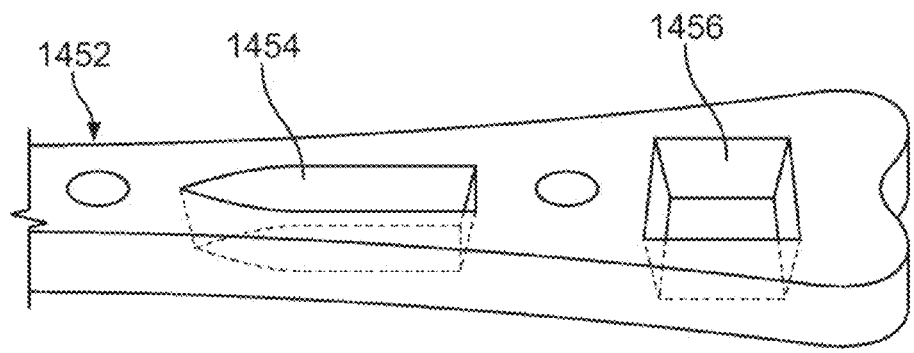
FIG. 202 shows an illustrative mounting member having openings for correspondingly-shaped inserts.

The features describe above may be applied to augments other than cup-shaped augments, as well as mounting members such as bone plates. For example, as shown in FIG. 202, in addition to or in lieu of traditional screw holes, openings 1454 and 1456 may be provided in a bone plate 1452 and correspondingly-shaped inserts (such as those shown in FIGS. 188-197) positioned in the plate 1452 to secure the plate 1452 to bone, as described above.

Figure 203:
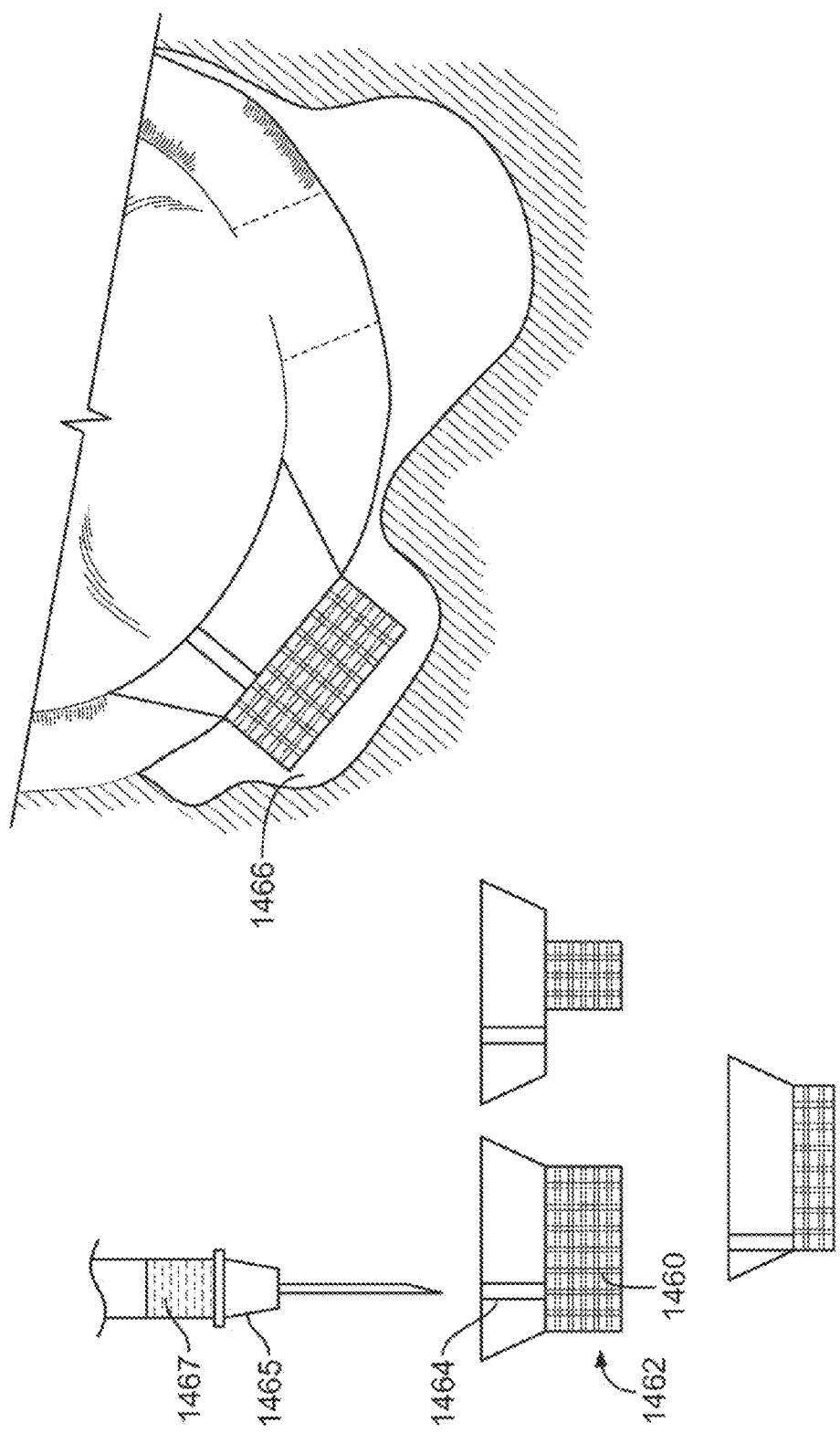
FIG. 203 shows illustrative inserts having lattice structures provided thereon.

FIG. 203 illustrates some embodiments of inserts that may be provided in the openings of the augments of, for example, FIGS. 185-187. Lattice structure is provided on the inserts (e.g., lattice structure 1460 of insert 1462). The inserts may have different amounts and configurations of lattice structure (e.g., some lattices may be large, small, deep, shallow, offset, etc.). The inserts may include a port (e.g., port 1464 of insert 1462) that extends through the insert. In use, the insert is secured in the augment (as discussed above), and the augment positioned so that the lattice structure of the insert extends into a bone void such as bone void 1466. A bone cement, injectable polymer (e.g., polyurethane) or bioresorbable material is injected into the bone void and around the lattice structure via the port in the insert. For example, an injector 1465 may be used to deposit an injectable curing material 1467, which may be one of the materials listed above, into lattice structure 1460 through port 1464 of insert 1462. The lattice structure serves to reinforce the injected material abler curing/setting.

Figure 204:
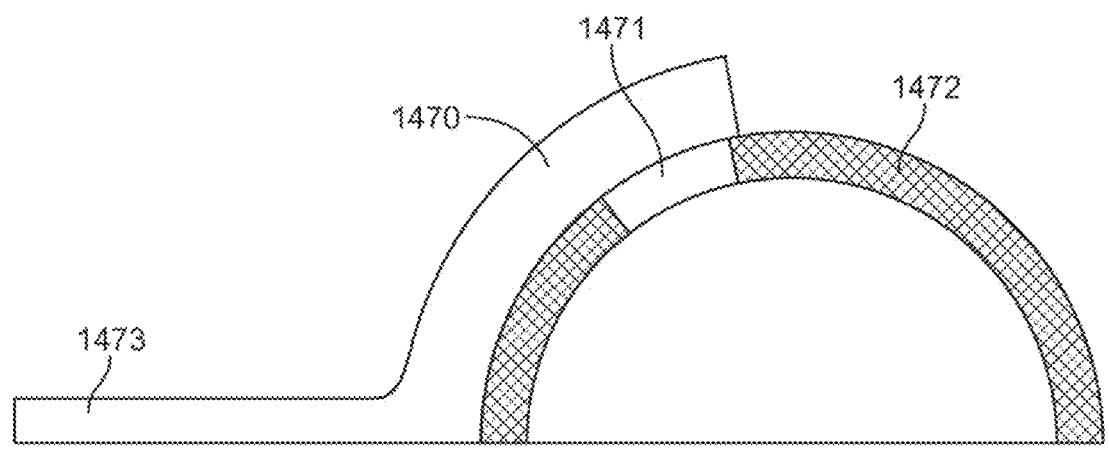
Figure 205:
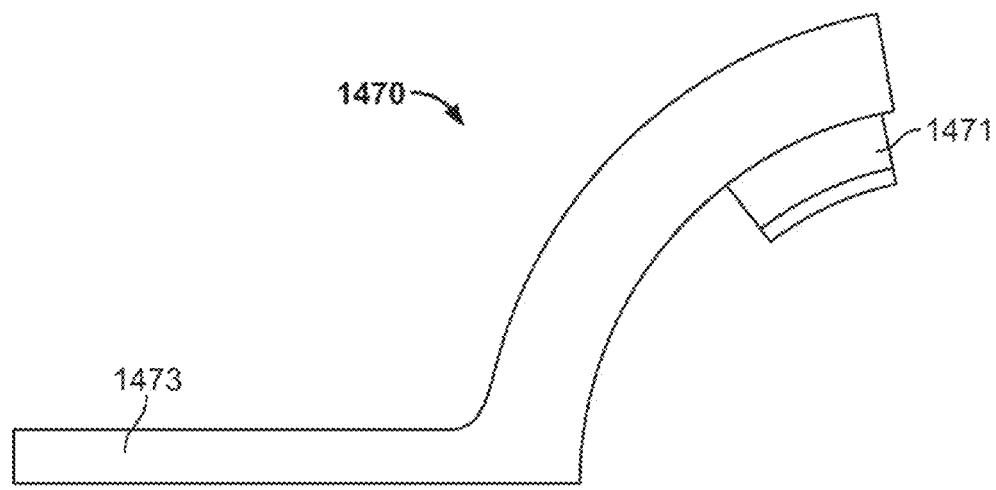

In FIGS. 204 and 205, a supplemental augment 1470 (shown in isolation in FIG. 205) is coupled to an augment 1472 (referred to here as the "primary augment" to avoid confusion) such as shown in FIGS. 185-187. A tongue 1471 extends from the supplemental augment 1470 and is of complementary shape to the opening in the primary augment 1472. The tongue 1471 is inserted into the opening of the primary augment 1472 to orient the supplemental augment 1470 properly relative to, and to retain the supplemental augment 1470 on, the primary augment 1472. In one possible use, the primary augment 1472 with attached supplemental augment 1470 is positioned adjacent a bone void in the acetabulum such that the flange 1473 of the supplemental augment 1470 extends adjacent healthy bone. Screws or other fixation means may be inserted through the flange 1473 to attach the primary 1472 and supplemental 1470 augment to bone and thereby retain the primary augment 1472 in position within the acetabulum. In some embodiments, a portion of the supplemental augment 1470 that spans the bone void may be shaped to fill at least a portion of the void.

Figure 206:
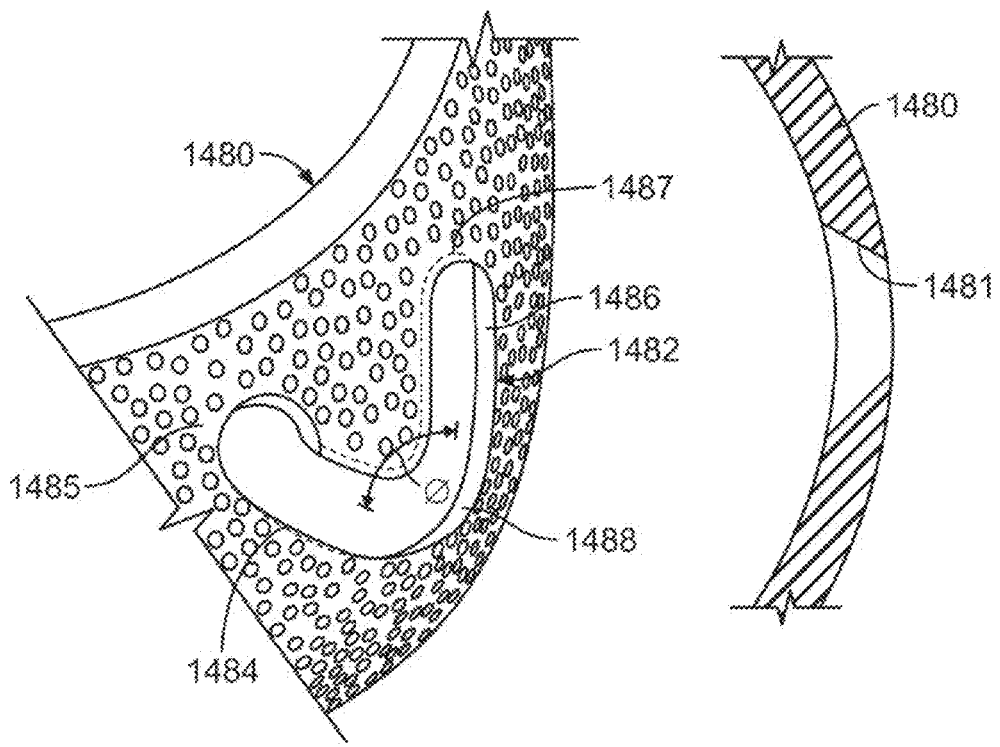
Figure 207:
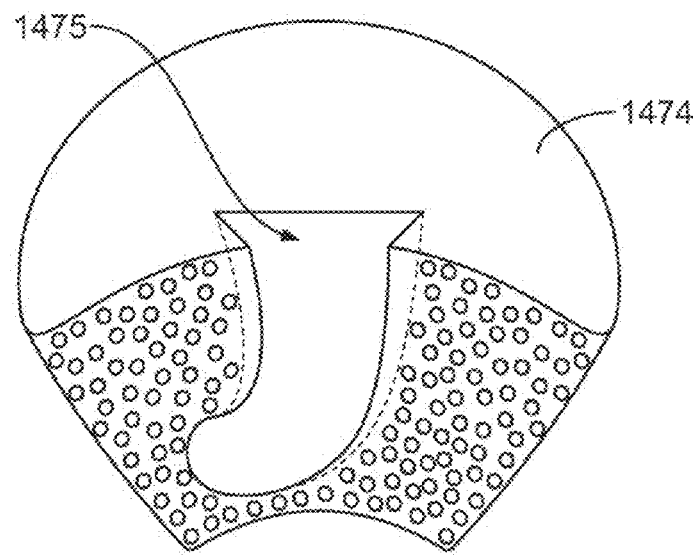
Figure 208:
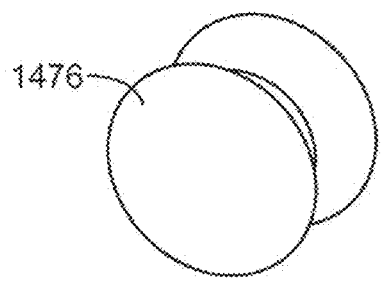

FIGS. 206-208 relate to augments that may be configured to attach to shells or cages with or without cement, and are also configured to allow fine positional adjustments for best bone lit, coverage, and stability. The augment can be placed on a periphery of a hemispherical acetabular shell, cage, or augment (a shell 1474 is illustrated). As shown in FIG. 206, the shell 1480 may include a track 1482 that is undercut so as to form a dovetail joint 1481 with the augment. The track 1482 may be provided as a j-shaped slot (as shown), T-shaped slot, H-shaped slot, or any other shape involving combinations of straight and/or carved segments. The track 1482 preferably includes at least two portions or slots, at least one of which can receive a complementary connecting member from the augment. As shown in FIG. 206, for example, the first portion or slot 1484 and second portion or slot 1486 join about common region 1488 but are separated out at distal ends 1485 and 1487 by angle $\Theta$, which is less than 180° in the example. The at least two portions thereby permit the augment to be adjustably positioned along the surface of the shell 1480 by sliding the augment (and its connector) along the track and securing it at the desired location. For example, the augment could be secured in one of the at least two portions (such as slot 1484), or the other of the at least two portions (such as slot 1486), or in between.

As shown in FIG. 207, the augment 1474 may include a channel 1475 that is shaped to receive a connecting member. In the illustrated embodiment of FIG. 208, the connecting member 1476 is a "V" button but connecting members having other shapes are contemplated. One side of the V button 1476 is positioned in the channel 1475 of the augment 1474, and the other side of the V button 1476 engages the track 1482 on the shell 1480 to thereby couple the augment 1474 to the shell 1480 and allow for variable positioning of the augment 1474 relative to the shell 1480. While the augment 1474 may be mechanically retained to the shell 1480 in this way, it also may be cemented to the shell 1480. To facilitate such retention, surfaces of the augment 1474 and/or shell 1480 may be textured to facilitate adherence of the cement on the augment 1474 and/or shell 1480.

FIG. 209 shows a "7-graft" type augment 1477 that spans a pelvic defect that enables screw fixation into the posterior portion of the pelvis. The augment includes an upraised portion 1478 for positioning adjacent a portion of the shell 1489 and an elongate portion 1479 for spanning a bone void or other pelvic defect 1490 and affixing to the sidewall of the pelvis into healthy bone (such as via screws) to thereby retain the shell in the acetabulum. The upraised portion 1478 can be affixed directly to the shell 1489 (such as via mechanical fixation methods such as screws) or can be cemented or otherwise adhered to the shell 1489.

Figure 210:
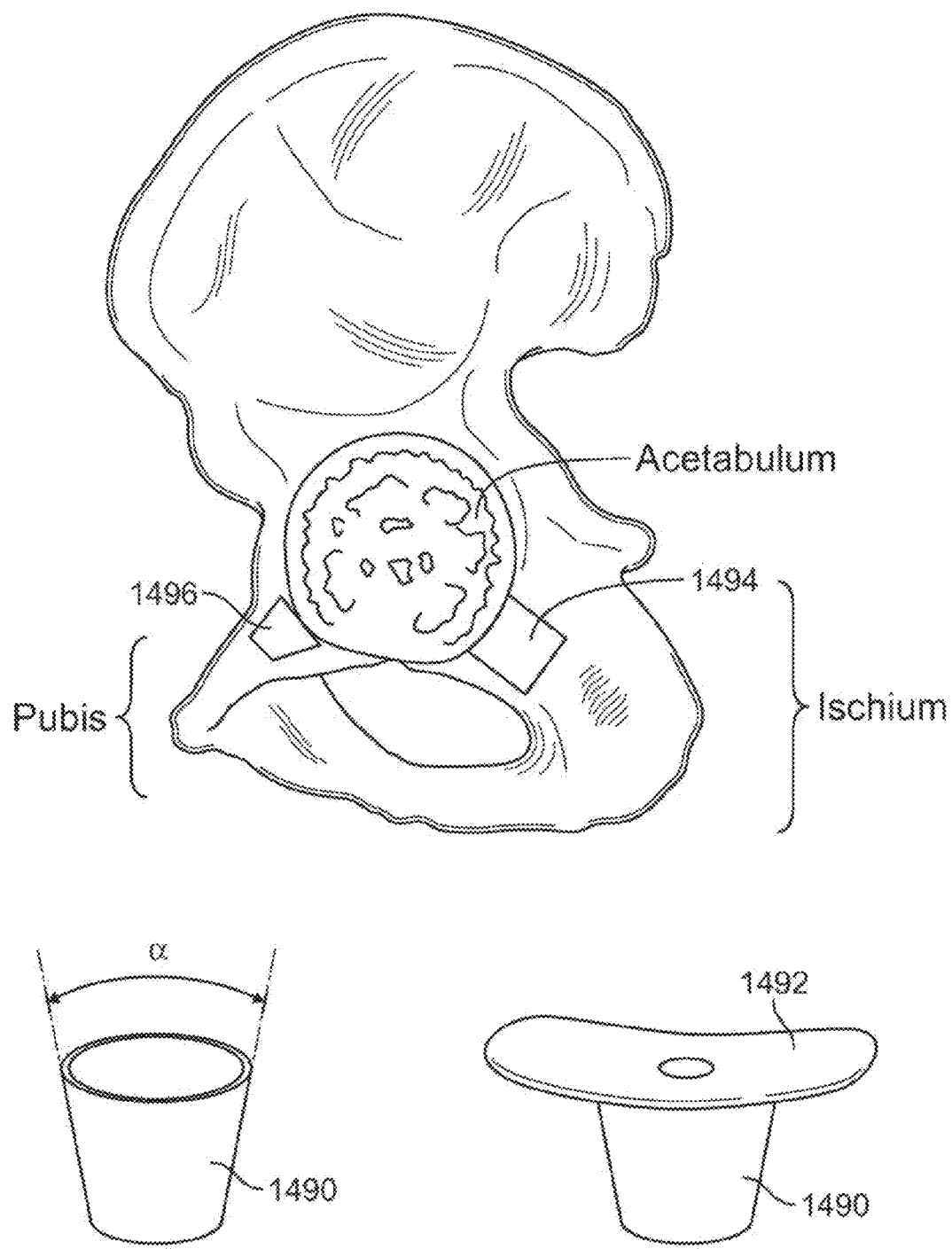

FIG. 210 illustrates a secondary augment 1490 for use with a primary augment. In use, the secondary augment 1490 is attached or coupled to the primary augment so as to extend off the primary augment. Bone surrounding the primary augment (such as the ischium) is prepared to received the secondary augment 1490, for example, at locations 1494 or 1496. In some embodiments, the ischium is reamed and the secondary augment 1490 is seated in the reamed out bone. In this way, the secondary augment 1490 helps to anchor the primary augment in the proper position within the acetabulum. The secondary augment 1490 is illustrated as conical in shape but can be of any shape suitable to accomplish its intended purpose. The secondary augment 1490 can be chemically (such as via adhesive) or mechanically (such as via screws) attached to the primary augment in any way, including those described herein. By way only of example, inserts (such as, but not limited to, those illustrated in FIGS. 194-198) may be positioned in the primary augment or shell (as described above) and the secondary augment 1490 may attach to the mounting structure provided on those inserts to thereby couple the secondary augment 1490 to the primary augment. Again, however, any coupling method is contemplated. In some embodiments, the secondary augment 1490 includes a wing 1492 to impart more stability to the primary/secondary augment construct.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in acetabular systems, may be applied to medical devices to be used in other surgical procedures including, but not limited to, spine arthroplasty, cranio-maxillofacial surgical procedures, knee arthroplasty, shoulder arthroplasty, as well as foot, ankle, hand, and extremities procedures.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A method of implanting an orthopedic device into bone, the method comprising:
   inserting an acetabular shell into a bone void in the bone;
   securing, by a first fixation element, the inserted acetabular shell to the bone;
   inserting an augment into the bone void and adjacent to the secured acetabular shell, at least a portion of the inserted augment inserted to a same depth into the bone void as at least opposing sides of the first fixation element such that the at least a portion of the augment extends around at least the opposing sides of the first fixation element; and
   applying a second fixation element to the shell and augment, wherein applying the second fixation element (1) locks the shell and augment together to form a unitary implant and (2) secures the unitary implant to the bone.

2. The method of claim 1, wherein the second fixation element comprises bone cement.

3. The method of claim 2, wherein the augment comprises a trough for receiving the bone cement, and applying the second fixation element comprises pouring cement down the trough, thereby binding the augment to the shell and to the patient's bone.

4. The method of claim 3, wherein the augment comprises an arcuate surface configured to contact an exterior surface of the shell, and wherein inserting the augment includes translating the augment along the exterior surface of the shell.

5. The method of claim 4, wherein applying the second fixation element comprises pouring a single volume of bone cement down the trough.

6. The method of claim 5, wherein pouring the single volume of bone cement comprises pouring the cement into a portal defined by the exterior surface of the shell and an end of the trough.

7. The method of claim 2, further comprising inserting a bone screw through the augment and into the bone after the bone cement sets.

8. The method of claim 1, wherein the augment is staple-shaped and includes a base portion and at least two protections extending from the base portion and spaced apart to define a gap therebetween.

9. A method of implanting an orthopedic device into bone, the method comprising:
   inserting an acetabular shell into a void in the bone;
   securing the acetabular shell to the bone by a fixation element;
   inserting an augment into the void and adjacent to the secured acetabular shell to a position at which the fixation element extends through a gap of the augment, the augment includes at least one trough for receiving bone cement, the trough positioned adjacent the acetabular shell, and wherein the inserting the augment includes displacing a portion of the augment to a depth in the void that is the same as a depth of at least opposing sides of the fixation element such that the portion of the augment extends around at least the opposing sides of the fixation element; and
   placing bone cement into the trough, thereby binding the augment to the acetabular shell to form a unitary implant within the void in the bone.

10. The method of claim 9, wherein the placing of the bone cement into the trough secures the augment and the acetabular shell to surrounding bone.

11. The method of claim 9, further comprising adjusting an orientation of the augment relative to the acetabular shell prior to the placing of the bone cement into the trough and binding the augment to the acetabular shell.

12. The method of claim 11, wherein the augment comprises an arcuate concave surface positioned in contact with an arcuate convex surface of the acetabular shell; and
   wherein the adjusting of the orientation of the augment relative to the acetabular shell comprises translating the arcuate concave surface of the augment along the arcuate convex surface of the acetabular shell.

13. The method of claim 9, wherein the placing of the bone cement into the trough comprises pouring a single volume of the bone cement into the trough.

14. The method of claim 9, wherein the at least one trough of the augment and an exterior surface of the acetabular shell define a portal for receiving the bone cement.

15. The method of claim 14, wherein the placing of the bone cement comprises pouring the bone cement into the portal defined by the at least one trough of the augment and the exterior surface of the acetabular shell.

16. The method of claim 9, further comprising inserting a bone screw through a bone screw opening in the augment and into the bone.

17. The method of claim 16, wherein the inserting of the bone screw through the bone screw opening and into the surrounding bone occurs after setting of the bone cement.

18. The method of claim 9, wherein the securing the acetabular shell to the bone includes inserting a fixation bone screw through an opening in the acetabular shell and into the bone.

19. The method of claim 18, wherein the augment includes a base portion and at least two protections extending from the base portion, the projections spaced apart to define the gap therebetween.

20. The method of claim 9, wherein the augment includes timing markings that are aligned with timing markings of the acetabular shell to properly align the augment relative to the acetabular shell.

21. The method of claim 9, wherein the augment includes timing markings that are aligned with timing markings of the acetabular shell to properly align the gap with the fixation element.

22. The method of claim 9, wherein the augment is staple-shaped and includes a base portion and at least two protections extending from the base portion and spaced apart to define the gap therebetween.

23. A method of implanting an orthopedic device into bone, the method comprising:
   inserting an acetabular shell into a void in the bone;
   inserting an augment into the void, the augment includes at least one trough for receiving bone cement, the trough positioned adjacent the acetabular shell; and
   placing bone cement into the trough, thereby binding the augment to the acetabular shell to form a unitary implant within the void in the bone, wherein the augment is staple-shaped and includes a base portion and at least two protections extending from the base portion and spaced apart to define a gap therebetween.

24. The method of claim 23, wherein the troughs are defined along a length of the projections and open onto an outer surface of the base portion.

25. The method of claim 23, wherein the augment comprises an arcuate concave surface defined by the base portion and/or the projections, the arcuate concave surface positioned in contact with an arcuate convex surface of the acetabular shell.

* * * * *